US012576147B2

(12) United States Patent
Levy et al.

(10) Patent No.: US 12,576,147 B2
(45) Date of Patent: Mar. 17, 2026

(54) RECOMBINANT PROTEINS WITH CD40 ACTIVATING PROPERTIES

(71) Applicants:INSERM (Institut National de la Santé et de la Recherche Médicale), Paris (FR); Université Paris est Cretéil Val de Marne, Cretéil (FR); Baylor Research Institute, Dallas, TX (US); Assistance Publique-Hôpitaux de Paris (APHP), Paris (FR)

(72) Inventors: Yves Levy, Paris (FR); Valentina Ceglia, Dallas, TX (US); Sandra Zurawski, Midlotian, TX (US); Gerard Zurawski, Midlothian, TX (US)

(73) Assignees: INSERM (INSTITUT NATIONAL DE LA SANTE ET DE LA RECHERCHE MEDICALE), Paris (FR); Université Paris est Cretéil Val de Marne, Cretéil (FR); Baylor Research Institute, Dallas, TX (US); Assistance Publique-Hôpitaux de Paris (APHP), Paris (FR)

( * ) Notice: Subject to any disclaimer, the term of this patent is extended or adjusted under 35 U.S.C. 154(b) by 1181 days.

(21) Appl. No.: 17/598,582

(22) PCT Filed: Mar. 26, 2020

(86) PCT No.: PCT/EP2020/058597
§ 371 (c)(1),
(2) Date: Sep. 27, 2021

(87) PCT Pub. No.: WO2020/193718
PCT Pub. Date: Oct. 1, 2020

(65) Prior Publication Data
US 2022/0175920 A1 Jun. 9, 2022

(30) Foreign Application Priority Data

Mar. 27, 2019 (EP) ..................................... 19305389
Dec. 5, 2019 (EP) ..................................... 19213891

(51) Int. Cl.
*A61K 39/395* (2006.01)
*A61K 39/00* (2006.01)
*A61K 39/385* (2006.01)
*A61P 31/18* (2006.01)
*C07K 14/705* (2006.01)
*C07K 16/28* (2006.01)

(52) U.S. Cl.
CPC ...... *A61K 39/39541* (2013.01); *A61K 39/385* (2013.01); *A61P 31/18* (2018.01); *C07K 14/70575* (2013.01); *C07K 16/2878* (2013.01); *A61K 2039/505* (2013.01); *A61K 2039/6056* (2013.01)

(58) Field of Classification Search
CPC ........... A61K 39/39541; A61K 39/385; A61K 2039/505; A61K 2039/6056; A61P 31/18; C07K 14/70575; C07K 16/2878
See application file for complete search history.

(56) References Cited

U.S. PATENT DOCUMENTS

| | | | | |
|---|---|---|---|---|
| 5,981,724 | A | 11/1999 | Armitage et al. | |
| 6,030,945 | A * | 2/2000 | Ashkenazi | A61P 43/00 514/18.9 |
| 6,746,668 | B2 * | 6/2004 | Ashkenazi | A61P 35/00 514/19.5 |
| 8,518,410 | B2 * | 8/2013 | Zurawski | A61P 31/18 424/188.1 |
| 9,102,734 | B2 * | 8/2015 | Zurawski | A61P 31/00 |
| 9,109,011 | B2 * | 8/2015 | Banchereau | A61K 47/6849 |
| 9,533,036 | B2 * | 1/2017 | Tang | C07K 14/005 |
| 9,562,104 | B2 * | 2/2017 | Banchereau | A61P 31/12 |
| 9,724,390 | B2 * | 8/2017 | Gurney | A61P 35/00 |
| 10,286,058 | B2 * | 5/2019 | Oh | C07K 16/2878 |
| 10,610,585 | B2 * | 4/2020 | Levy | A61K 39/21 |
| 2003/0021808 | A1 | 1/2003 | Tripp | |

(Continued)

FOREIGN PATENT DOCUMENTS

| | | |
|---|---|---|
| CN | 106103483 A | 11/2016 |
| WO | 00/39283 A1 | 7/2000 |

(Continued)

OTHER PUBLICATIONS

Bowie, J. U., Reidhaar-Olson, J. F., Lim, W. A., & Sauer, R. T. (1990). Deciphering the Message in Protein Sequences: Tolerance to Amino Acid Substitutions. Science (American Association for the Advancement of Science), 247(4948), 1306-1310. (Year: 1990).*

(Continued)

*Primary Examiner* — Janet L Andres
*Assistant Examiner* — Carey Alexander Stuart
(74) *Attorney, Agent, or Firm* — WCF IP

(57) ABSTRACT

CD40 activating proteins comprising recombinant proteins with CD40 agonist antibodies or their antigen-binding fragments fused or linked to CD40 ligand are provided. The CD40 activating proteins may further comprise at least one antigen. Uses for the CD40 activating proteins include inducing immune responses directed to delivered antigens such as viral or cancer antigens. Properties of the CD40 activating protein may include the ability to induce proliferation of B cells or secretion of cytokines, such as IL-6, IL-12 and/or IL-15.

17 Claims, 31 Drawing Sheets
Specification includes a Sequence Listing.

(56) References Cited

U.S. PATENT DOCUMENTS

| | | | | |
|---|---|---|---|---|
| 2003/0099644 A1* | 5/2003 | Ahuja | .............. | C07K 14/70575 514/18.9 |
| 2004/0235074 A1* | 11/2004 | Siegall | .................... | A61P 19/02 424/152.1 |
| 2007/0025982 A1* | 2/2007 | Ledbetter | ............... | A61K 39/12 424/130.1 |
| 2007/0128223 A1* | 6/2007 | Tang | ........................ | A61P 31/16 424/93.2 |
| 2009/0117111 A1* | 5/2009 | Aukerman | .............. | A61P 35/00 424/139.1 |
| 2009/0304706 A1* | 12/2009 | Lu | ........................... | A61P 37/00 424/144.1 |
| 2010/0291082 A1 | 11/2010 | Zurawski et al. | | |
| 2012/0039916 A1 | 2/2012 | Zurawski et al. | | |
| 2015/0368350 A1* | 12/2015 | Tykocinski | ........ | C07K 16/2878 424/134.1 |
| 2021/0260165 A1* | 8/2021 | Alam | ................... | A61K 38/191 |

FOREIGN PATENT DOCUMENTS

| | | | |
|---|---|---|---|
| WO | 2005/017148 | A1 | 2/2005 |
| WO | 2012/149356 | A2 | 11/2012 |
| WO | 2017/145355 | A1 | 9/2014 |
| WO | 2015106281 | A1 | 7/2015 |
| WO | 2016/177771 | A1 | 11/2016 |
| WO | 2017/165464 | A1 | 9/2017 |
| WO | 2017/184619 | A2 | 10/2017 |

OTHER PUBLICATIONS

Winkler, K., Kramer, A., Kuttner, G., Seifert, M., Scholz, C., Wessner, H., Schneider-Mergener, J., & Hohne, W. (2000). Changing the Antigen Binding Specificity by Single Point Mutations of an Anti-p24 (HIV-1) Antibody. The Journal of Immunology (1950), 165(8), 4505-4514. (Year: 2000).*

Kussie, P., Parhami-Seren, B., Wysocki, L., & Margolies, M. (1994). A single engineered amino acid substitution changes antibody fine specificity. The Journal of Immunology (1950), 152(1), 146-152. (Year: 1994).*

Chen, Z., Wang, J., Bao, L., Guo, L., Zhang, W., Xue, Y., Zhou, H., Xiao, Y., Wang, J., Wu, F., Deng, Y., Qin, C., & Jin, Q. (2015). Human monoclonal antibodies targeting the haemagglutinin glycoprotein can neutralize H7N9 influenza virus. Nature communications, 6, 6714. (Year: 2015).*

Sela-Culang, I., Kunik, V., & Ofran, Y. (2013). The Structural Basis of Antibody-Antigen Recognition. Frontiers in Immunology, 4, 302-302. (Year: 2013).*

Tsuchiya, Y., & Mizuguchi, K. (2016). The diversity of H3 loops determines the antigen-binding tendencies of antibody CDR loops. Protein science : a publication of the Protein Society, 25(4), 815-825. (Year: 2016).*

Collis, A. V., Brouwer, A. P., & Martin, A. C. (2003). Analysis of the antigen combining site: correlations between length and sequence composition of the hypervariable loops and the nature of the antigen. Journal of molecular biology, 325(2), 337-354. (Year: 2003).*

Dondelinger, M., Filée, P., Sauvage, E., Quinting, B., Muyldermans, S., Galleni, M., & Vandevenne, M. S. (2018). Understanding the Significance and Implications of Antibody Numbering and Antigen-Binding Surface/Residue Definition. Frontiers in Immunology, 9, 2278-2278. (Year: 2018).*

Sirin, S., Apgar, J. R., Bennett, E. M., & Keating, A. E. (2016). AB-Bind: Antibody binding mutational database for computational affinity predictions. Protein Science, 25(2), 393-409. https://doi.org/10.1002/pro.2829 (Year: 2016).*

Vonderheide, R. H. (2020). CD40 Agonist Antibodies in Cancer Immunotherapy. Annual Review of Medicine, 71(1), 47-58. (Year: 2020).*

Naseri, S. et al. (2024). CD40 stimulation via CD40 ligand enhances adenovirus-mediated tumour immunogenicity including 'find-me', 'eat-me', and 'kill-me' signalling. Journal of Cellular and Molecular Medicine, 28(7), e18162-n/a (Year: 2024).*

Whitmire, J. K., Slifka, M. K., Grewal, I. S., Flavell, R. A., & Ahmed, R. (1996). CD40 ligand-deficient mice generate a normal primary cytotoxic T-lymphocyte response but a defective humoral response to a viral infection. Journal of Virology, 70(12), 8375-8381. (Year: 1996).*

Sun, P., Celluzzi, C. M., Marovich, M., Subramanian, H., Eller, M., Widjaja, S., Palmer, D., Porter, K., Sun, W., & Burgess, T. (2006). CD40 Ligand Enhances Dengue Viral Infection of Dendritic Cells: A Possible Mechanism for T Cell-Mediated Immunopathology. Journal of Immunology, 177(9), 6497-6503. (Year: 2006).*

Norton, T. D., Tada, T., Leibowitz, R., van der Heide, V., Homann, D., & Landau, N. R. (2020). Lentiviral-Vector-Based Dendritic Cell Vaccine Synergizes with Checkpoint Blockade to Clear Chronic Viral Infection. Molecular Therapy, 28(8), 1795-1805. (Year: 2020).*

Gupta et al.; "Design of vaccine adjuvants incorporating TNF superfamily ligands and TNF superfamily molecular mimics"; Immunologic Research, vol. 57, No. 1, Nov. 7, 2013, pp. 303-310.

* cited by examiner

Pa$ent 1     2818 an' -CD40_12E12 HIVpep5 Gen2

Pa$ent 1     2818 an' -CD40_12E12 HIVpep5 Gen2
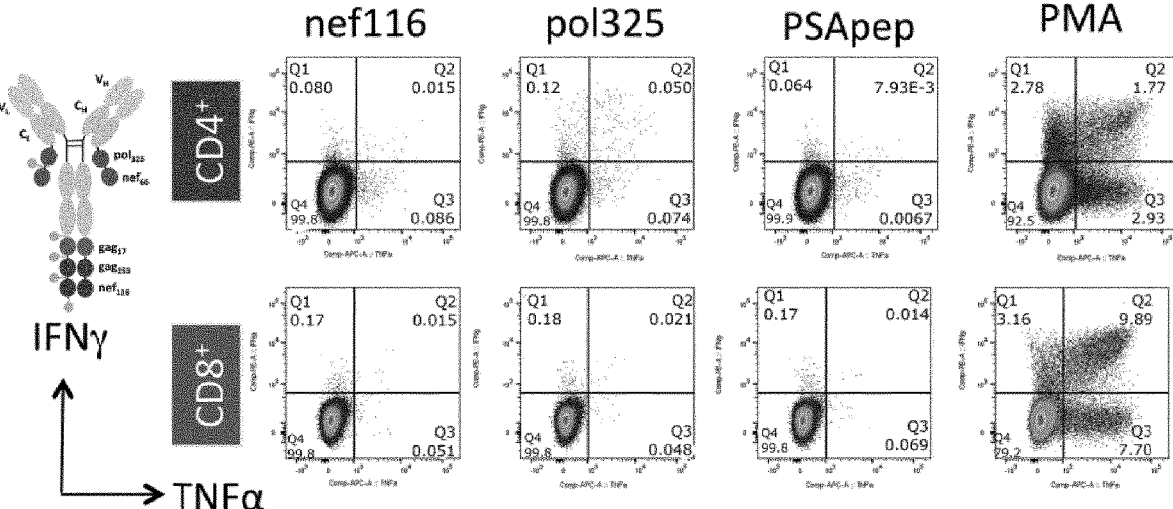
Figure 15 (continuation)

3498 an' -CD40 11B6-CD40L HIVpep5 Gen1
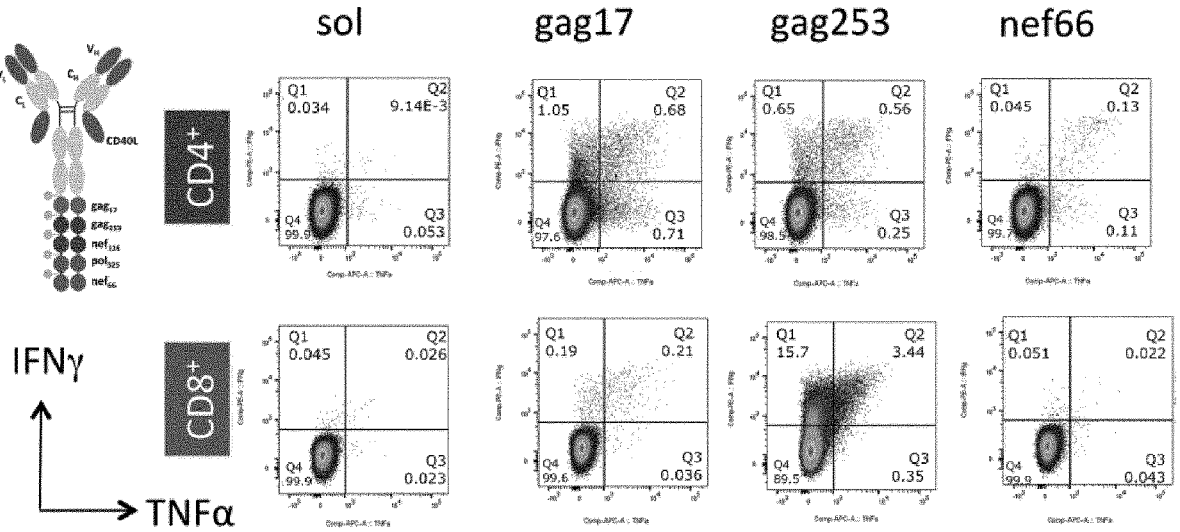
Figure 15 (continuation)

3498 an' -CD40 11B6-CD40L HIVpep5 Gen1
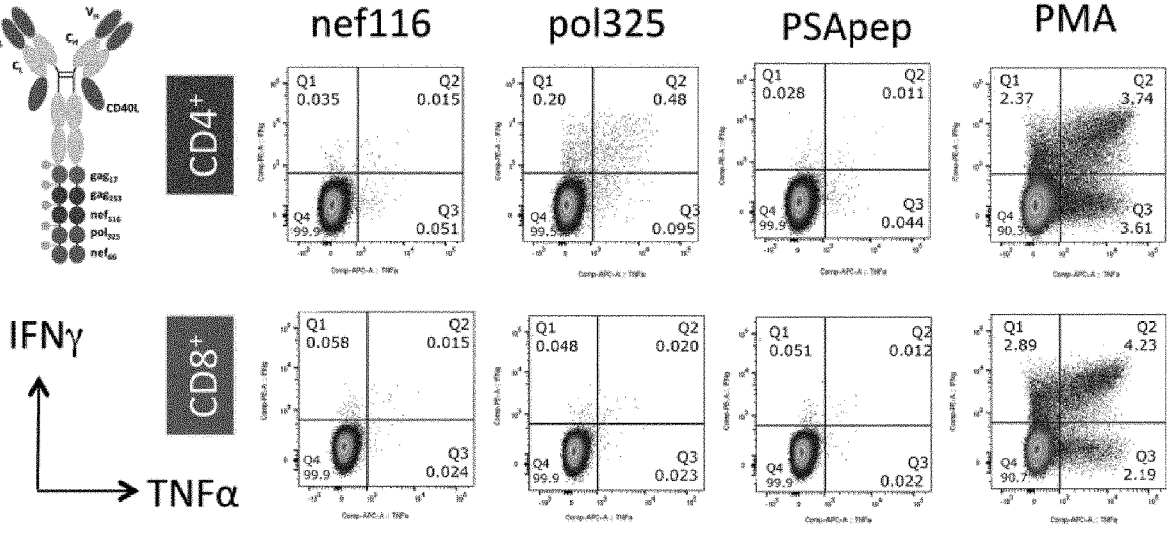
Figure 15 (continuation)

Example A1                              Example A3

Example A2                              Example A4

Example A5

A15

RECOMBINANT PROTEINS WITH CD40 ACTIVATING PROPERTIES

SEQUENCE LISTING

This application includes as the Sequence Listing the complete contents of the accompanying text filed "Sequence.txt", created Jun. 26, 2025, containing 258,000 bytes, hereby incorporated by reference.

The disclosure relates to the field of CD40 activating proteins. More specifically, disclosed herein are recombinant proteins based on CD40 agonist antibodies with their antigen-binding fragments fused or linked to CD40 ligand (CD40L). Also disclosed is the advantageous use of such CD40 activating proteins, in particular for inducing immune responses directed to delivered antigens such as viral or cancer antigens.

BACKGROUND

CD40 is a potent activating tumor necrosis factor receptor superfamily member expressed on antigen-presenting cells (APCs) and B cells. Dendritic cells (DCs) respond to infections by internalizing antigens and activating pathogen-associated molecular patterns (PAMPs), and thus present foreign antigens on their major histocompatibility complex (MHC) molecules to antigen-specific T cells, initiating a cycle of DC maturation via CD40 ligand (CD40L) expressed on the activated T cell, which then directs cellular and humoral antigen-specific T and B cell responses to the pathogen [Elgueta et al., 2009]. Agonistic anti-CD40 antibodies are in clinical development based on the notion of directly activating APCs to stimulate immune responses either against intrinsic antigens, e.g., tumor associated antigens (TAAs), or as an adjuvant to vaccines [Dahan et al., 2016, Thompson et al., 2015, reviewed by Vonderheide and Glennie, 2017]. Directly linking antigens to anti-CD40 antibodies by chemical conjugation [Bar et al., 2003], non-covalent assembly [Flamar et al., 2013], or direct fusion [Flamar et al., 2014] elicits potent antigen-specific cellular and humoral immunity at very low antigen doses in a wide array of in vitro and in vivo settings [Flamar et al., 2013, Flamar et al., 2014, Yin et al., 2016, Yin et al., 2017]. In particular, antigen-targeting to CD40 elicits superior cellular T cell responses compared to targeting other receptors, likely due to accumulation within the early endosome compartment, as distinct to the rapid antigen entry into late endosomes characterized by targeting other DC receptors. [Yin et al., 2016, Chattergee et al., 2012].

Beyond primary screening to identify CD40-reactive monoclonal antibodies that have the most potent agonist activity, e.g., inducing cytokine secretion or CD86 surface expression on human DCs, maximizing the agonist efficacy and utility of clinical candidate anti-CD40 antibodies typically involves affinity maturation of the H and L chain combining regions [Mangsbo et al., 2014], and enhancing cross-linking of the constant region with FcR [Dahan et al., 2016]. Screening can also identify potent agonists without any need for Fc interaction [He at al., 2016], which may be problematic for human platelet activation if FcγRIIA interaction is maintained [Dahan et al., 2016]. Agonistic anti-CD40 antibodies can either bind to sites that overlap the CD40L interacting region, or may interact with a site distinct from its ligand-binding region [Gladue et al., 2011, Dahan et al., 2016, He et al., 2016], but it is not clear if this distinction has clinical relevance.

Potent activation of CD40 is not required for efficient Class I and Class II presentation of antigens via CD40-targeting in vitro [Chattergee et al., 2012, Flamar et al., 2014], however in vivo efficacy requires co-administration of Toll-like receptor (TLR) activating agents such as poly IC [Zurawski et al., 2017, Cheng et al., 2017]. However, these in vitro and in vivo studies did not utilize anti-CD40 antibody-antigen complexes or fusions with full CD40 agonist activity, and the clear benefit of agonistic anti-CD40 antibody combined with poly IC for peptide-based vaccination in non-human primates [Thompson et al., 2015] suggests CD40-targeting of antigens may be further improved by fully agonistic anti-CD40 targeting vehicles. There is further a need to provide single molecules with high potency as agonist CD40-targeting vehicles. Disclosed herein is the nature of soluble CD40L co-operation with certain agonistic anti-CD40 vehicles for enhancing CD40 activation efficacy of both anti-CD40 antibodies and anti-CD40 antibody-antigen fusion proteins. It is further herein disclosed that a method that combines both, anti-CD40 antibody and CD40L agonist fragment, into a single entity, confers at least similar or even superior potency to that observed with the two separate agents co-administered. Such CD40 activating proteins may be of great value in therapy and to adjuvant immune responses directed to administered antigens.

SUMMARY

The disclosure relates to a CD40 activating protein comprising at least the following protein domains:
   (i) a CD40 agonist antibody or an antigen-binding fragment thereof (αCD40); and,
   (ii) the CD40 binding-domain of CD40L (CD40L).

In specific embodiments, said CD40 agonist antibody binds specifically to human CD40 and has at least one or more of the following properties:
   (i) it induces the proliferation of B cells, as measured in vitro by flow cytometric analysis or by analysis of replicative dilution of CFSE-labelled cells; or,
   (ii) it induces the secretion of cytokines, such as IL-6, IL-12 and/or IL-15 cytokine as measured in vitro with a dendritic cell activation assay.

In specific embodiments, said CD40 binding-domain of CD40L is a fragment of CD40L comprising SEQ ID NO: 14.

In specific embodiments, said CD40 binding-domain of CD40L is fused to the C-terminus of a light or heavy chain of said CD40 agonist antibody or its antigen-binding fragment.

In specific embodiments, said CD40 activating protein comprises a heavy and light chain of CD40 agonist IgG antibody, preferably Fc-null and di-sulphide stabilized IgG4 or mutated silent IgG antibody.

In specific embodiments, said CD40 activating protein further comprises a peptide linker between CD40L and the light or heavy chain of said CD40 agonist antibody or its antigen-binding fragment, preferably a flexible linker FlexV1 of SEQ ID NO: 15.

In specific embodiments, said CD40 agonist antibody is selected from the following antibodies:
   (i) a humanized antibody comprising the HCDR1 of SEQ ID NO: 27, HCDR2 of SEQ ID NO: 28, HCDR3 of SEQ ID NO: 29, LCEDR1 of SEQ ID NO: 30, LCDR2 of SEQ ID NO: 31 and LCDR3 of SEQ ID NO: 32;
   (ii) a humanized antibody comprising VH and VL domains of SEQ ID NO: 21 and SEQ ID NO: 22, respectively;

(iii) an antibody that competes for binding to CD40 expressing cells with at least one of the antibodies identified in (i) or (ii); or, (iv) an antibody that binds to the same epitope as one of the antibodies identified in (i) or (ii).

In specific embodiments, one or more antigens are fused to the heavy or light chain of said CD40 agonist antibody or its antigen-binding fragment.

Typically, said one or more antigens are viral, bacterial, or cancer antigens fused (either directly via peptide linkage, or non-covalently via e.g., dockerin-cohesin technology) to the heavy or light chain of a CD40 agonist antibody.

In specific embodiments, the CD40 activating protein comprises a light chain of the formula αCD40Light-PL-CD40L and a heavy chain of the formula αCD40Heavy-(PL-Ag)x, wherein αCD40Light is a light chain of said CD40 agonist antibody;

αCD40Heavy is a heavy chain of said CD40 agonist antibody;

PL is a bond or a peptide linker, either identical or different, preferably FlexV1 of SEQ ID NO: 15;

Ag is a viral or cancer antigen, either identical or different;

x is an integer from 1 to 20, for example from 3, 4, or 5;

CD40L is the binding domain of the ligand of CD40, for example the CD40-binding domain of CD40L comprising SEQ ID NO: 14; and, – is a bond.

In specific embodiments, said viral antigens are selected from HIV peptide antigens, preferably the HIV-1 antigens, such as GNG of SEQ ID NO: 48 or HIV5pep of SEQ ID NO:57.

The disclosure also relates to a pharmaceutical composition, comprising the CD40 activating protein as defined above and one or more pharmaceutically acceptable excipients.

The disclosure further relates to the CD40 activating protein for use as a vaccine. In particular, said CD40 activating protein may be used in enhancing T cell specific response in a subject, in particular CD8+ T cell specific response against a viral antigen.

Said CD40 activating protein may also be used in eliciting B cell proliferation and/or inducing cytokine proliferation of dendritic cells in a subject.

DETAILED DESCRIPTION

Definitions

In order that the present disclosure may be more readily understood, certain terms are first defined. Additional definitions are set forth throughout the detailed description.

As used herein, the term "CD40" has its general meaning in the art and refers to human CD40 polypeptide receptor including CD40 of SEQ ID NO: 13. In specific embodiments, CD40 is the isoform of the human canonical sequence as reported by UniProtKB-P25942 (also referred as human TNR5). The ectodomain of CD40 which is recognized by certain anti-CD40 antibodies may typically be comprised between residues at position 21 and position 193 of SEQ ID NO: 13.

As used herein, the term "CD40L" has its general meaning in the art and refers to human CD40L polypeptide, for example, as reported by UniProtKB-P25942, including its CD40-binding domain of SEQ ID NO: 14. CD40L may be expressed as a soluble polypeptide and is the natural ligand of CD40 receptor.

As used herein, the term "protein" refers to any organic compounds made of amino acids arranged in one or more linear chains (also referred as "polypeptide chains") and folded into a globular form. The amino acids in such polypeptide chain are joined together by the peptide bonds between the carboxyl and amino groups of adjacent amino acid residues. The term "protein" further includes, without limitation, peptides, single chain polypeptide or any complex proteins consisting primarily of two or more chains of amino acids. It further includes, without limitation, glycoproteins or other known post-translational modifications. It further includes known natural or artificial chemical modifications of natural proteins, such as without limitation, glycoengineering, pegylation, hesylation and the like, incorporation of non-natural amino acids, amino acid modification for chemical conjugation or other molecule, etc. . . . .

As used herein, a "complex protein" refers more specifically to a protein which is made of at least two polypeptide chains, wherein said at least two polypeptide chains are associated together under appropriate conditions via either non-covalent binding or covalent binding, for example, by disulphide bridge or peptide bond.

A "heterodimeric protein" refers to a protein that is made of at least two polypeptide chains, forming a complex protein, wherein said two polypeptide chains have different amino acid sequences.

The terms "polypeptide," "peptide" and "protein" expressly include glycoproteins, as well as non-glycoproteins. In specific embodiments, the term "polypeptide" and "protein" refers to any polypeptide or protein that can be encoded by a gene and translated using cell expression system and DNA recombinant means, such as mammalian host cell expression system.

The term "recombinant protein", as used herein, includes proteins that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) fusion proteins isolated from a host cell transformed to express the corresponding protein, e.g., from a transfectoma, etc. . . . .

As used herein, the term "fusion protein" refers to a recombinant protein comprising at least one polypeptide chain which is obtained or obtainable by genetic fusion, for example by genetic fusion of at least two gene fragments encoding separate functional domains of distinct proteins.

The term "antibody" as used herein refers to immunoglobulin molecules and immunologically active portions of immunoglobulin molecules, i.e., molecules that contain an antigen binding site that immunospecifically binds to an antigen.

In natural antibodies of rodents and primates, two heavy chains are linked to each other by disulfide bonds, and each heavy chain is linked to a light chain by a disulfide bond. There are two types of light chains, lambda (1) and kappa (k). There are five main heavy chain classes (or isotypes) which determine the functional activity of an antibody molecule: IgM, IgD, IgG, IgA and IgE. Each chain contains distinct sequence domains. In typical IgG antibodies, the light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL)

and heavy (CH) chains confer important biological properties such as antibody chain association, secretion, transplacental mobility, complement binding, and binding to Fc receptors (FcR).

The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity, determining regions (CDRs). Occasionally, residues from nonhypervariable or framework regions (FR) can participate in the antibody binding site, or influence the overall domain structure and hence the combining site. Complementarity Determining Regions or CDRs refer to amino acid sequences that together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, typically includes six CDRs, comprising the CDRs set from each of a heavy and a light chain V region. Framework Regions (FRs) refer to amino acid sequences interposed between CDRs. Accordingly, the variable regions of the light and heavy chains typically comprise 4 framework regions and 3 CDRs of the following sequence: FR1-CDR1-FR2-CDR2-FR3-CDR3-FR4.

The residues in antibody variable domains are conventionally numbered according to a system devised by Kabat et al. This system is set forth in Kabat et al., 1987, in Sequences of Proteins of Immunological Interest, US Department of Health and Human Services, NIH, USA (Kabat et al., 1992, hereafter "Kabat et al."). The Kabat residue designations do not always correspond directly with the linear numbering of the amino acid residues in SEQ ID sequences. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence. The CDRs of the heavy chain variable domain are located at residues 31-35 (H-CDR1), residues 50-65 (H-CDR2) and residues 95-102 (H-CDR3) according to the Kabat numbering system. The CDRs of the light chain variable domain are located at residues 24-34 (L-CDR1), residues 50-56 (L-CDR2) and residues 89-97 (L-CDR3) according to the Kabat numbering system. For the agonist antibodies described hereafter, the CDRs have been determined using CDR finding algorithms from www.bioinf.org.uk—see the section entitled «"How to identify the CDRs by looking at a sequence"» within the Antibodies pages. The predicted CDRs of some agonist antibodies, such as 11B6, 12E2, 12B4, CP (CP-870,893 from Pfizer) or 24A3 are described in the Examples below.

The term "antigen-binding fragment" of an antibody (or simply "antibody fragment"), as used herein, refers to full length or one or more fragments of an antibody that retain the ability to specifically bind to an antigen (e.g., the ectodomain of CD40). It has been shown that the antigen-binding function of an antibody can be performed by fragments of a full-length antibody. Examples of binding fragments encompassed within the term "antigen-binding fragment" of an antibody include a Fab fragment, a monovalent fragment consisting of the $V_L$, $V_H$, $C_L$ and CH1 domains; a F(ab)$_2$ fragment, a bivalent fragment comprising two Fab fragments linked by a disulfide bridge at the hinge region; a Fd fragment consisting of the $V_H$ and CH1 domains; a Fv fragment consisting of the $V_L$ and $V_H$ domains of a single arm of an antibody; a dAb fragment (Ward et al., 1989 Nature 341:544-546), which consists of a $V_H$ domain, or any fusion proteins comprising such antigen-binding fragments.

Furthermore, although the two domains of the Fv fragment, $V_L$ and $V_H$, are coded for by separate genes, they can be joined, using recombinant methods, by a synthetic linker that enables them to be made as a single chain protein in which the $V_L$ and $V_H$ regions pair to form monovalent molecules (known as single chain Fv (scFv); see e.g., Bird et al., 1988 Science 242:423-426; and Huston et al., 1988 Proc. Natl. Acad. Sci. 85:5879-5883). Such single chain antibodies are also intended to be encompassed within the term "antigen-binding fragment" of an antibody. These antibody fragments are obtained using conventional techniques known to those of skill in the art, and the fragments are screened for utility in the same manner as are intact antibodies.

As used herein, the term "IgG Fc region" is used to define the C-terminal region of an immunoglobulin heavy chain, including native sequence Fc region and variant Fc regions. The human IgG heavy chain Fc region is generally defined as comprising the amino acid residue from position C226 or from P230 to the carboxyl-terminus of the IgG antibody.

The numbering of residues in the Fc region is that of the EU index of Kabat. The C-terminal lysine (residue K447) of the Fc region may be removed, for example, during production or purification of the antibody. Accordingly, a composition of antibodies of the invention may comprise antibody populations with all K447 residues removed, antibody populations with no K447 residues removed, and antibody populations having a mixture of antibodies with and without the K447 residue.

The term "$K_{assoc}$" or "$K_a$", as used herein, is intended to refer to the association rate of a particular antibody-antigen interaction, whereas the term "$K_{dis}$" or "$K_d$," as used herein, is intended to refer to the dissociation rate of a particular antibody-antigen interaction.

The term "$K_D$", as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A method for determining the $K_D$ of a protein or an antibody is by using surface plasmon resonance, for example by using a biosensor system such as a Biacore® system.

As used herein, the term "binding specificity" refers to the ability of an antibody to detectably bind to an antigen recombinant polypeptide, such as recombinant CD40 polypeptide, with a $K_D$ of 100 nM or less, 10 nM or less, 5 nM or less, as measured by Surface Plasmon Resonance (SPR) measurements, for example as determined in the Examples.

An antibody that "does not cross-react with a particular antigen" is intended to refer to an antibody that binds to that antigen, with a $K_D$ of 100 nM or greater, or a $K_D$ of 1 mM or greater, or a $K_D$ of 10 mM or greater, said affinity being measured for example using similar Surface Plasmon Resonance (SPR) measurements, as disclosed in the Examples. In certain embodiments, such antibodies that do not cross-react with the antigen exhibit essentially undetectable binding against these proteins in standard binding assays.

The isolated CD40 activating protein according to the present disclosure is a protein that has binding specificity to CD40 and activating or agonist properties with respect to CD40 receptor. A CD40 activating protein may have cross-reactivity to other antigens, such as related CD40 molecules from other species. Moreover, in specific embodiments, an isolated CD40 activating protein may be substantially free of other cellular material and/or chemicals.

The phrases "an antibody recognizing an antigen" and "an antibody having specificity for an antigen" are used interchangeably herein with the term "an antibody which binds specifically to an antigen".

Specificity can further be exhibited by, e.g., an about 10:1, about 20:1, about 50:1, about 100:1, 10.000:1 or greater ratio of affinity/avidity in binding to the specific antigen versus nonspecific binding to other irrelevant molecules (in this case the specific antigen is a CD40 polypeptide). The term "affinity", as used herein, means the strength of the binding of an antibody to an epitope.

The present disclosure relates to the unexpected finding that fusion proteins of CD40L with certain CD40 agonist antibodies (e.g., derived from agonist mAb 11B6 or 12B4 as described in WO2010/104748), exhibit superior CD40 activating properties compared to the corresponding agonist antibody alone or the combined administration of such agonist antibody with soluble CD40L (sCD40L).

"Humanized antibody" as used herein, refers broadly to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies may include amino acid residues not encoded by human germline immunoglobulin sequences (e.g., mutations introduced by random or site-specific mutagenesis in vitro or by somatic mutation in vivo), for example in the CDRs. The antibodies as used herein may include amino acid residues not encoded by human sequences (e.g., mutations introduced by random or site-specific mutagenesis in vitro or by somatic mutation in vivo). In particular, the term "humanized antibody" includes antibodies that comprise a silent variant of Fc IgG region.

In specific embodiments, the term «humanized antibody» include antibodies which have the 6 CDRs of a murine antibody, but humanized framework and constant regions.

More specifically, the term "humanized antibody", as used herein, may include antibodies in which CDR sequences derived from the germline of another mammalian species, such as a mouse, have been grafted onto human framework sequences.

As used herein, a «CD40 agonist» antibody is intended to refer to an antibody that increase CD40 mediated signalling activity in the absence of CD40L in a cell-based assay, such as the B cell proliferation assay. Such assay is described in more details in the examples below.

As used herein, the term "silent" antibody refers to an antibody that exhibits no or low ADCC activity. As used herein, the term "ADCC" or "antibody dependent cell cytotoxicity" activity refers to cell depleting activity. ADCC activity can be measured by ADCC assays as described in the literature.

Silenced effector functions can be obtained by mutation in the Fc region of the antibodies and have been described in the Art: Strohl 2009 (LALA & N297A); Baudino 2008, D265A (Baudino et al., J. Immunol. 181 (2008): 6664-69, Strohl, CO Biotechnology 20 (2009): 685-91). Examples of silent Fc IgG1 antibodies comprise L234A and L235A mutations in the IgG1 Fc amino acid sequence.

As used herein, a protein or antibody with «CD40 activating» properties refers to a protein or antibody that is able to increase CD40 mediated signaling activity. In particular, as used herein, a protein with CD40 activating properties has at least one or more of the following properties:

(i) it induces the proliferation of B cell, as measured in vitro by flow cytometric analysis, for example as measured with the B cell proliferation assay described in the Examples below e.g., by analysis of replicative dilution of CFSE-labelled cells;

(ii) it induces the secretion of cytokines, such as IL-6, IL-12, or IL-15, as measured in vitro with a dendritic cell activation assay described in the Examples below.

In specific embodiment, said CD40 activating protein of the present disclosure has at least the same activating properties as a soluble version of CD40L, the natural ligand of CD40 receptor.

In specific embodiments, said CD40 activating protein includes a CD40 binding domain of CD40L which is not a trimeric form.

In specific embodiments, said CD40 activating protein of the present disclosure is tetravalent with respect to CD40 binding.

In specific embodiments, said CD40 activating protein includes a bivalent CD40 agonist antibody with one monomeric CD40 binding domain of CD40L covalently or non-covalently bound to each arm of said bivalent antibody, preferably via the C-terminal part of each arm of the bivalent antibody, either the light chain or heavy chain of each arm.

In other specific embodiments, said CD40 activating protein of the present disclosure has at least similar activating properties as a reference CD40 agonist antibody being typically selected among the following CD40 agonist (including partial agonist) antibodies: 11B6, 12B4, CP-870,893 or 24A3, typically 11B6 antibody or a humanized version.

In other specific embodiments, said CD40 activating protein of the present disclosure has at least similar activating properties, and may be even at least 10-fold, at least 50-fold, or at least 100-fold more active than Mega sCD40L, a known trimer version of soluble CD40L, for eliciting secretion of cytokines as measured in the dendritic cell activation assay as described in the Examples below.

As used herein, the term «Mega sCD40L» refers to the trimeric CD40 ligand molecules linked via the collagen domain of Adiponectin/ACRP30/AdipoQ, also marketed as MEGACD40L® and described in Kornbluth et al., 2012.

In other specific embodiment, said CD40 activating protein of the present disclosure has at least the same activating properties as a combined composition of soluble CD40L with the same CD40 agonist antibody (or its antigen-binding fragment) as present in said CD40 activating protein.

As used herein, the term, "optimized" means that a nucleotide sequence has been altered to encode an amino acid sequence using codons that are preferred in the production cell or organism, generally a eukaryotic cell, for example, a Chinese Hamster Ovary cell (CHO) or a human cell. The optimized nucleotide sequence is engineered to retain completely or as much as possible the amino acid sequence originally encoded by the starting nucleotide sequence. The amino acid sequences encoded by optimized nucleotide sequences are also referred to as optimized.

As used herein, the percent identity between the two sequences is a function of the number of identical positions shared by the sequences (i. e., % identity=number of identical positions/total number of positions×100), taking into account the number of gaps, and the length of each gap, which need to be introduced for optimal alignment of the two sequences. The comparison of sequences and determination of percent identity between two sequences can be accomplished using a mathematical algorithm, as described below.

The percent identity between two amino acid sequences can be determined using the Needleman and Wunsch algorithm (NEEDLEMAN, and Wunsch).

The percent identity between two nucleotide or amino acid sequences may also be determined using for example algorithms such as EMBOSS Needle (pair wise alignment; available at www.ebi.ac.uk). For example, EMBOSS Needle may be used with a BLOSUM62 matrix, a "gap open penalty" of 10, a "gap extend penalty" of 0.5, a false "end gap penalty", an "end gap open penalty" of 10 and an "end gap extend penalty" of 0.5. In general, the "percent identity" is a function of the number of matching positions divided by the number of positions compared and multiplied by 100. For instance, if 6 out of 10 sequence positions are identical between the two compared sequences after alignment, then the identity is 60%. The % identity is typically determined over the whole length of the query sequence on which the analysis is performed. Two molecules having the same primary amino acid sequence or nucleic acid sequence are identical irrespective of any chemical and/or biological modification.

As used herein, the term "subject" includes any human or nonhuman animal. The term "nonhuman animal" includes all vertebrates, e.g., mammals and non-mammals, such as nonhuman primates, sheep, dogs, cats, horses, cows, chickens, am phibians, reptiles, etc.

As used herein, "Dendritic Cells" (DCs) refers to any member of a diverse population of morphologically similar cell types found in lymphoid or non-lymphoid tissues. These cells are characterized by their distinctive morphology and high levels of surface MHC-class II expression. These cells can be isolated from a number of tissue sources, and conveniently, from peripheral blood, as described in the Examples below.

The CD40 Activating Protein of the Present Disclosure

The present disclosure relates to a CD40 activating protein comprising at least the following protein domains:

(i) a CD40 agonist antibody (αCD40) or an antigen-binding fragment thereof; and, (ii) the CD40 binding domain of CD40L (CD40L), typically of SEQ ID NO: 14 or its functional fragment with at least 90%, 95% or 100% identity to SEQ ID NO: 14.

In certain embodiments, the CD40 binding domain of CD40L (preferably as a monomeric form) is covalently or non-covalently attached to the C-terminus of a light or heavy chain of said CD40 agonist antibody or its antigen-binding fragment, optionally via a linker, such as a peptidic or chemical linker. In one embodiment, the CD40 binding-domain of CD40L is non-covalently attached to the C-terminus of the light chain of a CD40 agonist antibody or its antigen-binding fragment.

In certain embodiments, the CD40 binding domain of CD40L is fused to the C-terminus of a light or heavy chain of said CD40 agonist antibody or its antigen-binding fragment, optionally via a linker, such as a peptidic linker. Typically, the CD40 binding-domain of CD40L is fused to the C-terminus of the light chain of a CD40 agonist antibody or its antigen-binding fragment, optionally via a linker, such as a peptidic linker.

In other specific embodiments, said CD40 binding domain of CD40L is conjugated to the CD40 agonist antibody or its antigen-binding fragment using chemical coupling. Several methods are known in the art for the attachment or conjugation of an antibody to its conjugate moiety. Examples of linker types that have been used to conjugate a moiety to an antibody include, but are not limited to, hydrazones, thioethers, esters, disulfides and peptide-containing linkers, such as valine-citruline linker. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D). For further discussion of types of linkers and methods for conjugating therapeutic agents to antibodies, see also Panowski et al., 2013 for a review on antibody drug conjugates.

In certain embodiments, said CD40 activating protein as disclosed herein is an antibody-like protein comprising a light chain of the formula αCD40Light-PL-CD40L and a heavy chain of the formula αCD40Heavy, wherein αCD40Light is a light chain of a CD40 agonist antibody;

αCD40Heavy is a heavy chain of a CD40 agonist antibody;

PL is a bond or a peptide linker, either identical or different, preferably FlexV1 of SEQ ID NO: 15;

CD40L is the CD40-binding domain of CD40 ligand, for example comprising SEQ ID NO: 14, or its functional fragment with at least 90%, 95% or 100% identity to SEQ ID NO: 14.

In a more specific embodiment, said CD40 activating protein as disclosed herein is an antibody-like protein comprising a light chain of the formula αCD40Light-PL-CD40L and a heavy chain of the formula αCD40Heavy-PL-BP1, wherein αCD40Light is a light chain of a CD40 agonist antibody;

αCD40Heavy is a heavy chain of a CD40 agonist antibody;

PL is a bond or a peptide linker, either identical or different, preferably FlexV1 of SEQ ID NO: 15;

BP1 is a first member of a binding pair BP1/BP2 to permit non-covalent coupling to a second member BP2 of said binding pair BP1/BP2.

In another specific embodiment, said CD40 activating protein as disclosed herein is an antibody-like protein comprising a heavy chain of the formula αCD40Heavy-PL-CD40L and a light chain of the formula αCD40Light-PL-BP1, wherein αCD40Light is a light chain of a CD40 agonist antibody;

αCD40Heavy is a heavy chain of a CD40 agonist antibody;

PL is a bond or a peptide linker, either identical or different, preferably FlexV1 of SEQ ID NO: 15;

BP1 is a first member of a binding pair BP1/BP2 to permit non-covalent coupling to a second member BP2 of said binding pair BP1/BP2.

Any binding pairs, typically binding pair of polypeptide domains known in the art may be used for the above embodiments of DC40 activating proteins. Examples of said binding pair BP1/BP2 include without limitation dockerin domain/cohesin domain, or mSA2/biotin, as described below.

In a more specific embodiment, said CD40 activating protein as disclosed herein is an antibody-like protein comprising a light chain of the formula αCD40Light-PL-CD40L and a heavy chain of the formula αCD40Heavy-PL-Doc, wherein αCD40Light is a light chain of a CD40 agonist antibody;

αCD40Heavy is a heavy chain of a CD40 agonist antibody;

PL is a bond or a peptide linker, either identical or different, preferably FlexV1 of SEQ ID NO: 15;

Doc is a dockerin domain or multiple domains to permit non-covalent coupling to cohesin fusion proteins as described in US20160031988A1 and US20120039916A1, for example comprising SEQ ID NO: 111, or any functional variant thereof.

In other specific embodiments, said CD40 activating protein as disclosed herein is an antibody-like protein comprising a light chain of the formula αCD40Light-PL-CD40L and a heavy chain of the formula αCD40Heavy-PL-mSA2, wherein αCD40Light is a light chain of a CD40 agonist antibody;

αCD40Heavy is a heavy chain of a CD40 agonist antibody;

PL is a bond or a peptide linker, either identical or different, preferably FlexV1 of SEQ ID NO: 15;

mSA2 is a monomeric streptavidin 2 domain to permit non-covalent coupling to biotin labelled or fusion proteins as described in Lim et al (Biotechnology Bioeng 2013, 110, 57-67), for example comprising SEQ ID NO: 168, or any functional variant thereof.

In other specific embodiments, said CD40 activating protein as disclosed herein is an antibody-like protein comprising a heavy chain of the formula αCD40Heavy-PL-CD40L and a light chain of the formula αCD40Light, wherein αCD40Light is a light chain of a CD40 agonist antibody;

αCD40Heavy is a heavy chain of a CD40 agonist antibody;

PL is a bond or a peptide linker, either identical or different, preferably FlexV1 of SEQ ID NO: 15;

CD40L is the CD40-binding domain of CD40 ligand, for example comprising SEQ ID NO:14, or its functional fragment with at least 90%, 95% or 100% identity to SEQ ID NO: 14.

In a other more specific embodiment, said CD40 activating protein as disclosed herein is an antibody-like protein comprising a heavy chain of the formula αCD40Heavy-PL-CD40L and a light chain of the formula αCD40Light-PL-Doc, wherein αCD40Light is a light chain of a CD40 agonist antibody;

αCD40Heavy is a heavy chain of a CD40 agonist antibody;

PL is a bond or a peptide linker, either identical or different, preferably FlexV1 of SEQ JD NO: 15;

Doc is a dockerin domain or multiple domains to permit non-covalent coupling to cohesin fusion proteins as described in US20160031988A1 and US20120039, 916A1, for example comprising SEQ ID NO:111, or any functional variant thereof.

In other specific embodiments, said CD40 activating protein as disclosed herein is an antibody-like protein comprising a heavy chain of the formula αCD40Heavy-PL-CD40L and a light chain of the formula αCD40Light-PL-mSA2, wherein αCD40Light is a light chain of a CD40 agonist antibody;

αCD40Heavy is a heavy chain of a CD40 agonist antibody;

PL is a bond or a peptide linker, either identical or different, preferably FlexV1 of SEQ ID NO: 15;

mSA2 is a monomeric streptavidin 2 domain to permit non-covalent coupling to biotin labelled or fusion proteins as described in Lim et al (Biotechnology Bioeng 2013, 110, 57-67), for example comprising SEQ ID NO:168, or any functional variant thereof.

Preferred embodiments of αCD40Light, αCD40Heavy, and CD40L are further described in the next sections.

In certain embodiments, said CD40 activating protein further comprises one or more antigens ««Ag»» fused or conjugated or coupled by non-covalent coupling to either the corresponding heavy or light chain of said CD40 agonist antibody or its antigen-binding fragment. Said antigens may be conjugated directly to a polypeptide chain of the CD40 activating protein, for example at the C-terminal end of a polypeptide chain of the CD40 activating protein, and, optionally via peptide linker, such as FlexV1, f1, f2, f3, or f4 as described below. They can be also coupled by non-covalent coupling, for example as included in cohesin fusion proteins for coupling with dockerin domain, and/or biotin fusion proteins for coupling with monomeric streptavidin 2 domain.

As used herein, the term ««antigen»» or ««Ag»» refers to any antigen that can be used in a vaccine, whether it involves a whole microorganism or a portion thereof, and various types: (e.g., peptide, protein, glycoprotein, polysaccharide, glycolipid, lipopeptide, etc). Thus, the term "antigen" refers to a molecule that can initiate a humoral and/or cellular immune response in a recipient of the antigen. The antigen is usually a key molecule encoded by a pathogen that causes a disease for which vaccination would be advantageous treatment.

In specific embodiments, the Ag is a peptide concatamer. The Ag may also comprise a polynucleotide, the sequence of which is chosen so as to encode the antigen whose expression by the individuals to which the polynucleotide is administered is desired, in the case of the immunization technique referred to as DNA immunization.

Typically, as used herein, the Ag is selected from a viral or other infectious disease antigen, or a cancer antigen.

In certain embodiments, the Ag is selected from infectious disease antigens selected from bacterial, viral, parasitic, and fungal antigens. Typically, the Ag is at least one viral antigen. For example, at least one viral antigen comprises peptides from an adenovirus, retrovirus, picornavirus, herpesvirus, rotaviruses, hantaviruses, coronavirus, togavirus, flavivirus, rhabdovirus, paramyxovirus, orthomyxovirus, bunyavirus, arenavirus, reovirus, papillomavirus, parvovirus, poxvirus, hepadnavirus, rotovirus or spongiform virus. In another aspect, the at least one viral antigen comprise peptides from at least one of HIV, CMV, hepatitis A, B, and C, influenza; measles, polio, smallpox, rubella, respiratory syncytial, herpes simplex, varicella zoster, Epstein-Barr, Japanese encephalitis, rabies, flu, or cold viruses.

In specific embodiments, said viral antigens are selected from one or more of the following antigenic domains: HIV-1 Gag p24 (SEQ ID NO: 45), Nef (SEQ ID NO: 46), and Gag p17 (SEQ ID NO: 47) (including the combination of the three antigens called GNG, see the detailed description of the amino acid sequence below) or the combination of HPV16 E6 and HPV16 E7 antigens (HPV 16 E6/E7) (also as referred to HPV, see the detailed amino acid sequence below).

GNG sequence is of the following formula: (from C-terminal to N-terminal): FlexV1-LE-gag17-VDf3-VD-nef-EF-f4-QF p24-6×His] (flexible linker sequences) wherein FlexV1 is a peptide linker of SEQ ID NO: 15;

LE is a dipeptide of Leu-Glu;

Gag17 is a HIV-1 viral antigen of the following amino acid sequence: MGARASILSGGELDR-WEKIRLRPGGNKQYKLKHIVWASRELER-FAVNPGL LETSEGCRQILGQLQPSLQTGSEELRS-LYNTVATLYCVHQRIEIKDTKEALD KIEEEQNKS (SEQ ID NO: 47);

VD is a dipeptidic linker of Valine and Aspartic acid;

f3 is a peptidic linker of the following amino acid sequence: TVTPTATATPSAIVTTITPTATTKP (SEQ ID NO: 53);

nef is a HIV-1 viral antigen of the following amino acid sequence MGGKWSKRSVVGWPTVRERMRRAE-PAADGVGAVSRDLEKHGAITSSNTA ANNAD-CAWLEAQEEEEVGFPVRPQVPLRPMTYKGALD-LSHFLKEKGGLEG LIYSQKRQDILDLWVYHTQGYFPDWQNYTPGP-GIRYPLTFGWCFKLVPVEP EKVEEA-NEGENNSLLHPMSLHGMDDPEREVLVWKFDSR-LAFHHMARELH PEYYKDC (SEQ ID NO: 46);

EF is a dipeptidic linker of glutamic acid and phenylala-nine;

f4 is a flexible linker TNGSITVAATAPTVTPTVNATP-SAA (SEQ ID NO: 54);

QF is a dipeptidic linker of glutamine and phenylalanine;

P24 is a HIV-1 viral antigen of the following amino acid sequence AQQAAADTGHSNQVSQNYPIVQ-NIQGQMVHQAISPRTLNAWVKVVEEKA FSPE-VIPMFSALSE-GATPQDLNTMLNTVGGHQAAMQMLKETINEE AAEWD RVHPVHAGPIAPGQMREPRGSDIAGTT-STLQEQIGWMTHNPPIPVGEIYKR WIILGLNKIVRMYSPTSILDIRQGPKEP-FRDYVDRFYKTLRAEQASQEVKNW MTETLL-VQNANPDCKTILKALGPGATLEEMMTACQGVG (SEQ ID NO: 45); and, 6-His is the C-terminal hexahistidine tag of HHHHHH (SEQ ID NO: 173).

A full amino acid sequence of GNG consists of SEQ ID NO: 48.

Alternative GNG sequences may be used, for example, using GNG sequences with the same HIV-1 peptide sequences but with other peptidic linkers.

HPV is of the following formula: Flex-v1-HPV16E6-HPV16E7-f1 wherein FlexV1 are as described above and HPV16E6-HPV16E7 has the following amino acid sequence:

```
                                     (SEQ ID NO: 56)
MHQKRTAMFQDPQERPRKLPQLCTELQTTIHDIILECVYCKQQLLRR

EVGDFAFRDLCIVYRDGNPYAVCDKCLKEYSKISEYRHYCYSVYGTT

LEQQYNKPLCDLLIRCINCQKPLCPEASMHGDTPTLHEYMLDLQPET

TDLYGYGQLNDSSEEEDEIDGPAGQAEPDRAHYNIVTFCCK.
``` f1 is the flexible linker of the following amino acid sequence

```
                                     (SEQ ID NO: 56)
     ASSSVSPTTSVHPTPTSVPPTPTKSSPAS.
```

A full amino acid sequence of HPV consists of SEQ ID NO: 57.

In other specific embodiments, said viral antigens are selected from one or more of the following HIV antigenic domains: Gag p17 (17-35) of SEQ ID NO:16, Gag p17-p24

(253-284) of SEQ ID NO: 17 and Nef (116-145) of SEQ ID NO:18, Pol 325-344 (RT 158-188) of SEQ ID NO: 19 and Nef (66-97) of SEQ ID NO: 20.

In preferred embodiments, said viral antigens are selected from the following combination of the 5 HIV antigenic domains: Gag p17 (17-35) of SEQ ID NO: 16, Gag p17-p24 (253-284) of SEQ ID NO: 17 and Nef (116-145) of SEQ ID NO:18, Pol 325-344 (RT 158-188) of SEQ ID NO: 19 and Nef (66-97) of SEQ ID NO: 20, also as comprised in the HIV5pep sequence of the following formula:

FlexV1-gag p17 (17-35)-f1-gag p17-p24 (253-284)-f2-nef (116-145)-f3-nef (66-97)-f4-Pol 325-344 (RT158-188), wherein FlexV1, f1, f2, f3, f4 are described above.

A specific embodiment of HIV5pep amino acid sequence is described in SEQ ID NO: 112.

In other specific embodiments, the Ag is selected from tumor associated antigens selected from CEA, prostate specific antigen (PSA), HER-2/neu, BAGE, GAGE, MAGE 1-4, 6 and 12, MUC-related protein (Mucin) (MUC-1, MUC-2, etc.), GM2 and GD2 gangliosides, ras, myc, tyrosinase, MART (melanoma antigen), MARCO-MART, cyclin Bl, cyclin D1, Pmel 17 (gpl00), GnT-V intron V sequence (N-acetylglucosaminyltransferase V intron V sequence), Prostate Ca psm, prostate serum antigen (PSA), PRAME (melanoma antigen), β-catenin, MUM-I-B (melanoma ubiquitous mutated gene product), GAGE (melanoma antigen) 1, BAGE (melanoma antigen) 2-10, C-ERB2 (Her2/neu), EBNA (Epstein-Barr Virus nuclear antigen) 1-6, gp75, human papilloma virus (HPV) E6 and E7, p53, lung resistance protein (LRP), Bcl-2, and Ki-67. In another aspect, the Ag is selected from tumor associated antigens comprising antigens from leukemias and lymphomas, neurological tumors such as astrocytomas or glioblastomas, melanoma, breast cancer, lung cancer, head and neck cancer, gastrointestinal tumors, gastric cancer, colon cancer, liver cancer, pancreatic cancer, genitourinary tumors such cervix, uterus, ovarian cancer, vaginal cancer, testicular cancer, prostate cancer or penile cancer, bone tumors, vascular tumors, or cancers of the lip, nasopharynx, pharynx and oral cavity, esophagus, rectum, gall bladder, biliary tree, larynx, lung and bronchus, bladder, kidney, brain and other parts of the nervous system, thyroid, Hodgkin's disease, non-Hodgkin's lymphoma, multiple myeloma and leukemia. Such tumor associated antigens include patient-specific tumor mutated proteins containing known or potential T cell epitopes.

In specific embodiments, the CD40 activating protein of the present disclosure refers to a complex protein comprising two heterodimers, each heterodimer consisting of one heavy and one light chains of amino acids, stably associated together, for example via one or more disulfide bonds. Typically, the heavy chain comprises at least the VH region, preferably at least the CH1-VH regions of a CD40 agonist antibody and the light chain comprises at least the VL region, preferably at least the CL-VL regions of said CD40 agonist antibody. At least, said heavy or light chain is fused or conjugated to at least the CD40 binding domain of CD40L, optionally via a linker, for example a peptidic linker.

In specific embodiments, said CD40 activating protein of the present disclosure comprises heavy and light chains of a CD40 agonist IgG antibody, including isotype constant region or IgG Fc region, preferably IgG4 or mutated silent IgG Fc.

In a more specific embodiment, said CD40 activating protein as disclosed herein is an antibody-like protein comprising a light chain of the formula αCD40Light-PL-CD40L and a heavy chain of the formula αCD40Heavy-(PL-Ag)x, wherein αCD40Light is a light chain of a CD40 agonist antibody;

αCD40Heavy is a heavy chain of a CD40 agonist antibody;

PL is a bond or a peptide linker, either identical or different, preferably FlexV1 of SEQ ID NOT: 15;

Ag is a viral or cancer antigen, either identical or different;

x is an integer from 1 to 20, for example from 3, 4, or 5;

CD40L is the binding domain of the ligand of CD40 comprising SEQ ID NO: 14 or a functional fragment thereof with at least 90%, 95% or 100% identity to SEQ ID NO: 14; and – is a covalent bond.

In another more specific embodiment, said CD40 activating protein as disclosed herein is an antibody-like protein comprising a heavy chain of the formula αCD40Heavy-PL-CD40L and a light chain of the formula αCD40Light-(PL-Ag)x, wherein αCD40Light is a light chain of a CD40 agonist antibody;

αCD40Heavy is a heavy chain of a CD40 agonist antibody;

PL is a bond or a peptide linker, either identical or different, preferably FlexV1 of SEQ ID NO: 15;

Ag is a viral or cancer antigen, either identical or different;

x is an integer from 1 to 20, for example from 3, 4, or 5;

CD40L is the binding domain of the ligand of CD40 comprising SEQ ID NO: 14 or a functional fragment thereof with at least 90%, 95% or 100% identity to SEQ ID NO: 14; and – is a covalent bond.

In specific embodiments, the PL is a peptide linker preferably ensuring optimal activating properties and yield in cell production.

In specific embodiments, the -(PL-Ag)x is located at the carboxy terminus of the heavy chain of said CD40 activating antibody-like protein.

Typically, a schematic representation of an embodiment of said CD40 activating protein is shown in FIG. 1. Preferred embodiments of αCD40Light, αCD40Heavy, and CD40L are further described in the next sections.

In certain embodiments, peptide linkers may incorporate glycosylation sites or introduce secondary structure. Additionally these linkers may increase the efficiency of expression or stability of the fusion protein and as a result the efficiency of antigen presentation to a dendritic cell. Such linkers may include the flexV1, f1, f2, f3 and/or f4 linkers. These examples and others are discussed in WO 2010/104747, the contents of which are incorporated herein by reference. In particular, flexV1 is a polypeptide of SEQ ID NO: 15.

In a more specific embodiment, said CD40 activating protein comprises PAB3405 CD40 agonist antibody consisting of SEQ ID NO: 1 and SEQ ID NO: 2.

In another specific embodiment, said CD40 activating protein comprises PAB3408 CD40 agonist antibody consisting of SEQ ID NO: 3 and SEQ ID NO: 4.

In another specific embodiment, said CD40 activating protein consists of a heavy chain polypeptide comprising SEQ ID NO: 5 and a light chain comprising SEQ ID NO: 6.

In another specific embodiment, said CD40 activating protein consists of a heavy chain polypeptide comprising SEQ ID NO: 5 and a light chain comprising SEQ ID NO: 8.

In another specific embodiment, said CD40 activating protein consists of a heavy chain polypeptide comprising SEQ ID NO: 9 and a light chain comprising SEQ ID NO: 10.

In another specific embodiment, said CD40 activating protein consists of a heavy chain polypeptide comprising SEQ ID NO: 11 and a light chain comprising SEQ ID NO: 12.

In another specific embodiment, said CD40 activating protein consists of a light chain polypeptide of SEQ ID NO: 109 and a heavy chain polypeptide of SEQ ID NO: 110.

CD40 activating proteins with amino acid sequences having at least 90%, for example, at least 95%, 96%, 97%, 98%, or 99% identity to any one of the above defined amino acid sequences are also part of the present disclosure.

The CD40 Agonist Antibody for Use in Preparing the Fusion Protein of Present Disclosure The skilled person may use CD40 agonist antibodies already known in the art or generate de novo novel CD40 activating antibodies using antibody screening technologies.

More specifically, said CD40 agonist antibody (or its antigen-binding fragment) for use in the CD40 activating protein of the present disclosure have one or more of the following advantageous properties:

(i) it binds to CD40 ectodomain with a $K_D$ of 500 nM or less, for example between 50 or less and 500 nM, as measured by SPR binding assay, for example as described in the Examples below;

(ii) it induces the proliferation of B cell, as measured in vitro by flow cytometric analysis, for example as measured with the B cell proliferation assay described in the Examples below; and/or (iii) it induces the secretion of cytokines, such as IL-6, IL-12, or IL-15, as measured in vitro with a dendritic cell activation assay described in the Examples below.

In specific embodiments, said CD40 agonist antibody has one or more of the following properties:

(i) it binds to CD40 ectodomain with a $K_D$ of 500 nM or less, for example between 50 and 500 nM, as measured by SPR, for example as described in the Examples below;

(ii) the proliferation of B cell as measured in a B cell proliferation assay with said agonist antibodies can be further increased, typically at least 10 fold, or at least 100 fold, in the presence of a suboptimal dose of soluble CD40L, for example using the assay as described in the Examples below; and/or, (iii) the secretion of cytokines, such as IL-6, IL-12, or IL-15, can be potentiated, typically at least 10 fold, or at least 100 fold, or at least 1000 fold, in the presence of a suboptimal dose of soluble CD40L, as measured in vitro with a dendritic cell activation assay, for example using the assay described in the Examples below.

In specific embodiment, a CD40 agonist antibody is an antibody which has CD40 mediated signaling activity in the absence of CD40L in a cell-based assay which is at least similar to the CD40 mediated signaling activity of a reference CD40 agonist antibody as measured in the same cell-based assay, said reference CD40 agonist antibody being typically selected among the following CD40 agonist antibodies: mAb1, mAb2, mAb3, mAb4, mAb5 and mAb6 as described below.

In specific embodiments, said CD40 agonist antibody does not compete with sCD40L for binding to CD40.

In specific embodiments, in the presence of a constant suboptimal amount (6 nM) of soluble human CD40L, a CD40 agonist antibody has an EC50 (as measured in the B cell proliferation assay described in the examples) that is between 1 and 200 fold the EC50 measured for CD40 agonist antibody mAb5 (CP-870,893), preferably between 1 and 150 fold, or between 1 and 100 fold.

In other specific embodiments, in the presence of a constant suboptimal amount (6 nM) of soluble human CD40L, a CD40 agonist antibody has an EC50 (as measured in the B cell proliferation assay described in the examples) that is equal or less than the EC50 of mAb 1 (11B6) antibody.

The relative EC50 values as measured in the B cell proliferation assay are further described in the Examples (see Tables for FIGS. 2 and 3).

To select novel CD40 agonist antibodies, a variety of methods of screening antibodies have been described in the Art. Such methods may be divided into in vivo systems, such as transgenic mice capable of producing fully human antibodies upon antigen immunization and in vitro systems, consisting of generating antibody DNA coding libraries, expressing the DNA library in an appropriate system for antibody production, selecting the clone that express antibody candidate that binds to the target with the affinity selection criteria and recovering the corresponding coding sequence of the selected clone.

These in vitro technologies are known as display technologies, and include without limitation, phage display, RNA or DNA display, ribosome display, yeast or mammalian cell display. They have been well described in the Art (for a review see for example: Nelson et al., 2010 Nature Reviews Drug discovery, "Development trends for human monoclonal antibody therapeutics" (Advance Online Publication) and Hoogenboom et al. in *Method in Molecular Biology* 178:1-37, O'Brien et al., ed., Human Press, Totowa, N.J., 2001). In one specific embodiment, human recombinant CD40 agonist antibodies are isolated using phage display methods for screening libraries of human recombinant antibody libraries with CD40 binding and agonist properties.

Repertoires of $V_H$ and $V_L$ genes or related CDR regions can be separately cloned by polymerase chain reaction (PCR) or synthesized by DNA synthesizer and recombined randomly in phage libraries, which can then be screened for antigen-binding clones. Such phage display methods for isolating human antibodies are established in the art or described in the examples below. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

In a certain embodiment, human antibodies directed against CD40 can be identified using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HuMAb Mouse® (Medarex, Inc.) contains human immunoglobulin gene miniloci that encode un-rearranged human heavy (μ and γ) and κ light chain immunoglobulin sequences, together with targeted mutations that inactivate the endogenous μ and κ chain loci (see e.g., Lonberg, et al., 1994 Nature 368(6474): 856-859).

In another embodiment, human CD40 agonist antibodies can be raised using a mouse that carries human immunoglobulin sequences on transgenes and transchomosomes such as a mouse that carries a human heavy chain transgene and a human light chain transchromosome. Such mice, referred to herein as "KM mice", are described in detail in PCT Publication WO 02/43478 to Ishida et al.

Monoclonal antibodies (mAbs) can also be produced by conventional monoclonal antibody methodology e.g., the standard somatic cell hybridization technique of Kohler and Milstein, 1975 Nature 256: 495. Many techniques for producing monoclonal antibody can be employed e.g., viral or oncogenic transformation of B lymphocytes.

An animal system for preparing hybridomas is the murine system. Hybridoma production in the mouse is a well established procedure. Immunization protocols and techniques for isolation of immunized splenocytes for fusion are known in the art. Fusion partners (e.g., murine myeloma cells) and fusion procedures are also known.

Chimeric or humanized antibodies can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art. See e.g., U.S. Pat. No. 5,225,539 to Winter, and U.S. Pat. Nos. 5,530,101; 5,585,089; 5,693,762 and 6,180,370 to Queen et al.

It is further contemplated that monoclonal antibodies may be further screened or optimized for their CD40 agonist properties as above defined. In particular, it is contemplated that monoclonal antibodies may have 1, 2, 3, 4, 5, 6, or more alterations in the amino acid sequence of 1, 2, 3, 4, 5, or 6 CDRs of monoclonal antibodies or humanized antibodies provided herein. It is contemplated that the amino acid in position 1, 2, 3, 4, 5, 6, 7, 8, 9, or 10 of CDR1, CDR2, CDR3, CDR4, CDR5, or CDR6 of the VJ or VDJ region of the light or heavy variable region of antibodies may have an insertion, deletion, or substitution with a conserved or non-conserved amino acid.

Such amino acids that can either be substituted or constitute the substitution are disclosed above.

CD40 agonist antibodies known in the art for use in preparing the CD40 activating proteins of the disclosure include the recombinant CD40 agonist antibodies mAb1, mAb2, mAb3, mAb4, mAb5 and mAb6, which are structurally characterized by their variable heavy and light chain amino acid and nucleotide sequences as described in the Tables 1 and 2 below:

TABLE 1

| Variable heavy and light chain amino acid sequences of mAb1-mAb6 | | |
|---|---|---|
| Antibody | VH Amino acid sequence | VL Amino acid sequence |
| mAb1 [11B6 VH/VkV2] | SEQ ID NO: 21 | SEQ ID NO: 22 |
| mAb2 [11B6 VHV3/VkV2] | SEQ ID NO: 23 | SEQ ID NO: 22 |
| mAb3 [12B4] | SEQ ID NO: 58 | SEQ ID NO: 59 |
| mAb4 [24A3] | SEQ ID NO: 60 | SEQ ID NO: 61 |
| mAb5 [CP870893] | SEQ ID NO: 62 | SEQ ID NO: 63 |
| mAb 6 [12E12] | SEQ ID NO: 64 | SEQ ID NO: 65 |

TABLE 2

Variable heavy and light chain nucleotide (nt) coding
sequences of mAb1-mAb6

| Antibody | VH Nt coding sequence | VL Nt coding sequence |
|---|---|---|
| mAb1 [11B6 VH/VkV2] | SEQ ID NO: 24 | SEQ ID NO: 25 |
| mAb2 [11B6 VHV3/VkV2] | SEQ ID NO: 26 | SEQ ID NO: 25 |
| mAb3 [12B4] | SEQ ID NO: 66 | SEQ ID NO: 67 |
| mAb4 [24A3] | SEQ ID NO: 68 | SEQ ID NO: 69 |
| mAb5 [CP870, 893] | SEQ ID NO: 70 | SEQ ID NO: 71 |
| mAb 6 [12E12] | SEQ ID NO: 72 | SEQ ID NO: 73 |

Other CD40 agonist antibodies which may be used include any chimeric or humanized antibodies comprising the 6 CDRs of the above defined mAb1, mAb2, mAb3, mAb4, mAb5 or mAb6.

Examples of the amino acid sequences of the VH CDR1s (also called HCDR1), VH CDR2s (also called HCDR2), VH CDR3s (also called HCDR1), VL CDR1s (also called LCDR1), VL CDR2s (also called LCDR2), VL CDR3s (also called HCDR3) of some CD40 agonist antibodies according to the disclosure are shown in Table 3.

In Table 3, the CDR regions of the antibodies of the present disclosure are delineated using the Kabat numbering (Kabat et al., 1992, hereafter "Kabat et al.").

TABLE 3

CDR regions of mAb1, mAb2, mAb3, mAb4,
mAb5 and mAb6 according to Kabat numbering

| Original antibody | HCDR1 | HCDR2 | HCDR3 | LCDR1 | LCDR2 | LCDR3 |
|---|---|---|---|---|---|---|
| mAb1 [11B6 VH/VkV2] | SEQ ID NO: 27 | SEQ ID NO: 28 | SEQ ID NO: 29 | SEQ ID NO: 30 | SEQ ID NO: 31 | SEQ ID NO: 32 |
| mAb2 [11B6 VHV3/VkV2] | SEQ ID NO: 27 | SEQ ID NO: 28 | SEQ ID NO: 29 | SEQ ID NO: 30 | SEQ ID NO: 31 | SEQ ID NO: 32 |
| mAb3 [12B4] | SEQ ID NO: 74 | SEQ ID NO: 75 | SEQ ID NO: 76 | SEQ ID NO: 77 | SEQ ID NO: 78 | SEQ ID NO: 79 |
| mAb4 [24A3] | SEQ ID NO: 80 | SEQ ID NO: 81 | SEQ ID NO: 82 | SEQ ID NO: 83 | SEQ ID NO: 84 | SEQ ID NO: 85 |
| mAb5 CP870893 | SEQ ID NO: 86 | SEQ ID NO: 87 | SEQ ID NO: 88 | SEQ ID NO: 89 | SEQ ID NO: 90 | SEQ ID NO: 91 |
| mAb6 [12E12] | SEQ ID NO: 92 | SEQ ID NO: 93 | SEQ ID NO: 94 | SEQ ID NO: 95 | SEQ ID NO: 96 | SEQ ID NO: 97 |

In specific embodiments, a CD40 agonist antibody is selected from the following antibodies:

(i) a humanized antibody comprising the 6 CDRs of mAb1, mAb2, mAb3, mAb4, mAb5 or mAb6;

(ii) a humanized antibody comprising VH and VL domains of SEQ ID NO: 21 and SEQ ID NO: 22 respectively;

(iii) an antibody that competes for binding to CD40 expressing cells with at least one of the antibodies identified in (i) or (ii), (iv) an antibody that binds to the same epitope as one of the antibodies identified in (i) or (ii).

In particular, in specific embodiments, a CD40 agonist antibody binds to an epitope region comprising or consisting of amino acid residues 36-59 of SEQ ID NO:13 (CDR1 region of CD40). More specifically, it binds to an epitope region comprising or consisting of amino acid residues 50-58 of CD40. In certain embodiments, a CD40 agonist antibody has direct contact to at least the following amino acid residues: E56 and E58. In other embodiments, a CD40 agonist antibody has direct contact to at least the following amino acid residues: D50 and E58.

Other examples of CD40 agonist antibodies are described in WO2010/009346, WO2010/104747 and WO2010/104749. Other anti-CD40 agonist antibodies in development include:

CP-870,893—a fully human IgG2 CD40 agonist antibody developed by Pfizer. It binds CD40 with a $K_D$ of $3.48 \times 10^{-10}$ M, but does not block binding of CD40L (see e.g., U.S. Pat. No. 7,338,660).

SGN-40 is a humanized IgG1 antibody developed by Seattle Genetics from mouse antibody clone S2C6, which was generated using a human bladder carcinoma cell line as the immunogen. It binds to CD40 with a KD of $1.0 \times 10^{-9}$ M and works through enhancing the interaction between CD40 and CD40L, thus exhibiting a partial agonist effect (Francisco J A, et al., Cancer Res, 60: 3225-31, 2000).

Also, US20120301488A1 by APEXIGEN describes another anti-CD40 agnostic mAb. AbbVie Biotherapeutics Inc United States Patent Application 20170342159 describes another agonist antibody.

CDX-1140, an agonist CD40 antibody by Celldex is another agonist antibody.

Any other known antibodies can be potentially combined with linked CD40L using the method revealed in this application to increase their biological activity.

Nucleic Acid Molecules Encoding the CD40 Activating Proteins of the Disclosure

Also disclosed herein are the nucleic acid molecules that encode the CD40 activating proteins of the present disclosure.

Examples of nucleic acid molecules are those encoding the variable light and heavy chain amino acid sequences of the CD40 activating antibody-like proteins as disclosed in the previous section, and using the genetic code and, optionally taking into account the codon bias depending on the host cell species.

Typically, nucleic acid molecules encoding the CD40 activating protein of the disclosure comprises coding sequences of CD40 agonist antibody consisting of SEQ ID NO 1 and SEQ ID NO 2, for example the nucleic acids of SEQ ID NO:33 and SEQ ID NO:34 respectively.

In specific embodiments, nucleic acid molecules encoding the CD40 activating protein comprises coding sequences of CD40 agonist antibody consisting of SEQ ID NO: 3 and SEQ ID NO: 4, for example the nucleic acids of SEQ ID NO: 35 and SEQ ID NO: 36, respectively.

In another specific embodiment, nucleic acid molecules encoding the CD40 activating protein comprising coding sequences encoding a heavy chain polypeptide comprising SEQ ID NO: 5 and a light chain comprising SEQ ID NO: 6, for example the nucleic acids of SEQ ID NO: 37 and SEQ ID NO: 38, respectively.

In another specific embodiment, nucleic acid molecules encoding the CD40 activating protein comprise coding sequences of a heavy chain polypeptide comprising SEQ ID NO: 5 and coding sequences of a light chain comprising SEQ ID NO: 8 for example the nucleic acids of SEQ ID NO: 39 and SEQ ID NO: 37, respectively.

In another specific embodiment, nucleic acid molecules encoding the CD40 activating protein comprise coding sequences of a heavy chain polypeptide comprising SEQ ID NO: 9 and coding sequences of a light chain comprising SEQ ID NO: 10 for example the nucleic acids of SEQ ID NO: 41 and SEQ ID NO: 42, respectively.

In another specific embodiment, nucleic acid molecules encoding the CD40 activating protein comprise coding sequences of a heavy chain polypeptide comprising SEQ ID NO: 11 and coding sequences of a light chain comprising SEQ ID NO: 12 for example the nucleic acids of SEQ ID NO: 43 and SEQ ID NO: 44, respectively.

In another specific embodiment, nucleic acid molecules encoding the CD40 activating protein comprise coding sequences of a heavy chain polypeptide comprising SEQ ID NO: 110 and coding sequences of a light chain comprising SEQ ID NO: 109 for example the nucleic acids of SEQ ID NO: 114 and SEQ ID NO: 113, respectively.

Nucleic acids encoding CD40 activating proteins of the disclosure with nucleotide sequences having at least 90%, for example, at least 95%, 96%, 97%, 98%, or 99% identity to any one of the above defined nucleotides sequences are also part of the present disclosure.

The present disclosure also pertains to nucleic acid molecules that derive from the latter sequences having been optimized for protein expression in mammalian cells, for example, CHO or HEK cell lines.

The nucleic acids may be present in whole cells, in a cell lysate, or may be nucleic acids in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art (Ausubel et al., 1988). A nucleic acid of the disclosure can be, for example, DNA or RNA and may or may not contain intronic sequences. In an embodiment, the nucleic acid may be present in a vector such as a phage display vector, or in a recombinant plasmid vector.

Nucleic acids of the disclosure can be obtained using standard molecular biology techniques. Once DNA fragments encoding, for example, VH and VL segments are obtained, these DNA fragments can be further manipulated by standard recombinant DNA techniques, for example to convert the variable region genes to full-length antibody chain genes, to Fab fragment genes or to an scFv gene.

Generation of Transfectomas Producing CD40 Activating Proteins

The CD40 activating proteins of the present disclosure can be produced in a host cell transfectoma using, for example, a combination of recombinant DNA techniques and gene transfection methods as is well known in the art (Morrison, 1985).

For example, to express the CD40 activating proteins, DNAs encoding said CD40 activating proteins can be obtained by standard molecular biology or biochemistry techniques (e.g., DNA chemical synthesis, PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that a gene is ligated into a vector such that transcriptional and translational control sequences within the vector serve their intended function of regulating the transcription and translation of the CD40 activating protein. The expression vector and expression control sequences are chosen to be compatible with the expression host cell used. If the CD40 activating proteins include distinct polypeptide, for example one sequence encoding a heavy chain of a CD40 activating antibody-like protein as disclosed in the above sections and another encoding a light chain of said CD40 activating antibody-like protein, the heavy and light chain encoding genes can be inserted into separate vector or, more typically, both genes are inserted into the same expression vector. The genes are inserted into the expression vector by standard methods (e.g., ligation of complementary restriction sites on the protein gene and vector, or blunt end ligation if no restriction sites are present).

Signal peptides may be further used for secretion of the polypeptides out of the expression cells, such as an immunoglobulin signal peptide or a heterologous signal peptide (i.e., a signal peptide from a non-immunoglobulin protein).

In addition, the recombinant expression vectors disclosed herein carry regulatory sequences that control the expression of the CD40 activating proteins in a host cell. The term "regulatory sequence" is intended to include promoters, enhancers and other expression control elements (e.g., polyadenylation signals) that control the transcription or translation of the respective genes. It will be appreciated by those skilled in the art that the design of the expression vector, including the selection of regulatory sequences, may depend on such factors as the choice of the host cell to be transformed, the level of expression of protein desired, etc. Regulatory sequences for mammalian host cell expression include viral elements that direct high levels of protein expression in mammalian cells, such as promoters, and/or enhancers derived from cytomegalovirus (CMV), Simian Virus 40 (SV40), adenovirus (e.g., the adenovirus major late promoter (AdMLP)), and polyoma. Alternatively, nonviral regulatory sequences may be used, such as the ubiquitin promoter or P-globin promoter. Still further, regulatory elements composed of sequences from different sources, such as the SRa promoter system, which contains sequences from the SV40 early promoter and the long terminal repeat of human T cell leukemia virus type 1.

Additionally, the recombinant expression vectors of the present disclosure may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Selectable marker genes include the dihydrofolate reductase (DHFR) gene (for use in dhfr– host cells with methotrexate selection/amplification) and the neo gene (for G418 selection).

For expression of the CD40 activating proteins, the expression vector is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. It is theoretically possible to express the binding proteins of the present disclosure in either prokaryotic or eukaryotic host cells. Expression of recombinant proteins in eukaryotic cells, for example mammalian host cells, yeast or filamentous fungi, is discussed because such eukaryotic cells, and in particular mammalian cells, are more likely than prokaryotic cells to assemble and secrete a properly folded and immunologically active antibody.

In one specific embodiment, a cloning or expression vector according to the disclosure comprises one or more of the nucleic acids as described in the previous section, operatively linked to suitable promoter sequences.

Mammalian host cells for expressing the recombinant antibodies of the disclosure include Chinese Hamster Ovary (CHO cells) including dhfr– CHO cells (described in Urlaub and Chasin, 1980) used with a DHFR selectable marker, CHOK1 dhfr+ cell lines, NSO myeloma cells, COS cells and SP2 cells, for example GS CHO cell lines together with GS Xceed™ gene expression system (Lonza), or HEK cells. When recombinant expression vectors encoding antibody genes are introduced into mammalian host cells, the antibodies are produced by culturing the host cells for a period of time sufficient for expression of the antibody in the host cells and, optionally, secretion of the antibody into the culture medium in which the host cells are grown. Antibodies can be recovered and purified for example from the culture medium after their secretion using standard protein purification methods.

In one specific embodiment, the host cell of the disclosure is a host cell transfected with an expression vector having the coding sequences of the CD40 activating proteins as disclosed in the previous section.

The latter host cells may then be further cultured under suitable conditions for the expression and production of said CD40 activating protein.

Pharmaceutical Compositions

In another aspect, the present disclosure provides a composition, e.g., a pharmaceutical composition, containing an CD40 activating protein, formulated together with a pharmaceutically acceptable carrier.

Pharmaceutical compositions disclosed herein also can be administered in combination therapy, i.e., combined with other agents. For example, the combination therapy can include CD40 activating protein of the present disclosure, combined with at least one anti-viral, anti-inflammatory, vaccine adjuvant and/or another anti-proliferative agent.

As used herein, "pharmaceutically acceptable carrier" includes any and all solvents, dispersion media, coatings, antibacterial and antifungal agents, isotonic and absorption delaying agents, and the like that are physiologically compatible. The carrier should be suitable for intravenous, intramuscular, subcutaneous, parenteral, spinal or epidermal administration (e.g., by injection or infusion). In one embodiment, the carrier should be suitable for subcutaneous route. Depending on the route of administration, the active compound, i.e., CD40 activating protein, may be coated in a material to protect the compound from the action of acids and other natural conditions that may inactivate the compound.

Sterile phosphate-buffered saline is one example of a pharmaceutically acceptable carrier. Other suitable carriers are well-known to those in the art. (Remington and Gennaro, 1995). Formulations may further include one or more excipients, preservatives, solubilizers, buffering agents, albumin to prevent protein loss on vial surfaces, etc.

The form of the pharmaceutical compositions, the route of administration, the dosage and the regimen naturally depend upon the condition to be treated, the severity of the illness, the age, weight, and sex of the patient, etc.

The pharmaceutical compositions of the disclosure can be formulated for a topical, oral, parenteral, intranasal, intravenous, intramuscular, subcutaneous or intraocular administration and the like.

Preferably, the pharmaceutical compositions contain vehicles, which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

To prepare pharmaceutical compositions, an effective amount of the CD40 activating protein may be dissolved or dispersed in a pharmaceutically acceptable carrier or aqueous medium.

The pharmaceutical forms suitable for injectable use include sterile aqueous solutions or dispersions; formulations including sesame oil, peanut oil or aqueous propylene glycol; and sterile powders or lyophilisates for the extemporaneous preparation of sterile injectable solutions or dispersions. In all cases, the form must be sterile and must be fluid to the extent that easy syringeability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

Pharmaceutically acceptable salts which may be used in the formulation include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

The CD40 activating protein may be formulated within a therapeutic mixture to comprise about 0.0001 to 1.0 milligrams, or about 0.001 to 0.1 milligrams, or about 0.1 to 1.0 or even 1.0 to about 10 milligrams per dose. Multiple doses can also be administered.

Vaccine Compositions

The disclosure also relates to a vaccine comprising a CD40 activating protein of the disclosure and a pharmaceutically acceptable vehicle.

As used herein, the term "vaccine" is intended to mean a composition which can be administered to humans or to animals in order to induce an immune response; this immune response can result in a production of antibodies or simply in the activation of certain cells, in particular antigen-presenting cells, T lymphocytes and B lymphocytes. In certain embodiments the vaccine is capable of producing an immune response that leads to the production of neutralizing antibodies in the patient with respect to the antigen provided in the vaccine. The vaccine can be a composition for prophylactic purposes or for therapeutic purposes, or both.

Vaccines may include an effective amount of the CD40 activating proteins of the disclosure, dissolved or dispersed in a pharmaceutically acceptable carrier or aqueous medium. Such compositions can also be referred to as inocula. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions. The vaccine compositions of the present disclosure may include classic pharmaceutical preparations. Dispersions also can be prepared in glycerol, liquid polyethylene glycols, and mixtures thereof and in oils. Under ordinary conditions of storage and use, these preparations contain a preservative to prevent the growth of microorganisms.

In addition, if desired, the vaccine can contain minor amounts of auxiliary substances such as wetting or emulsifying agents, pH buffering agents, and/or adjuvants which enhance the effectiveness of the vaccine. Examples of adjuvants that may be effective include but are not limited to: aluminum hydroxide, N-acetyl-muramyl-L-threonyl-D-isoglutamine (thr-MDP), N-acetyl-nor-muramyl-L-alanyl-D-isoglutamine, MTP-PE and RIBI, which contains three components extracted from bacteria, monophosphoryl lipid A, trehalose dimycolate and cell wall skeleton (MPL+TDM+CWS) in a 2% squalene/Tween 80 emulsion. Other examples of adjuvants include DDA (dimethyldioctadecylammonium bromide), Freund's complete and incomplete adjuvants and QuilA. In addition, immune modulating substances such as lymphokines (e.g., IFN-[gamma], IL-2 and IL-12) or synthetic IFN-[gamma] inducers such as poly I:C or poly ICLC (Hiltonol) can be used in combination with adjuvants described herein.

In certain embodiments, the adjuvant may be selected among poly ICLC, CpG, LPS, Immunoquid, PLA, GLA or cytokine adjuvants such as IFNα. In other embodiments the adjuvant may be a toll-like receptor agonist (TLR). Examples of TLR agonists that may be used comprise TLR1 agonist, TLR2 agonist, TLR3 agonist, TLR4 agonist, TLR5 agonist, TLR6 agonist, TLR7 agonist, TLR8 agonist or TLR9 agonist.

The vaccine preparation of CD40 activating protein as the active immunogenic ingredient, may be prepared as injectables, either as liquid solutions or suspensions; solid forms suitable for solution in, or suspension in, liquid prior to infection can also be prepared. The preparation may be emulsified, encapsulated in liposomes. The active immunogenic ingredients are often mixed with carriers which are pharmaceutically acceptable and compatible with the active ingredient.

Methods of Use of the CD40 Activating Proteins of the Disclosure

By eliciting an immune response to the antigen(s) present in the CD40 activating proteins, the CD40 activating proteins of the disclosure may be useful as a drug, in particular for treating or preventing cancer or infectious disorders.

In some embodiments, the CD40 activating proteins may be used in a method for treating or preventing from a viral infection or cancer disorder in a subject comprising administering a CD40 activating protein of the disclosure to the subject.

Yet further aspects relate to a method for eliciting and/or enhancing B cell and/or T cell response against a viral or tumor associated antigen, in a subject in need thereof, comprising administering to said subject in need thereof, a CD40 activating protein or vaccine of the disclosure.

Further aspects relate to a method for inducing IgG binding antibody responses to the antigens in a subject in need thereof, the method comprising administering the CD40 activating protein of the disclosure or the vaccine composition of the disclosure.

In some embodiments, the method further comprises administration of an immunostimulant. In some embodiments, the immunostimulant is administered sequentially or concomitantly to a vaccine or therapeutic composition.

In some embodiments, the immunostimulant is mixed with a vaccine composition extemporaneously prior to injection of the vaccine composition to the subject.

Additionally, the methods of the disclosure may also comprise the administration of one or more adjuvants. The adjuvants may be attached or conjugated directly or indirectly to one or more of the vaccine components, such as an antigen or CD40 activating protein. In other embodiments, the adjuvants may be provided or administered separately from the vaccine composition. In certain embodiments the adjuvant is poly ICLC, CpG, LPS, Immunoquid, PLA, GLA or cytokine adjuvants such as IFNα. In other embodiments the adjuvant may be a toll-like receptor agonist (TLR). Examples of TLR agonists that may be used comprise TLR1 agonist, TLR2 agonist, TLR3 agonist, TLR4 agonist, TLR5 agonist, TLR6 agonist, TLR7 agonist, TLR8 agonist or TLR9 agonist.

In some embodiments, the administration comprises intradermal, intramuscular, or subcutaneous administration.

In some embodiments, the viral vaccine, e.g., a CD40 activating protein comprising a viral antigen, is used in a method for potentiating an immune response to at least one viral epitope comprising administering to a patient such viral vaccine as described herein.

In some embodiments, such viral vaccine is used to prevent healthy subject to be infected by said virus, comprising administering such viral vaccine of the present disclosure, e.g. to a healthy subject, not infected by said virus (preventive treatment). In other embodiments, the viral vaccine of the present disclosure is used in a method of treating a patient in the early stages of the viral infection comprising administering to a patient said viral vaccine.

It is contemplated that at least one viral antigen elicits at least one of a humoral and/or a cellular immune response in a host, preferably a human patient or a primate.

Administration of vaccines or pharmaceutical compositions according to the present disclosure will be via any common route so long as the target tissue is available via that route in order to maximize the delivery of antigen to a site for maximum (or in some cases minimum) immune response. Administration of vaccines will generally be by orthotopic, intradermal, mucosally, subcutaneous, intramuscular, intraperitoneal or intravenous injection. Other areas for delivery include: oral, nasal, buccal, rectal, vaginal or topical. Vaccines of the disclosure are preferably administered parenterally, by injection, for example, either subcutaneously or intramuscularly.

Vaccines or pharmaceutical compositions of the present disclosure may be administered in a manner compatible with the dosage formulation, and in such amount as will be prophylactically and/or therapeutically effective. The quantity to be administered depends on the subject to be treated, including, e.g., capacity of the subject's immune system to synthesize antibodies, and the degree of protection or treatment desired. Suitable dosage ranges are of the order of several hundred micrograms active ingredient per vaccination with a range from about 0.1 mg to 1000 mg, such as in the range from about 1 mg to 300 mg, or in the range from about 10 mg to 50 mg.

Precise amounts of active ingredient required to be administered depend on the judgment of the practitioner and may be peculiar to each subject. It will be apparent to those of skill in the art that the therapeutically effective amount of CD40 activating proteins of this disclosure will depend, inter alia, upon the administration schedule, the unit dose of antigen administered, whether the CD40 activating protein is administered in combination with other therapeutic agents, the immune status and health of the recipient, and the therapeutic activity of the particular CD40 activating protein.

A vaccine may typically be given in a single dose schedule or in a multiple dose schedule. A multiple dose schedule is one in which a primary course of vaccination may include, e.g., 1-10 separate doses, followed by other doses given at subsequent time intervals required to maintain and or reinforce the immune response, for example, at 1-4 months for a second dose, and if needed, a subsequent dose(s) after several months. Periodic boosters at intervals of 1-5 years, usually 3 years, are desirable to maintain the desired levels of protective immunity. The course of the immunization can be followed by in vitro proliferation assays of peripheral blood lymphocytes (PBLs) co-cultured with the antigen, and by measuring the levels of IFN-[gamma] released from the primed lymphocytes. The assays may be performed using conventional labels, such as radionucleotides, enzymes, fluorescent labels and the like. These techniques are known to one skilled in the art and can be found in U.S. Pat. Nos. 3,791,932, 4,174,384 and 3,949,064.

A vaccine may be provided in one or more "unit doses". Unit dose is defined as containing a predetermined-quantity of the vaccine calculated to produce the desired responses in association with its administration, i.e., the appropriate route and treatment regimen. The quantity to be administered, and the particular route and formulation, are within the skill of those in the clinical arts. The subject to be treated may also be evaluated, in particular, the state of the subject's immune system and the protection desired. A unit dose need not be administered as a single injection but may include continuous infusion over a set period of time. The amount of vaccine delivered can vary from about 0.001 to about 0.05 mg/kg body weight, for example between 0.1 to 5 mg per subject.

Further aspects relate to a kit comprising a CD40 activating protein of the disclosure, a nucleic acid of the disclosure, an expression vector of the disclosure, or a host cell of the disclosure, and; optionally, instructions for use of the kit. The kit may be used to perform the methods described herein. In some embodiments, the kit is for eliciting a T cell response and/or a B cell response in a subject; wherein the kit comprises the CD40 activating protein of the disclosure or the vaccine of the disclosure.

The disclosure will be further illustrated by the following examples. However, these examples should not be interpreted in any way as limiting the scope of the present invention.

DESCRIPTION OF THE FIGURES

FIGS. 2 and 5 contain replicated data for Ab and Ab+sCD40L.

EXAMPLES

1. Methods

Method for MDDC Preparation—Protocol

Figure 1:
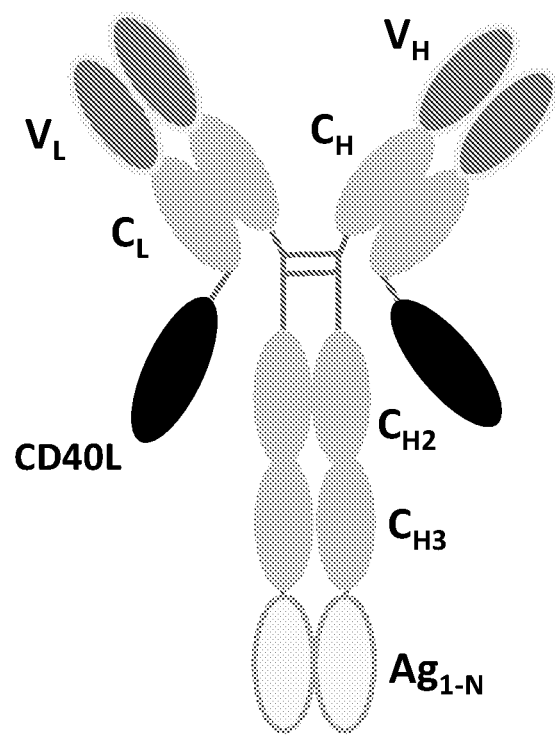
FIG. 1: A cartoon illustrating the anti-Receptor antibody-Ligand fusion concept exemplified by anti-CD40 11B6-human CD40 IgG4. Shown are relevant domains: $V_L$ are the light chain variable regions; $V_H$ are the heavy chain variable regions; $C_H$ are the H chain constant regions 1-3; $C_L$ are the light chain constant regions; linker sequences and key disulfide bonds are represented by grey lines. The invention anticipated alternate form of fusion including Ligand fused to H chain C-termini and diverse antibody forms and isotypes.

1 M human blood monocytes/mL were cultured in a six well plate (2 mL per well) in RPMI medium+10% FBS+10 ng/mL human IL-4+100 ng/mL human GM-CSF.

Half of the medium was changed at day 2 and at day 4, maintaining the same concentration of IL-4 and GM-CSF. Cells were harvested at day 5 without scraping but with gentle washing and plated in a 96 well v bottom plate in 200 uL at 100,000 cells per well. Typically, 1M DCs were derived from 2M monocytes. Different concentrations of the anti-CD40 mAbs or anti-CD40 IgG4 fusion proteins and 10 ng/mL IL-4 and 100 ng/mL GM-CSF were added, and after 24 or 48 hours supernatants were tested for secreted cytokines a nd the cells were stained for cell surface activation markers.

Surface Plasmon Resonance (SPR) Binding Assay—PROTOCOL

Surface plasmon resonance (SPR) assay binding measurements were performed on a SensiQ Pioneer instrument (SensíQ Technologies, Inc., Oklahoma City, OK, USA). Protein A or Protein G (100 μg/mL in 10 mM NaAc pH4.5) were immobilized using amine coupling chemistry on COOH2 or COOH5 sensor chips at 25° C. following the manufacturer's recommended protocols. Running buffer was 10 mM HEPES, 3.4 mM EDTA, 0.005% Tween 20, 8.8 g/L NaCl, pH 7.5. Subsequently, Channel 1 was used to inject anti-CD40 mAbs at a concentration of 125 nM (Injection Fast, 10 μL/min for 4 min); Channel 1-2 were used to inject a dilution series of cohesin-human CD40 ectodomain protein (P3398) (25, 12.5, 6.25, 3.125, 1.6, 0.8 nM at 25 uL/min for 2 min); finally, surfaces were regenerated through injection of 20 mM NaOH for 1 min (25 μL). The binding data were analyzed with Qdat software (SensíQ Technologies, Inc.).

T Cell Expansion—PROTOCOL

After been thawed and washed, 2M PBMC were cultured at 37'C in presence of $O_2$ in 1 mL cRPMI+10% AB serum in a 24 well flat bottom plate. Cells were treated with different concentrations (1 nM, 0.1 nM and 0.01 nM) of αCD40 abs or controls. In order to have enough T cells at the end of the culture, the conditions were done in triplicate. At day 2, 1 mL of cRPMI+10% AB serum and IL-2 at a final concentration of 100 U/mL were added to each well. Half media was changed at day 4 and at day 6 adding fresh IL-2 without doubling the concentration. Cells were let rest until day 10, when they were harvested and washed twice in PBS with 2 mM EDTA. Cells were subsequently resuspended in cRPMI+10% AB serum in a volume which allowed an equal distribution of the cells between the conditions needed, with a final volume of 200 μL per condition, counted and let them rest O/N at 37'C in presence of $O_2$ in 50 mL tubes.

At day 11, cells were plated in a 96 well plate V bottom and re-stimulated with 2 μM peptides or controls for one hour at 37'C in presence of $O_2$. After one hour, 0.175 μL of Golgi Stop and 0.45 μL of Brefeldin in a volume of 50 μL of cRPMI+10% AB serum were added in each well and the cells were incubated for additional 4 hours. Subsequently, cells were spin down and ICS staining was performed using the following antibodies: αCD3 BV711, αCD4 Pe-Cy7, αCD8 Pacific Blue, αCD56 Pe-Cy5, αCD16 APC-H7, αCD45 Pacific Orange, αNKG2C Alexa Fluor 700, αNKG2D PECF594, αCD69 FITC, αTNF-α APC, αINF-γ PE. Aqua was used as viability dye. After staining, cells were resuspended in BD fixative and analyzed at BD LSR II Flow Cytometer.

B Cell Proliferation Assay—PROTOCOL

Human PBMCs were thawed using benzonaide 1:10 in RPMI medium (1 μL in 5 mL), the cells were wash 2× in PBS and resuspended to have a Cf 10 M/mL in PBS, then stained with CSFE Cf 1.25 μM (Ci=5 mM) for 7 min RT in the dark. Labeling was stopped by adding 10 mL FBS and leave the cells in the cold for 5 min, then washed 2× in PBS, and resuspended in RPMI medium with 10% FBS to distribute 1M cells/mL per well. Human IL-4 (10 ng/mL) and human IL-21 (5 ng/mL) were added to the cells along with various amounts of anti-CD40 mAbs or anti-CD40 IgG4 fusion proteins. 6 Days. CD19 APC: 1 μl; CD27 APC-H7: 1 μl; CD38 PE-Cy7: 0.5 μl; Live/Dead Aqua: 1 μl.

Dendritic Cell Activation Assay—PROTOCOL

1 M human blood monocytes/mL were cultured in a six well plate (2 mL per well) in RPMI medium+10% FBS+10 ng/mL human IL-4+100 ng/mL human GM-CSF. Half of the medium was changed at day 2 and at day 4, maintaining the same concentration of IL-4 and GM-CSF. Cells were harvested at day 5 without scraping but with gentle washing and plated in a 96 well v bottom plate in 200 μL at 100,000 cells per well. Typically, 1M DCs were derived from 2M monocytes. Different concentrations of the anti-CD40 mAbs or anti-CD40 IgG4 fusion proteins and 10 ng/mL IL-4 and 100 ng/mL GM-CSF were added, and after 24 or 48 hours supernatants were tested for secreted cytokines and the cells were stained for cell surface activation markers.

T Cell Expansion Assay with HIV5 Long Peptides: ICS—PROTOCOL

All culture is done in 10% AB (unfiltered) in cRPMI:
cRPMI
Hepes (1M) [12.5 ml per 500 ml]
NEAA (10×) [5 ml per 500 ml]
2ME (1000×) [450 μl per 500 ml; 50 uM final]
NaPyruvate (10×) [5 ml per 500 ml]
Pen Strep (10,000 U/10,000 U) [5 ml per 500 ml]
pH to 7.4 with NaOH
Thaw cells with 10% AB cRPMI (with 50 U benzonase in initial dilution of cells) Wash 2× with 1×PBS, 2 mM EDTA. Resuspend cells in 10% AB cRPMI at a concentration of 2×10e6/ml in a 50 ml loose capped tube and allow cells to rest overnight, at 37 C CO2 5%.

Next day (Day 0): Recount and adjust, based on viability/density, to 2×10e6/ml (per well)*

Day 0: Plate cells in 24 well plate:

Target for about 6 wells per test molecule condition (so you have enough cells at end of T cell expansion—You also need a set of 'cells only' without test molecule, as control for re-stimulation)

(Typically this will require 6×10e7 donor PBMC's, if testing 4 different test molecules and a negative cell only control)

Plate cells in a 24 well plate at 2×10e6/well (1 ml at set up)* in 10% AB cRPMI

Add test molecules at 1 nM "final"**

this can be done in 50 ul vol to add to the 1 ml of cells OR adjust cell vol for 'equal vol' addition of cells and test molecules (500 μl+500 ul)*

**Range for test molecules has been tested between 30 nM and 0.1 nM: For our comparative vaccine assessment, we are using 1 nM, final.

Make fresh from concentrated stock and do not store at low protein concentrations.

Day 2: Following culture set up and protein stimulation, add 1 ml of 10% AB cRPMI containing IL2 (so that final IL-2 concentration in well is 100 U/ml)

Day 4: Remove 1 ml and add 1 ml of 100 U/ml IL2 in 10% AB cRPMI

Day 6: Remove 1 ml and add 1 ml of 100 U/ml IL2 in 10% AB cRPMI

Day 8: Harvest all pools per test molecule condition (depending on test molecule, cell number and type/morphology will vary). Wash away IL2 (2× wash with 1×PBS, 2 mM EDTA). Resuspend cells in 10% AB cRPMI at a concentration of 2×10e6/ml in a 50 ml loose capped tube and allow cells to rest overnight, at 37 C CO2 5%.

Day 9: Filter (cells aggregate with CD40L constructs), count and dispense equal amount of cells (per total cells accumulated per donor) to allow for re-stimulation with peptides. (Cell count/viability will vary per PBMC donor; peptide conditions remain the same) Typically, cells are about 1-5 million per test point, depending on the donor. Cells will be plated at 100 ul vol.

Set up peptide stimulation in a 96 well-V-bottom plate:

100 μl of cells (~1-5×10e6 per 100 μl)+100 μl of peptide (or solvent/control SEB) in V-bottom 96 well plate: (7 conditions divided across each donor)

Solvent (highest vol of highest amount of peptide used), Peptides at 10 uM (can use at 2 uM to 10 uM), SEB at 2 μg/ml. 1 hour at 37 C, CO2 5%.

After 1 hour of stimulation at 37 C, CO2 5%, add 50 μl of 10% AB cRPMI media containing 0.175 μl Golgi stop/0.45 ul of BrefeldinA: (BD Golgi Stop, Cat 51-2092KZ; BrefeldinA, Cat 420601)

After 4 hours at 37 C, CO2 5%, proceed with Intracellular staining:

Intracellular Staining Protocol:

Continuing in 96 well V bottom plate, post peptide re-stimulation, Golgi/BFA block:

Wash cells (1× w/200 μl 1×PBS): (Cfg 1600 RPM 10 min; flick plate to remove wash)

Resuspend cells in 50 μL Aqua* (1 ul Aqua/50 μl of 1×PBS per sample needed) for 20 min at 4'C.

Wash cells (1× in 200 μl with FACS Buffer): (Cfg 1600 RPM 10 min; flick plate to remove wash)

Stain cells in a cocktail of cell surface markers: (αCD3 Per-CP 3 μL, αCD4 PE-Cy7 0.5 μL and αCD8 Pacific Blue 1 μL) in a total volume of 50 μL/sample in FACS Buffer for 30 min in ice.

Wash cells (2× with FACS Buffer): (Cfg 1600 RPM 10 min; flick plate to remove wash)

Resuspend cells in 200 μL of Cytofix/Cytoperm** solution for 20 min at 4'C.

Subsequently, spin cells, then wash cells 2× in 1× Filtered (0.45 μm) Perm/Wash solution Stain cells in a cocktail of anti-cytokines: (αTNFα APC 1 μL and αINFY PE 2 μL) in a total volume of 50 μL Perm/Wash/sample.

Incubate for 30 min at RT

Wash cells (2× with Perm/Wash** buffer): (Cfg 1600 RPM 10 min; flick plate to remove wash)

Resuspend in BD Fixative (~200 μl per sample).

**BD Fixation/Permeabilization Kit Cat #554714

FACS Buffer: PBS+2% FCS or BSA+2 mM EDTA

BD Fixative Stabilizing Fixative 3× concentrate: 1:3 in water Cat #338036

*Aqua Live/Dead Invitrogen L34966 (reconstitute 50 ul DMSO per tube, use 1 μl/sample)

CD40 Receptor Cluster Formation Assay—Protocol.

ExpiCHO-S cells (Thermo Fisher) stably expressing a human CD40-eGFP or a human CD40-mCherry fusion protein were used as a model to study CD40 cluster formation. The cells were incubated in CD CHO/M5 media (Gibco) at a concentration of 1E6 cells/mL in a 6 well plate with rounded cover slides of 25 mm diameter (Electron Microscopy Science) at 37° C. in the presence of 10 nM anti-CD40 antibody. After 1 hour the cover slides were gently washed with PBS twice and then resuspended in 1% PFA (Thermo Fisher) for 10 min at room temperature. Two more washes in PBS followed, and finally the cover slides were mounted on super frosted microscope slides (Fisher-brand) using ProLong Gold antifade reagent with DAPI (Invitrogen). The slides were left o/n at room temperature in the dark. The day after, the slides were imaged by Leica TCS SP5 Confocal Microscopy and subsequently analyzed with ImageJ software.

Anti-CD40 mAb Internalization Assay Protocol.

CHO cells stably transfected with a CET 1019 HS-puro-SceI vector (Millipore Sigma) carrying a human CD40 cDNA insert (NM_001250.6 residues 31 to 864, C928) were grown in CD CHO/M5 media (Gibco) with puromycin selection to establish a bulk stably transfected cell population. Cells were dispensed in culture media with 1% BSA (250K in 50 μl) in V bottom 96 well plates and 100 nM of each test mAb fused at the H-chain C-terminus to a flex V1 Doc Var1 module (Flamar et al., 2012) in non-covalent association with a Cohesin-mCherry fusion protein (C3808, LDITH6 residues fused to a Cohesin domain from cellulo-somal-scaffolding protein A [*Hungateiclostridium thermocellum*] WP_065674352.1 residues 1044-1213 with a f1 flexible linker AVY25163.1 residues 580-608 to mCherry ANF29837.1 residues 330-562 preceded by codons encoding ML and followed by a KEPEA sequence used for C-tag affinity matrix CaptureSelect™ (Thermo Fisher, 191307005) purification of the encoded secreted protein. The tested antibodies saturate CD40 binding sites on these cells at 100 nM (data not shown). At 30 min intervals, the labeled antibody complex was added to cells kept at 37° C. in a cell culture incubator, and at the last (zero) time point an equal volume of ice cold PBS was added to all time points with centrifugation at 1600 rpm for 6 min with liquid removal by flicking. Then 110 μl of cold PBS was added to one time course row (for total binding analysis) and 100 μl of ice cold 0.1M Glycine, 0.1 M NaCl pH 2.5 was added to a parallel time course row (i.e, acid stripping treatment to selectively remove cell surface bound mAb). After 1 min, 10 μl of 1M Tris HCl pH 9 was added to the acid treatment row to neutralize the acid and a further 100 μl cold PBS was added to all rows followed by centrifugation at 1600 rpm for 6 min with liquid removal by flicking. Note that mCherry fluorescence is not compromised by the acid treatment in this time frame (data not shown). After a final wash in PBS, cells were resuspended in 100 μl of PBS and 75 μl was dispensed into Black Fluor Micro 2 plates (Thermo Fisher) for reading fluorescence at Ex 570_Em 625 nM in a SpectraMax Paradigm instrument (Molecular Devices).

```
SEQUENCE NAMING CONVENTION EXEMPLIFIED:
11B6-5
PAB3405
rAB-pIRES2[mAnti-CD40-11B6.1C3-VH-v2-LV-hIgG4H-C-]
rAB-IRES2-CI2[mAnti-CD40-11B6.1C3-Vκ-v2-LV-hIgGK-C]
C3677 rAB-pIRES2[mAnti-CD40-11B6.1C3-VH-v2-LV-hIgG4H-C
                                                          SEQ ID NO: 1

EVQLVQSGAEVKKPGASVKISCKASGYSFTGYYMHWVKQAHGQGLEWIGRINPY

NGATSYNQNFKDRATLTVDKSTSTAYMELSSLRSEDTAVYYCAREDYVYWGQGT

TVTVSSAKTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVESKYGPPC

PPCPAPEFEGGPSVFLFPPKPKDTLMISRTPEVTCVVVDVSQEDPEVQFNWYVDGV

EVHNAKTKPREEQFNSTYRVVSVLTVLHQDWLNGKEYKCKVSNKGLPSSIEKTIS

KAKGQPREPQVYTLPPSQEEMTKNQVSLTCLVKGFYPSDIAVEWESNGQPENNYK

TTPPVLDSDGSFFLYSRLTVDKSRWQEGNVFSCSVMHEALHNHYTQKSLSLSLGK

AS-

+C3862 rAB-IRES2-CI2
C3682 rAB-IRES2-CI2[mAnti-CD40-11B6.1C3-Vκ-v2-LV-hIgGK-C]
                                                          SEQ ID NO: 2

DVVMTQSPLSLPVTLGQPASISCRSSQSLVHSNGNTYLHWYQQRPGQSPRLLIYKV

SNRFSGVPDRFSGSGSGTDFTLKISRVEAEDVGVYFCSQSTHVPWTFGGGTKLEIK

RTVAAPSVFIFPPSDEQLKSGTASVVCLLNNFYPREAKVQWKVDNALQSGNSQES

VTEQDSKDSTYSLSSTLTLSKADYEKHKVYACEVTHQGLSSPVTKSFNRGECAS-

PAB3408
11B6-8
rAB-pIRES2[mAnti-CD40-11B6.1C3-VH-v3-LV-hIgG4H-C]
rAB-IRES2-CI2[mAnti-CD40-11B6.1C3-Vκ-v2-LV-hIgGK-C]
C3678 rAB-pIRES2[mAnti-CD40-11B6.1C3-VH-v3-LV-hIgG4H-C]
                                                          SEQ ID NO: 3

EVQLVQSGAEVKKPGASVKVSCKASGYSFTGYYMHWVRQAPGQGLEWIGRINPY

NGATSYNQNFKDRVTLTVDKSTSTAYMELSSLRSEDTAVYYCAREDYVYWGQGT

TVTVSSAKTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVESKYGPPC

PPCPAPEFEGGPSVFLFPPKPKDTLMISRTPEVTCVVVDVSQEDPEVQFNWYVDGV
```

-continued

EVHNAKTKPREEQFNSTYRVVSVLTVLHQDWLNGKEYKCKVSNKGLPSSIEKTIS

KAKGQPREPQVYTLPPSQEEMTKNQVSLTCLVKGFYPSDIAVEWESNGQPENNYK

TTPPVLDSDGSFFLYSRLTVDKSRWQEGNVFSCSVMHEALHNHYTQKSLSLSLGK

AS

C3682 rAB-IRES2-CI2[mAnti-CD40-11B6.1C3-Vκ-v2-LV-hIgGK-C]

SEQ ID NO: 4

DVVMTQSPLSLPVTLGQPASISCRSSQSLVHSNGNTYLHWYQQRPGQSPRLLIYKV

SNRFSGVPDRFSGSGSGTDFTLKISRVEAEDVGVYFCSQSTHVPWTFGGGTKLEIK

RTVAAPSVFIFPPSDEQLKSGTASVVCLLNNFYPREAKVQWKVDNALQSGNSQES

VTEQDSKDSTYSLSSTLTLSKADYEKHKVYACEVTHQGLSSPVTKSFNRGECAS

From these two were derived the two variants with CD40L attached:
PAB3470
rAB-cetHS-puro[mAnti-CD40-11B6.1C3-Vκ-v2-LV-hIgGK-C-Flex-v1-
hCD40Ligand]
rAB-cetHS-puro[mAnti-CD40-11B6.1C3-VH-v2-LV-hIgG4H-C]
C3724rAB-cetHS-puro[mAnti-CD40-11B6.1C3-Vκ-v2-LV-hIgGK-C-Flex-v1-
hCD40Ligand]

SEQ ID NO: 5

DVVMTQSPLSLPVTLGQPASISCRSSQSLVHSNGNTYLHWYQQRPGQSPRLLIYKV

SNRFSGVPDRFSGSGSGTDFTLKISRVEAEDVGVYFCSQSTHVPWTFGGGTKLEIK

RTVAAPSVFIFPPSDEQLKSGTASVVCLLNNFYPREAKVQWKVDNALQSGNSQES

VTEQDSKDSTYSLSSTLTLSKADYEKHKVYACEVTHQGLSSPVTKSFNRGECASQ

TPTNTISVTPTNNSTPTNNSNPKPNPASMQKGDQNPQIAAHVISEASSKTTSVLQW

AEKGYYTMSNNLVTLENGKQLTVKRQGLYYIYAQVTFCSNREASSQAPFIASLCL

KSPGRFERILLRAANTHSSAKPCGQQSIHLGGVFELQPGASVFVNVTDPSQVSHGT

GFTSFGLLKL

+C3725 rAB-cetHS-puro[mAnti-CD40-11B6.1C3-VH-v2-LV-hIgG4H-C]

SEQ ID NO: 6

EVQLVQSGAEVKKPGASVKISCKASGYSFTGYYMHWVKQAHGQGLEWIGRINPY

NGATSYNQNFKDRATLTVDKSTSTAYMELSSLRSEDTAVYYCAREDYVYWGQGT

TVTVSSAKTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVESKYGPPC

PPCPAPEFEGGPSVFLFPPKPKDTLMISRTPEVTCVVVDVSQEDPEVQFNWYVDGV

EVHNAKTKPREEQFNSTYRVVSVLTVLHQDWLNGKEYKCKVSNKGLPSSIEKTIS

KAKGQPREPQVYTLPPSQEEMTKNQVSLTCLVKGFYPSDIAVEWESNGQPENNYK

TTPPVLDSDGSFFLYSRLTVDKSRWQEGNVFSCSVMHEALHNHYTQKSLSLSLGK

AS-

PAB3471
rAB-cetHS-puro[mAnti-CD40-11B6.1C3-Vκ-v2-LV-hIgGK-C-Flex-v1-hCD40Ligand]
rAB-cetHS-puro[mAnti-CD40-11B6.1C3-VH-v3-LV-hIgG4H-C]
C3724 rAB-cetHS-puro[mAnti-CD40-11B6.1C3-Vκ-v2-LV-hIgGK-C-Flex-v1-
hCD40Ligand]

SEQ ID NO: 5

DVVMTQSPLSLPVTLGQPASISCRSSQSLVHSNGNTYLHWYQQRPGQSPRLLIYKV

SNRFSGVPDRFSGSGSGTDFTLKISRVEAEDVGVYFCSQSTHVPWTFGGGTKLEIK

RTVAAPSVFIFPPSDEQLKSGTASVVCLLNNFYPREAKVQWKVDNALQSGNSQES

VTEQDSKDSTYSLSSTLTLSKADYEKHKVYACEVTHQGLSSPVTKSFNRGECASQ

TPTNTISVTPTNNSTPTNNSNPKPNPASMQKGDQNPQIAAHVISEASSKTTSVLQW

AEKGYYTMSNNLVTLENGKQLTVKRQGLYYIYAQVTFCSNREASSQAPFIASLCL

-continued

KSPGRFERILLRAANTHSSAKPCGQQSIHLGGVFELQPGASVFVNVTDPSQVSHGT

GFTSFGLLKL

+C3726 rAB-cetHS-puro[mAnti-CD40-11B6.1C3-VH-v3-LV-hIgG4H-C]

SEQ ID NO: 8

EVQLVQSGAEVKKPGASVKVSCKASGYSFTGYYMEIWVRQAPGQGLEWIGRINPY

NGATSYNQNFKDRVTLTVDKSTSTAYMELSSLRSEDTAVYYCAREDYVYWGQGT

TVTVSSAKTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVESKYGPPC

PPCPAPEFEGGPSVFLFPPKPKDTLMISRTPEVTCVVVDVSQEDPEVQFNWYVDGV

EVHNAKTKPREEQFNSTYRVVSVLTVLHQDWLNGKEYKCKVSNKGLPSSIEKTIS

KAKGQPREPQVYTLPPSQEEMTKNQVSLTCLVKGFYPSDIAVEWESNGQPENNYK

TTPPVLDSDGSFFLYSRLTVDKSRWQEGNVFSCSVMHEALHNHYTQKSLSLSLGK

AS

We selected PAB3470 to attach HIV-5pep
PAB3499 (no CD40L)
rAB-cetHS-puro[mAnti-CD40-11B6.1C3-VH-v2-LV-hIgG4H-C-Flex-v1-Pep-gag17-
f1-gag253-f2-nef116-f3-nef66-f4-pol158]
rAB-cetHS-puro[mAnti-CD40-11B6.1C3-Vĸ-v2-LV-hIgGK-C]
C3735 rAB-cetHS-puro[mAnti-CD40-11B6.1C3-VH-v2-LV-hIgG4H-C-Flex-v1-Pep-
gag17-f1-gag253-f2-nef116-f3-nef66-f4-pol158]

SEQ ID NO: 9

EVQLVQSGAEVKKPGASVKISCKASGYSFTGYYMHWVKQAHGQGLEWIGRINPY

NGATSYNQNFKDRATLTVDKSTSTAYMELSSLRSEDTAVYYCAREDYVYWGQGT

TVTVSSAKTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVESKYGPPC

PPCPAPEFEGGPSVFLFPPKPKDTLMISRTPEVTCVVVDVSQEDPEVQFNWYVDGV

EVHNAKTKPREEQFNSTYRVVSVLTVLHQDWLNGKEYKCKVSNKGLPSSIEKTIS

KAKGQPREPQVYTLPPSQEEMTKNQVSLTCLVKGFYPSDIAVEWESNGQPENNYK

TTPPVLDSDGSFFLYSRLTVDKSRWQEGNVFSCSVMHEALHNHYTQKSLSLSLGK

ASQTPTNTISVTPTNNSTPTNNSNPKPNPASEKIRLRPGGKKKYKLKHIVASSSVSPT

TSVHPTPTSVPPTPTKSSPASNPPIPVGEIYKRWIILGLNKIVRMYSPTSILDASPTSTP

ADSSTITPTATPTATPTIKGASHTQGYFPDWQNYTPGPGVRYPLTFGWLYKLASTV

TPTATATPSAIVTTITPTATTKPASVGFPVTPQVPLRPMTYKAAVDLSHFLKEKGGL

ASTNGSITVAATAPTVTPTVNATPSAAASAIFQSSMTKILEPFRKQNPDIVIYQYMD

DLYAS

+C3739 rAB-cetHS-puro[mAnti-CD40-11B6.1C3-Vĸ-v2-LV-hIgGK-C9+

SEQ ID NO: 10

DVVMTQSPLSLPVTLGQPASISCRSSQSLVHSNGNTYLHWYQQRPGQSPRLLIYKV

SNRFSGVPDRFSGSGSGTDFTLKISRVEAEDVGVYFCSQSTHVPWTFGGGTKLEIK

RTVAAPSVFIFPPSDEQLKSGTASVVCLLNNFYPREAKVQWKVDNALQSGNSQES

VTEQDSKDSTYSLSSTLTLSKADYEKHKVYACEVTHQGLSSPVTKSFNRGECAS

PAB3498 rAB-cetHS-puro[mAnti-CD40-11B6.1C3-VH-v2-LV-hIgG4H-C-Flex-v1-Pep-
gag17-f1-gag253-f2-nef116-f3-nef66-f4-pol158]
rAB-cetHS-puro[mAnti-CD40-11B6.1C3-Vĸ-v2-LV-hIgGK-C-Flex-v1-hCD40Ligand]
C3735 rAB-cetHS-puro[mAnti-CD40-11B6.1C3-VH-v2-LV-hIgG4H-C-Flex-v1-Pep-gag17-f1-
gag253-f2-nef116-f3-nef66-f4-pol158]

SEQ ID NO: 11

EVQLVQSGAEVKKPGASVKISCKASGYSFTGYYMHWVKQAHGQGLEWIGRINPY

NGATSYNQNFKDRATLTVDKSTSTAYMELSSLRSEDTAVYYCAREDYVYWGQGT

-continued

TVTVSSAKTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVESKYGPPC

PPCPAPEFEGGPSVFLFPPKPKDTLMISRTPEVTCVVVDVSQEDPEVQFNWYVDGV

EVHNAKTKPREEQFNSTYRVVSVLTVLHQDWLNGKEYKCKVSNKGLPSSIEKTIS

KAKGQPREPQVYTLPPSQEEMTKNQVSLTCLVKGFYPSDIAVEWESNGQPENNYK

TTPPVLDSDGSFFLYSRLTVDKSRWQEGNVFSCSVMHEALHNHYTQKSLSLSLGK

ASQTPTNTISVTPTNNSTPTNNSNPKPNPASEKIRLRPGGKKKYKLKHIVASSSVSPT

TSVHPTPTSVPPTPTKSSPASNPPIPVGEIYKRWIILGLNKIVRMYSPTSILDASPTSTP

ADSSTITPTATPTATPTIKGASHTQGYFPDWQNYTPGPGVRYPLTFGWLYKLASTV

TPTATATPSAIVTTITPTATTKPASVGFPVTPQVPLRPMTYKAAVDLSHFLKEKGGL

ASTNGSITVAATAPTVTPTVNATPSAAASAIFQSSMTKILEPFRKQNPDIVIYQYMD

DLYAS

+C3524 rAB-cetHS-puro[mAnti-CD40-11B6.1C3-Vκ-v2-LV-hIgGK-C-Flex-v1-
hCD40Ligand]

SEQ ID NO: 12

DVVMTQSPLSLPVTLGQPASISCRSSQSLVHSNGNTYLHWYQQRPGQSPRLLIYKV

SNRFSGVPDRFSGSGSGTDFTLKISRVEAEDVGVYFCSQSTHVPWTFGGGTKLEIK

RTVAAPSVFIFPPSDEQLKSGTASVVCLLNNFYPREAKVQWKVDNALQSGNSQES

VTEQDSKDSTYSLSSTLTLSKADYEKHKVYACEVTHQGLSSPVTKSFNRGECASQ

TPTNTISVTPTNNSTPTNNSNPKPNPASMQKGDQNPQIAAHVISEASSKTTSVLQW

AEKGYYTMSNNLVTLENGKQLTVKRQGLYYIYAQVTFCSNREASSQAPFIASLCL

KSPGRFERILLRAANTHSSAKPCGQQSIHLGGVFELQPGASVFVNVTDPSQVSHGT

GFTSFGLLKL

Seq ID NO: 13: CD40L
MVRLPLQCVLWGCLLTAVHPEPPTACREKQYLINSQCCSLCQPGQKLVSDCTEFT

ETECLPCGESEFLDTWNRETHCHQHKYCDPNLGLRVQQKGTSETDTICTCEEGWH

CTSEACESCVLHRSCSPGFGVKQIATGVSDTICEPCPVGFFSNVSSAFEKCHPWTSC

ETKDLVVQQAGTNKTDVVCGPQDRLRALVVIPIIFGILFAILLVLVFIKKVAKKPTN

KAPHPKQEPQEINFPDDLPGSNTAAPVQETLHGCQPVTQEDGKESRISVQERQ

Leader or Signal sequence 1-20;
Ectodomain residues 21-193;
Transmembrane sequence 194-215;
Cytoplasmic sequence 216-277.
This is the isoform that has been chosen as the "canonical" sequence as reported by
UniProtKB—P25942 (TNR5_HUMAN) which also describes sequence variants.
Other CD40 antibodies: Variable domain sequences for HC and KC
The amino acid at the end of the H chain V regions is usu-
ally a Lysine, but may be more
typically replaced by Serine (as in the CP sequence—this has no effect on activity)
12B4 HC [manti-CD40_12B4.2C10_H-LV-hIgG4H-C]

(SEQ ID NO: 98)

EVQLQQSGPELVKPGASVKMSCKASGYTFTDYVLHWVKQKPGQGLEWIGYINP

YNDGTKYNEKFKGKATLTSDKSSTAYMELSSLTSEDSAVYYCARGYPAYSGY

AMDYWGQGTSVTVSSAK

12B4 KC [manti-CD40_12B4.2C10_K-LV-hIgGK-C]

(SEQ ID NO: 99)

DIQMTQTTSSLSASLGDRVTISCRASQDISNYLNWYQQKPDGTVKLLIYYTSRLHS

GVPSRFSGSGSGTDYSLTISNLEQEDIATYFCHHGNTLPWTFGGGTK

12E12 HC [manti-CD40_12E12.3F3_H-V-hIgG4H-C]

(SEQ ID NO: 100)

-continued

EVKLVESGGGLVQPGGSLKLSCATSGFTFSDYYMYWVRQTPEKRLEWVAYINSG

GGSTYYPDTVKGRFTISRDNAKNTLYLQMSRLKSEDTAMYYCARRGLPFHAMD

YWGQGTSVTVSSAK

12E12 KC [manti-CD40_12E12.3F3_K-V-hIgGK-C]

(SEQ ID NO: 101)

DIQMTQTTSSLSASLGDRVTISCSASQGISNYLNWYQQKPDGTVKLLIYYTSILHS

GVPSRFSGSGSGTDYSLTIGNLEPEDIATYYCQQFNKLPPTFGGGTK

12E12 H2 Humanized HC [hAnti-CD40VH2-LV-hIgG4H-C]

(SEQ ID NO: 102)

EVKLVESGGGLVQPGGSLKLSCATSGFTFSDYYMYWVRQAPGKGLEWVAYINS

GGGSTYYPDTVKGRFTISRDNAKNTLYLQMNSLRAEDTAVYYCARRGLPFHAM

DYWGQGTLVTVSSAK

12E12 H3 Humanized HC [hAnti-CD40VH3-LV-hIgG4H-C]

(SEQ ID NO: 103)

EVQLVESGGGLVQPGGSLKLSCATSGFTFSDYYMYWVRQAPGKGLEWVAYINS

GGGSTYYPDTVKGRFTISRDNAKNTLYLQMNSLRAEDTAVYYCARRGLPFHAM

DYWGQGTLVTVSSAK

12E12 K2 Humanized KC [hAnti-CD40VK2-LV-hIgGK-C]

(SEQ ID NO: 104)

DIQMTQSPSSLSASVGDRVTITCSASQGISNYLNWYQQKPGKAVKLLIYYTSILHS

GVPSRFSGSGSGTDYTLTISSLQPEDFATYYCQQFNKLPPTFGGGTK

Pfizer HC [manti-hCD40_CP870893H-LV-hIgG4H-C]

(SEQ ID NO: 105)

QVQLVQSGAEVKKPGASVKVSCKASGYTFTGYYMHWVRQAPGQGLEWMGWI

NPDSGGTNYAQKFQGRVTMTRDTSISTAYMELNRLRSDDTAVYYCARDQPLGY

CTNGVCSYFDYWGQGTLVTVSSAS

Pfizer KC [manti-hCD40_CP870893K-LV-hIgGK-C]

(SEQ ID NO: 106)

DIQMTQSPSSVSASVGDRVTITCRASQGIYSWLAWYQQKPGKAPNLLIYTASTLQ

SGVPSRFSGSGSGTDFTLTISSLQPEDFATYYCQQANIFPLTFGGGTK

24A3 HC [manti-hCD40_24A3.3F1_H-LV-hIgG4H-C]

(SEQ ID NO: 107)

DVQLQESGPDLVKPSQSLSLTCTVTGYSITSDYSWHWIRQFPGNKLEWMGYIYYS

GSTNYNPSLKSRISITRDTSKNQFFLQLNSVTTEDSATYFCARFYYGYSFFDYWGQ

GTTLTVSSAK

24A3 KC [manti-hCD40_24A3.3F1_K-LV-hIgGK-C]

(SEQ ID NO: 108)

QIVLTQSPAFMSASPGEKVTMTCSASSSVSYMHWYQQKSGTSPKRWIYDTSKLAS

GVPARFSGSGSGTSYSLTISSMEAEDAATYYCQQWSSNPLTFGAGTK

11B6 hCD40L Humanized HC fused to a dockerin domain—which when paired with
11B6 hCD40L Humanized KC [mAnti-CD40-11B6.1C3-Vκ-v2-LV-hIgGK-C-Flex-v1-
hCD40Ligand]makes humanized 11B6-CD40L-Dockerin for non-covalent coupling to
any cohesin-antigen fusion.
Complete sequence (C3724) <u>FlexV1</u> <u>hCD40L</u>

(SEQ ID NO: 109)

DVVMTQSPLSLPVTLGQPASISCRSSQSLVHSNGNTYLHWYQQRPGQSPRLLIYK
VSNRFSGVPDRFSGSGSGTDFTLKISRVEAEDVGVYFCSQSTHVPWTFGGGTKLEI
KRTVAAPSVFIFPPSDEQLKSGTASVVCLLNNFYPREAKVQWKVDNALQSGNSQE
SVTEQDSKDSTYSLSSTLTLSKADYEKHKVYACEVTHQGLSSPVTKSFNRGECASQ
<u>TPTNTISVTPTNNSTPTNNSNPKPNPAS</u><u>MQKGDQNPQIAAHVISEASSKTTSVLQW</u>

<u>AEKGYYTMSNNLVTLENGKQLTVKRQGLYYIYAQVTFCSNREASSQAPFIASLCL</u>

<u>KSPGRFERILLRAANTHSSAKPCGQQSIHLGGVFELQPGASVFVNVTDPSQVSHGT</u>

-continued

GFTSPGLLKL

11B6 hCD40L Humanized HC [mAnti-CD40-11B6.1C3-VH-v2-LV-hIgG4H-C-
CthermoDockerin](C3737) [CthermoDockerin]

(SEQ ID NO: 110)

EVQLVQSGAEVKKPGASVKISCKASGYSFTGYYMHWVKQAHGQGLEWIGRINP
YNGATSYNQNFKDRATLTVDKSTSTAYMELSSLRSEDTAVYYCAREDYVYWGQ
GTTVTVSSAKTKGPSVFPLAPCSRSTSESTAALGCLVKDYFPEPVTVSWNSGALTS
GVHTFPAVLQSSGLYSLSSVVTVPSSSLGTKTYTCNVDHKPSNTKVDKRVESKYG
PPCPPCPAPEFEGGPSVFLFPPKPKDTLMISRTPEVTCVVVDVSQEDPEVQFNWYV
DGVEVHNAKTKPREEQFNSTYRVVSVLTVLHQDWLNGKEYKCKVSNKGLPSSIE
KTISKAKGQPREPQVYTLPPSQEEMTKNQVSLTCLVKGFYPSDIAVEWESNGQPEN
NYKTTPPVLDSDGSFFLYSRLTVDKSRWQEGNVFSCSVMHEALHNHYTQKSLSLS
LGKASNSPQNEVLYGDVNDDGKVNSTDLTLLKRYVLKAVSTLPSSKAEKNADVN

RDGRVDSSDVTILSRYLIRVIEDLPI

Flex linkers amino acid sequences:
(flexV1, SEQ ID NO: 15)
QTPTNTISVTPTNNSTPTNNSNPKPNP (f1, SEQ ID NO: 56)
ASSSVSPTTSVHPTPTSVPPTPTKSSPAS (f2, SEQ ID NO: 130)
PTSTPADSSTITPTATPTATPTIKG (f3, SEQ ID NO: 53)
TVTPTATATPSAIVTTITPTATTKP (f4, SEQ ID NO: 54)
TNGSITVAATAPTVTPTVNATPSAA

2. Results

Some Agonist Including Partial Agonist Anti-CD40 Antibodies can Synergize with Soluble CD40L for CD40 Activation.

Figure 2:
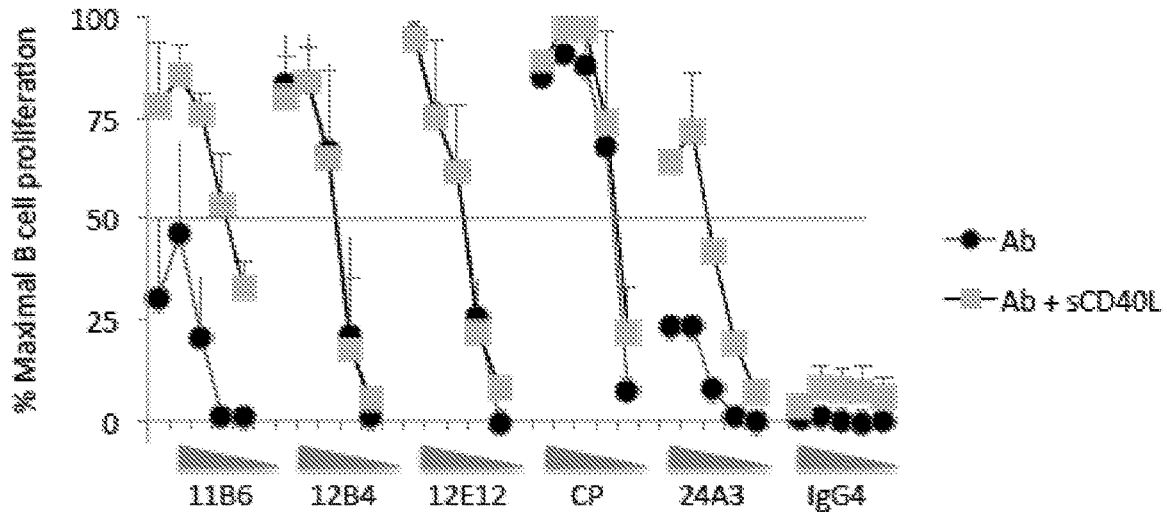
FIG. 2. Proliferative response of human B cells to a dose range of anti-CD40 antibodies incubated with and without a constant low dose of soluble human CD40L. Human PBMCs were incubated with human IL-4, human IL-21, and a dose range of various human IgG4 isotype-matched antibodies (shown left to right: 10, 1, 0.1, 0.01 nM), and the extent of proliferation was determined after 6 days by flow cytometric analysis of CFSE dilution. Curves with black filled circle symbols are response to antibody dose, curves with grey filled square symbols are response to antibody dose in the presence of 100 ng/ml (6 nM) soluble human CD40L. Data represent averages 7 (11B6, 12B4, CP, IgG4) or 3 (12E12, 24A3) independent experiments on different donors normalized for maximum proliferation (80±22%) versus baseline replication without antibody or sCD40L (range 6±4%) or without antibody but with sCD40L (11±7%).

CD40 expressed on B cells, when engaged by CD40L expressed on antigen-activated CD4+ helper T cells secreting cytokines interleukin-4 and interleukin-21, drives the proliferation of B cells, events that are typically confined to germinal centers of lymphoid organs. We tested a matched panel of anti-human CD40 antibodies formatted as human IgG4 and human κ light chain for their efficacy in driving proliferation of human peripheral B cells in the presence of IL-4 and IL-21 (FIG. 2). These antibodies covered a >100-fold range of agonist efficacies with rank order CP>12E12≥12B4>11B6>24A3 (CP is CP-870,893, a Pfizer Inc. antibody tested in various clinical trials, (Vonderheide et al., 2013).

Repeating this assay in the presence of a fixed suboptimal concentration of soluble CD40L (sCD40L) had no effect on the dose-response of the 12B4 and 12E12 antibodies, slightly increased the potency of the CP antibody, but synergized with the 11B6 and 24A3 antibodies to greatly (≥100-fold) increase their efficacy (FIG. 2). The synergistic co-operation of these two weak CD40 agonist signals suggests that the interaction of these specific mAbs with CD40 potentiates productive interaction with CD40L, or visa versa. Synergism between substances that activate distinct receptors on a single cell is a well-known phenomenon, e.g., co-operative effects can be observed between agonistic anti-CD40 mAbs and FcRII (Dahan, et al., 2016), but in this case our two activating agents are acting on the same receptor type.

| Antibody (hIgG4) | 11B6 | 12B4 | | 12E12 | | CP | | 24A3 |
|---|---|---|---|---|---|---|---|---|
| EC$_{50}$ (nM) B cell | ≥10 | >0.1 | <1 | >0.1 | <1 | >0.01 | <0.1 | >10 |
| EC$_{50}$/EC$_{50}$ CP | ≥100 | ≈10 | | ≈10 | | 1 | | ≥1000 |
| EC$_{50}$ w/sCD40L (nM) | ≥0.1 | >0.1 | <1 | >0.1 | <1 | >0.01 | <0.1 | ≥1 <10 |
| Δ w/sCD40L (fold) | ≥100 | ≈0 | | ≈0 | | ≈0 | | ≈100 |

Table for FIG. 2. Limits for the efficacious dose for 50% of maximum B cell proliferation (EC$_{50}$) are given as nanomolar values (nM).
Also calculated are EC$_{50}$ ratio relative to the CP-870, 893 (CP) strong agonist antibody; EC$_{50}$ value in the presence of a constant suboptimal amount (6 nM) of soluble human CD40L; and fold difference (Δ) in EC$_{50}$ value in the presence of a constant suboptimal amount (6 nM) of soluble human CD40L.

Figure 3:
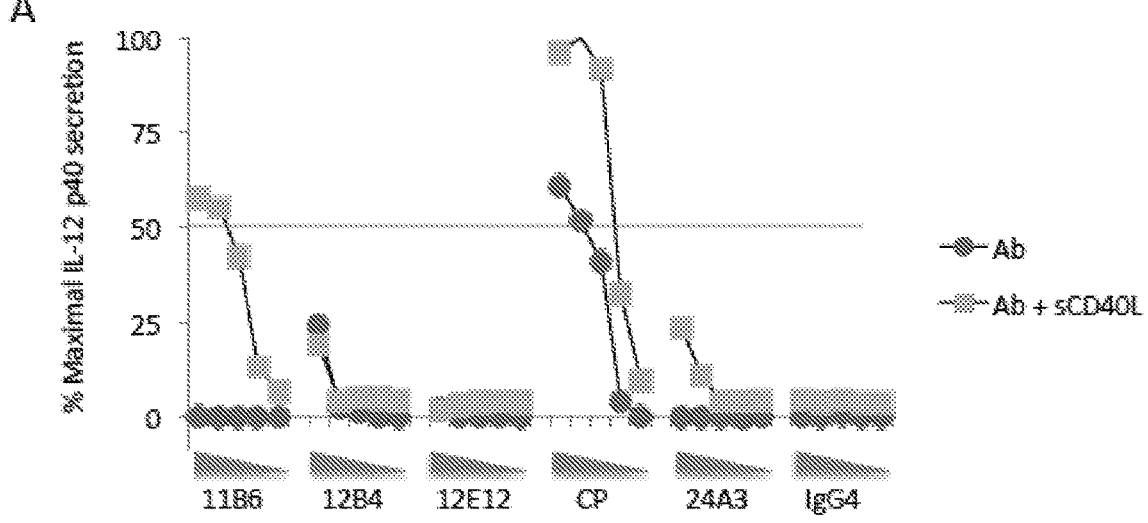
FIG. 3. Cytokine secretion response of human MDDCs to a dose range of anti-CD40 IgG4 antibodies incubated with and without a constant low dose of soluble CD40L. Human MCDCs were cultured with a dose range (shown left to right: 10, 1, 0.1, 0.01, 0.001 nM) of each anti-CD40 mAb and the extent of cytokine secretion was determined after 2 days. Maximum responses were set at 100%. Curves with black circle symbols are response to antibody alone, curves with grey square symbols are responses to antibody in the presence of 1 µg/ml soluble human CD40L (60 nM). Data represent a single experiment normalized relative to the maximum secretion of each cytokine tested (panel A, IL-12 p40, 561 ng/ml; panel B, IL-15, 62 ng/ml). A similar dose response trend was observed for IL-6 secretion (446 pg/ml maximum, and 30 pg/ml response to sCD40L).
Figure 3:
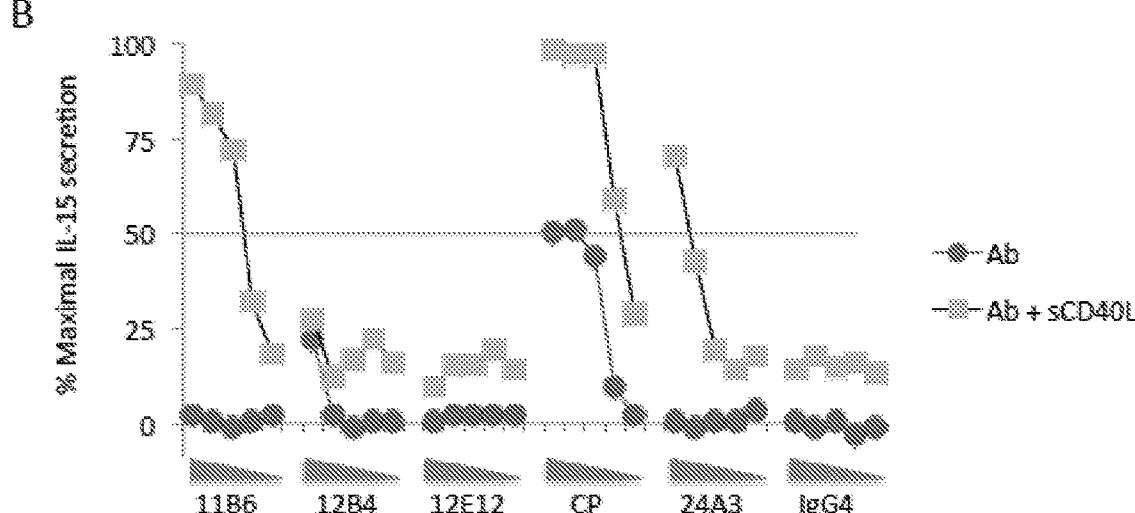

Sentinel dendritic cells (DCs), when exposed to foreign antigens and pathogen-derived danger signals, process and present antigen peptides in their major histocompatibility molecules (MHC) to cognate antigen-specific T cells (Hivroz et al., 2012). CD40 expressed on the dendritic cells interacts with CD40L expressed on adjacent antigen-activated T cells, and this event is critical for initiating immunity, partly via increasing expression of cell surface DC activation molecules (e.g, CD68 and HLA) and invoking secretion of inflammatory cytokines by the DCs (Ma and Clark, 2009). Thus we, assayed the panel of anti-CD40 human IgG4 mAbs for their ability to initiate cytokine secretion on matured human monocyte-derived DC (MDDC). As with the B cell proliferation assay, these antibodies elicited cytokine production over a similar >1000-fold range of efficacies with a similar rank order CP>12B4≥12E12>11B6>24A3 (FIG. 3). When assayed with a sub-optimal dose of sCD40L, there was no effect on the dose-response of the 12B4 and 12E12 antibodies. However, low dose sCD40L increased the potency of the CP antibody by ≈100-fold, while strong synergy for DC activation (≥100-fold) was again observed between sCD40L and the 11B6 and 24A3 antibodies (FIG. 3). The difference in efficacy between antibody alone and antibody with sCD40L was greater than observed with the B cell proliferation assay, indicating a greater potential for co-operation between these two agonist types on MDDCs.

| Antibody (hIgG4) | 11B6 | 12B4 | 12E12 | CP | 24A3 |
|---|---|---|---|---|---|
| EC$_{50}$ (nM) cytokines | >>10 | >10 | >>10 | ≈0.1 | >>10 |
| EC$_{50}$/EC$_{50}$ CP | >1000 | ≥100 | >1000 | 1 | >1000 |
| EC$_{50}$ w/sCD40L (nM) | ≈≥0.1 | >10 ≥100 | >>10 >0.1 <1 | ≥0.01 | ≥10 |
| Δ w/sCD40L (fold) | >1000 | ≅0 | ≅0 | ≈100 | >1000 |

Table for FIG. 3. Limits for the efficacious dose for 50% of maximum secretion of IL-40 p40 or IL-15 by MDDCs (EC$_{50}$) are given as nanomolar values (nM). Also calculated are EC$_{50}$ ratio relative to the CP-870, 893 (CP) strong agonist antibody; EC$_{50}$ value in the presence of a constant suboptimal amount (6 nM) of soluble human CD40L; and fold difference (Δ) in EC$_{50}$ value in the presence of a constant suboptimal amount (60 nM) of soluble human CD40L.

The panel of anti-human CD40 mAbs we studied all bind with relatively high affinity to CD40 as determined by surface plasmon resonance (SPR), with rank order for on-rate of 11B6>12B4>12E12>24A3>CP and rank order for off-rate 12B4>11B6>24A3>12E12>CP (Table 1). Previous studies with agonistic anti-CD40 antibodies have shown no apparent correlation between these kinetic parameters and activation potential (Hagar et al., 2003) and the SPR data for the mAbs with in this study are in accord with this conclusion.

TABLE 4

Kinetic parameters and affinity constants for the interaction between immobilized anti-human CD40 IgG4 mAbs and liquid phase soluble human CD40 ectodomain. Surface plasmon resonance analysis of the kinetics of soluble liquid phase human CD40 ectodomain with immobilized antibody was performed as described in Materials and Methods.

| mAb | 11B6 | 12B4 | 12E12 | CP | 24A3 |
|---|---|---|---|---|---|
| Kd (nM) | 217 | 100 | 33 | 71 | 97 |
| Ka (M$^{-1}$s$^{-1}$) | 3.0E+05 | 2.5E+05 | 1.5E+05 | 4.6E+04 | 8.3E+04 |
| kd (s$^{-1}$) | 6.4E-02 | 2.7E-02 | 4.6E-03 | 2.2E-03 | 8.0E-03 |

One possible mechanism for the synergy between sCD40L and anti-CD40 mAb activation of CD40 could be via their access to separate sites on the CD40 ectodomain. It is known that the agonistic anti-CD40L mAb CDX-1140 interacts with CD40 at a site distinct from CD40L and similar synergy between sCD40L and this mAb was observed (He et al., 2016).

Figure 4:
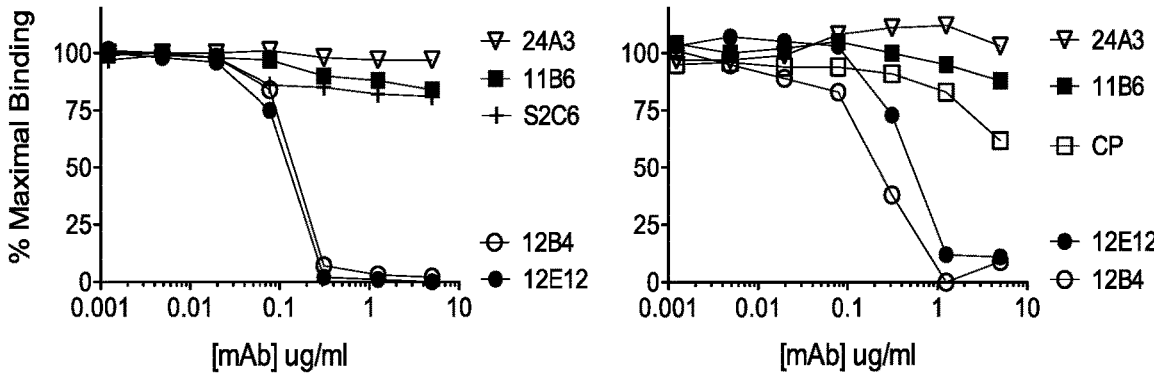
FIG. 4. Anti-CD40 antibody inhibition of CD40L binding. A titration series of anti-human CD40 mouse (left panel) or human IgG4 (right panel) mAbs was added to a constant amount (2 µg/ml) of human CD40 ectodomain human Fc (left panel) or mouse Fc (right panel) fusion protein at 2 µg/ml and the mixture was incubated on ice 1 hour, then added to an equal volume of 200K human CD40L stably-transfected L cells, incubated on ice for 1 hour, washed, incubated with goat anti-mouse (upper panel) or anti-human (lower panel) IgG-PE reagent, washed again, and analyzed on a FACS Array instrument. Loss of binding indicates that the test mAb binds to soluble CD40 in a manner that interferes with binding to cell surface CD40L.

Thus we tested our panel of anti-human CD40 IgG4 antibodies for their ability to prevent the binding of CD40 to CD40L expressed on the surface of L cells. The 12B4 and 12E12 antibodies in stoichiometric amounts prevented CD40 binding to cell surface CD40L, while >20-fold higher levels of the CP antibody were required to even partially block CD40 binding to CD40L, while the 11B6 and 24A3 antibodies had a minimal effect on CD40L binding to CD40 even at the highest mAb doses (FIG. 4).

These data were consistent for these mAbs either as the original mouse antibodies or reformatted as hIgG4. Based on their affinity constants (Table 4) all of these antibodies would have fully occupied CD40 binding sites at the key discriminating concentration of 1 μg/ml where 12E12 and 12B4 mAbs fully block CD40L binding. These data show that the 12B4 and 12E12 mAbs bind to sites on CD40 that are absolutely required for CD40-CD40L interaction, while the CP, 11B6, and 24A3 mAbs bind to CD40 sites with minimal interference to CD40-CD40L interaction.

Thus synergy between sCD40L and anti-CD40 mAb for B cell and DC activation is associated with simultaneous access of both these agonists to distinct parts of CD40L.

Antigens Fused to Agonistic Anti-CD40 mAbs can Dull CD40 Activation Efficacy but Some Anti-CD40 mAb-Antigen Fusions Synergize with sCD40L to Restore CD40 Activation Potency.

Fusion of antigens to the C-terminus of chimeric or humanized agonistic antibodies can dull or eliminate the agonistic property of the parent antibody [Flamar et al., 2013]. A panel of anti-CD40 antibodies matched to the human IgG4 isotype with and without concatenated strings of HIV-1 long T cell epitope-rich peptides from the Gag, Nef, and Pol gene regions grafted to their H and/or L chain C-termini [Flamar et al., 2013] were tested for their relative efficacy in evoking human B cell proliferation and human dendritic cell activation.

Figure 5:
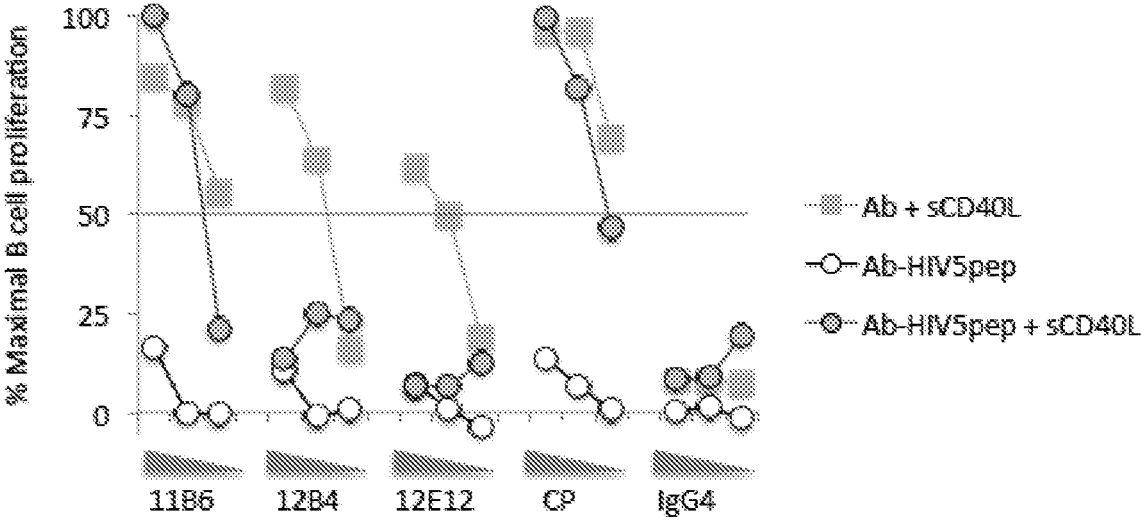
FIG. 5. Proliferative response of human B cells to a dose range of anti-CD40 HIV5pep antigen fusion proteins incubated with and without a constant low dose of soluble CD40L. Human PBMCs were incubated with human IL-4, human IL-21, and a dose range of the mAbs or fusion proteins (shown left to right: 10, 1, 0.1 nM), then the extent of proliferation was determined after 6 days by flow cytometry analysis of CFSE dilution. Curves with solid grey square symbols are response to parental hIgG4 antibody dose in the presence of 100 ng/ml (6 nM) soluble human CD40L, curves with empty circle symbols are responses to antibody-HIV5pep fusion protein doses, and curves with grey filled circle symbols symbols are response to doses of the antibody-HIV5pep fusion proteins in the presence of 100 ng/ml (6 nM) soluble human CD40L. Data represent a single experiment normalized for maximum proliferation (58%) versus baseline replication without antibody or sCD40L (range 6%) or without antibody but with sCD40L (12.5%). For reference the proliferative B cell responses elicited by these antibodies without fused antigen and with and without added sCD40L are shown replicated in FIG. 2.

The agonistic 11B6, 12B4, 12E12, and CP IgG4 mAbs became very weak agonists for eliciting B cell proliferation when the concatenated five HIV-1 long peptide regions interspersed with glycosylated flexible linkers were grafted to their H chain C-termini (FIG. 5). Addition of suboptimal levels of sCD40L restored the B cell proliferation potency of the 11B6-HIV5pep and CP-HIV5pep mAbs to the levels characteristic of the analogous 'naked' anti-CD40 11B6 and CP mAbs incubated with sCD40L, but had no significant effect on the 12B4-HIV5pep or 12E12-HIV5pep mAbs (FIG. 5).

Figure 6:
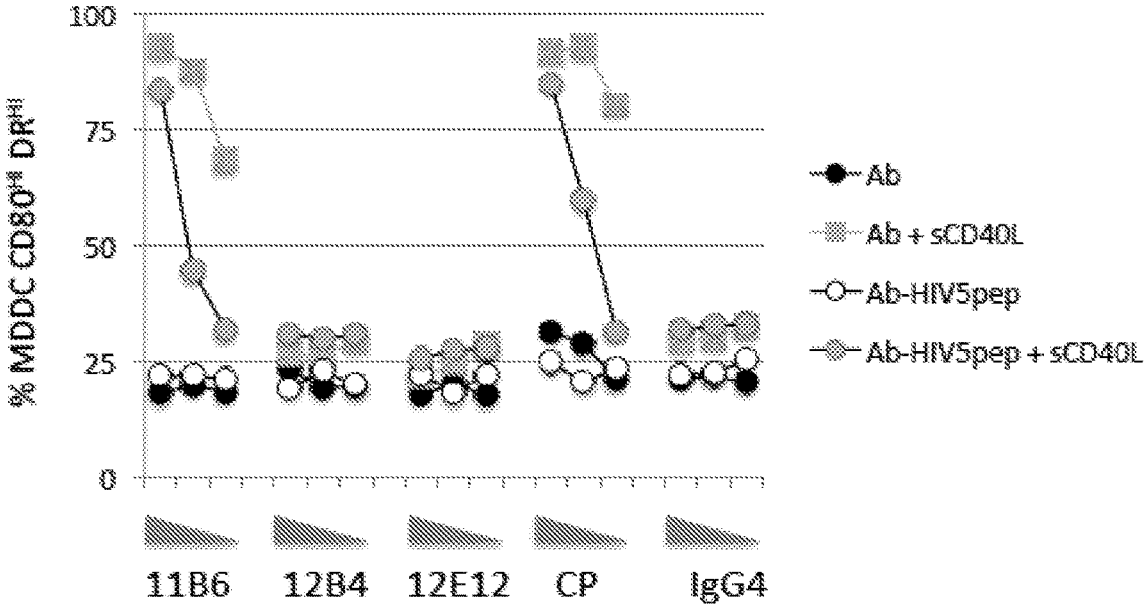
FIG. 6. Cell surface activation marker response of human MDDCs to a dose range of anti-CD40 IgG4 antibodies with and without fused HIV5pep antigens, and incubated with and without a constant low dose of soluble CD40L. Human MDDCs with a dose range (shown left to right: 10, 1, 0.1 nM) of each anti-CD40 mAb and anti-CD40.HIV5pep fusion protein antibody in the presence or absence of 100 ng/ml (6 nM) soluble human CD40L and the percentage of cells with high expression of CD86 and DR determined by flow cytometry. Curves with black filled circle symbols are responses to antibody alone, curves with filled grey square symbols are responses to antibody in the presence of soluble human CD40L, curves empty circle symbols are responses to antibody fused to HIV5pep alone, and curves with grey filled circle symbols are responses to antibodies fused to HIV5pep in the presence of soluble human CD40L. Data are from a single representative experiment.

These same four anti-CD40-HIV5pep fusion proteins were also of very low potency for up-regulation of activation markers on MDDCs, and a suboptimal level of sCD40L potentiated the activity of the 11B6-HIV5pep and CP-HIV5pep, but had no effect on the 12B4-HIV5pep or 12E12-HIV5pep fusion proteins (FIG. 6). However, the extent of sCD40L potentiation was ~5-10 fold less than that observed with the 11B6 and CP 'naked' mAbs (FIG. 6).

sCD40L Co-Operates with Anti-CD40.HIV5Pep to Expand Antigen-Specific Memory CD8$^+$ T Cells in PBMCs from HIV-1-Infected Individuals.

PBMC and DC-T cell co-culture systems are useful in vitro assays for validating DC-targeting prototype vaccine constructs, in particular for selecting the best receptor to target e.g., for cellular T cell response (Yin et al., 2016), as well as confirming the efficacy of the selected fused antigen for eliciting a broad range of T cell peptide specificities for both CD4$^+$ and CD8$^+$ T cell responses across a range of HLA types (Flamar et al., 2013). Based on such tests CD40-targeting is particularly attractive, however the potential contribution of activation of CD40 concomitant with the characteristic antigen internalization into the early endosome DC compartment has not been addressed (Chattergee et al., 2012; Yin et al., 2016).

We tested the efficiency of anti-CD40 mAbs fused to HIV5pep for HIV-1 antigen-specific T cell expansion in HIV-1$^+$ donor PBMC cultures with and without a low dose

US 12,576,147 B2

Figure 7:
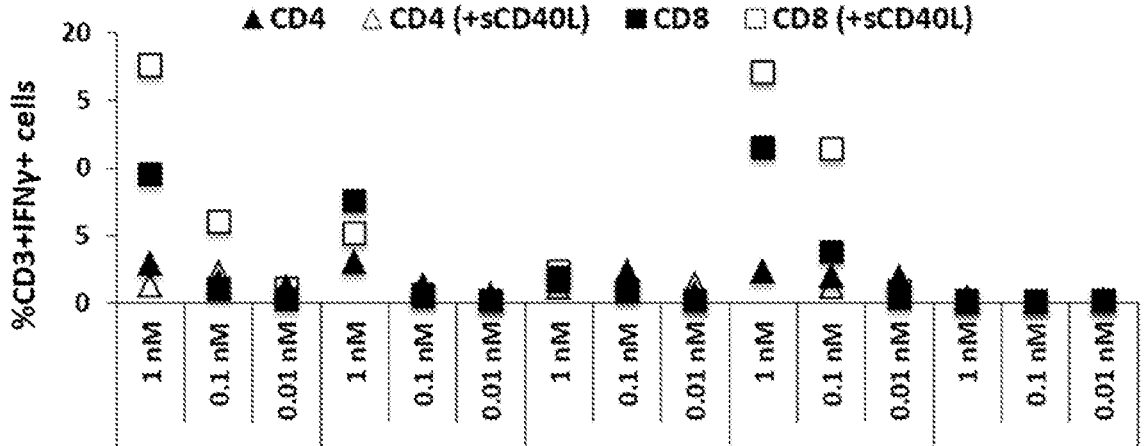
FIG. 7. Expansion by CD40-targeted HIV5pep of HIV-1-specific T cells in HIV-1-infected donor PBMC cultures incubated with and without sCD40. HIV-1+ donor PBMCs were cultured with a dose range of anti-CD40.HIV5pep fusion proteins (from left to right 1, 0.1, 0.01 nM) with and without a low dose of sCD40L (100 ng/ml; 6 nM) and IL-2 for 9 days, followed by stimulation with a pool of the five HIV-1 Gag, Nef, and Pol long peptides for 6 h with BFA, then analyzed by ICS. The data show the percentage at the end of the culture of antigen-specific CD8+ and CD4+ T cells producing IFNγ in response to peptide stimulation. The Y axis shows the percentage of IFNY+ CD3+CD4+ or CD3+ CD8+ cells.

53 54 of sCD40L. A striking augmentation of antigen-specific CTL expansion was observed via co-administration of suboptimal level of sCD40L with anti-CD40 11B6 and CP HIV5pep vaccines, but not with the anti-CD40 12E12 and 12B4 HIV5pep vaccines (FIG. 7).

CD40L Fused to Agonist Anti-CD40 Antibodies can Maximize CD40 Activation.

Synergistic cooperation between sCD40L and agonistic anti-CD40 mAbs may be a valuable property in vivo, e.g., via allowing the CD40L on activated T cells access to CD40 on DCs already occupied by the mAb. Alternatively, agonistic anti-CD40 mAb and sCD40L could be delivered simultaneously in vivo for possible therapeutic benefit via the enhanced CD40 activation observed in vitro.

Trimeric sCD40L has shown efficacy in preclinical studies (Stone et al., 2009) and may become available in the future for actual clinical validation of combining sCD40L with synergizing agonistic mAbs.

Here we explored the novel concept of physically associating sCD40L with agonistic mAb by direct fusion with an obvious potential benefit of establishing a single agent highly active agonist. For this purpose, the entire ectodomain of human CD40L was fused to the L chain C-termini of the anti-CD40 mAbs via a glycosylation-rich flexible linker sequence (called flex V1 or ASQTPTNTISVTPTNN-STPTNNSNPKPNPAS (SEQ ID NO: 15); Flamar et al., 2013). These 'bivalent' anti-CD40-CD40L mAbs were efficiently expressed in 293 and CHO cells as homogeneous secreted products (data not shown).

Figure 8:
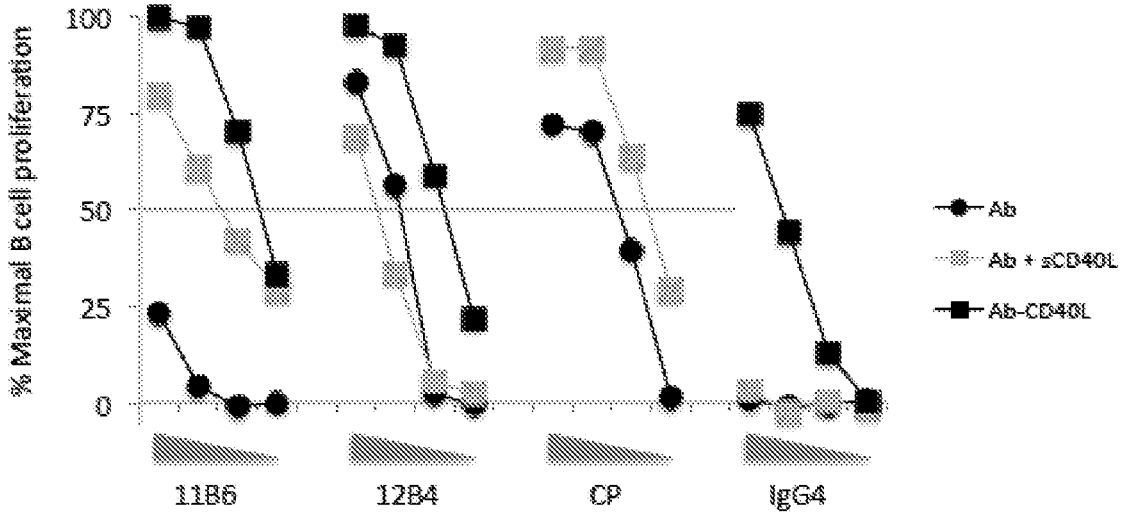
FIG. 8. Proliferative response of human B cells to a dose range of anti-CD40 hIgG4 mAbs with or without directly fused CD40L or incubated with a constant low dose of soluble CD40L. Human PBMCs were incubated with human IL-4, human IL-21, and a dose range of the mAbs or fusion proteins (shown left to right: 10, 1, 0.1, 0.01 nM), then the extent of proliferation was determined after 6 days by flow cytometry analysis of CFSE dilution. Curves with black filled circle symbols are response to hIgG4 antibody doses, curves with grey filled square symbols are responses to hIgG4 antibody doses in the presence of 100 ng/ml (6 nM) soluble human CD40L, and curves with black filled square symbols are response to doses of the hIgG4 antibodies with directly fused CD40L. Data represent a single experiment normalized for maximum proliferation (95%) versus baseline replication without antibody or sCD40L (10%) or without antibody but with sCD40L (44.5%).

Anti-CD40 IgG4 mAbs 11B6 and 12B4 fused to CD40L were tested relative to the non-fused mAbs for their efficacy in eliciting B cell proliferation. Both of these CD40L fused mAbs were highly potent in this assay, matching the efficacy of the highly potent CP mAb co-administered with suboptimal sCD40L (see FIG. 2). In both cases the CD40L adduct greatly increased the potency of the parent mAb (>1,000-fold for 11B6 and >100-fold for 12B4) and the increase for the 11B6 mAb was >10-fold more robust that when co-administered with sCD40L (FIG. 8). CD40L fused to the control IgG4 mAb was also active in inducing B cell proliferation, but ~10-fold less than the 11B6 and 12B4-CD40L fusion proteins (FIG. 8), highlighting the benefit of combining via direct linkage CD40L with anti-CD40 antibody binding.

Figure 9:
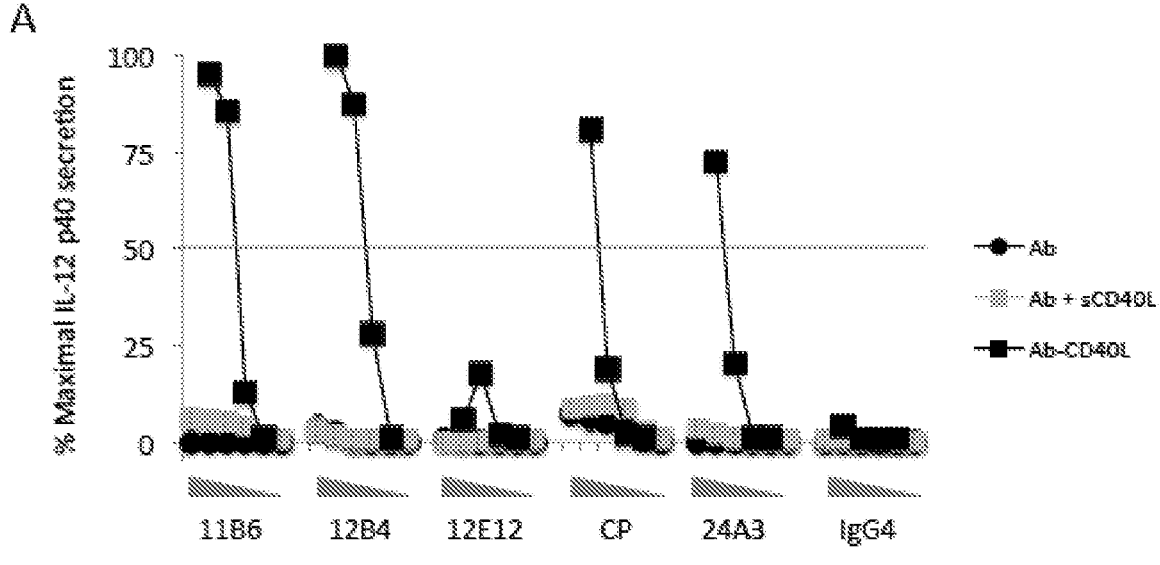
FIG. 9. Cytokine secretion responses of human MDDCs to a dose range of anti-CD40 IgG4 antibodies with and without directly fused human CD40L and incubated with or without a constant low dose of soluble CD40L. Human MCDCs were cultured with a dose range (shown left to right: 100, 10, 1, 0.1, 0.01, 0.001 nM) of each anti-CD40 mAb or control mAb and the extent of cytokine secretion determined after 2 days. Curves with black filled circle symbols are responses to antibody alone, curves with grey filled square square symbols are responses to antibody in the presence of 1 µg/ml (6 nM) soluble human CD40L, and curves with black filled square symbols are responses to antibodies directly fused to human CD40L. Data represent a single experiment normalized relative to the maximum secretion of each cytokine tested. For the left hand panels the maximal values were: IL-6, 469 ng/ml; IL-12p40, 561 ng/ml; IL-15, 62 ng/ml). For the right hand panels the maximal values were: IL-6, 6192 ng/ml; IL-12p40, 5776 ng/ml; IL-15, 194 ng/ml). Note that the data for Ab and Ab+sCD40 L is identical to that represented in FIG. 3.
Figure 9:
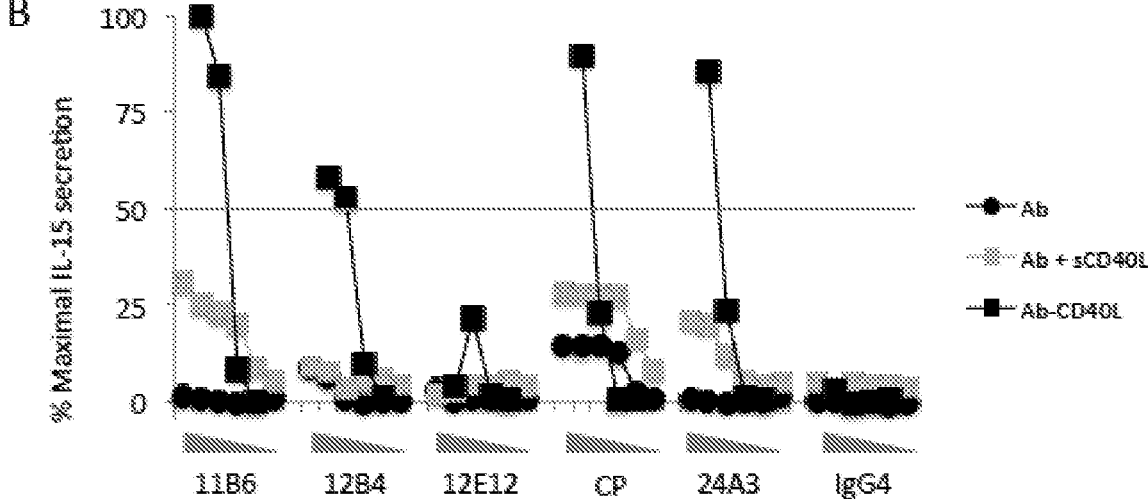

A full panel of anti-CD40 IgG4 mAbs fused to CD40L was tested relative to the non-fused mAbs for their efficacy in eliciting DC activation. Remarkably, directly linking CD40L to all the mAbs except 12E12 dramatically increased their efficacy (i.e., the maximal response) compared to the synergy observed with adding unlinked sCD40L to the 11B6, CP, and 24A3 mAbs (FIG. 9). Furthermore, consistent with the B cell proliferation assay mAb 12B4, which competes directly with CD40L for CD40 occupancy, also benefited greatly from CD40L fusion (FIG. 9). Note that hCD40L directly fused to a control (non-DC binding) IgG4 had only minimal activity on MDDCs, suggesting that the CD40L-antiCD40 mAb fusion approach is preferentially efficacious for DC activation.

Directly Linking CD40L to Agonistic Anti-CD40 mAb 11B6 Increases Affinity and Activation Efficacy.

We used SPR analysis to probe the impact upon the CD40 binding kinetics of anti-CD40 11B6 and anti-CD40 12E12 mAbs of CD40L fused to their L chain C-termini by immobilizing them onto a protein A/G surface and flowing soluble human CD40 ectodomain over them in the liquid phase. The CD40L adduct on the anti-CD40 12E12 mAb did not significantly alter the antibody on- or off-rates compared to the parental anti-CD40 12E12 mAb (data not shown). This was expected since the anti-CD40 12E12 mAb competes for the CD40L binding site on CD40, and a human IgG4 control mAb with CD40L fused in a similar manner to the L chain showed no detectable binding to CD40 in this format (data not shown). In contrast, the CD40L adduct on the anti-CD40 11B6 mAb significantly altered the antibody off-rate compared to the parental anti-CD40 11b6 mAb (data not shown). Specifically, while the on-rate was marginally impacted, the off-rate decreased by ~15-fold, indicating cooperatively between the anti-CD40 mAb and CD40L in binding to CD40.

Agonistic Properties of Anti-CD40 mAbs Dulled by Antigen Fusion can be Restored Via Direct Fusion of CD40L to their Light Chain C-Termini.

Figure 10A:
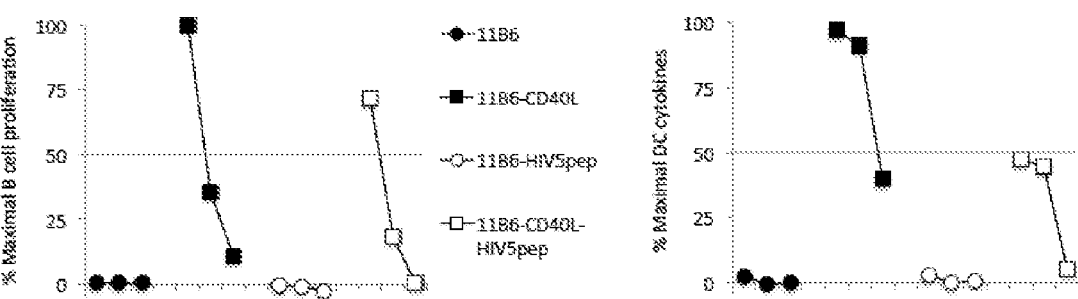
FIG. 10A. Responses of human B cells and MDDCs to a dose range of anti-CD40 11B6 mAbs fused either at the H chain C-terminus to HIV5pep antigen and/or with human CD40L fused to the L chain C-terminus. Human PBMCs or MDDCs were incubated with a dose range (shown left to right: 10, 1, 0.1 nM) of each IgG4 mAb and the extent of B cell proliferation (left panel) or MDDC cytokine secretion (right panel) was determined. These are the results of single experiments where the maximal extent of B cell proliferation was 31% with a 4% baseline, while the cytokine production data are averages of percentage maximal production for IL-6 (610 pg/ml), IL-15 (2,250 pg/ml), TNFα (27,500 pg/ml), IL-12 p40 (9,900 pg/ml), and IL-12 p70 (3,300 pg/ml) within the experiment.
Figure 10B:
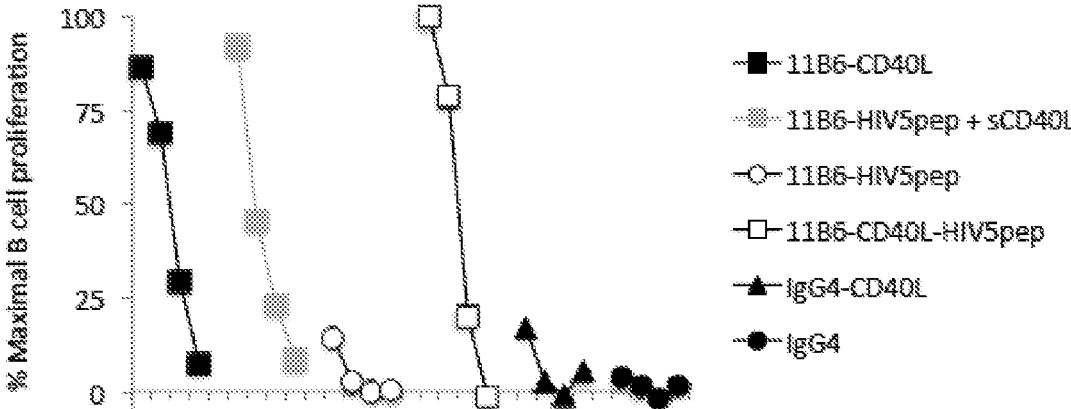
FIG. 10B. Proliferative response of human B cells to dose range of antibodies or antibody fusion proteins. Human PBMCs were incubated with human IL-4, human IL-21, and a dose range (left to right, 10, 1, 0.1, 0.01 nM) and the extent of proliferation was determined after 6 days by flow cytometric analysis of CFSE dilution. Curves are response to antibody dose. Data represent average values for two donors each normalized for maximum proliferation (31% and 28% of the B cell replicated in response to the maximal signal, while baseline cells only values were 3.5% and 3.6%). 11B6-HIV5pep+sCD40L titration series was 11B6-HIV5pep supplemented with a constant dose of 1 µg/ml (60 nM) soluble CD40L.

Agonistic properties of anti-CD40 mAbs can be reduced or eliminated via fusion to some antigens. For example, the HIV5pep antigens fused to the H chain C-termini greatly reduce agonistic properties when carried by 11B6, 12B4, or 12E12 mAb vehicles, but co-administered sCD40L potentiates the activity of the anti-CD40 11B6 HIV5pep fusion protein (FIGS. 5 and 6). In a similar manner, fusion of CD40L to the L chain of the anti-CD40 11B6-HIV5pep protein also potentiates activity for B cell proliferation and MDDC cytokine production (FIG. 10A). FIG. 10B shows that anti-CD40 11B6 bearing the HIV5pep antigens at the H chain C-terminus (11B6-HIV5pep in FIG. 12) has minimal efficacy for CD40 activation as determined by the B cell proliferation assay. However, addition of a low dose of sCD40L (11B6-HIV5pep+sCD40L) or fusion of human CD40L to the L chain C-terminus (11B6-CD40L-HIV5pep) results in highly potent CD40 activation, to a greater extent that can be achieved by the CP-870,893 IgG4 antibody.

| Antibody (hIgG4) | 11B6-CD40L | 11B6-HIV5 pep + sCD40L | 11B6-HIV5pep | 11B6-CD40L HIV5pep | IgG4-CD40L |
|---|---|---|---|---|---|
| EC$_{50}$ (nM) B cell | >0.1 <1 | >1 <10 | >10 | >0.1 <1 | >10 |

Table for FIG. 10-B. Limits for the efficacious dose for 50% of maximum B cell proliferation (EC$_{50}$) are given as nanomolar values (nM).

Anti-CD40 11B6 mAb Directly Fused to CD40L is a Superior Agonist Compared to a Highly Active Dimer-Trimer Form of Soluble CD40L.

Figure 10C:
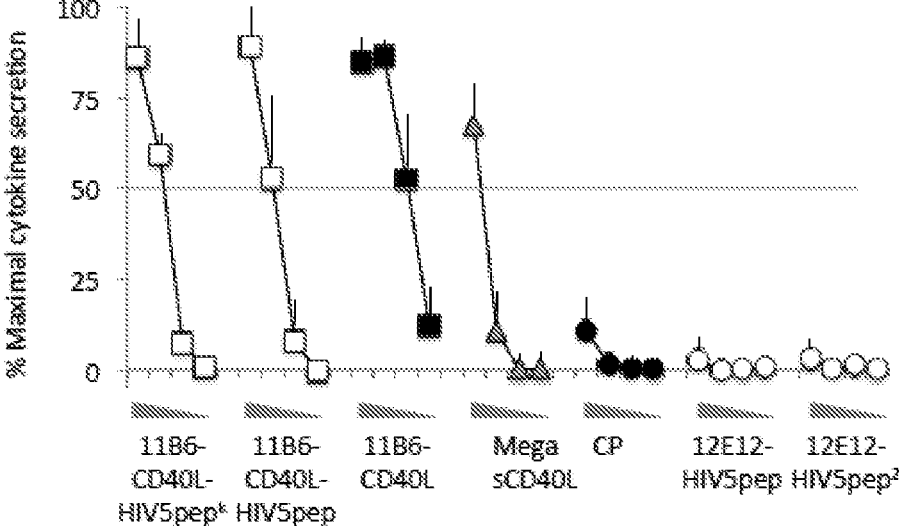
FIG. 10C. Responses of human MDDCs to a dose range of Mega sCD40L and anti-CD40 11B6-CD40L mAbs with and without HIV5pep antigen fused to the H chain C-termini. Human MDDCs were incubated with a dose range (shown left to right: 10, 1, 0.1, 0.01 nM) of each IgG4 mAb or Mega sCD40L and the extent of cytokine secretion was determined at 24 h The results presented are averaged data over three experiments using two different donors where the maximal extent of cytokine production was normalized to the maximal signal and then averaged for IL-12 p40, TNFα, and IL-15 secretion. The averaged maximal production values were IL-12 p40 (14,236 pg/ml), TNFα (37,145 pg/ml), and IL-15 (295 pg/ml). The error bars are standard deviation of the mean. 11B6-CD40L-HIV5pep carries the 5 concatenated HIV-1 antigen regions on the IgG4 H chain termini as previously described (Flamar et al., 2013) while 11B6-CD40L-HIV5pep[k] has two of the five antigen regions on one H chain and three on the other H chain using knob-in-hole technology (Flamar et al., 2018; Ridgway et al., 1996).

MEGACD40L® (Mega sCD40L) is a widely used (Kornbluth et al., 2012) high activity protein in which two trimeric CD40 ligand molecules are artificially linked via the collagen domain of Adiponectin/ACRP30/AdipoQ (see Miconnet and Pantaleo, Vaccine 2008). FIG. 10C shows responses of human MDDCs to a dose range of Mega sCD40L and anti-CD40 11B6-CD40L mAbs with and without HIV5pep antigen fused to the H chain C-terminus. Anti-CD40 11B6-CD40L was ≈100-fold more active than Mega sCD40L for eliciting cytokine secretion in this assay, as well as ≈100-fold more active than Mega sCD40L co-administered with 10 nM anti-CD40 11B6, indicating that physical linkage of anti-CD40 11B6 with CD40L was essential for this very high activity. Importantly, anti-CD40 11B6-CD40L linked to the HIV5pep antigens via the H chain C-terminus was also ≈10-fold more active than Mega sCD40L.

| Antibody (hIgG4) | 11B6-CD40L-HIV5pep[k] | 11B6-CD40L-HIV5pep | Mega sCD40L | 11B6-CD40L |
|---|---|---|---|---|
| EC$_{50}$ (nM) IL-12 p40 | >0.1 ≤1 | >0.1 ≤1 | >1 <10 | >0.01 ≤0.1 |

-continued

| Antibody (hIgG4) | 11B6-CD40L-HIV5pep$^k$ | 11B6-CD40L-HIV5pep | Mega sCD40L | 11B6-CD40L |
|---|---|---|---|---|
| EC$_{50}$/11B6-CD40L | ≅10 | ≅10 | ~100 | 1 |
| EC$_{50}$ (nM)TNFα | >0.1 ≤1 | >0.1 ≤1 | >1 <10 | >0.01 ≤0.1 |
| EC$_{50}$/11B6-CD40L | ≈10 | ≅10 | ~100 | 1 |
| EC$_{50}$ (nM) IL-15 | >0.1 ≤1 | >0.1 ≤1 | ≥1 ≤10 | >0.01 ≤0.1 |
| EC$_{50}$/11B6-CD40L | ≈10 | ≅10 | ~100 | 1 |

Table for FIG. 10C. Limits for the efficacious dose for 50% of maximum cytokine secretion (EC$_{50}$) are given as nanomolar values (nM).

Figure 11:
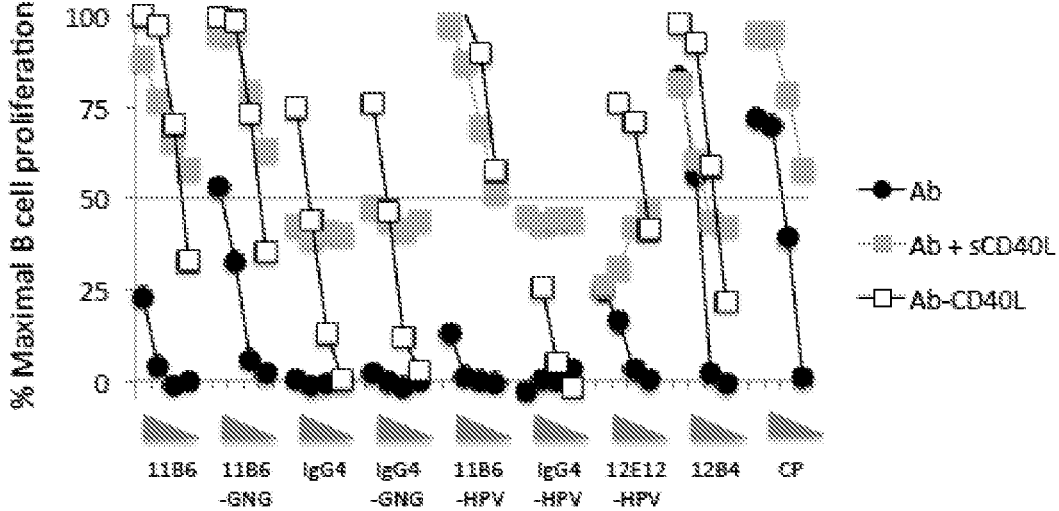
FIG. 11. Proliferative response of human B cells to a dose range of anti-CD40 or control antibodies fused at the H chain C-terminus to HIV-1 Gag p24, Nef, and Gag p17 or HPV16 E6/E7 antigens with and without human CD40L fused to the L chain C-terminus or co-cultured with a constant low dose of soluble CD40L. Human PBMCs were incubated with human IL-4, human IL-21, and a dose range (shown left to right: 10, 1, 0.1, 0.01 nM) and the extent of proliferation was determined after 6 days by flow cytometric analysis of CFSE dilution. Curves with black filled circle symbols are responses to dose of the indicated antibody or antibody-antigen fusion protein, curves with grey filled square symbols are responses doses to of the indicated antibody or antibody-antigen fusion protein in the presence of 1 µg/ml (60 nM) soluble human CD40L, and curves with empty square symbols are responses to doses of the antibody-CD40L or antibody-CD40L-antigen fusion proteins. Data represent a single experiment normalized for maximum proliferation (95%) versus baseline proliferation without antibody (10%).

To test if CD40L fusion to agonistic anti-CD40 mAb L chain C-termini could also increase their agonist potency while fused to other antigens, we compared their agonistic activities when fused at their H chain C-termini to concatenated HIV-1 Gag p24 Nef Gag p17 (called GNG) or HPV 16 E6/E7 (called HPV) antigens with or without CD40L directly fused to the L chain. These two antigens did not significantly dull the low potency of B cell CD40 activation of the parent 11B6 mAb, but CD40L L chain fusion potentiated the activation to levels equal to co-administered sCD40 (FIG. 11). The 11B6 mAb fused to GNG at the H chain C-termini and CD40L at the L chain C-termini was equipotent for MDDC activation compared to the 11B6-CD40L mAb without fused antigen, and both 11B6 and 11B8-GNG synergized strongly with sCD40L), while 11B6-CD40L-GNG was equal in potency to 11B6-GNG+sCD40 (FIG. 11). These data were similar for 11B6 fused to the HPV antigens in that CD40L fused to the L chain restored the full agonist activity seen with 11B6-HPV+sCD40 (FIG. 11). These 11B6-CD40L-antigen fusions were equipotent to strong agonist activities observed with the 12B4-CD40L mAb, as well as the CD mAb+sCD40L. Interestingly the 12E12-HPV mAb interferes with sCD40L action, but the anti-CD40 12E12-CD40L-HPV mAb format restored strong agonist activity (FIG. 11).

Figure 12:
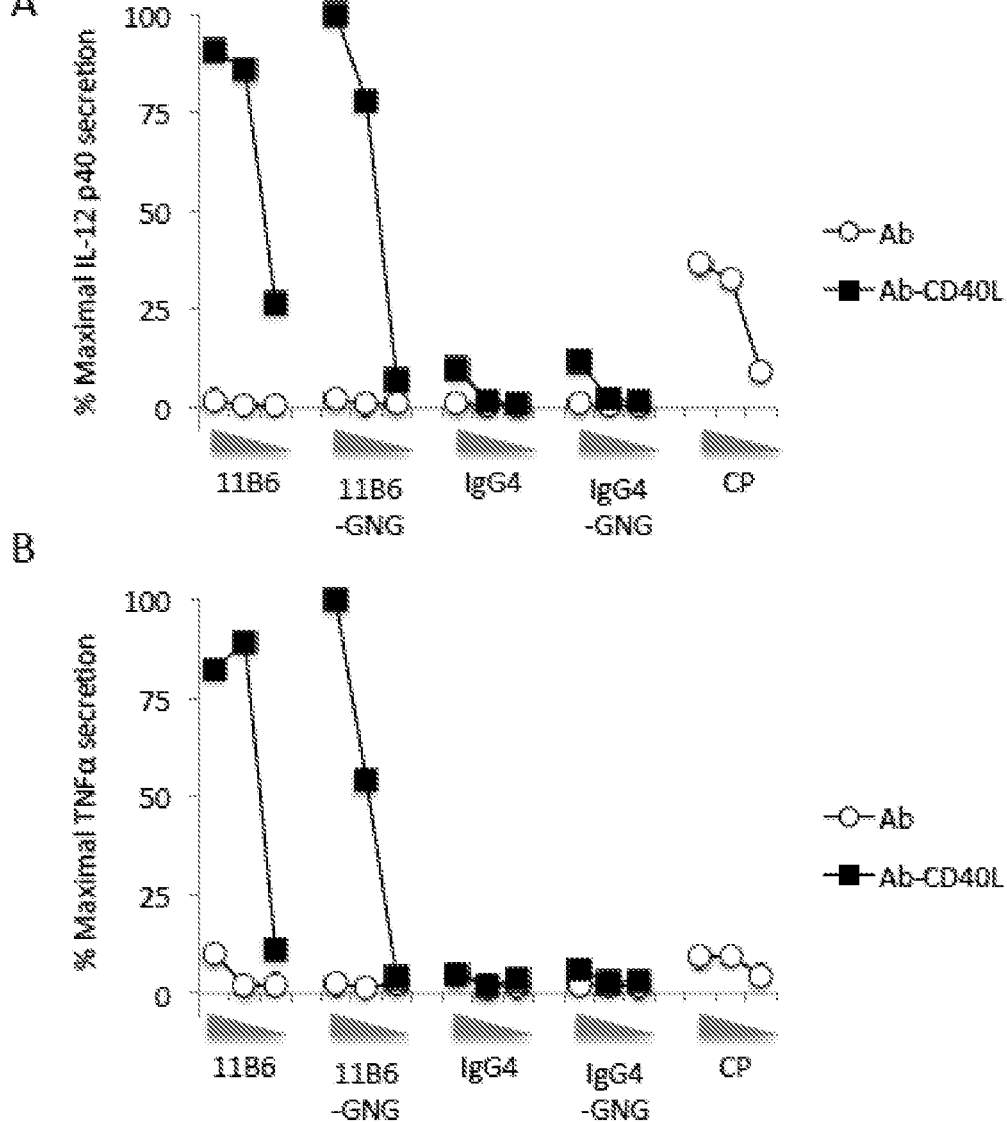
FIG. 12. Cytokine secretion responses of human MDDCs to a dose range of anti-CD40 or anti-CD40-GNG fusion antibodies with and without directly fused human CD40L. Human MCDCs were cultured with a dose range (shown left to right: 10, 1, 0.1 nM) of each mAb and the extent of cytokine secretion was determined after 2 days. Curves with open circle symbols are dose responses to antibody or antibody-antigen fusion proteins, curves with black filled square symbols are dose responses to antibodies or antibody-antigen fusion proteins directly fused to human CD40L. Data represent a single experiment normalized relative to the maximum secretion of each cytokine tested. The maximal values were: IL-10, 30 ng/ml; IL-12p40, 359 ng/ml; IL-15, 36 ng/ml, TNFα, 6134 ng/ml).

The full 'high' agonist activity observed on B cell proliferation with the anti-CD40 11B6-CD40L-GNG protein was recapitulated by the high cytokine secretion responses of MDDCs to 11B6-CD40L-GNG in contrast to very weak agonist activity of 11B6-GNG (FIG. 12). Note that the efficacy of the 11B6-CD40L molecules is strikingly higher than the standard full agonist anti-CD40 CP IgG4 antibody. Anti-CD40.Gag p17-Nef-Gag p24 Vaccine Directly Linked to CD40L Increases Specific Memory CD8$^+$ T Cell Responses In Vitro.

Figure 13:
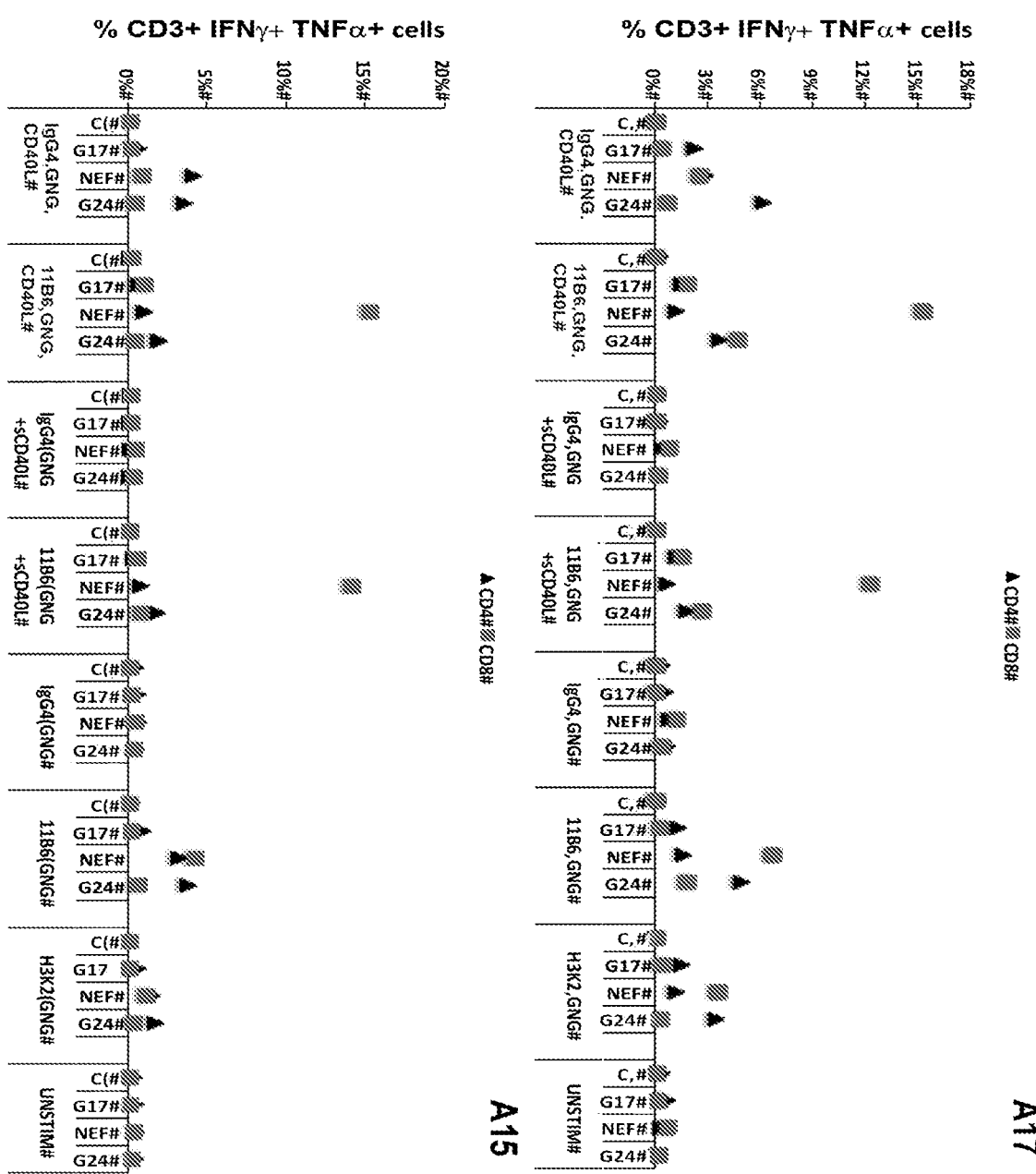
FIG. 13. CD40-targeted Gag p17-Nef-Gag p24 with and without soluble CD40L or fused CD40L expansion of HIV-1-specific T cells in HIV-1-infected donor PBMC cultures. HIV-1[+] donor PBMCs were cultured for 9 days with IL-2 and anti-CD40-GNG and control IgG4-GNG fusion proteins (0.1 nM) with and without soluble CD40L (0.1 nM) or directly linked CD40L, followed by stimulation with Gag and Nef overlapping peptides for 6 h with BFA, then analyzed by ICS. The upper panel shows data for donor A17, the lower is the data for donor A15.

To test directly if the improved agonist properties of anti-CD40 11B6-GNG mAb with linked CD40L impacted the efficacy of HIV-1-specific T cell expansion, HIV-1-infected donor PBMCs were incubated with a low doses of anti-CD40 11B6-GNG-CD40L and various control GNG fusion mAbs for 9 days with IL-2 feeding followed by stimulation with pools of peptides from Gag p17, Gag p24, and Nef. In both donors the 11B6-GNG mAbs with directly linked CD40L or co-administered sCD40L elicited strikingly superior Nef-specific CD8$^+$ T cell responses (FIG. 13).

Figure 14:
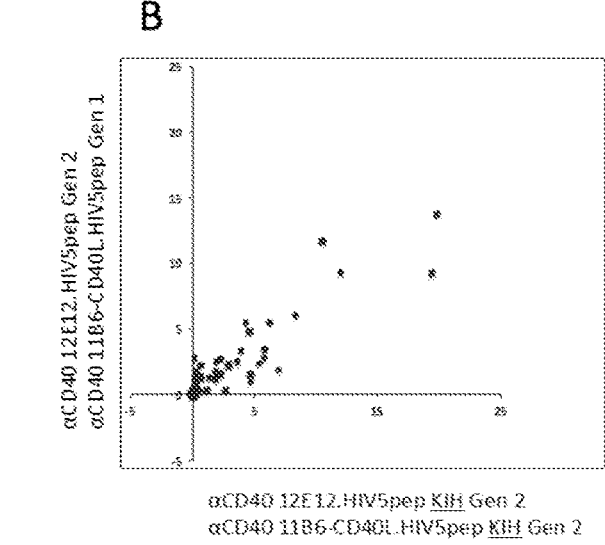
FIG. 14. CD40-targeted HIV5pep antigens with fused CD40L preferentially expand HIV-1-specific CD8[+] T cell responses in HIV-1-infected donor PBMC cultures. HIV-1[+] donor PBMCs were cultured for 9 days with IL-2 and anti-CD40 HIV5pep fusion proteins (1 nM; 2 nM for KIH proteins), followed by stimulation with long peptides specific for each of the five HIV-1 gag, nef, and pol regions for 6 h with BFA, then analyzed by ICS. This combined data from an experiment with each of the four indicated proteins tested on four donors. A. Each point represents the % value for IFNγ[+] TNFα[+] HIV5pep-specific CD8[+] (squares) or CD4[+] (diamonds) T cells for each response specific to each long peptide elicited in each donor comparing αCD40 11B6-CD40L.HIV5pep KIH Gen 2 and to αCD40 11B6-CD40L.HIV5pep Gen 1 (X axis) to αCD40 12E12.HIV5pep KIH Gen 2 (X axis) and αCD40 12E12.HIV5pep Gen 2 (Y axis). High values for a nef66 response in one donor are not shown (58,44 versus 35,44). B. A comparison of HIV5pep KIH constructs versus non-KIH constructs showed no significant differences in HIV5pep-specific CD4[+] or CD8[+] T cell responses.
Figure 15:
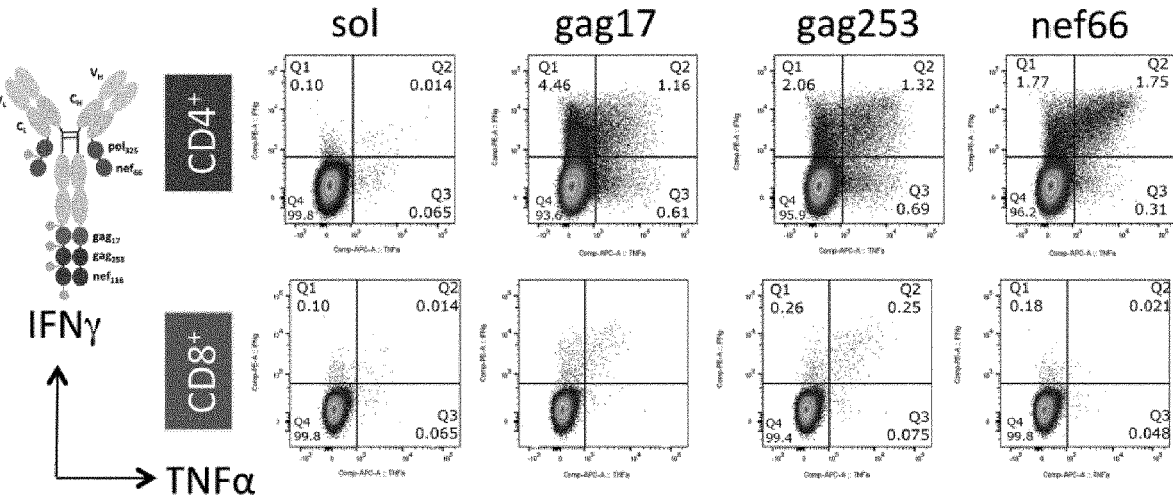
FIG. 15. CD40-targeted HIV5pep antigens with and without fused CD40L tested via in vitro expansion of HIV-1-specific T cells in HIV-1-infected donor PBMC cultures. HIV-1[+] donor patient 1 PBMCs were cultured for 9 days with IL-2 and anti-CD40 HIV5pep fusion proteins (1 nM), followed by stimulation with long peptides specific for each of the five HIV-1 gag, nef, and pol regions for 6 h with BFA, then analyzed by intracellular cytokine staining (ICS). This is ICS data from an experiment with two of the four indicated proteins tested on one of the donors shown in FIG. 14. PSApep and sol indicate, respectively, non-relevant peptide and solvent negative controls and PMA represents polyclonal stimulation by Phorbol 12-Myristate 13-Acetate and Ionomycin. For each ICS panel the Y axis shows INFY staining intensity, the X axis shows TNFα staining intensity.

To test directly if the improved agonist properties of anti-CD40 11B6-HIV5pep mAbs with linked CD40L impacted the efficacy of HIV-1-specific T cell expansion, HIV-1-infected donor PBMCs were incubated with a low doses of anti-CD40 11B6-GNG-CD40L and various control GNG fusion mAbs for 9 days with IL-2 feeding followed by stimulation with individual long peptides corresponding to the five Gag p17, Gag p24, Nef, and Pol epitope components of HIV5pep. The general trend for elicited HIV-1 peptide-specific T cell responses was that the 11B6-HIV5pep mAbs with directly linked CD40L elicited superior HIV-1-specific CD8$^+$ T cell responses and lesser HIV-1-specific CD4$^+$ T cell responses (FIG. 14).

The in vitro culture system combining anti-CD40 DC targeting vaccine with sCD40L has potential value for enhancing yields of e.g., ex vivo expanded CTL for cellular therapy applications. However, as an in vivo vaccine strategy this is constrained by the need to co-administer two different protein agents associated with potentially complex dosing/pharmacokinetic, GMP production, and licensing issues. The novel bivalent antibody format of directly linking CD40L to anti-CD40 DC-targeting mAbs solves this issue.

Expansion by CD40-Targeted GNG Antigen of HIV-1-Specific T Cells in HIV-1-Infected Donor PBMC Cultures.

Figure 26:
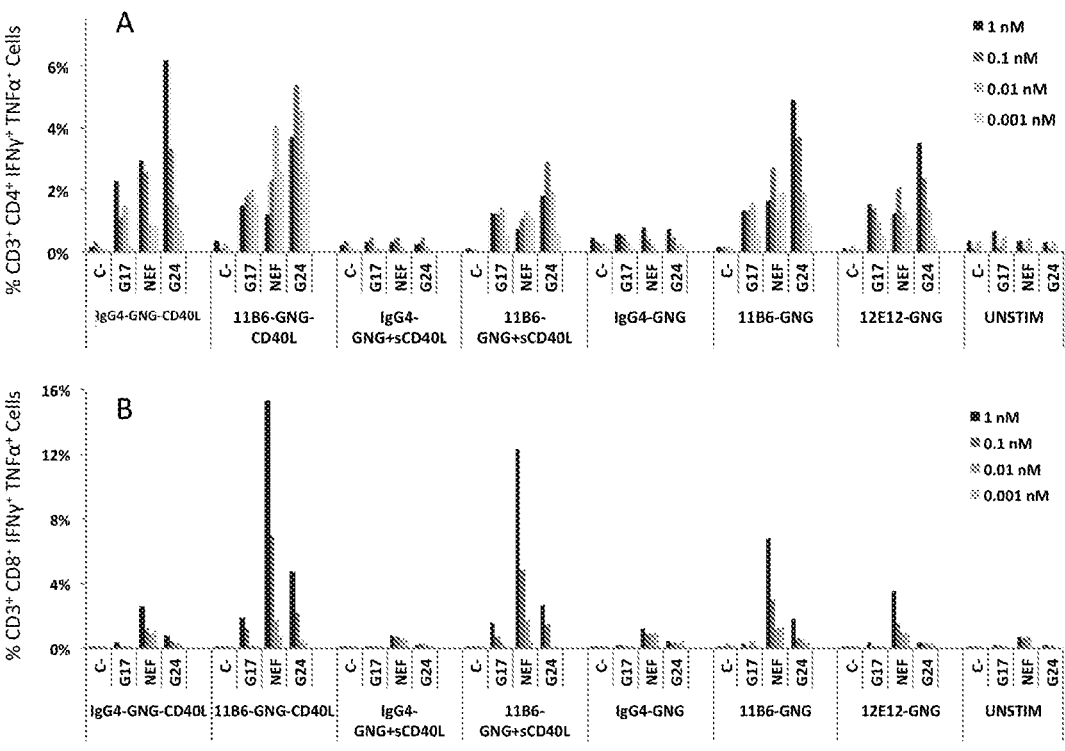
FIG. 26. Expansion by CD40-targeted GNG antigen of HIV-1-specific T cells in HIV-1-infected donor PBMC cultures. HIV-1+ donor PBMCs were cultured with a dose range of anti-CD40-GNG fusion proteins (from left to right 1, 0.1, 0.01 nM) with and without a low dose of sCD40L (100 ng/ml; 6 nM) and IL-2 for 9 days, followed by stimulation with a pools HIV-1 Gag p17, Nef, and Gag p24 peptides for 6 h, then analyzed by ICS. The data show the percentage at the end of the culture of antigen-specific (A) CD4+ and (B) CD8+ T cells producing IFNγ+TNFα in response to peptide stimulation FIG. 27. Expansion by CD40-targeted GNG antigen of HIV-1-specific T cells in HIV-1-infected donor PBMC cultures. HIV-1+ donor PBMCs were cultured with a dose range of anti-CD40-GNG fusion proteins (from left to right 1, 0.1, 0.01 nM) with and without a low dose of sCD40L (100 ng/ml; 6 nM) and IL-2 for 9 days, followed by stimulation with a pools HIV-1 Gag p17, Nef, and Gag p24 peptides for 6 h, then analyzed by ICS. The data show the percentage at the end of the culture of antigen-specific (A) CD4+ and (B) CD8+ T cells producing IFNγ+TNFα in response to peptide stimulation. Panels C and D show, respectively, antigen-specific CD4+ and CD8+ T cell collated responses from three patients to the three highest doses were added across all three peptide regions tested and normalized to the highest response for each patient, then averaged. The indicated significant differences were based on unpaired tests with Welch's corrections.
Figure 27:
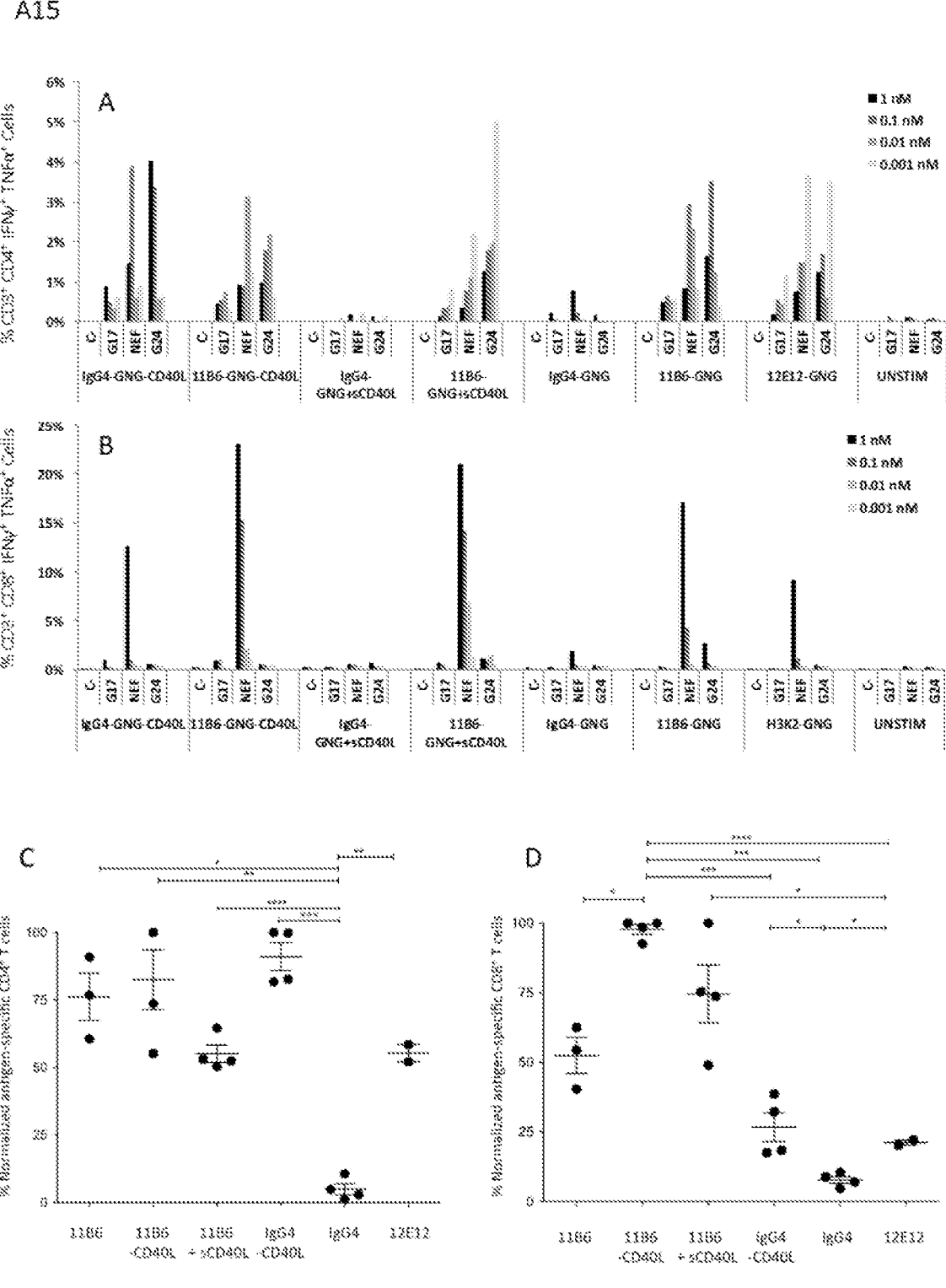

HIV-1$^+$ donor PBMCs were cultured with a dose range of anti-CD40-GNG fusion proteins (from left to right 1, 0.1, 0.01 nM) with and without a low dose of sCD40L (100 ng/ml; 6 nM) and IL-2 for 9 days, followed by stimulation with a pools HIV-1 Gag p17, Nef, and Gag p24 peptides for 6 h, then analyzed by ICS. The data show the percentage at the end of the culture of antigen-specific (A) CD4$^+$ and (B) CD8$^+$ T cells producing IFNγ+TNFα in response to peptide stimulation (see FIG. 26). Similar data was observed using PBMCs from two other donors (FIG. 27).

Figure 28:
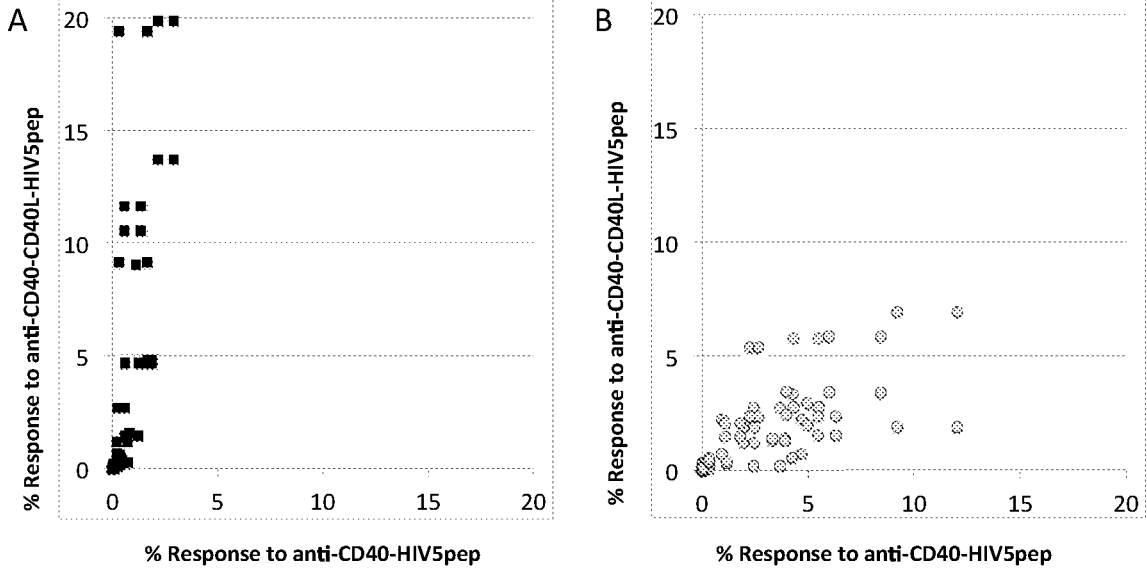
FIG. 28. Anti-CD40-CD40L targeted HIV5pep antigens preferentially expand many HIV-1-specific CD8+ T cell responses in HIV-1-infected donor PBMC cultures. HIV-1+ donor PBMCs were cultured for 9 days with IL-2 and anti-CD40 HIV5pep fusion proteins (1 nM; 2 nM for KIH proteins), followed by stimulation with long peptides specific for each of the five HIV-1 gag, nef, and pol regions for 6 h with BFA, then analyzed by ICS. This is collated data from experiments with each of the indicated protein pairs tested on four donors. Each point represents the % value for IFNγ++TNFα+ HIV5pep-specific CD8+ (panel A, black filled squares) or CD4+ (panel B, open grey circles) T cells for each response specific to each long peptide elicited in each donor comparing anti-CD40 11B6-CD40L-HIV5pep KIH Gen 2 and anti-CD40 11B6-CD40L-HIV5pep Gen 1 (Y axis) to anti-CD40 12E12-HIV5pep KIH Gen 2 and anti-CD40 12E12-HIV5pep Gen 2 (X axis). Panel A highlights the responses that were ≤20% of the expanded culture and excludes the potent patient 2 response to the nef66 peptide (38±7% elicited by anti-CD40 11B6-CD40L-HIV5pep vaccines versus 48±10% elicited by anti-CD40-HIV5pep vaccines. Panel B shows the whole dataset.

Anti-CD40-CD40L Targeted HIV5Pep Antigens Preferentially Expand Many HIV-1-Specific CD8$^+$ T Cell Responses in HIV-1-Infected Donor PBMC Cultures HIV-1$^+$ donor PBMCs were cultured for 9 days with IL-2 and anti-CD40 HIV5pep fusion proteins (1 nM; 2 nM for KIH proteins), followed by stimulation with long peptides specific for each of the five HIV-1 gag, nef, and pol regions for 6 h with BFA, then analyzed by ICS. FIG. 28 shows collated data from experiments with each of the indicated protein pairs tested on four donors. Each point represents the % value for IFNγ$^+$+TNFα$^+$ HIV5pep-specific CD8$^+$ (panel A, black filled squares) or CD4$^+$ (panel B, open grey circles) T cells for each response specific to each long peptide elicited in each donor comparing anti-CD40 11B6-CD40L-HIV5pep KIH Gen 2 and anti-CD40 11B6-CD40L-HIV5pep Gen 1 (Y axis) to anti-CD40 12E12-HIV5pep KIH Gen 2 and anti-CD40 12E12-HIV5pep Gen 2 (X axis). Panel A highlights the responses that were ≤20% of the expanded culture and excludes the potent patient 2 response to the nef66 peptide (38±7% elicited by anti-CD40 11B6-CD40L-HIV5pep vaccines versus 48±10% elicited by anti-CD40-HIV5pep vaccines. Panel B shows the whole dataset.

Fusion of CD40L to Anti-CD40 11B6 Augments Adjuvant-Free Antibody Response in an In Vivo Mouse Model.

Figure 16:
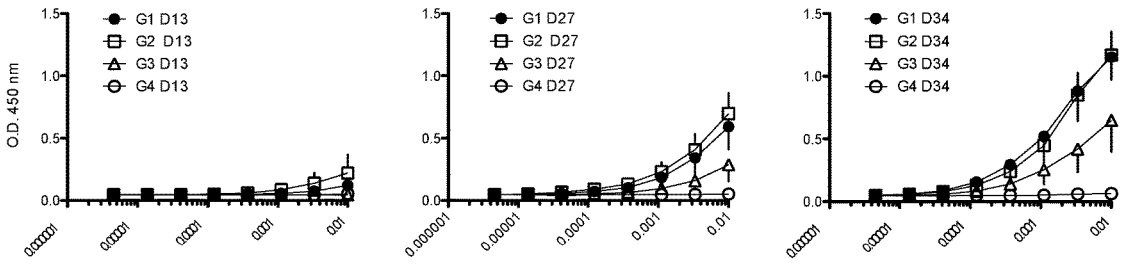
FIG. 16. CD40-targeted HIV-1 gp140 antigen with and without fused CD40L elicit gp140-specific serum IgG responses in human CD40 transgenic mice. Taconic CD40 homozygous transgenic mice (strain 12692) were vaccinated via intraperitoneal injection with (Group 1, G1) anti-CD40 11B6-CD40L directly fused to HIV-1 gp140, (Group 2, G2) anti-CD4011B6-CD40L-dockerin complexed with cohesin-gp140, (Group 3, G3) anti-CD4011B6-dockerin complexed with cohesin gp140, or (Group 4, G4) cohesin gp140. Dose was normalized to be the molar equivalent of 1 g of the Group 2 vaccine, except for the non-targeting control Group 3 (2 µg or ≅3 molar equivalents). Vaccination was at Day 1, Day 14, and Day 21 with small blood draws taken at Day 13 (D13), Day 27 (D27) and Day 34 (D34). The graphs show serial dilutions of sera analyzed for anti-gp140 IgG reactivity by ELISA as described in Zurawski et al., 2016 except that anti-mouse IG-HRP reagent was the detecting reagent. Group sizes were G1, n=3 and G2-4, n=4). Directional error bars are S.E. of the mean.

To test the potential of combining CD40L fusion to anti-CD40 11B6 antibody for increasing vaccine efficacy, human CD40 transgenic mice were vaccinated with anti-CD40 11B6 delivery vehicles coupled to HIV-1 Env gp140, with and without the CD40L light chain fusion. Vaccination with anti-CD40 11B6-CD40L directly fused to gp140 was compared to vaccination with anti-CD40 11B6-CD40L non-covalently coupled to a cohesion-gp140 fusion protein, to anti-CD40 11B6 non-covalently coupled to a cohesion-gp140 fusion protein, and to non-CD40 targeted cohesin-gp140. Both anti-CD40 11B6-CD40L non-covalently coupled to cohesion-gp140 fusion protein and anti-CD40 11B6-CD40L directly fused to gp140 elicited serum anti-gp140 IgG titers that were detected as early as 1 week after a single vaccination, and both vaccines increase responses to similar extents after subsequent two vaccinations (FIG. 16). Vaccination with anti-CD40 11B6 non-covalently linked to cohesin-gp140 elicited serum anti-gp140 IgG titers that were detected only after a second vaccination, and responses increased further after the third vaccination, but the titers were significantly reduced compared to the two anti-CD40. 11B6-CD40L-based vaccines. Non-targeted cohesin-gp140 failed to elicit any detectable anti-gp140 IgG responses even after three vaccinations using a three-fold molar excess of gp140 compared to the CD40-targeting vaccines. These results should be considered in the context of results in the non-human primate model, where anti-CD40 12E12-gp140 vaccinations elicited only modest anti-gp140 IgG responses compared to the same vaccine co-administered with the adjuvant poly IC (Zurawski et al., 2016). The mouse data suggest the likelihood that CD40L linked to the anti-CD40 11B6-gp140 construct confers 'adjuvant-like' property to this protein vaccine.

Anti-CD40 11B6-CD40L Elicits Potent Activation of CD40 in an In Vivo Mouse Model.

Figure 17:
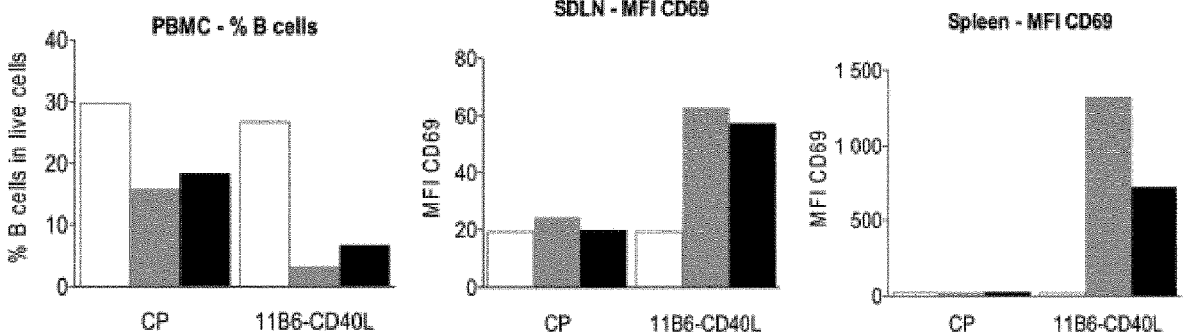
FIG. 17. Effects of anti-CD40 CP and anti-CD40 11B6-CD40L on B cells in human CD40 transgenic mice. CP-870, 893 hIgG4 (CP) and anti-CD40 11B6-CD40L (11B6-CD40L) were administered to mice. Wild type (WT, white bars) or human CD40 BAC transgenic mice on either a wild type (hCD40 Taconic strain, black bars) or CD40 KO (ImmuRx hCD40 strain, grey bars) C57BL/6 backgrounds were injected (intraperitoneal) with CP-870,893 hIgG4 (CP, 10 µg 0.5 mg/Kg) or the molar equivalent of anti-CD40 11B6-CD40L (11B6-CD40L) and were sacrificed 24 h later. Blood was collected for PBMC preparation, and cells were prepared from skin draining lymph node and spleen, then cells were analyzed by flow cytometry. B cell activation was characterized by analysis of the activation marker CD69. The data are the average for two animals in each of the 6 groups.

CP-870,893 infusion in cancer patients undergoing chemotherapy triggers immune activation detected by increased plasma inflammatory cytokines (i.e., cytokine release syndrome), increased B cell expression of co-stimulatory molecules, and transient depletion of B cells (Beatty et al., 2013). In these patients, dose-limiting toxicity was determined to be 0.2 mg/kg, although 0.3 mg/kg was the limit determined in patients receiving this anti-CD40 agonist alone (Vonderheide et al., 2016). To appraise the biological activity of anti-CD40 11B6-CD40L in vivo, we tested the short-term (24 h) effects of CP-870,893 hIgG4 and anti-CD40 11B6-CD40L at a dose of 10 μg (≈0.5 mg/Kg). Wild type or human CD40 BAC transgenic mice on either a wild type (Taconic strain) or CD40 KO (ImmuRx strain) C57BL/6 background were injected (intraperitoneal) with CP-870,893 hIgG4 or the molar equivalent of anti-CD40 11B6-CD40L and were sacrificed 24 h later. Blood was collected for assay of cytokines (serum via Luminex®) and cells from PBMC, skin draining lymph node, and spleen, were analyzed by flow cytometry. B cells were characterized by analysis of the activation markers CD69, MHC-II, OX40L and CD86. The results are shown in FIG. 17 and show that while CP-870,893 hIgG4 has minimal or no activity in these tests, of anti-CD40 11B6-CD40L elicits robust B cell depletion associated with activation, as well as cytokine secretion as detected in the circulation. These data predict that very low doses of anti-CD40 11B6-CD40L compared to CP-870,893 would be required when used clinically as an adjuvant in e.g., cancer therapy.

Fusion of CD40L to Anti-CD40 11B6 Increases Both Efficacy and Potency of Cell Killing Directed by CD40 Ectodomain Fused to FAS Transmembrane and Intracellular Domains.

Figure 18:
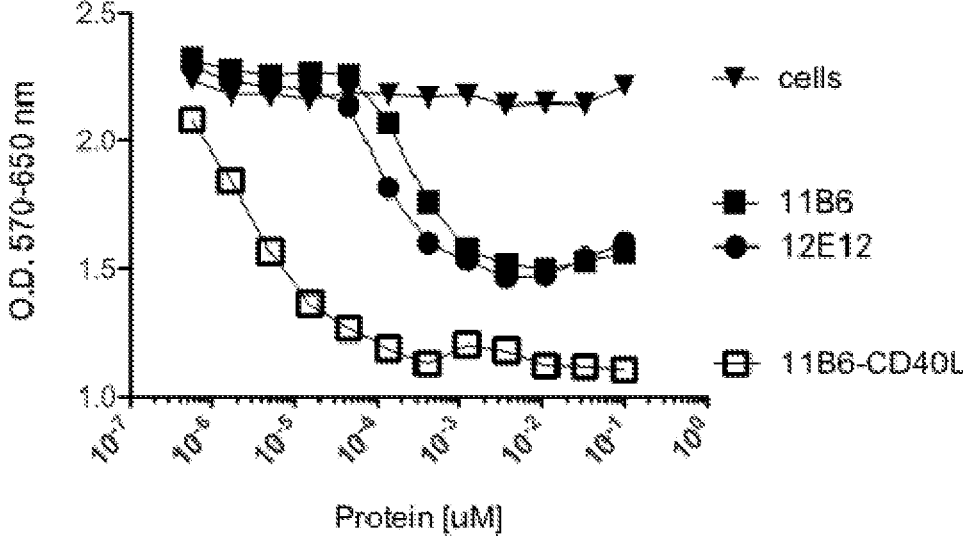
FIG. 18. Fusion of CD40L to anti-CD40 11B6 increases both efficacy and potency of cell killing directed by CD40 ectodomain fused to FAS transmembrane and intracellular domains. CHO cells stably transfected with a human CD40-FAS fusion construct incubated for 48 h with a dilution series of anti-CD40 IgG4 antibodies. Cells were then incubated with MTT for colorimetric detection of mitochondrial reduction activity, an indicator of cell viability. Non-transfected CHO cells are not affected by any of these tested agents (not shown).

FAS (CD95) belongs to the tumor necrosis factor receptor (TNF-R) family that contain an intra-cellular 'death domain' and can trigger apoptosis in response to its physiological ligand, FASL (Strasser et al., 2009). We constructed a fusion protein expressing human CD40 ectodomain residues 21-193 fused to human FAS residues 187-350 and established stably transfected Chinese Hamster Ovary (CHO) cells expressing the CD40 ectodomain linked to the FAS transmembrane and intracellular domains. CD40 agonists elicit killing of these cells as determined by loss of mitochondrial reduction of the tetrazolium salt MTT (3-(4,5-dimethylthiazol-2-yl)-2,5-diphenyl tetrazolium bromide) (Mossman, 1983). In this assay anti-CD40 11B6 IgG4 and anti-CD40 12E12 IgG4 show similar efficacy (as determined by maximal decrease in MTT reduction) and similar potency ($EC_{50}$≈2.5 nM and 1 nM, respectively), but anti-CD40 11B6-CD40L IgG4 has increased efficacy (i.e., greater maximal decrease in MTT reduction) and significantly increased potency (EC50≈2.5 pM) (FIG. 18). This data reinforces conclusions drawn from tests of the superiority of anti-CD4011B6-CD40L efficacy seen in B cell and DC assays.

Anti-CD40 11B6-CD40L Enhances CD40-Mediated Clustering and Internalization

We compared the rate and extent of CD40-mediated internalization of anti-CD40 11B6-CD40L versus anti-CD40 12E12. These two antibodies are well matched for their binding to CD40 based on SPR analysis (KD of 12 and 28 nM, respectively, FIG. 24), but they differ dramatically in potency of CD40 activation (FIGS. 9,18). Since ligand engagement leads to the formation of cross-linked CD40 lipid rafts (clusters) on the cell membrane, an event followed by CD40 internalization and downstream signaling (Wang et al. 2015), we compared the ability of anti-CD40 11B6-CD40L versus anti-CD40 12E12 to cluster and internalize cell surface CD40.

Figure 23:
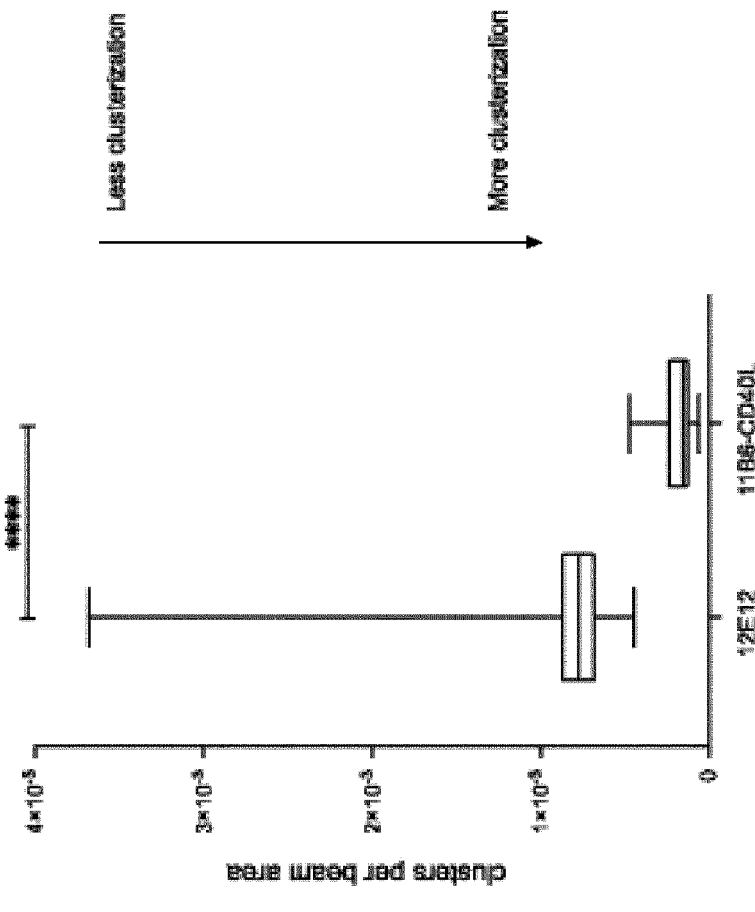
FIG. 23. Anti-CD40 11B6-CD40L enhances CD40 cluster formation. Human CD40-mCherry CHO cells were incubated in culture media for 1 hour alone (top panels), with 10 nM anti-CD40 12E12 (middle panels) or with 10 nM anti-CD40 11B6-CD40L (bottom panels) at 37° C. on cover slides. The cells were then fixed with 1% PFA, washed and mounted on super frosted slides using ProLong Gold antifade reagent with DAPI. The images were taken with put images taken at UTSW and analyzed with FIJI software (open sources from ImageJ) for quantification of clusters per beam area. An average of 5 cells per each group were analyzed performing spatial image correlation spectroscopy, analyzing three 32×32 squares per each cell. The protocol used takes advantage of autocorrelation and image mathematical functions of FIJI software to quantitates the fluorescent intensity of labeled receptors as a function of the beam area of the confocal microscope, to provide a quantitative measure of the state of target molecule aggregation (clusterization) on the cell surface (Parslow et al., 2018, *J Vis Exp*. 2018; (138):57164). MDDC were incubated for 6 hours in culture media at 37° C. on cover slides with 100 nM anti-CD40 11B6-CD40L-Dock_Coh-eGFP or with 100 nM anti-CD40 23E12-Dock_Coh-eGFP. The cells were then washed, fixed, permealized, stained for anti-EEA1 or anti-Lamp1, washed and mounted on super frosted slides using ProLong Gold antifade reagent with DAPI. Images were taken with and analyzed using FIJI software for quantification of clusters per beam area as previously described. Eight images for anti-CD40 11B6-CD40L treatment, using four 32×32 squares per image, and seven images for anti-CD40 12E12 treatment, using four or five 32×32 squares each, were used for the analyses (right). The scale difference between left and right is due to difference in the fluorescence intensity between the pictures, that were taken at different moments, and that are of different cell types (not comparable). However, the statistical significance between the treatments is the same in the different cell types used (p value <0.0001).
Figure 23:
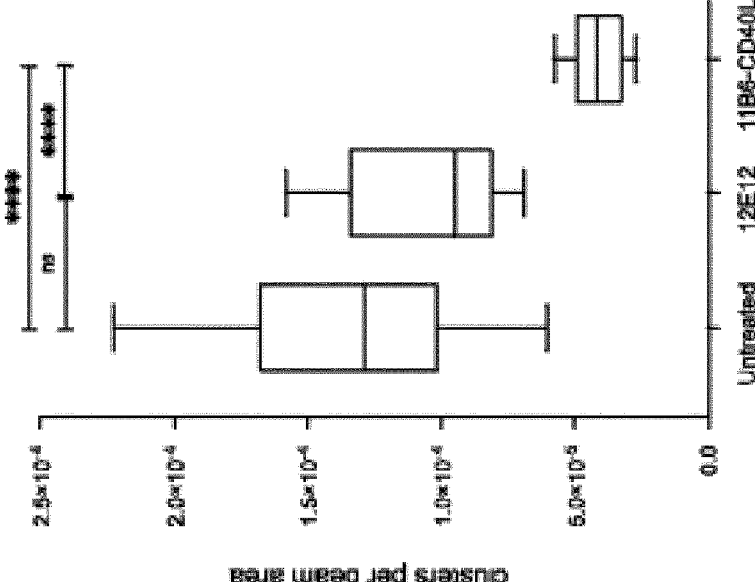

We first compared the ability of these two anti-CD40 antibodies to induce the formation of cross-linked CD40 lipid rafts (clusters) on the cell membrane. We used CHO cells expressing a human CD40-eGFP fusion protein or a human CD40-mCherry fusion as a model to visualize cluster formation through confocal microscopy. Treating the cells for 1 hour at 37° C. with 10 nM anti-CD4011B6-CD40L induced stronger CD40 cluster formation compared to the same treatment with anti-CD40 12E12 (FIG. 23). This data is concordant with the increased signaling potency of the anti-CD40 11B6-CD40L antibody since CD40 clustering is likely the initial trigger for CD40 activation.

Figure 24:
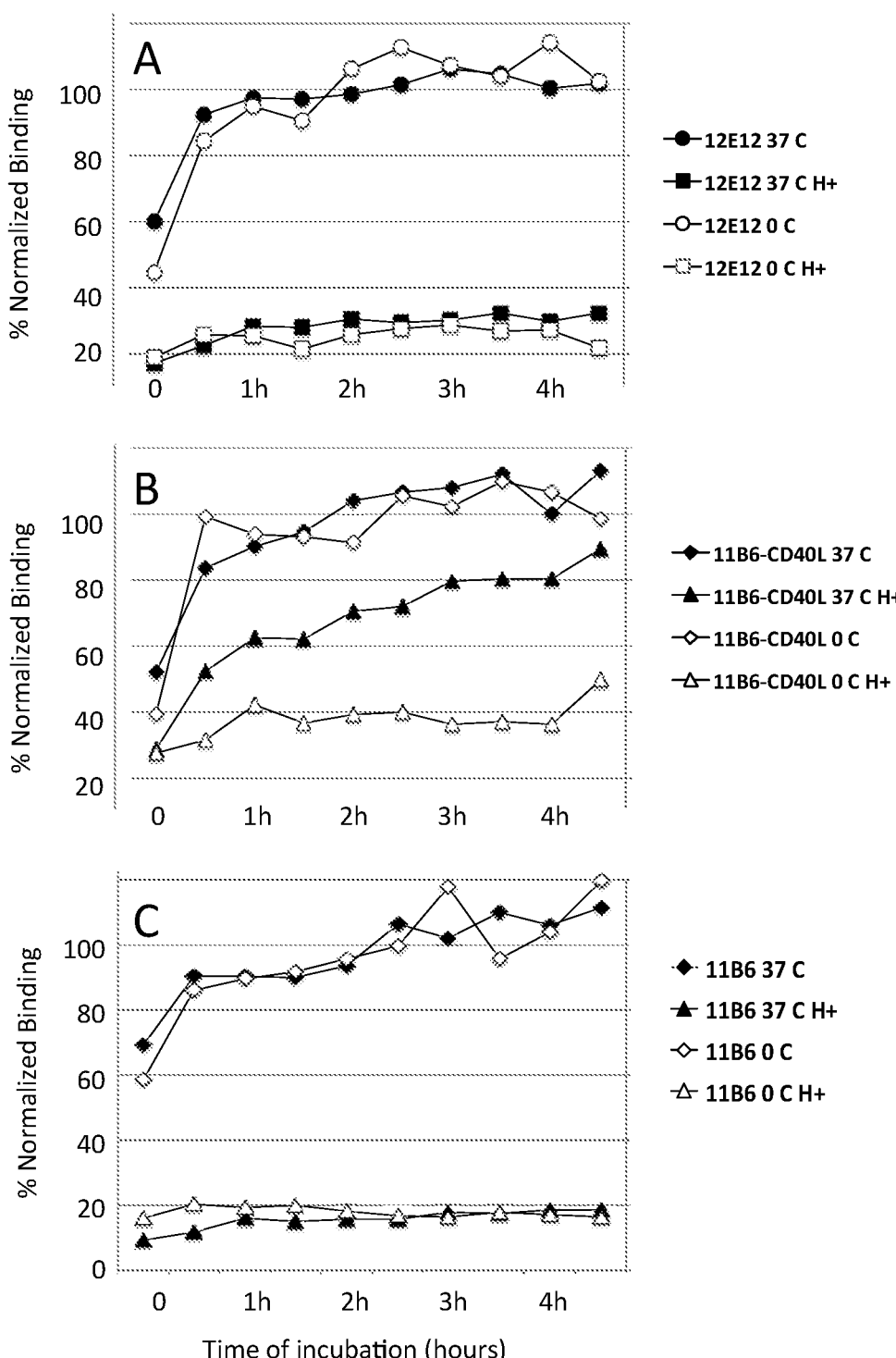
FIG. 24. Anti-CD40 11B6-CD40L enhances CD40-mediated internalization. Human CD40-CHO cells were incubated in culture medium for various times with 100 nM mCherry-labeled anti-CD40 12E12 (A), anti-CD40 11B6-CD40L (B) or anti-CD40 11B6 (C) at either 37° C. or 0° C. Cells were then either washed with PBS or treated with isotonic acid stripping buffer (pH 2.5) for 1 min, neutralized and then washed with PBS. Total or acid-resistant (i.e., internalized) label was then measured by fluorescence. Signal for total binding from the 30-270 min time points was averaged and set to 100% to normalize the data between three independent replicate experiments. Background fluorescence values with cells alone or 100 nM mCherry not conjugated to anti-CD40 mAbs were 2±1%. The detectable binding at the zero time point reflects binding occurring during the initial ~6 min centrifugation and washing step.

We then used CHO cells expressing human CD40 as a model and assayed anti-CD40-mediated binding and internalization of a non-covalently attached mCherry module. Binding of both antibodies was rapid and reached saturation within ~30 min at 37° C. and at 0° C. (FIGS. 24 A and B). Treating the cells in cold isotonic acid buffer (pH 2.5) for one minute removed ~75% of the cell-associated anti-CD40 12E12 label when binding was performed at 0° C. (FIG. 24 A). When binding was performed at 37° C., there was a trend (residual label 29±3% versus 26±3%, n.s.) to greater label retention at 37° C., perhaps reflecting slight internalization. In contrast, when anti-CD40 11B6-CD40L binding was performed at 0° C., the acid stripping removed only ~60% of the cell-associated label versus the 26±3% observed with the anti-CD40 12E12 mAb, and this difference between the two mAbs is significant (p<0.0001, FIG. 24 B) indicating anti-CD40 11B6-CD40L internalization is readily detectable even at 0° C. Internalization of the anti-CD40 11B6-CD40L label was much greater at 37° C., with acid-resistant label increasing from 50-90% over the 4.5 hour time course (FIG. 24 B). Thus, anti-CD40 11B6-CD40L internalizes to a much greater extent than anti-CD40 12E12, with significant internalization detectable even at 0° C. This property is a sole result of the CD40L adduct since the binding and internalization properties of the anti-CD40 11B6 mAb without fusion to CD40L were very similar to the anti-CD40 12E12 mAb (FIG. 24 C).

Anti-CD40 11B6 Recognizes an Epitope on CD40 that is Distinct from Anti-CD40 12E12 and Anti-CD40 CP.

Figure 19:
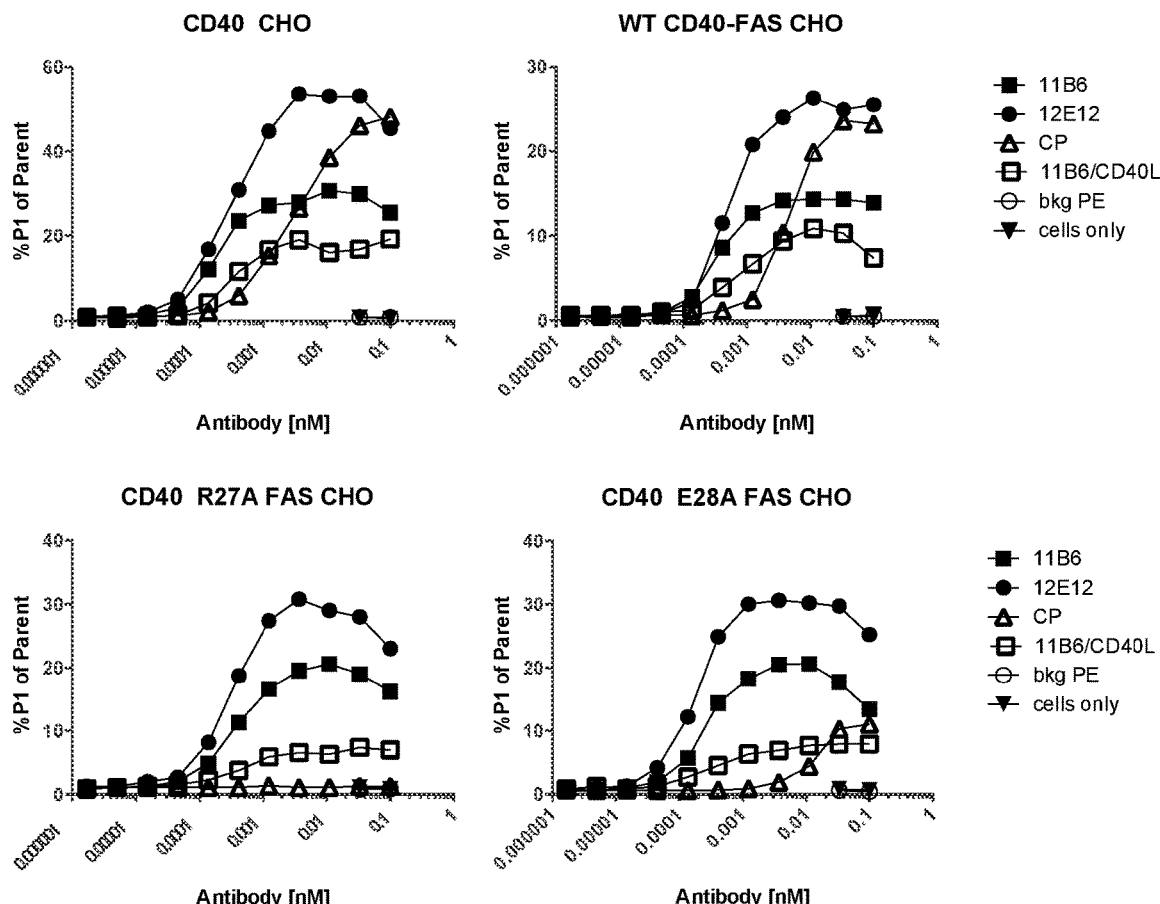
FIG. 19. Analysis of anti-CD40 mAb binding to CHO cells expressing CD40 ectodomain fusion proteins. CHO cells (250K) stably transfected with an expression plasmid expressing human CD40 or CD40 ectodomain fused to FAS transmembrane and intracellular residues were 250K per point (with specific cell type) were incubated with a dilution series of anti-CD40 antibodies starting at 0.1 µM final (3× dilution over 11 wells). Binding was for 1 h on ice followed by 2× washing with 1×PBS, 2% FCS, 2 mM EDTA (also the binding buffer), then probed with goat anti-human IgG PE (Prozyme: Phycolink goat anti-hIgG-RPE) at a dilution of 1:500, followed by 2× washing with above buffer. Samples were analyzed on a FACS Array (BD Biosciences): Calculated % P1 used a gate set at the above background cells only with PE (parent) histogram. All events from sample/specific events in the P1 gate give the stated % P1 values. WT CD40-FAS CHO are cells expressing the wild type (non-mutated) CD40 ectodomain fused to FAS. CD40 R27A and E28A FAS are cells with mutated CD40 ectodomain.

Yu et al. (2018) summarized the knowledge of relationships between agonist anti-CD40 mAbs and their sites of interaction with CD40. For example, anti-CD40 CP binds within the CD40 CRD1 region (i.e., no binding if removed) and also binding is lost when residues 23-37 are deleted or residues 27-28 RE are replaced with AA. Also, Singh et al. (1998) reported that individual substitutions of the negatively charged residues Glu74, Asp84, and Glu117 in CD40 disrupted CD40L binding. This mapping shows distinct sites of interaction on CD40 for CD40L versus the CP antibody. Using the method of Wan et al., 2012, residues R27 and E28 were individually replaced with A and the mutated CD40 ectodomains were tested for binding to anti-CD40 CP, anti-CD40 12E12, and anti-CD40 11B6 (±CD40L). As expected, the R27A and E28A mutations abrogated or greatly reduced binding to the anti-CD40 CP mAb (FIG. 19). However, these mutations did not affect binding of anti-CD40 11B6 or 12E12 mAbs. The data clearly differentiate the binding sites on CD40 of the anti-CD40 CP mAb from the anti-CD40 11B6 or 12E12 mAbs.

Epitope Mapping of Anti-CD40 Agonistic Antibody 12E12 and 11B6

Two approaches were used to define CD40 residues that were important for interaction/binding to the two claimed antibodies (12E12 and 11B6), as well as to differentiate them from the other agonistic antibody CP-870,893 (referred herein as CP). The first approach is based on PepScan (Netherland based company) "Precision Epitope Mapping" platform. The second approach built upon the PepScan data by undertaking Ala-scanning mutagenesis of selected hydrophilic residues of the human CD40 ectodomain coupled to antibody binding analysis.

Using these approaches, the aim was to identify differences in epitopes on CD40 specific to these three antibodies.

Six 12E12 binding peptide regions were identified from Pepscan analysis and the Ala mutagenesis covered charged residues in all but one of these peptides (which has no highly charged residues):

```
                               (SEQ ID NO: 153)
    PPTACREKQYLINSQ;

(SEQ ID NO: 154
    QCCSLCQPGQ;

(SEQ ID NO: 155)
    DTWNRETHCHQHKYC;

(SEQ ID NO: 156)
    HKSCSPGFGVKQI;

(SEQ ID NO: 157)
    KCHPWTSCETKD;

(SEQ ID NO: 158)
    CHQHKYCDPNLGL
```

Nine 11B6 binding peptide regions were highlighted and the Ala mutagenesis covered charged residues in 8 of these 9 peptides (excluding one which has no highly charged residues):

```
                               (SEQ ID NO: 159)
    INSQCCSLCQPGQ;

(SEQ ID NO: 160)
    CLPCGESEFLDTWNR;

(SEQ ID NO: 161)
    DTWNRETHCH;
```

```
             -continued
                               (SEQ ID NO; 162)
    CHQHKYCDPNLGLK;

(SEQ ID NO: 163)
    HCTSEACESCVLHK;

(SEQ ID NO: 164)
    LHKSCSPGFGVK;

(SEQ ID NO: 165)
    HPWTSCETKDLVVQQ;

(SEQ ID NO: 166)
    TDKTDVVCGPQDR;

(SEQ ID NO: 167)
    PTACREKQYLINSQ
```

Figure 25:
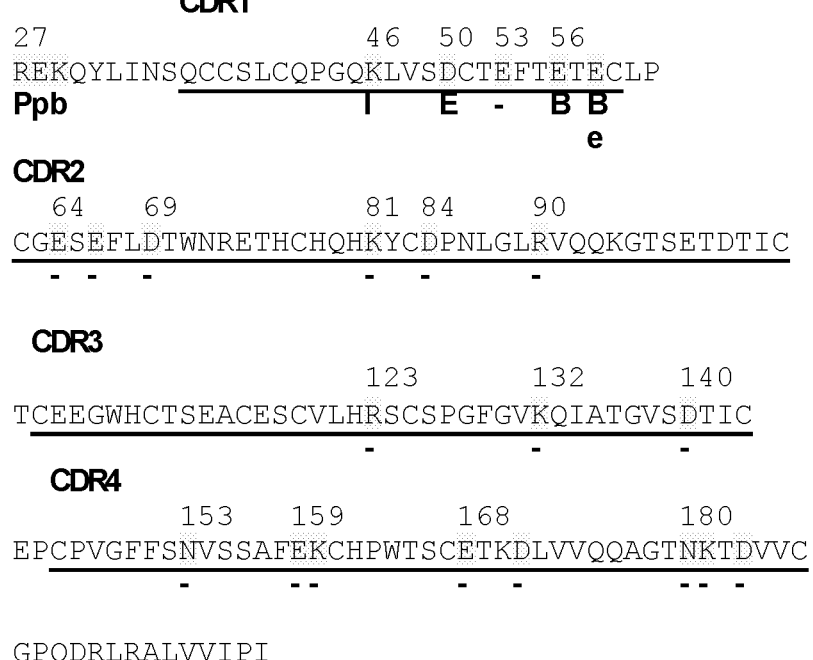
FIG. 25: SEQ ID NO: 172 is shown. Data derived from the Ala-mutagenesis study. Underlined are the four CDR structural homology regions of CD40. Residue numbers for some of the mutations are shown. Grey highlights show the residues that were changed. P is the Pfizer CP mAb; E is 12E12; B is 11B6; L is 11B6-CD40L; – means no effect on any mAb tested; a small letter below the sequence indicates reduced binding; letter in CAPS means no binding.

The data derived from the Ala-mutagenesis study are summarized in FIG. 25, showing SEQ ID NO: 172. Underlined are the four CDR structural homology regions of CD40. Residue numbers for some of the mutations are shown. Grey highlights show the residues that were changed. P is the Pfizer CP mAb; E is 12E12; B is 11B6; L is 11B6-CD40L; – means no effect on any mAb tested; a small letter below the sequence indicates reduced binding; letter in CAPS means no binding.

The mutagenesis did result in discriminating with high confidence the epitopes for CP, 11B6, and 12E12 binding—even though all three mAbs had clear epitope components in the CDR1 region. This CP interaction was disrupted by changes in residues R27 and E28 (verifying published information); 11B6 interaction involved interaction with residue K29, as well as E56 and E58; the combined 11B6-CD40L binding was specifically abrogated by the K46A change; and the 12E12 interaction was dependent on D50 and E58. Thus, the data show some overlap of epitopes for these three mAbs, but distinct differences in key contact sites.

Other Examples of the Fusion Proteins of the Present Disclosure

Figure 22:
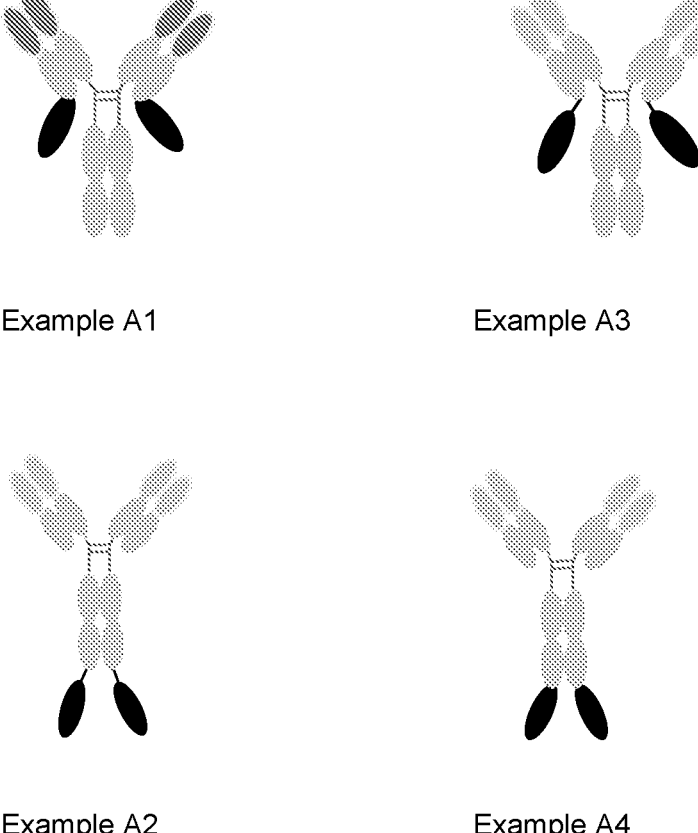
FIG. 22. This figure shows cartoons representing the structure of each fusion proteins, with antigens either at the C-terminus of light or heavy chains, and/or with the presence of flexible linker.
Figure 22:
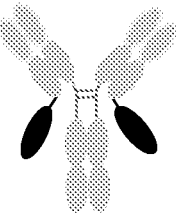

The following alternative fusion proteins A1-A5 have been prepared. The FIG. 22 shows cartoons representing the structure of each fusion proteins, with the antigens either at the C-terminus of light or heavy chains, and/or with the presence of flexible linker.

Example A1: Anti-CD40 11B6 with CD40L on the L Chain C-Terminus

PAB3588 C3334 (SEQ ID NO:131)×C3792 (SEQ ID NO: 133)

[manti-CD40_11B6.1C3_H-LV-hIgG4H-C-Nhe-Not] [manti-CD40_11B6.1C3_Syn_K-LV-hIgGK-C-hCD40Ligand]

Example A2: Anti-CD40 Humanized 11B6 with Flex-CD40L on the H Chain C-Terminus

PAB3618 C3823 (SEQ ID NO: 135)×C3739 (SEQ ID NO: 137)

[mAnti-CD40-11B6.1C3-VH-v2-LV-hIgG4H-C-Flex-v1-hCD40Ligand][mAnti-CD40-11B6.1C3-Vκ-v2-LV-hIgGK-C]

Example A3: Anti-CD40 Humanized 11B6 with Flex-CD40L on the L Chain C-Terminus PAB3475 C3724 (SEQ ID NO: 139)×C3726 (SEQ ID NO: 141)
[mAnti-CD40-11B6.1C3-Vκ-v2-LV-hIgGK-C-Flex-v1-hCD40Ligand][mAnti-CD40-11B6.1C3-VH-v3-LV-hIgG4H-C]

Example A4: Anti-CD40 Humanized 11B6 with CD40L on the H Chain C-Terminus

PAB3615 C3821 (SEQ ID NO: 143)×C3739 (SEQ ID NO: 137)
[mAnti-CD40-11B6.1C3-VH-v2-LV-hIgG4H-C-hCD40Ligand][mAnti-CD40-11B6.1C3-Vκ-v2-LV-hIgGK-C]

Example A5: Anti-CD40 Humanized 11B6 with Flex-CD40L on the L Chain C-Terminus PAB3470 C3724 (SEQ ID NO: 139)×C3725 (SEQ ID NO: 145)
[mAnti-CD40-11B6.1C3-Vκ-v2-LV-hIgGK-C-Flex-v1-hCD40Ligand][mAnti-CD40-11B6.1C3-VH-v2-LV-hIgG4H-C]
Super Agonist Properties are Observed Irrespective of the Position of the CD40L at Either the C-Terminus of the L Chain or the C-Terminus of the H Chain and of the Presence or Absence of a Flexible Linker Joining Sequence.

Figure 20:
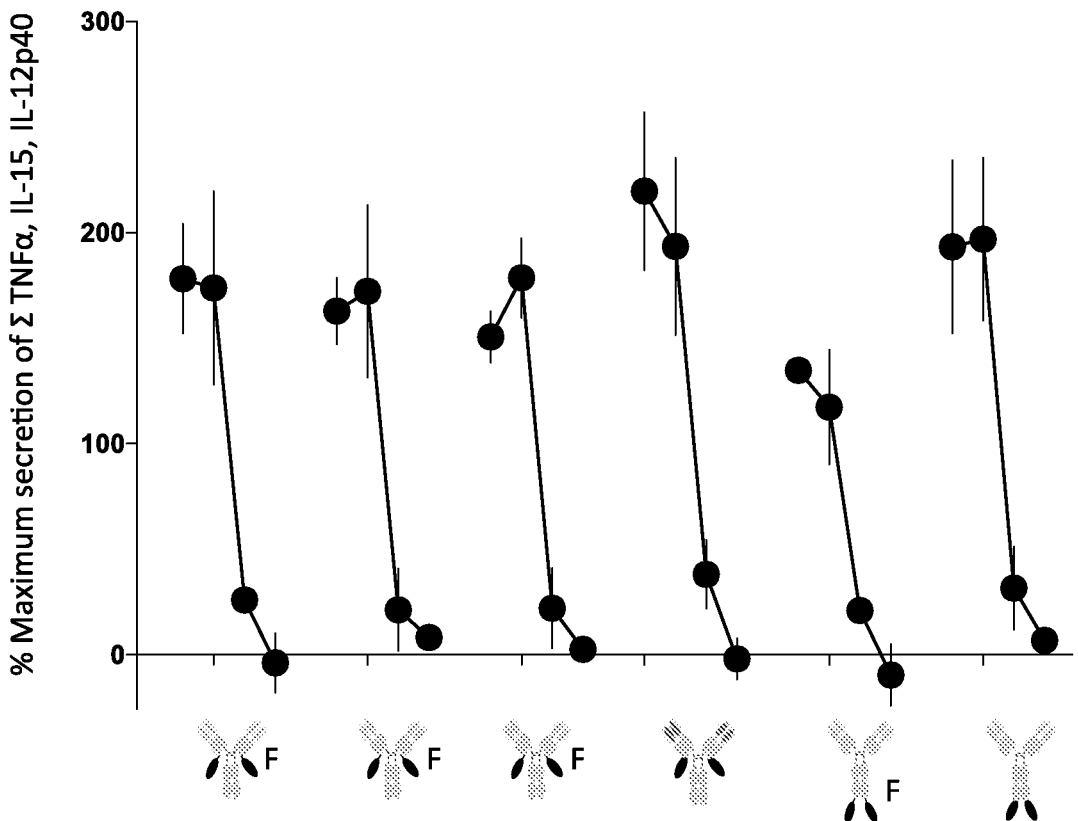
FIG. 20. Cytokine secretion responses of human myeloid-derived dendritic cells (MDDCs) to a dose range of anti-CD40 11B6 IgG4 antibodies with directly fused human CD40L fused to H or L chain C-termini with and without a flexible linker region. Human MDDCs were cultured with a dose range (shown left to right: 10, 1, 0.1, 0.01 nM) of each anti-CD40 11B6-CD40L isoform and the extent of cytokine secretion determined after 24 h. Data represent a summation of the values for each cytokine tested normalized to the highest value within the experiment and averaged for replicated responses with two different donors. Error bars are the standard error of the mean. The cartoons shown below each titration series indicate the L chain or H chain CD40L fusion isoforms and F indicates the presence of the Flex V1 linker.

Human MDDCs were cultured with a dose range (shown left to right in FIG. 20: 10, 1, 0.1, 0.01 nM) of each anti-CD40 11B6-CD40L isoform and the extent of cytokine secretion was determined after 24 h. Data in FIG. 20 represent a summation of the values for each cytokine tested normalized to the highest value within the experiment and averaged for replicated responses with two different donors. Error bars are the standard error of the mean. The cartoons shown below each titration series indicate the L chain or H chain CD40L fusion isoforms and F indicates the presence of the Flex V1 linker. The results show no significant differences between the values for each dose across this series.

Superagonist Activity of CD40L Fused to Anti-CD40 Antibody is Independent of CD40L Positioning as Defined by Efficacy and Potency of Cell Killing Directed by CD40 Ectodomain Fused to FAS Transmembrane and Intracellular Domains.

Figure 21:
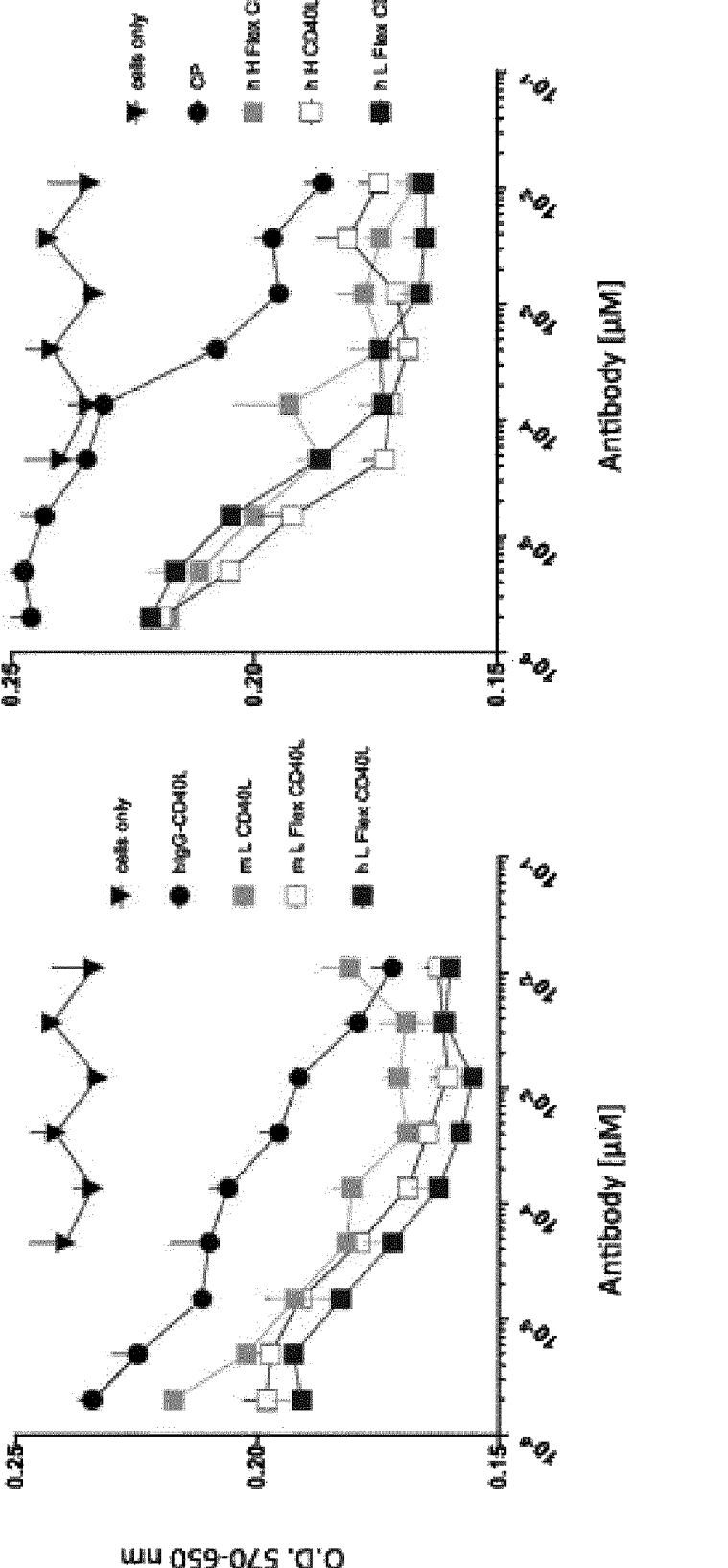
FIG. 21. Superagonist activity of CD40L fused to anti-CD40 11B6 is independent of CD40L positioning as defined by efficacy and potency of cell killing directed by CD40 ectodomain fused to FAS transmembrane and intracellular domains. CHO cells stably transfected with a construct (Mam-cetHS-puro[hCD40—Ecto hFas-TM-IC], SEQ ID NO: 151) for expressing human CD40 ectodomain fused to FAS transmembrane and intracellular residues were incubated for 48 h with a dilution series of anti-CD40 IgG4 antibodies. Cells were then incubated with MTT for colorimetric detection of mitochondrial reduction activity. In the graph h indicated humanized 11B6 mAb, m indicates the original mouse V region.

FAS (CD95) belongs to the tumor necrosis factor receptor (TNF-R) family that contain an intra-cellular 'death domain' and can trigger apoptosis in response to its physiological ligand, FASL (Strasser et al., 2009). We constructed a fusion protein expressing human CD40 ectodomain residues 21-193 fused to human FAS residues 187-350 and established stably transfected Chinese Hamster Ovary (CHO) cells expressing the CD40 ectodomain linked to the FAS transmembrane and intracellular domains. CD40 agonists elicit killing of these cells as determined by loss of mitochondrial reduction of the tetrazolium salt MTT (3-(4,5-dimethylthiazol-2-yl)-2,5-diphenyl tetrazolium bromide) (Mossman, 1983). FAS and CD40 are in the same TNF-R family and mechanisms of receptor activation (external to the cell) are similar—but the intracellular signalling pathways are different, i.e., apoptosis versus selected cytokine and cell surface marker activation). This fusion construct provides a convenient surrogate assay format for analysis of CD40 activation based on transfected CHO cells. In this assay anti-CD40 11B6 IgG4 and anti-CD40 12E12 IgG4 show similar efficacy (as determined by maximal decrease in MTT reduction) and similar potency ($EC_{50} \approx 2.5$ nM and 1 nM, respectively), but anti-CD40 11B6-CD40L IgG4 has increased efficacy (i.e., greater maximal decrease in MTT reduction) and significantly increased potency ($EC_{50} \approx 2.5$ pM) (FIG. 21). Thus, CD40L fusion to the partial agonist anti-CD40 11B6 mAb can greatly increase the potency and efficacy for on three distinct CD40-bearing cell types.

| | Tables 5 and 6: Useful sequences for practicing the invention | |
|---|---|---|
| SEQ ID | Type | Brief description |
| 1 | aa | Amino acid sequence of PAB3405 heavy chain C3677 [mAnti-CD40-11B6.1.C3-VH-v2-LV-hIgG4H-C] |
| 2 | aa | Amino acid sequence of PAB3405 light chain C3862 [mAnti-CD40-11B6.1C3-Vk-v2-LV-hIgGK-C] |
| 3 | aa | Amino acid sequence of PAB3408 heavy chain C3678 [mAnti-CD40-11B6.1C3-VH-v3-LV-hIgG4H-C] |
| 4 | aa | Amino acid sequence of PAB3408 light chain C3682 [mAnti-CD40-11B6.1C3-Vκ-v2-LV-hIgGK-C] |
| 5 | aa | Amino acid sequence of PAB3470 and PAB3471 light chain C3724 [mAnti-CD40-11B6.1C3-Vκ-v2-LV-hIgGK-C-Flex-v1-hCD40Ligand] |
| 6 | aa | Amino acid sequence of PAB3470 heavy chain C3725 [mAnti-CD40-11B6.1C3-VH-v2-LV-hIgG4H-C] |
| 7 | aa | Nucleotide coding sequence of human CD40 (SEQ ID NO: 13) |
| 8 | aa | Amino acid sequence of PAB3471 heavy chain C3726 [mAnti-CD40-11B6.1C3-VH-v3-LV-hIgG4H-C] |
| 9 | aa | Amino acid sequence of PAB3499 heavy chain C3735 [mAnti-CD40-11B6.1C3-VH-v2-L-V-hIgG4H-C-Flex-v1-Pep-gag17-f1-gag253-f2-nef116-f3-nef66-f4-pol158] |
| 10 | aa | Amino acid sequence of PAB3499 light chain C3739 [mAnti-CD40-11B6.1C3-Vκ-v2-LV-hIgGK-C] |
| 11 | aa | Amino acid sequence of PAB3498 heavy chain C3735 [mAnti-CD40-11B6.1C3-VH-v2-L-V-hIgG4H-C-Flex-v1-Pep-gag17-f1-gag253-f2-nef116-f3-nef66-f4-pol158] |
| 12 | aa | Amino acid sequence of PAB3498 light chain C3524 [mAnti-CD40-11B6.1C3-Vk-v2-LV-hIgGK-C-Flexv1-hCD40L] |

-continued

| Tables 5 and 6: Useful sequences for practicing the invention | | |
|---|---|---|
| SEQ ID | Type | Brief description |
| 13 | aa | Full amino acid sequence of human CD40 |
| 14 | aa | Amino acid sequence of CD40 binding domain of human CD40L |
| 15 | aa | Amino acid sequence of FlexV1 peptidic linker |
| 16 | aa | Amino acid sequence of Gag p17 (17-35) |
| 17 | aa | Amino acid sequence of Gag p17-p24 (253-284) |
| 18 | aa | Amino acid sequence of Nef (116-145) |
| 19 | aa | Amino acid sequence of Pol 325-344 (RT 158-188) |
| 20 | aa | Amino acid sequence of Nef (66-97) |
| 21 | aa | Amino acid sequence of variable heavy chain region (VH) (v2) of Humanized 11B6 |
| 22 | aa | Amino acid sequence of variable light chain (VL) Vk (v2) of humanized 11B6 VL |
| 23 | aa | Amino acid sequence of variable heavy chain region VH (v3) of humanied 11B6 |
| 24 | nt | Nucleotide sequence encoding SEQ ID NO: 21 |
| 25 | nt | Nucleotide sequence encoding SEQ ID NO: 22 |
| 26 | nt | Nucleotide sequence encoding SEQ ID NO: 23 |
| 27 | aa | Amino acid sequence of HCDR1 of Humanized 11B6 VH V2 |
| 28 | aa | Amino acid sequence of HCDR2 of Humanized 11B6 VH V2 |
| 29 | aa | Amino acid sequence of HCDR3 of Humanized 11B6 VH V2 |
| 30 | aa | Amino acid sequence of LCDR1 of Humanized 11B6 VkV2 |
| 31 | aa | Amino acid sequence of LCDR2 of Humanized 11B6 VkV2 |
| 32 | aa | Amino acid sequence of LCDR3 of Humanized 11B6 VkV2 |
| 33 | nt | Nucleotide sequenc of PAB3405 heavy chain |
| 34 | nt | Nucleotide sequenc of PAB3405 light chain |
| 35 | nt | Coding Sequence of SEQ ID NO: 3 |
| 36 | nt | Coding Sequence of SEQ ID NO: 4 |
| 37 | nt | Coding Sequence of SEQ ID NO: 5 |
| 38 | nt | Coding Sequence of SEQ ID NO: 6 |
| 39 | nt | Coding sequence of SEQ ID NO: 8 |
| 40 | aa | Amino acid of mAb 12E12 HC [manti-CD40_12E12.3F3_H-V-hIgG4H-C] |
| 41 | nt | Coding Sequence of SEQ ID NO: 9 |
| 42 | nt | Coding Sequence of SEQ ID NO: 10 |
| 43 | nt | Coding Sequence of SEQ ID NO: 11 |
| 44 | nt | Coding Sequence of SEQ ID NO: 12 |
| 45 | aa | Amino acid sequence of Gag p24 as used in GNG |
| 46 | aa | Amino acid sequence of Nef as used in GNG |
| 47 | aa | Amino acid sequence of Gag p17 as used in GNG |
| 48 | aa | Amino acid sequence of GNG as used in the example |
| 49 | nt | Nucleotide sequence of Gag p24 as used in GNG |
| 50 | nt | Nucleotide sequence of Nef as used in GNG |
| 51 | nt | Nucleotide sequence of Gag p17 as used in GNG |
| 52 | nt | Nucleotide sequence of GNG as used in the example |
| 53 | aa | Amino acid sequence of flexible linker f3 |
| 54 | aa | Amino acid sequence of flexible linker f4 |
| 55 | aa | Amino acid sequence of HV16E6HPV16E7 as used in HPV sequence |
| 56 | aa | Amino acid sequence of flexible linker f1 |
| 57 | aa | Full amino acid sequence of HPV sequence |
| 58 | aa | VH amino acid sequence of mAb3 (12B4) |
| 59 | aa | VL amino acid sequence of mAb3 (12B4) |
| 60 | aa | VH amino acid sequence of mAb4 (24A3 HC) [manti-hCD40_24A3.3F1_H-LV-hIgG4H-C] |
| 61 | aa | VL amino acid sequence of mAb4 (24A3 KC) [manti-hCD40_24A3.3F1_K-LV-hIgGK-C] |
| 62 | aa | VH amino acid sequence of mAb5 (CP) [manti-hCD40_CP870893H-LV-hIgG4H-C] |
| 63 | aa | VL amino acid sequence of mAb5 (CP) [manti-hCD40_CP870893K-LV-hIgGK-C] |
| 64 | aa | VH amino acid sequence of mAb6 (12E12 H3 Humanized HC [hAnti-CD40VH3-LV-hIgG4H-C]) |
| 65 | aa | VL amino acid sequence of mAb6 (Humanized K2 12E12) |
| 66 | nt | Coding sequence of SEQ ID NO: 58 |
| 67 | nt | Coding sequence of SEQ ID NO: 59 |
| 68 | nt | Coding sequence of SEQ ID NO: 60 |
| 69 | nt | Coding sequence of SEQ ID NO: 61 |
| 70 | nt | Coding sequence of SEQ ID NO: 62 |
| 71 | nt | Coding sequence of SEQ ID NO: 63 |
| 72 | nt | Coding sequence of SEQ ID NO: 64 |
| 73 | nt | Coding sequence of SEQ ID NO: 65 |
| 74 | aa | HCDR1 amino acid sequence of mAb3 (12B4) |
| 75 | aa | HCDR2 amino acid sequence of mAb3 (12B4) |
| 76 | aa | HCDR3 amino acid sequence of mAb3 (12B4) |
| 77 | aa | LCR1 amino acid sequence of mAb3 (12B4) |
| 78 | aa | LCDR2 amino acid sequence of mAb3 (12B4) |

-continued

| | | Tables 5 and 6: Useful sequences for practicing the invention |
|---|---|---|
| SEQ ID | Type | Brief description |
| 79 | aa | LCDR3 amino acid sequence of mAb3 (12B4) |
| 80 | aa | HCDR1 amino acid sequence of mAb4 (24A3) |
| 81 | aa | HCDR2 amino acid sequence of mAb4 (24A3) |
| 82 | aa | HCDR3 amino acid sequence of mAb4 (24A3) |
| 83 | aa | LCDR1 amino acid sequence of mAb4 (24A3) |
| 84 | aa | LCDR2 amino acid sequence of mAb4 (24A3) |
| 85 | aa | LCDR3 amino acid sequence of mAb4 (24A3) |
| 86 | aa | HCDR1 amino acid sequence of mAb5 (CP) |
| 87 | aa | HCDR2 amino acid sequence of mAb5 (CP) |
| 88 | aa | HCDR3 amino acid sequence of mAb5 (CP) |
| 89 | aa | LCDR1 amino acid sequence of mAb5 (CP) |
| 90 | aa | LCDR2 amino acid sequence of mAb5 (CP) |
| 91 | aa | LCDR3 amino acid sequence of mAb5 (CP) |
| 92 | aa | HCDR1 amino acid sequence of mAb6 (humanized 12E12) |
| 93 | aa | HCDR2 amino acid sequence of mAb6 (humanized 12E12) |
| 94 | aa | HCDR3 amino acid sequence of mAb6 (humanized 12E12) |
| 95 | aa | LCDR1 amino acid sequence of mAb6 (humanized 12E12) |
| 96 | aa | LCDR2 amino acid sequence of mAb6 (humanized 12E12) |
| 97 | aa | LCDR3 amino acid sequence of mAb6 (humanized 12E12) |
| 98 | aa | 12B4 HC [manti-CD40_12B4.2C10_H-LV-hIgG4H-C] |
| 99 | aa | 12B4 KC [manti-CD40_12B4.2C10_K-LV-hIgGK-C] |
| 100 | aa | 12E12 HC [manti-CD40_12E12.3F3_H-V-hIgG4H-C] |
| 101 | aa | 12E12 KC [manti-CD40_12E12.3F3_K-V-hIgGK-C] |
| 102 | aa | 12E12 H2 Humanized HC [hAnti-CD40VH2-LV-hIgG4H-C] |
| 103 | aa | 12E12 H3 Humanized HC [hAnti-CD40VH3-LV-hIgG4H-C] |
| 104 | aa | 12E12 K2 Humanized KC [hAnti-CD40VK2-LV-hIgGK-C] |
| 105 | aa | Pfizer HC [manti-hCD40_CP870893H-LV-hIgG4H-C] |
| 106 | aa | Pfizer KC [manti-hCD40_CP870893K-LV-hIgGK-C] |
| 107 | aa | 24A3 HC [manti-hCD40_24A3.3F1_H-LV-hIgG4H-C] |
| 108 | aa | 24A3 KC [manti-hCD40_24A3.3F1_K-LV-hIgGK-C] |
| 109 | aa | Complete sequence (C3724) FlexV1 hCD40L |
| 110 | aa | 11B6 hCD40L Humanized HC [mAnti-CD40-11B6.1C3-VH-v2-LV-hIgG4H-C-CthermoDockerin] (C3737) (CthermoDockerin) |
| 111 | aa | Amino acid sequence of CthermoDockerin |
| 112 | aa | Amino acid sequence of HIV5pep |
| 113 | nt | Coding sequence of SEQ ID NO: 109 |
| 114 | nt | Coding sequence of SEQ ID NO: 110 |
| 115 | nt | Coding sequence of SEQ ID NO: 112 |
| 116 | aa | C3336 rAB-cetHS-puro-CI2[manti-CD40_11B6.1C3_H-LV-hIgG4H-C-Flex-v1-HPV16E6-HPV16E7-f1] |
| 117 | aa | C3735 rAB-cetHS-puro[mAnti-CD40-11B6.1C3-VH-v2-LV-hIgG4H-C-Flex-v1-Pep-gag17-f1-gag253-f2-nef116-f3-nef66-f4-pol158] |
| 118 | nt | Coding sequence of SEQ ID NO: 117 |
| 119 | aa | 12E12 KC [manti-CD40_12E12.3F3_K-V-hIgGK-C] |
| 120 | nt | Coding sequence of SEQ ID NO: 119 |
| 121 | aa | C3678 [mAnti-CD40-11B6.1C3-VH-v3-LV-hIgG4H-C] |
| 122 | aa | C3682 [mAnti-CD40-11B6.1C3-Vκ-v2-LV-hIgGK-C] |
| 123 | aa | C3724 [mAnti-CD40-11B6.1C3-Vκ-v2-LV-hIgGK-C-Flex-v1-hCD40Ligand] |
| 124 | aa | C566 Ecoli-pET28 [Cohesin-var1-FluM1-6xHis] Cohesin mutant (Cys to Ala change; C38A) fused to Influenza matrix protein 1 |
| 125 | nt | Coding sequence of SEQ ID NO: 124 |
| 126 | nt | Coding sequence of SEQ ID NO: 40 |
| 127 | aa | Coding sequence of SEQ ID NO: 102 |
| 128 | nt | Coding sequence of SEQ ID NO: 121 |
| 129 | nt | Coding sequence of SEQ ID NO: 122 |
| 130 | aa | Flex linker amino acid sequence |
| 131 | aa | C3334 [manti-CD40_11B6.1C3_H-LV-hIgG4H-C-Nhe-Not] |
| 132 | nt | Coding sequence of SEQ ID NO: 130 |
| 133 | aa | C3792 [manti-CD40_11B6.1C3_Syn_K-LV-hIgGK-C-hCD40Ligand] |
| 134 | nt | Coding sequence of SEQ ID NO: 132 |
| 135 | aa | C3823 [mAnti-CD40-11B6.1C3-VH-v2-LV-hIgG4H-C-Flex-v1-hCD40Ligand] |
| 136 | nt | Coding sequence of SEQ ID NO: 134 |
| 137 | aa | C3739 [mAnti-CD40-11B6.1C3-Vκ-v2-LV-hIgGK-C] |
| 138 | nt | Coding sequence of SEQ ID NO: 136 |
| 139 | aa | C3724 [mAnti-CD40-11B6.1C3-Vκ-v2-LV-hIgGK-C-Flex-v1-hCD40Ligand] |
| 140 | nt | Coding sequence of SEQ ID NO: 138 |
| 141 | aa | C3726 [mAnti-CD40-11B6.1C3-VH-v3-LV-hIgG4H-C] |
| 142 | nt | Coding sequence of SEQ ID NO: 140 |
| 143 | aa | C3821 [mAnti-CD40-11B6.1C3-VH-v2-LV-hIgG4H-C-hCD40Ligand] |
| 144 | nt | Coding sequence of SEQ ID NO: 142 |
| 145 | aa | C3725 [mAnti-CD40-11B6.1C3-VH-v2-LV-hIgG4H-C] |

-continued

Tables 5 and 6: Useful sequences for practicing the invention

| SEQ ID | Type | Brief description |
|---|---|---|
| 146 | nt | Coding sequence of SEQ ID NO: 144 |
| 147 | aa | C3678 [mAnti-CD40-11B6.1C3-VH-v3-LV-hIgG4H-C] |
| 148 | nt | Coding sequence of SEQ ID NO: 146 |
| 149 | aa | C3682 [mAnti-CD40-11B6.1C3-V$_K$-v2-LV-hIgGK-C] |
| 150 | nt | Coding sequence of SEQ ID NO: 148 |
| 151 | aa | Mam-cetHS-puro[hCD40--Ecto hFas-TM-IC] |
| 152 | nt | Coding sequence of SEQ ID NO: 151 |
| 153 | aa | 12E12 binding peptide regions identified from Pepscan |
| 154 | aa | 12E12 binding peptide regions identified from Pepscan |
| 155 | aa | 12E12 binding peptide regions identified from Pepscan |
| 156 | aa | 12E12 binding peptide regions identified from Pepscan |
| 157 | aa | 12E12 binding peptide regions identified from Pepscan |
| 158 | aa | 12E12 binding peptide regions identified from Pepscan |
| 159 | aa | 11B6 binding peptide regions identified from Pepscan |
| 160 | aa | 11B6 binding peptide regions identified from Pepscan |
| 161 | aa | 11B6 binding peptide regions identified from Pepscan |
| 162 | aa | 11B6 binding peptide regions identified from Pepscan |
| 163 | aa | 11B6 binding peptide regions identified from Pepscan |
| 164 | aa | 11B6 binding peptide regions identified from Pepscan |
| 165 | aa | 11B6 binding peptide regions identified from Pepscan |
| 166 | aa | 11B6 binding peptide regions identified from Pepscan |
| 167 | aa | 11B6 binding peptide regions identified from Pepscan |
| 168 | aa | monomeric streptavidin 2 domain |
| 169 | nt | Nucleotide coding sequence of monomeric streptavidin 2 domain |
| 170 | aa | C3948:rAB-cetHS-puro[hIgG4H-Flex-v1-S.Aureusmono-Streptavidin-EPEA] |
| 171 | nt | Coding sequence of C3948 |

TABLE 6

| SEQ ID NO: | Full Sequence |
|---|---|
| 1 | EVQLVQSGAEVKKPGASVKISCKASGYSFTGYYMHWVKQAHGQGLEWI<br>GRINPYNGATSYNQNFKDRATLTVDKSTSTAYMELSSLRSEDTAVYYCAR<br>EDYVYWGQGTTVTVSSAKTKGPSVFPLAPCSRSTSESTAALGCLVKDYFP<br>EPVTVSWNSGALTSGVHTFPAVLQSSGLYSLSSVVTVPSSSLGTKTYTCNV<br>DHKPSNTKVDKRVESKYGPPCPPCPAPEFEGGPSVFLFPPKPKDTLMISRTP<br>EVTCVVVDVSQEDPEVQFNWYVDGVEVHNAKTKPREEQFNSTYRVVSVL<br>TVLHQDWLNGKEYKCKVSNKGLPSSIEKTISKAKGQPREPQVYTLPPSQEE<br>MTKNQVSLTCLVKGFYPSDIAVEWESNGQPENNYKTTPPVLDSDGSFFLY<br>SRLTVDKSRWQEGNVFSCSVMHEALHNHYTQKSLSLSLGKAS |
| 2 | DVVMTQSPLSLPVTLGQPASISCRSSQSLVHSNGNTYLHWYQQRPGQSPR<br>LLIYKVSNRFSGVPDRFSGSGSGTDFTLKISRVEAEDVGVYFCSQSTHVPW<br>TFGGGTKLEIKRTVAAPSVFIFPPSDEQLKSGTASVVCLLNNFYPREAKVQ<br>WKVDNALQSGNSQESVTEQDSKDSTYSLSSTLTLSKADYEKHKVYACEV<br>THQGLSSPVTKSFNRGECAS |
| 3 | EVQLVQSGAEVKKPGASVKVSCKASGYSFTGYYMHWVRQAPGQGLEWI<br>GRINPYNGATSYNQNFKDRVTLTVDKSTSTAYMELSSLRSEDTAVYYCAR<br>EDYVYWGQGTTVTVSSAKTKGPSVFPLAPCSRSTSESTAALGCLVKDYFP<br>EPVTVSWNSGALTSGVHTFPAVLQSSGLYSLSSVVTVPSSSLGTKTYTCNV<br>DHKPSNTKVDKRVESKYGPPCPPCPAPEFEGGPSVFLFPPKPKDTLMISRTP<br>EVTCVVVDVSQEDPEVQFNWYVDGVEVHNAKTKPREEQFNSTYRVVSVL<br>TVLHQDWLNGKEYKCKVSNKGLPSSIEKTISKAKGQPREPQVYTLPPSQEE<br>MTKNQVSLTCLVKGFYPSDIAVEWESNGQPENNYKTTPPVLDSDGSFFLY<br>SRLTVDKSRWQEGNVFSCSVMHEALHNHYTQKSLSLSLGKAS |
| 4 | DVVMTQSPLSLPVTLGQPASISCRSSQSLVHSNGNTYLHWYQQRPGQSPR<br>LLIYKVSNRFSGVPDRFSGSGSGTDFTLKISRVEAEDVGVYFCSQSTHVPW<br>TFGGGTKLEIKRTVAAPSVFIFPPSDEQLKSGTASVVCLLNNFYPREAKVQ<br>WKVDNALQSGNSQESVTEQDSKDSTYSLSSTLTLSKADYEKHKVYACEV<br>THQGLSSPVTKSFNRGECAS |
| 5 | DVVMTQSPLSLPVTLGQPASISCRSSQSLVHSNGNTYLHWYQQRPGQSPR<br>LLIYKVSNRFSGVPDRFSGSGSGTDFTLKISRVEAEDVGVYFCSQSTHVPW<br>TFGGGTKLEIKRTVAAPSVFIFPPSDEQLKSGTASVVCLLNNFYPREAKVQ<br>WKVDNALQSGNSQESVTEQDSKDSTYSLSSTLTLSKADYEKHKVYACEV<br>THQGLSSPVTKSFNRGECASQTPTNTISVTPTNNSTPTNNSNPKPNPASMQ<br>KGDQNPQIAAHVISEASSKTTSVLQWAEKGYYTMSNNLVTLENGKQLTV |

TABLE 6-continued

| SEQ ID NO: | Full Sequence |
|---|---|

KRQGLYYIYAQVTFCSNREASSQAPFIASLCLKSPGRFERILLRAANTHSSA
KPCGQQSIHLGGVFELQPGASVFVNVTDPSQVSHGTGFTSFGLLKL

6　EVQLVQSGAEVKKPGASVKISCKASGYSFTGYYMHWVKQAHGQGLEWI
GRINPYNGATSYNQNFKDRATLTVDKSTSTAYMELSSLRSEDTAVYYCAR
EDYVYWGQGTTVTVSSAKTKGPSVFPLAPCSRSTSESTAALGCLVKDYFP
EPVTVSWNSGALTSGVHTFPAVLQSSGLYSLSSVVTVPSSSLGTKTYTCNV
DHKPSNTKVDKRVESKYGPPCPPCPAPEFEGGPSVFLFPPKPKDTLMISRTP
EVTCVVVDVSQEDPEVQFNWYVDGVEVHNAKTKPREEQFNSTYRVVSVL
TVLHQDWLNGKEYKCKVSNKGLPSSIEKTISKAKGQPREPQVYTLPPSQEE
MTKNQVSLTCLVKGFYPSDIAVEWESNGQPENNYKTTPPVLDSDGSFFLY
SRLTVDKSRWQEGNVFSCSVMHEALHNHYTQKSLSLSLGKAS

7　ATGGTTCGTCTGCCTCTGCAGTGCGTCCTCTGGGGCTGCTTGCTGACCG
CTGTCCATCCAGAACCACCCACTGCATGCAGAGAAAAACAGTACCTAA
TAAACAGTCAGTGCTGTTCTTTGTGCCAGCCAGGACAGAAACTGGTGA
GTGACTGCACAGAGTTCACTGAAACGGAATGCCTTCCTTGCGGTGAAA
GCGAATTCCTAGACACCTGGAACAGAGAGACACACTGCCACCAGCAC
AAATACTGCGACCCCAACCTAGGGCTTCGGGTCCAGCAGAAGGGCACC
TCAGAAACAGACACCATCTGCACCTGTGAAGAAGGCTGGCACTGTACG
AGTGAGGCCTGTGAGAGCTGTGTCCTGCACCGCTCATGCTCGCCCGGC
TTTGGGGTCAAGCAGATTGCTACAGGGGTTTCTGATACCATCTGCGAG
CCCTGCCCAGTCGGCTTCTTCTCCAATGTGTCATCTGCTTTCGAAAAT
GTCACCCTTGGACAAGCTGTGAGACCAAAGACCTGGTTGTGCAACAGG
CAGGCACAAACAAGACTGATGTTGTCTGTGGTCCCCAGGATCGGCTGA
GAGCCCTGGTGGTGATCCCCATCATCTTCGGGATCCTGTTTGCCATCCT
CTTGGTGCTGGTCTTTATCAAAAAGGTGGCCAAGAAGCCAACCAATAA
GGCCCCCCACCCCAAGCAGGAACCCCAGGAGATCAATTTTCCCGACGA
TCTTCCTGGCTCCAACACTGCTGCTCCAGTGCAGGAGACTTTACATGGA
TGCCAACCGGTCACCCAGGAGGATGGCAAAGAGAGTCGCATCTCAGTG
CAGGAGAGACAG

8　EVQLVQSGAEVKKPGASVKVSCKASGYSFTGYYMHWVRQAPGQGLEWI
GRINPYNGATSYNQNFKDRVTLTVDKSTSTAYMELSSLRSEDTAVYYCAR
EDYVYWGQGTTVTVSSAKTKGPSVFPLAPCSRSTSESTAALGCLVKDYFP
EPVTVSWNSGALTSGVHTFPAVLQSSGLYSLSSVVTVPSSSLGTKTYTCNV
DHKPSNTKVDKRVESKYGPPCPPCPAPEFEGGPSVFLEPPKPKDTLMISRTP
EVTCVVVDVSQEDPEVQFNWYVDGVEVHNAKTKPREEQFNSTYRVVSVL
TVLHQDWLNGKEYKCKVSNKGLPSSIEKTISKAKGQPREPQVYTLPPSQEE
MTKNQVSLTCLVKGFYPSDIAVEWESNGQPENNYKTTPPVLDSDGSFFLY
SRLTVDKSRWQEGNVFSCSVMHEALHNHYTQKSLSLSLGKAS

9　EVQLVQSGAEVKKPGASVKISCKASGYSFTGYYMHWVKQAHGQGLEWI
GRINPYNGATSYNQNFKDRATLTVDKSTSTAYMELSSLRSEDTAVYYCAR
EDYVYWGQGTTVTVSSAKTKGPSVFPLAPCSRSTSESTAALGCLVKDYFP
EPVTVSWNSGALTSGVHTFPAVLQSSGLYSLSSVVTVPSSSLGTKTYTCNV
DHKPSNTKVDKRVESKYGPPCPPCPAPEFEGGPSVFLEPPKPKDTLMISRTP
EVTCVVVDVSQEDPEVQFNWYVDGVEVHNAKTKPREEQFNSTYRVVSVL
TVLHQDWLNGKEYKCKVSNKGLPSSIEKTISKAKGQPREPQVYTLPPSQEE
MTKNQVSLTCLVKGFYPSDIAVEWESNGQPENNYKTTPPVLDSDGSFFLY
SRLTVDKSRWQEGNVFSCSVMHEALHNHYTQKSLSLSLGKASQTPTNTIS
VTPTNNSTPTNNSNPKPNPASEKIRLRPGGKKKYKLKHIVASSSVSPTTSVH
PTPTSVPPTPTKSSPASNPPIPVGEIYKRWIILGLNKIVRMYSPTSILDASPTS
TPADSSTITPTATPTATPTIKGASHTQGYFPDWQNYTPGPGVRYPLTFGWL
YKLASTVTPTATATPSAIVTTITPTATTKPASVGFPVTPQVPLRPMTYKAA
VDLSHFLKEKGGLASTNGSITVAATAPTVTPTVNATPSAAASAIFQSSMTK
ILEPFRKQNPDIVIYQYMDDLYAS

10　DVVMTQSPLSLPVTLGQPASISCRSSQSLVHSNGNTYLHWYQQRPGQSPR
LLIYKVSNRFSGVPDRFSGSGSGTDFTLKISRVEAEDVGVYFCSQSTHVPW
TFGGGTKLEIKRTVAAPSVFIFPPSDEQLKSGTASVVCLLNNFYPREAKVQ
WKVDNALQSGNSQESVTEQDSKDSTYSLSSTLTLSKADYEKHKVYACEV
THQGLSSPVTKSFNRGECAS

11　EVQLVQSGAEVKKPGASVKISCKASGYSFTGYYMHWVKQAHGQGLEWI
GRINPYNGATSYNQNFKDRATLTVDKSTSTAYMELSSLRSEDTAVYYCAR
EDYVYWGQGTTVTVSSAKTKGPSVFPLAPCSRSTSESTAALGCLVKDYFP
EPVTVSWNSGALTSGVHTFPAVLQSSGLYSLSSVVTVPSSSLGTKTYTCNV
DHKPSNTKVDKRVESKYGPPCPPCPAPEFEGGPSVFLEPPKPKDTLMISRTP
EVTCVVVDVSQEDPEVQFNWYVDGVEVHNAKTKPREEQFNSTYRVVSVL
TVLHQDWLNGKEYKCKVSNKGLPSSIEKTISKAKGQPREPQVYTLPPSQEE
MTKNQVSLTCLVKGFYPSDIAVEWESNGQPENNYKTTPPVLDSDGSFFLY
SRLTVDKSRWQEGNVFSCSVMHEALHNHYTQKSLSLSLGKASQTPTNTIS
VTPTNNSTPTNNSNPKPNPASEKIRLRPGGKKKYKLKHIVASSSVSPTTSVH
PTPTSVPPTPTKSSPASNPPIPVGEIYKRWIILGLNKIVRMYSPTSILDASPTS
TPADSSTITPTATPTATPTIKGASHTQGYFPDWQNYTPGPGVRYPLTFGWL

TABLE 6-continued

SEQ
ID
NO: Full Sequence

```
    YKLASTVTPTATATPSAIVTTITPTATTKPASVGFPVTPQVPLRPMTYKAA
    VDLSHFLKEKGGLASTNGSITVAATAPTVTPTVNATPSAAASAIFQSSMTK
    ILEPFRKQNPDIVIYQYMDDLYAS

12  DVVMTQSPLSLPVTLGQPASISCRSSQSLVHSNGNTYLHWYQQRPGQSPR
    LLIYKVSNRFSGVPDRFSGSGSGTDFTLKISRVEAEDVGVYFCSQSTHVPW
    TFGGGTKLEIKRTVAAPSVFIFPPSDEQLKSGTASVVCLLNNFYPREAKVQ
    WKVDNALQSGNSQESVTEQDSKDSTYSLSSTLTLSKADYEKHKVYACEV
    THQGLSSPVTKSFNRGECASQTPTNTISVTPTNNSTPTNNSNPKPNPASMQ
    KGDQNPQIAAHVISEASSKTTSVLQWAEKGYYTMSNNLVTLENGKQLTV
    KRQGLYYIYAQVTFCSNREASSQAPFIASLCLKSPGRFERILLRAANTHSSA
    KPCGQQSIHLGGVFELQPGASVFVNVTDPSQVSHGTGFTSFGLLKL

13  MVRLPLQCVLWGCLLTAVHPEPPTACREKQYLINSQCCSLCQPGQKLVSD
    CTEFTETECLPCGESEFLDTWNRETHCHQHKYCDPNLGLRVQQKGTSETD
    TICTCEEGWHCTSEACESCVLHRSCSPGFGVKQIATGVSDTICEPCPVGFFS
    NVSSAFEKCHPWTSCETKDLVVQQAGTNKTDVVCGPQDRLRALVVIPIIF
    GILFAILLVLVFIKKVAKKPTNKAPHPKQEPQEINFPDDLPGSNTAAPVQET
    LHGCQPVTQEDGKESRISVQERQ

14  MQKGDQNPQIAAHVISEASSKTTSVLQWAEKGYYTMSNNLVTLENGKQL
    TVKRQGLYYIYAQVTFCSNREASSQAPFIASLCLKSPGRFERILLRAANTHS
    SAKPCGQQSIHLGGVFELQPGASVFVNVTDPSQVSHGTGFTSFGLLKL

15  QTPTNTISVTPTNNSTPTNNSNPKPNP

16  EKIRLRPGGKKKYKLKHIV

17  NPPIPVGEIYKRWIILGLNKIVRMYSPTSILD

18  HTQGYFPDWQNYTPGPGVRYPLTFGWLYKL

19  AIFQSSMTKILEPFRKQNPDIVIYQYMDDLY

20  VGFPVTPQVPLRPMTYKAAVDLSHFLKEKGGL

21  EVQLVQSGAEVKKPGASVKISCKASGYSFTGYYMHWVKQAHGQGLEWI
    GRINPYNGATSYNQNFKDRATLTVDKSTSTAYMELSSLRSEDTAVYYCAR
    EDYVYWGQGTTVTVSSAKTKGPSVFPLAPCSRSTSESTAALGCLVKDYFP
    EPVTVSWNSGALTSGVHTFPAVLQSSGLYSLSSVVTVPSSSLGTKTYTCNV
    DHKPSNTKVDKRVESKYGPPCPPCPAPEFEGGPSVFLFPPKPKDTLMISRTP
    EVTCVVVDVSQEDPEVQFNWYVDGVEVHNAKTKPREEQFNSTYRVVSVL
    TVLHQDWLNGKEYKCKVSNKGLPSSIEKTISKAKGQPREPQVYTLPPSQEE
    MTKNQVSLTCLVKGFYPSDIAVEWESNGQPENNYKTTPPVLDSDGSFFLY
    SRLTVDKSRWQEGNVFSCSVMHEALHNHYTQKSLSLSLGKAS

22  DVVMTQSPLSLPVTLGQPASISCRSSQSLVHSNGNTYLHWYQQRPGQSPR
    LLIYKVSNRFSGVPDRFSGSGSGTDFTLKISRVEAEDVGVYFCSQSTHVPW
    TFGGGTKLEIKRTVAAPSVFIFPPSDEQLKSGTASVVCLLNNFYPREAKVQ
    WKVDNALQSGNSQESVTEQDSKDSTYSLSSTLTLSKADYEKHKVYACEV
    THQGLSSPVTKSFNRGECAS

23  EVQLVQSGAEVKKPGASVKVSCKASGYSFTGYYMHWVRQAPGQGLEWI
    GRINPYNGATSYNQNFKDRVTLTVDKSTSTAYMELSSLRSEDTAVYYCAR
    EDYVYWGQGTTVTVSSAKTKGPSVFPLAPCSRSTSESTAALGCLVKDYFP
    EPVTVSWNSGALTSGVHTFPAVLQSSGLYSLSSVVTVPSSSLGTKTYTCNV
    DHKPSNTKVDKRVESKYGPPCPPCPAPEFEGGPSVFLFPPKPKDTLMISRTP
    EVTCVVVDVSQEDPEVQFNWYVDGVEVHNAKTKPREEQFNSTYRVVSVL
    TVLHQDWLNGKEYKCKVSNKGLPSSIEKTISKAKGQPREPQVYTLPPSQEE
    MTKNQVSLTCLVKGFYPSDIAVEWESNGQPENNYKTTPPVLDSDGSFFLY
    SRLTVDKSRWQEGNVFSCSVMHEALHNHYTQKSLSLSLGKAS

24  GAGGTCCAGCTGGTGCAATCTGGAGCTGAGGTGAAGAAGCCTGGGGCT
    TCAGTGAAGATATCCTGCAAGGCTTCTGGATACTCCTTCACTGGCTACT
    ACATGCACTGGGTGAAGCAGGCCCATGGACAAGGGCTTGAGTGGATTG
    GAAGGATTAATCCTTACAATGGTGCTACTAGCTACAACCAGAACTTCA
    AGGACAGAGCCACCTTGACTGTAGACAAGTCCACGAGCACAGCCTACA
    TGGAGCTCAGCAGCCTGAGGTCTGAGGACACGGCAGTCTATTACTGTG
    CAAGAGAGGACTACGTACTGGGGCCAAGGCACCACGGTCACCGTCT
    CCTCAGCCAAAACGAAGGGCCCATCCGTCTTCCCCCTGGCGCCCTGCT
    CCAGGAGCACCTCCGAGAGCACAGCCGCCCTGGGCTGCCTGGTCAAGG
    ACTACTTCCCCGAACCGGTGACGGTGTCGTGGAACTCAGGCGCCCTGA
    CCAGCGGCGTGCACACCTTCCCGGCTGTCCTACAGTCCTCAGGACTCTA
    CTCCCTCAGCAGCGTGGTGACCGTGCCCTCCAGCAGCTTGGGCACGAA
    GACCTACACCTGCAACGTAGATCACAAGCCCAGCAACACCAAGGTGG
    ACAAGAGAGTTGAGTCCAAATATGGTCCCCCATGCCCACCCTGCCCAG
```

TABLE 6-continued

| SEQ ID NO: | Full Sequence |
|---|---|

CACCTGAGTTCGAAGGGGGACCATCAGTCTTCCTGTTCCCCCCAAAAC
CCAAGGACACTCTCATGATCTCCCGGACCCCTGAGGTCACGTGCGTGG
TGGTGGACGTGAGCCAGGAAGACCCCGAGGTCCAGTTCAACTGGTACG
TGGATGGCGTGGAGGTGCATAATGCCAAGACAAAGCCGCGGGAGGAG
CAGTTCAACAGCACGTACCGTGTGGTCAGCGTCCTCACCGTCCTGCAC
CAGGACTGGCTGAACGGCAAGGAGTACAAGTGCAAGGTCTCCAACAA
AGGCCTCCCGTCCTCCATCGAGAAAACCATCTCCAAAGCCAAAGGGCA
GCCCCGAGAGCCACAGGTGTACACCCTGCCCCCATCCCAGGAGGAGAT
GACCAAGAACCAGGTCAGCCTGACCTGCCTGGTCAAAGGCTTCTACCC
CAGCGACATCGCCGTGGAGTGGGAGAGCAATGGGCAGCCGGAGAACA
ACTACAAGACCACGCCTCCCGTGCTGGACTCCGACGGCTCCTTCTTCCT
CTACAGCAGGCTAACCGTGGACAAGAGCAGGTGGCAGGAGGGGAATG
TCTTCTCATGCTCCGTGATGCATGAGGCTCTGCACAACCACTACACACA
GAAGAGCCTCTCCCTGTCTCTGGGTAAAGCTAGCTGA

25 GATGTTGTGATGACCCAATCTCCACTCTCCCTGCCTGTCACCCTTGGAC
AGCCGGCCTCCATCTCTTGCAGGTCTAGTCAGAGCCTTGTACACAGTA
ATGGAAACACCTATTTACATTGGTACCAGCAGAGACCAGGCCAGTCTC
CAAGGCTCCTGATCTACAAAGTTTCCAACCGATTTTCTGGGGTCCCAGA
CAGGTTCAGTGGCAGTGGATCAGGGACAGATTTCACACTCAAGATCAG
CAGAGTGGAGGCTGAAGATGTTGGAGTTTATTTCTGCTCTCAAAGTAC
ACATGTTCCTTGGACGTTCGGCGGAGGGACCAAGCTCGAGATCAAACG
AACTGTGGCTGCACCATCTGTCTTCATCTTCCCGCCATCTGATGAGCAG
TTGAAATCTGGAACTGCCTCTGTTGTGTGCCTGCTGAATAACTTCTATC
CCAGAGAGGCCAAAGTACAGTGGAAGGTGGATAACGCCCTCCAATCG
GGTAACTCCCAGGAGAGTGTCACAGAGCAGGACAGCAAGGACAGCAC
CTACAGCCTCAGCAGCACCCTGACGCTGAGCAAAGCAGACTACGAGA
AACACAAAGTCTATGCCTGCGAAGTCACCCATCAGGGCCTGAGCTCGC
CCGTCACAAAGAGCTTCAACAGGGGAGAGTGTGCTAGCTGA

26 GAGGTCCAGCTGGTGCAATCTGGAGCTGAGGTGAAGAAGCCTGGGGCT
TCAGTGAAGGTCTCCTGCAAGGCTTCTGGATACTCCTTCACTGGCTACT
ACATGCACTGGGTGCGACAGGCCCCTGGACAAGGGCTTGAGTGGATTG
GAAGGATTAATCCTTACAATGGTGCTACTAGCTACAACCAGAACTTCA
AGGACAGAGTCACCTTGACTGTAGACAAGTCCACGAGCACAGCCTACA
TGGAGCTCAGCAGCCTGAGGTCTGAGGACACGGCAGTCTATTACTGTG
CAAGAGAGGACTACGTGTACTGGGGCCAAGGCACCACGGTCACCGTCT
CCTCAGCCAAAACGAAGGGCCCATCCGTCTTCCCCCTGGCGCCCTGCT
CCAGGAGCACCTCCGAGAGCACAGCCGCCCTGGGCTGCCTGGTCAAGG
ACTACTTCCCCGAACCGGTGACGGTGTCGTGGAACTCAGGCGCCCTGA
CCAGCGGCGTGCACACCTTCCCGGCTGTCCTACAGTCCTCAGGACTCTA
CTCCCTCAGCAGCGTGGTGACCGTGCCCTCCAGCAGCTTGGGCACGAA
GACCTACACCTGCAACGTAGATCACAAGCCCAGCAACACCAAGGTGG
ACAAGAGAGTTGAGTCCAAATATGGTCCCCCATGCCCACCCTGCCCAG
CACCTGAGTTCGAAGGGGGACCATCAGTCTTCCTGTTCCCCCCAAAAC
CCAAGGACACTCTCATGATCTCCCGGACCCCTGAGGTCACGTGCGTGG
TGGTGGACGTGAGCCAGGAAGACCCCGAGGTCCAGTTCAACTGGTACG
TGGATGGCGTGGAGGTGCATAATGCCAAGACAAAGCCGCGGGAGGAG
CAGTTCAACAGCACGTACCGTGTGGTCAGCGTCCTCACCGTCCTGCAC
CAGGACTGGCTGAACGGCAAGGAGTACAAGTGCAAGGTCTCCAACAA
AGGCCTCCCGTCCTCCATCGAGAAAACCATCTCCAAAGCCAAAGGGCA
GCCCCGAGAGCCACAGGTGTACACCCTGCCCCCATCCCAGGAGGAGAT
GACCAAGAACCAGGTCAGCCTGACCTGCCTGGTCAAAGGCTTCTACCC
CAGCGACATCGCCGTGGAGTGGGAGAGCAATGGGCAGCCGGAGAACA
ACTACAAGACCACGCCTCCCGTGCTGGACTCCGACGGCTCCTTCTTCCT
CTACAGCAGGCTAACCGTGGACAAGAGCAGGTGGCAGGAGGGGAATG
TCTTCTCATGCTCCGTGATGCATGAGGCTCTGCACAACCACTACACACA
GAAGAGCCTCTCCCTGTCTCTGGGTAAAGCTAGCTGA

27 GYSFTGYYMH

28 RINPYNGATSYNQNFKDR

29 EDYVY

30 RSSQSLVHSNGNTYLH

31 KVSNRFS

32 SQSTHVPWT

33 GAGGTCCAGCTGGTGCAATCTGGAGCTGAGGTGAAGAAGCCTGGGGCT
TCAGTGAAGATATCCTGCAAGGCTTCTGGATACTCCTTCACTGGCTACT
ACATGCACTGGGTGAAGCAGGCCCATGGACAAGGGCTTGAGTGGATTG
GAAGGATTAATCCTTACAATGGTGCTACTAGCTACAACCAGAACTTCA
AGGACAGAGCCACCTTGACTGTAGACAAGTCCACGAGCACAGCCTACA

TABLE 6-continued

| SEQ ID NO: | Full Sequence |
|---|---|

TGGAGCTCAGCAGCCTGAGGTCTGAGGACACGGCAGTCTATTACTGTG
CAAGAGAGGACTACGTGTACTGGGGCCAAGGCACCACGGTCACCGTCT
CCTCAGCCAAAACGAAGGGCCCATCCGTCTTCCCCCTGGCGCCCTGCT
CCAGGAGCACCTCCGAGAGCACAGCCGCCCTGGGCTGCCTGGTCAAGG
ACTACTTCCCCGAACCGGTGACGGTGTCGTGGAACTCAGGCGCCCTGA
CCAGCGGCGTGCACACCTTCCCGGCTGTCCTACAGTCCTCAGGACTCTA
CTCCCTCAGCAGCGTGGTGACCGTGCCCTCCAGCAGCTTGGGCACGAA
GACCTACACCTGCAACGTAGATCACAAGCCCAGCAACACCAAGGTGG
ACAAGAGAGTTGAGTCCAAATATGGTCCCCCATGCCCACCCTGCCCAG
CACCTGAGTTCGAAGGGGGACCATCAGTCTTCCTGTTCCCCCCAAAAC
CCAAGGACACTCTCATGATCTCCCGGACCCCTGAGGTCACGTGCGTGG
TGGTGGACGTGAGCCAGGAAGACCCCGAGGTCCAGTTCAACTGGTACG
TGGATGGCGTGGAGGTGCATAATGCCAAGACAAAGCCGCGGGAGGAG
CAGTTCAACAGCACGTACCGTGTGGTCAGCGTCCTCACCGTCCTGCAC
CAGGACTGGCTGAACGGCAAGGAGTACAAGTGCAAGGTCTCCAACAA
AGGCCTCCCGTCCTCCATCGAGAAAACCATCTCCAAAGCCAAAGGGCA
GCCCCGAGAGCCACAGGTGTACACCCTGCCCCCATCCCAGGAGGAGAT
GACCAAGAACCAGGTCAGCCTGACCTGCCTGGTCAAAGGCTTCTACCC
CAGCGACATCGCCGTGGAGTGGGAGAGCAATGGGCAGCCGGAGAACA
ACTACAAGACCACGCCTCCCGTGCTGGACTCCGACGGCTCCTTCTTCCT
CTACAGCAGGCTAACCGTGGACAAGAGCAGGTGGCAGGAGGGGAATG
TCTTCTCATGCTCCGTGATGCATGAGGCTCTGCACAACCACTACACACA
GAAGAGCCTCTCCCTGTCTCTGGGTAAAGCTAGC<u>TGA</u>

34  GATGTTGTGATGACCCAATCTCCACTCTCCCTGCCTGTCACCCTTGGAC
AGCCGGCCTCCATCTCTTGCAGGTCTAGTCAGAGCCTTGTACACAGTA
ATGGAAACACCTATTTACATTGGTACCAGCAGAGACCAGGCCAGTCTC
CAAGGCTCCTGATCTACAAAGTTTCCAACCGATTTTCTGGGGTCCCAGA
CAGGTTCAGTGGCAGTGGATCAGGGACAGATTTCACACTCAAGATCAG
CAGAGTGGAGGCTGAAGATGTTGGAGTTTATTTCTGCTCTCAAAGTAC
ACATGTTCCTTGGACGTTCGGCGGAGGGACCAAGCTCGAGATCAAACG
AACTGTGGCTGCACCATCTGTCTTCATCTTCCCGCCATCTGATGAGCAG
TTGAAATCTGGAACTGCCTCTGTTGTGTGCCTGCTGAATAACTTCTATC
CCAGAGAGGCCAAAGTACAGTGGAAGGTGGATAACGCCCTCCAATCG
GGTAACTCCCAGGAGAGTGTCACAGAGCAGGACAGCAAGGACAGCAC
CTACAGCCTCAGCAGCACCCTGACGCTGAGCAAAGCAGACTACGAGA
AACACAAAGTCTATGCCTGCGAAGTCACCCATCAGGGCCTGAGCTCGC
CCGTCACAAAGAGCTTCAACAGGGGAGAGTGTGCTAGCTGA

35  GAGGTCCAGCTGGTGCAATCTGGAGCTGAGGTGAAGAAGCCTGGGGCT
TCAGTGAAGGTCTCCTGCAAGGCTTCTGGATACTCCTTCACTGGCTACT
ACATGCACTGGGTGCGACAGGCCCCTGGACAAGGGCTTGAGTGGATTG
GAAGGATTAATCCTTACAATGGTGCTACTAGCTACAACCAGAACTTCA
AGGACAGAGTCACCTTGACTGTAGACAAGTCCACGAGCACAGCCTACA
TGGAGCTCAGCAGCCTGAGGTCTGAGGACACGGCAGTCTATTACTGTG
CAAGAGAGGACTACGTGTACTGGGGCCAAGGCACCACGGTCACCGTCT
CCTCAGCCAAAACGAAGGGCCCATCCGTCTTCCCCCCTGGCGCCCTGCT
CCAGGAGCACCTCCGAGAGCACAGCCGCCCTGGGCTGCCTGGTCAAGG
ACTACTTCCCCGAACCGGTGACGGTGTCGTGGAACTCAGGCGCCCTGA
CCAGCGGCGTGCACACCTTCCCGGCTGTCCTACAGTCCTCAGGACTCTA
CTCCCTCAGCAGCGTGGTGACCGTGCCCTCCAGCAGCTTGGGCACGAA
GACCTACACCTGCAACGTAGATCACAAGCCCAGCAACACCAAGGTGG
ACAAGAGAGTTGAGTCCAAATATGGTCCCCCATGCCCACCCTGCCCAG
CACCTGAGTTCGAAGGGGGACCATCAGTCTTCCTGTTCCCCCCAAAAC
CCAAGGACACTCTCATGATCTCCCGGACCCCTGAGGTCACGTGCGTGG
TGGTGGACGTGAGCCAGGAAGACCCCGAGGTCCAGTTCAACTGGTACG
TGGATGGCGTGGAGGTGCATAATGCCAAGACAAAGCCGCGGGAGGAG
CAGTTCAACAGCACGTACCGTGTGGTCAGCGTCCTCACCGTCCTGCAC
CAGGACTGGCTGAACGGCAAGGAGTACAAGTGCAAGGTCTCCAACAA
AGGCCTCCCGTCCTCCATCGAGAAAACCATCTCCAAAGCCAAAGGGCA
GCCCCGAGAGCCACAGGTGTACACCCTGCCCCCATCCCAGGAGGAGAT
GACCAAGAACCAGGTCAGCCTGACCTGCCTGGTCAAAGGCTTCTACCC
CAGCGACATCGCCGTGGAGTGGGAGAGCAATGGGCAGCCGGAGAACA
ACTACAAGACCACGCCTCCCGTGCTGGACTCCGACGGCTCCTTCTTCCT
CTACAGCAGGCTAACCGTGGACAAGAGCAGGTGGCAGGAGGGGAATG
TCTTCTCATGCTCCGTGATGCATGAGGCTCTGCACAACCACTACACACA
GAAGAGCCTCTCCCTGTCTCTGGGTAAAGCTAGCTGA

36  GATGTTGTGATGACCCAATCTCCACTCTCCCTGCCTGTCACCCTTGGAC
AGCCGGCCTCCATCTCTTGCAGGTCTAGTCAGAGCCTTGTACACAGTA
ATGGAAACACCTATTTACATTGGTACCAGCAGAGACCAGGCCAGTCTC
CAAGGCTCCTGATCTACAAAGTTTCCAACCGATTTTCTGGGGTCCCAGA
CAGGTTCAGTGGCAGTGGATCAGGGACAGATTTCACACTCAAGATCAG
CAGAGTGGAGGCTGAAGATGTTGGAGTTTATTTCTGCTCTCAAAGTAC
ACATGTTCCTTGGACGTTCGGCGGAGGGACCAAGCTCGAGATCAAACG
AACTGTGGCTGCACCATCTGTCTTCATCTTCCCGCCATCTGATGAGCAG

TABLE 6-continued

SEQ
ID
NO: Full Sequence

```
    TTGAAATCTGGAACTGCCTCTGTTGTGTGCCTGCTGAATAACTTCTATC
    CCAGAGAGGCCAAAGTACAGTGGAAGGTGGATAACGCCCTCCAATCG
    GGTAACTCCCAGGAGAGTGTCACAGAGCAGGACAGCAAGGACAGCAC
    CTACAGCCTCAGCAGCACCCTGACGCTGAGCAAAGCAGACTACGAGA
    AACACAAAGTCTATGCCTGCGAAGTCACCCATCAGGGCCTGAGCTCGC
    CCGTCACAAAGAGCTTCAACAGGGGAGAGTGTGCTAGCTGA

37  GATGTTGTGATGACCCAATCTCCACTCTCCCTGCCTGTCACCCTTGGAC
    AGCCGGCCTCCATCTCTTGCAGGTCTAGTCAGAGCCTTGTACACAGTA
    ATGGAAACACCTATTTACATTGGTACCAGCAGAGACCAGGCCAGTCTC
    CAAGGCTCCTGATCTACAAAGTTTCCAACCGATTTTCTGGGGTCCCAGA
    CAGGTTCAGTGGCAGTGGATCAGGGACAGATTTCACACTCAAGATCAG
    CAGAGTGGAGGCTGAAGATGTTGGAGTTTATTTCTGCTCTCAAAGTAC
    ACATGTTCCTTGGACGTTCGGCGGAGGGACCAAGCTCGAGATCAAACG
    AACTGTGGCTGCACCATCTGTCTTCATCTTCCCGCCATCTGATGAGCAG
    TTGAAATCTGGAACTGCCTCTGTTGTGTGCCTGCTGAATAACTTCTATC
    CCAGAGAGGCCAAAGTACAGTGGAAGGTGGATAACGCCCTCCAATCG
    GGTAACTCCCAGGAGAGTGTCACAGAGCAGGACAGCAAGGACAGCAC
    CTACAGCCTCAGCAGCACCCTGACGCTGAGCAAAGCAGACTACGAGA
    AACACAAAGTCTATGCCTGCGAAGTCACCCATCAGGGCCTGAGCTCGC
    CCGTCACAAAGAGCTTCAACAGGGGAGAGTGTGCTAGTCAGACCCCCA
    CCAACACCATCAGCGTGACCCCCACCAACAACAGCACCCCCACCAACA
    ACAGCAACCCCAAGCCCAACCCCGCTAGCATGCAGAAGGGAGACCAG
    AACCCTCAGATCGCAGCTCACGTCATCTCCGAGGCTTCTTCCAAGACC
    ACCTCCGTGCTCCAGTGGGCTGAAAAGGGATACTACACCATGAGCAAC
    AACCTGGTGACACTGGAGAACGGCAAGCAGCTCACAGTCAAGCGGCA
    GGGCCTTTACTACATCTATGCCCAGGTGACCTTCTGCTCCAACAGGGA
    GGCCTCCAGCCAGGCCCCTTTCATTGCCTCTCTGTGTCTCAAGAGCCCA
    GGCAGATTCGAGAGGATTCTCCTGCGCGCCGCCAATACACACAGTCA
    GCCAAACCCTGCGGGCAACAGTCAATTCACCTGGGGGGGGTCTTTGAG
    TTGCAGCCAGGGGCCAGTGTCTTCGTGAACGTGACAGATCCCAGTCAG
    GTGAGCCATGGCACTGGCTTTACTAGCTTTGGGTTGCTGAAACTGTGA

38  GAGGTCCAGCTGGTGCAATCTGGAGCTGAGGTGAAGAAGCCTGGGGCT
    TCAGTGAAGATATCCTGCAAGGCTTCTGGATACTCCTTCACTGGCTACT
    ACATGCACTGGGTGAAGCAGGCCCATGGACAAGGGCTTGAGTGGATTG
    GAAGGATTAATCCTTACAATGGTGCTACTAGCTACAACCAGAACTTCA
    AGGACAGAGCCACCTTGACTGTAGACAAGTCCACGAGCACAGCCTACA
    TGGAGCTCAGCAGCCTGAGGTCTGAGGACACGGCAGTCTATTACTGTG
    CAAGAGAGGACTACGTGTACTGGGGCCAAGGCACCACGGTCACCGTCT
    CCTCAGCCAAAACGAAGGGCCCATCCGTCTTCCCCCTGGCGCCCTGCT
    CCAGGAGCACCTCCGAGAGCACAGCCGCCCTGGGCTGCCTGGTCAAGG
    ACTACTTCCCCGAACCGGTGACGGTGTCGTGGAACTCAGGCGCCCTGA
    CCAGCGGCGTGCACACCTTCCCGGCTGTCCTACAGTCCTCAGGACTCTA
    CTCCCTCAGCAGCGTGGTGACCGTGCCCTCCAGCAGCTTGGGCACGAA
    GACCTACACCTGCAACGTAGATCACAAGCCCAGCAACACCAAGGTGG
    ACAAGAGAGTTGAGTCCAAATATGGTCCCCCATGCCCACCCTGCCCAG
    CACCTGAGTTCGAAGGGGGACCATCAGTCTTCCTGTTCCCCCCAAAAC
    CCAAGGACACTCTCATGATCTCCCGGACCCCTGAGGTCACGTGCGTGG
    TGGTGGACGTGAGCCAGGAAGACCCCGAGGTCCAGTTCAACTGGTACG
    TGGATGGCGTGGAGGTGCATAATGCCAAGACAAAGCCGCGGGAGGAG
    CAGTTCAACAGCACGTACCGTGTGGTCAGCGTCCTCACCGTCCTGCAC
    CAGGACTGGCTGAACGGCAAGGAGTACAAGTGCAAGGTCTCCAACAA
    AGGCCTCCCGTCCTCCATCGAGAAAACCATCTCCAAAGCCAAAGGGCA
    GCCCCGAGAGCCACAGGTGTACACCCTGCCCCCATCCCAGGAGGAGAT
    GACCAAGAACCAGGTCAGCCTGACCTGCCTGGTCAAAGGCTTCTACCC
    CAGCGACATCGCCGTGGAGTGGGAGAGCAATGGGCAGCCGGAGAACA
    ACTACAAGACCACGCCTCCCGTGCTGGACTCCGACGGCTCCTTCTTCCT
    CTACAGCAGGCTAACCGTGGACAAGAGCAGGTGGCAGGAGGGGAATG
    TCTTCTCATGCTCCGTGATGCATGAGGCTCTGCACAACCACTACACACA
    GAAGAGCCTCTCCCTGTCTCTGGGTAAAGCTAGCTGA

39  GATGTTGTGATGACCCAATCTCCACTCTCCCTGCCTGTCACCCTTGGAC
    AGCCGGCCTCCATCTCTTGCAGGTCTAGTCAGAGCCTTGTACACAGTA
    ATGGAAACACCTATTTACATTGGTACCAGCAGAGACCAGGCCAGTCTC
    CAAGGCTCCTGATCTACAAAGTTTCCAACCGATTTTCTGGGGTCCCAGA
    CAGGTTCAGTGGCAGTGGATCAGGGACAGATTTCACACTCAAGATCAG
    CAGAGTGGAGGCTGAAGATGTTGGAGTTTATTTCTGCTCTCAAAGTAC
    ACATGTTCCTTGGACGTTCGGCGGAGGGACCAAGCTCGAGATCAAACG
    AACTGTGGCTGCACCATCTGTCTTCATCTTCCCGCCATCTGATGAGCAG
    TTGAAATCTGGAACTGCCTCTGTTGTGTGCCTGCTGAATAACTTCTATC
    CCAGAGAGGCCAAAGTACAGTGGAAGGTGGATAACGCCCTCCAATCG
    GGTAACTCCCAGGAGAGTGTCACAGAGCAGGACAGCAAGGACAGCAC
    CTACAGCCTCAGCAGCACCCTGACGCTGAGCAAAGCAGACTACGAGA
    AACACAAAGTCTATGCCTGCGAAGTCACCCATCAGGGCCTGAGCTCGC
    CCGTCACAAAGAGCTTCAACAGGGGAGAGTGTGCTAGTCAGACCCCCA
```

TABLE 6-continued

| SEQ ID NO: | Full Sequence |
|---|---|

CCAACACCATCAGCGTGACCCCCACCAACAACAGCACCCCCACCAACA
ACAGCAACCCCAAGCCCAACCCCGCTAGCATGCAGAAGGGGAGACCAG
AACCCTCAGATCGCAGCTCACGTCATCTCCGAGGCTTCTTCCAAGACC
ACCTCCGTGCTCCAGTGGGCTGAAAAGGGATACTACACCATGAGCAAC
AACCTGGTGACACTGGAGAACGGCAAGCAGCTCACAGTCAAGCGGCA
GGGCCTTTACTACATCTATGCCCAGGTGACCTTCTGCTCCAACAGGGA
GGCCTCCAGCCAGGCCCCTTTCATTGCCTCTCTGTGTCTCAAGAGCCCA
GGCAGATTCGAGAGGATTCTCCTGCGCGCCGCCAATACACACAGCTCA
GCCAAACCCTGCGGGCAACAGTCAATTCACCTGGGGGGGGTCTTTGAG
TTGCAGCCAGGGGCCAGTGTCTTCGTGAACGTGACAGATCCCAGTCAG
GTGAGCCATGGCACTGGCTTTACTAGCTTTGGGTTGCTGAAACTGTGA

40  EVKLVESGGGLVQPGGSLKLSCATSGFTFSDYYMYWVRQTPEKRLEWVA
    YINSGGGSTYYPDTVKGRFTISRDNAKNTLYLQMSRLKSEDTAMYYCARR
    GLPFHAMDYWGQGTSVTVSSAK

41  GAGGTCCAGCTGGTGCAATCTGGAGCTGAGGTGAAGAAGCCTGGGGCT
    TCAGTGAAGGTCTCCTGCAAGGCTTCTGGATACTCCTTCACTGGCTACT
    ACATGCACTGGGTGCGACAGGCCCCTGGACAAGGGCTTGAGTGGATTG
    GAAGGATTAATCCTTACAATGGTGCTACTAGCTACAACCAGAACTTCA
    AGGACAGAGTCACCTTGACTGTAGACAAGTCCACGAGCACAGCCTACA
    TGGAGCTCAGCAGCCTGAGGTCTGAGGACACGGCAGTCTATTACTGTG
    CAAGAGAGGACTACGTGTACTGGGGCCAAGGCACCACGGTCACCGTCT
    CCTCAGCCAAAACGAAGGGCCCATCCGTCTTCCCCCTGGCGCCCTGCT
    CCAGGAGCACCTCCGAGAGCACAGCCGCCCTGGGCTGCCTGGTCAAGG
    ACTACTTCCCCGAACCGGTGACGGTGTCGTGGAACTCAGGCGCCCTGA
    CCAGCGGCGTGCACACCTTCCCGGCTGTCCTACAGTCCTCAGGACTCTA
    CTCCCTCAGCAGCGTGGTGACCGTGCCCTCCAGCAGCTTGGGCACGAA
    GACCTACACCTGCAACGTAGATCACAAGCCCAGCAACACCAAGGTGG
    ACAAGAGAGTTGAGTCCAAATATGGTCCCCCATGCCCACCCTGCCCAG
    CACCTGAGTTCGAAGGGGGACCATCAGTCTTCCTGTTCCCCCCAAAAC
    CCAAGGACACTCTCATGATCTCCCGGACCCCTGAGGTCACGTGCGTGG
    TGGTGGACGTGAGCCAGGAAGACCCCGAGGTCCAGTTCAACTGGTACG
    TGGATGGCGTGGAGGTGCATAATGCCAAGACAAAGCCGCGGGAGGAG
    CAGTTCAACAGCACGTACCGTGTGGTCAGCGTCCTCACCGTCCTGCAC
    CAGGACTGGCTGAACGGCAAGGAGTACAAGTGCAAGGTCTCCAACAA
    AGGCCTCCCGTCCTCCATCGAGAAAACCATCTCCAAAGCCAAAGGGCA
    GCCCCGAGAGCCACAGGTGTACACCCTGCCCCCATCCCAGGAGGAGAT
    GACCAAGAACCAGGTCAGCCTGACCTGCCTGGTCAAAGGCTTCTACCC
    CAGCGACATCGCCGTGGAGTGGGAGAGCAATGGGCAGCCGGAGAACA
    ACTACAAGACCACGCCTCCCGTGCTGGACTCCGACGGCTCCTTCTTCCT
    CTACAGCAGGCTAACCGTGGACAAGAGCAGGTGGCAGGAGGGGAATG
    TCTTCTCATGCTCCGTGATGCATGAGGCTCTGCACAACCACTACACACA
    GAAGAGCCTCTCCCTGTCTCTGGGTAAAGCTAGCTGA

42  GATGTTGTGATGACCCAATCTCCACTCTCCCTGCCTGTCACCCTTGGAC
    AGCCGGCCTCCATCTCTTGCAGGTCTAGTCAGAGCCTTGTACACAGTA
    ATGGAAACACCTATTTACATTGGTACCAGCAGAGACCAGGCCAGTCTC
    CAAGGCTCCTGATCTACAAAGTTTCCAACCGATTTTCTGGGGTCCCAGA
    CAGGTTCAGTGGCAGTGGATCAGGGACAGATTTCACACTCAAGATCAG
    CAGAGTGGAGGCTGAAGATGTTGGAGTTTATTTCTGCTCTCAAAGTAC
    ACATGTTCCTTGGACGTTCGGCGGAGGGACCAAGCTCGAGATCAAACG
    AACTGTGGCTGCACCATCTGTCTTCATCTTCCCGCCATCTGATGAGCAG
    TTGAAATCTGGAACTGCCTCTGTTGTGTGCCTGCTGAATAACTTCTATC
    CCAGAGAGGCCAAAGTACAGTGGAAGGTGGATAACGCCCTCCAATCG
    GGTAACTCCCAGGAGAGTGTCACAGAGCAGGACAGCAAGGACAGCAC
    CTACAGCCTCAGCAGCACCCTGACGCTGAGCAAAGCAGACTACGAGA
    AACACAAAGTCTATGCCTGCGAAGTCACCCATCAGGGCCTGAGCTCGC
    CCGTCACAAAGAGCTTCAACAGGGGAGAGTGTGCTAGCTGA

43  GAGGTCCAGCTGGTGCAATCTGGAGCTGAGGTGAAGAAGCCTGGGGCT
    TCAGTGAAGATATCCTGCAAGGCTTCTGGATACTCCTTCACTGGCTACT
    ACATGCACTGGGTGAAGCAGGCCCATGGACAAGGGCTTGAGTGGATTG
    GAAGGATTAATCCTTACAATGGTGCTACTAGCTACAACCAGAACTTCA
    AGGACAGAGCCACCTTGACTGTAGACAAGTCCACGAGCACAGCCTACA
    TGGAGCTCAGCAGCCTGAGGTCTGAGGACACGGCAGTCTATTACTGTG
    CAAGAGAGGACTACGTGTACTGGGGCCAAGGCACCACGGTCACCGTCT
    CCTCAGCCAAAACGAAGGGCCCATCCGTCTTCCCCCCTGGCGCCCTGCT
    CCAGGAGCACCTCCGAGAGCACAGCCGCCCTGGGCTGCCTGGTCAAGG
    ACTACTTCCCCGAACCGGTGACGGTGTCGTGGAACTCAGGCGCCCTGA
    CCAGCGGCGTGCACACCTTCCCGGCTGTCCTACAGTCCTCAGGACTCTA
    CTCCCTCAGCAGCGTGGTGACCGTGCCCTCCAGCAGCTTGGGCACGAA
    GACCTACACCTGCAACGTAGATCACAAGCCCAGCAACACCAAGGTGG
    ACAAGAGAGTTGAGTCCAAATATGGTCCCCCATGCCCACCCTGCCCAG
    CACCTGAGTTCGAAGGGGGACCATCAGTCTTCCTGTTCCCCCCAAAAC
    CCAAGGACACTCTCATGATCTCCCGGACCCCTGAGGTCACGTGCGTGG

TABLE 6-continued

| SEQ ID NO: | Full Sequence |
|---|---|

```
    TGGTGGACGTGAGCCAGGAAGACCCCGAGGTCCAGTTCAACTGGTACG
    TGGATGGCGTGGAGGTGCATAATGCCAAGACAAAGCCGCGGGAGGAG
    CAGTTCAACAGCACGTACCGTGTGGTCAGCGTCCTCACCGTCCTGCAC
    CAGGACTGGCTGAACGGCAAGGAGTACAAGTGCAAGGTCTCCAACAA
    AGGCCTCCCGTCCTCCATCGAGAAAACCATCTCCAAAGCCAAAGGGCA
    GCCCCGAGAGCCACAGGTGTACACCCTGCCCCCATCCCAGGAGGAGAT
    GACCAAGAACCAGGTCAGCCTGACCTGCCTGGTCAAAGGCTTCTACCC
    CAGCGACATCGCCGTGGAGTGGGAGAGCAATGGGCAGCCGGAGAACA
    ACTACAAGACCACGCCTCCCGTGCTGGACTCCGACGGCTCCTTCTTCCT
    CTACAGCAGGCTAACCGTGGACAAGAGCAGGTGGCAGGAGGGGAATG
    TCTTCTCATGCTCCGTGATGCATGAGGCTCTGCACAACCACTACACACA
    GAAGAGCCTCTCCCTGTCTCTGGGTAAAGCTAGTCAGACCCCCACCAA
    CACCATCAGCGTGACCCCCACCAACAACAGCACCCCCACCAACAACAG
    CAACCCCAAGCCCAACCCCGCTAGTGAGAAGATCCGGCTGCGGCCCGG
    CGGCAAGAAGAAGTACAAGCTGAAGCACATCGTGGCTAGTAGCAGCG
    TGAGCCCCACCACCAGCGTGCACCCCACCCCCACCAGCGTGCCCCCCA
    CCCCCACCAAGAGCAGCCCCGCTAGTAACCCCCCCATCCCCGTGGGCG
    AGATCTACAAGCGGTGGATCATCCTGGGCCTGAACAAGATCGTGCGGA
    TGTACAGCCCCACCAGCATCCTGGACGCTAGTCCCACCAGCACCCCCG
    CCGACAGCAGCACCATCACCCCCACCGCCACCCCCACCGCCACCCCCA
    CCATCAAGGGCGCTAGTCACACCCAGGGCTACTTCCCCGACTGGCAGA
    ACTACACCCCCGGCCCCGGCGTGCGGTACCCCCTGACCTTCGGCTGGC
    TGTACAAGCTGGCTAGTACCGTGACCCCCACCGCCACCGCCACCCCCA
    GCGCCATCGTGACCACCATCACCCCCACCGCCACCACCAAGCCCGCTA
    GTGTGGGCTTCCCCGTGACCCCCCAGGTGCCCCTGCGGCCCATGACCT
    ACAAGGCCGCCGTGGACCTGAGCCACTTCCTGAAGGAGAAGGGCGGC
    CTGGCTAGTACCAACGGCAGCATCACCGTGGCCGCCACCGCCCCCACC
    GTGACCCCCACCGTGAACGCCCACCCCCAGCGCCGCCGCTAGTGCCATC
    TTCCAGAGCAGCATGACCAAGATCCTGGAGCCCTTCCGGAAGCAGAAC
    CCCGACATCGTGATCTACCAGTACATGGACGACCTGTACGCTAGCTGA
```

```
44  GATGTTGTGATGACCCAATCTCCACTCTCCCTGCCTGTCACCCTTGGAC
    AGCCGGCCTCCATCTCTTGCAGGTCTAGTCAGAGCCTTGTACACAGTA
    ATGGAAACACCTATTTACATTGGTACCAGCAGAGACCAGGCCAGTCTC
    CAAGGCTCCTGATCTACAAAGTTTCCAACCGATTTTCTGGGGTCCCAGA
    CAGGTTCAGTGGCAGTGGATCAGGGACAGATTTCACACTCAAGATCAG
    CAGAGTGGAGGCTGAAGATGTTGGAGTTTATTTCTGCTCTCAAAGTAC
    ACATGTTCCTTGGACGTTCGGCGGAGGGACCAAGCTCGAGATCAAACG
    AACTGTGGCTGCACCATCTGTCTTCATCTTCCCGCCATCTGATGAGCAG
    TTGAAATCTGGAACTGCCTCTGTTGTGTGCCTGCTGAATAACTTCTATC
    CCAGAGAGGCCAAAGTACAGTGGAAGGTGGATAACGCCCTCCAATCG
    GGTAACTCCCAGGAGAGTGTCACAGAGCAGGACAGCAAGGACAGCAC
    CTACAGCCTCAGCAGCACCCTGACGCTGAGCAAAGCAGACTACGAGA
    AACACAAAGTCTATGCCTGCGAAGTCACCCATCAGGGCCTGAGCTCGC
    CCGTCACAAAGAGCTTCAACAGGGGAGAGTGTGCTAGTCAGACCCCCA
    CCAACACCATCAGCGTGACCCCCACCAACAACAGCACCCCCACCAACA
    ACAGCAACCCCAAGCCCAACCCCGCTAGCATGCAGAAGGGAGACCAG
    AACCCTCAGATCGCAGCTCACGTCATCTCCGAGGCTTCTTCCAAGACC
    ACCTCCGTGCTCCAGTGGGCTGAAAAGGGATACTACACCATGAGCAAC
    AACCTGGTGACACTGGAGAACGGCAAGCAGCTCACAGTCAAGCGGCA
    GGGCCTTTACTACATCTATGCCCAGGTGACCTTCTGCTCCAACAGGGA
    GGCCTCCAGCCAGGCCCCTTTCATTGCCTCTCTGTGTCTCAAGAGCCCA
    GGCAGATTCGAGAGGATTCTCCTGCGCGCCGCCAATACACACAGCTCA
    GCCAAACCCTGCGGGCAACAGTCAATTCACCTGGGGGGGGTCTTTGAG
    TTGCAGCCAGGGGCCAGTGTCTTCGTGAACGTGACAGATCCCAGTCAG
    GTGAGCCATGGCACTGGCTTTACTAGCTTTGGGTTGCTGAAACTGTGA
```

```
45  AQQAAADTGHSNQVSQNYPIVQNIQGQMVHQAISPRTLNAWVKVVEEKA
    FSPEVIPMFSALSEGATPQDLNTMLNTVGGHQAAMQMLKETINEEAAEW
    DRVHPVHAGPIAPGQMREPRGSDIAGTTSTLQEQIGWMTHNPPIPVGEIYK
    RWIILGLNKIVRMYSPTSILDIRQGPKEPFRDYVDRFYKTLRAEQASQEVK
    NWMTETLLVQNANPDCKTILKALGPGATLEEMMTACQGVG
```

```
46  MGGKWSKRSVVGWPTVRERMRRAEPAADGVGAVSRDLEKHGAITSSNT
    AANNADCAWLEAQEEEEVGFPVRPQVPLRPMTYKGALDLSHF'LKEKGGL
    EGLIYSQKRQDILDLWVYHTQGYFPDWQNYTPGPGIRYPLTFGWCFKLVP
    VEPEKVEEANEGENNSLLHPMSLHGMDDPEREVLVWKFDSRLAFHHMAR
    ELHPEYYKDC
```

```
47  MGARASILSGGELDRWEKIRLRPGGNKQYKLKHIVWASRELERFAVNPGL
    LETSEGCRQILGQLQPSLQTGSEELRSLYNTVATLYCVHQRIEIKDTKEALD
    KIEEEQNKS
```

```
48  ASQTPTNTISVTPTNNSTPTNNSNPKPNPASLEMGARASILSGGELDRWEKI
    RLRPGGNKQYKLKHIVWASRELERFAVNPGLLETSEGCRQILGQLQPSLQ
    TGSEELRSLYNTVATLYCVHQRIEIKDTKEALDKIEEEQNKSVDTVTPTAT
```

SEQ
ID
NO: Full Sequence

```
     ATPSAIVTTITPTATTKPVDMGGKWSKRSVVGWPTVRERMRRAEPAADG
     VGAVSRDLEKHGAITSSNTAANNADCAWLEAQEEEEVGFPVRPQVPLRP
     MTYKGALDLSHF'LKEKGGLEGLIYSQKRQDILDLWVYHTQGYFPDWQNY
     TPGPGIRYPLTFGWCFKLVPVEPEKVEEANEGENNSLLHPMSLHGMDDPE
     REVLVWKFDSRLAFHHMARELHPEYYKDCEFTNGSITVAATAPTVTPTVN
     ATPSAAQFAQQAAADTGHSNQVSQNYPIVQNIQGQMVHQAISPRTLNAW
     VKVVEEKAFSPEVIPMFSALSEGATPQDLNTMLNTVGGHQAAMQMLKET
     INEEAAEWDRVHPVHAGPIAPGQMREPRGSDIAGTTSTLQEQIGWMTHNP
     PIPVGEIYKRWIILGLNKIVRMYSPTSILDIRQGPKEPFRDYVDRFYKTLRAE
     QASQEVKNWMTETLLVQNANPDCKTILKALGPGATLEEMMTACQGVGH
     HHHHH
```

49  GCACAGCAAGCAGCAGCTGACACAGGACACAGCAATCAGGTCAGCCA
    AAATTACCCTATAGTGCAGAACATCCAGGGGCAAATGGTACATCAGGC
    CATATCACCTAGAACTTTAAATGCATGGGTAAAAGTAGTAGAAGAGAA
    GGCTTTCAGCCCAGAAGTGATACCCATGTTTTCAGCATTATCAGAAGG
    AGCCACCCCACAAGATTTAAACACCATGCTAAACACAGTGGGGGGAC
    ATCAAGCAGCCATGCAAATGTTAAAAGAGACCATCAATGAGGAAGCT
    GCAGAATGGGATAGAGTGCATCCAGTGCATGCAGGGCCTATTGCACCA
    GGCCAGATGAGAGAACCAAGGGGAAGTGACATAGCAGGAACTACTAG
    TACCCTTCAGGACAAATAGGATGGATGACACATAATCCACCTATCCC
    AGTAGGAGAAATCTATAAAAGGTGGATAATCCTGGGATTAAATAAAAT
    AGTAAGAATGTATAGCCCTACCAGCATTCTGGACATAAGACAAGGACC
    AAAGGAACCCTTTAGAGACTATGTAGACCGATTCTATAAAACTCTAAG
    AGCCGAGCAAGCTTCACAAGAGGTAAAAAATTGGATGACAGAAACCT
    TGTTGGTCCAAAATGCGAACCCAGATTGTAAGACTATTTTAAAAGCAT
    TGGGACCAGGAGCGACACTAGAAGAAATGATGACAGCATGTCAGGGA
    GTGGGG

50  ATGGGAGGCAAATGGAGTAAAAGAAGTGTTGTGGGTTGGCCAACTGT
    GAGAGAAAGAATGAGAAGGGCTGAACCAGCCGCTGATGGTGTAGGTG
    CTGTGTCACGAGATCTGGAAAAACACGGAGCAATAACATCCTCTAATA
    CCGCCGCAAATAACGCAGACTGTGCCTGGCTCGAAGCTCAAGAAGAA
    GAAGAAGTCGGATTCCCCGTGCGACCCCAAGTTCCCCTCAGACCAATG
    ACTTATAAAGGCGCTCTGGATCTTAGCCACTTTCTTAAAGAAAAAGGA
    GGACTGGAAGGACTTATTTATTCACAAAAAAGACAAGACATCCTCGAT
    TTGTGGGTATATCATACTCAAGGTTATTTCCCAGACTGGCAAAATTATA
    CTCCTGGACCCGGCATTCGATATCCCCTTACCTTTGGATGGTGCTTTAA
    ACTTGTCCCCGTCGAACCTGAAAAAGTAGAAGAAGCAAATGAAGGCG
    AAAATAATTCACTGCTCCACCCTATGTCACTGCACGGAATGGATGACC
    CCGAACGCGAAGTTCTGGTATGGAAATTTGATTCAAGACTTGCTTTTCA
    CCACATGGCTAGAGAACTTCACCCCGAATATTATAAAGACTGT

51  ATGGGTGCGAGAGCGTCAATATTAAGCGGTGGCGAATTAGATAGATGG
    GAAAAAATTCGGTTAAGGCCAGGGGGAAACAAACAATATAAATTAAA
    ACATATAGTATGGGCAAGCAGGGAGCTAGAACGATTCGCAGTTAATCC
    TGGCCTGTTAGAAACATCAGAAGGCTGTAGACAAATACTGGGACAGCT
    ACAACCATCCCTTCAGACAGGATCAGAAGAACTTAGATCATTATATAA
    TACAGTAGCAACCCTCTATTGTGTGCATCAAAGGATAGAGATAAAAGA
    CACCAAGGAAGCTTTAGACAAGATAGAGGAAGAGCAAAACAAAAGT

52  GCTAGTCAGACCCCCACCAACACCATCAGCGTGACCCCCACCAACAAC
    AGCACCCCCACCAACAACAGCAACCCCAAGCCCAACCCCGCTAGCCTC
    GAGATGGGTGCGAGAGCGTCAATATTAAGCGGTGGCGAATTAGATAG
    ATGGGAAAAAATTCGGTTAAGGCCAGGGGGAAACAAACAATATAAAT
    TAAAACATATAGTATGGGCAAGCAGGGAGCTAGAACGATTCGCAGTTA
    ATCCTGGCCTGTTAGAAACATCAGAAGGCTGTAGACAAATACTGGGAC
    AGCTACAACCATCCCTTCAGACAGGATCAGAAGAACTTAGATCATTAT
    ATAATACAGTAGCAACCCTCTATTGTGTGCATCAAAGGATAGAGATAA
    AAGACACCAAGGAAGCTTTAGACAAGATAGAGGAAGAGCAAAACAAA
    AGTGTCGATACCGTGACCCCCACCGCCACCGCCACCCCCAGCGCCATC
    GTGACCACCATCACCCCCACCGCCACCACCAAGCCCGTCGACATGGGA
    GGCAAATGGAGTAAAAGAAGTGTTGTGGGTTGGCCAACTGTGAGAGA
    AAGAATGAGAAGGGCTGAACCAGCCGCTGATGGTGTAGGTGCTGTGTC
    ACGAGATCTGGAAAAACACGGAGCAATAACATCCTCTAATACCGCCGC
    AAATAACGCAGACTGTGCCTGGCTCGAAGCTCAAGAAGAAGAAGAAG
    TCGGATTCCCCGTGCGACCCCAAGTTCCCCTCAGACCAATGACTTATAA
    AGGCGCTCTGGATCTTAGCCACTTTCTTAAAGAAAAAGGAGGACTGGA
    AGGACTTATTTATTCACAAAAAAGACAAGACATCCTCGATTTGTGGGT
    ATATCATACTCAAGGTTATTTCCCAGACTGGCAAAATTATACTCCTGGA
    CCCGGCATTCGATATCCCCTTACCTTTGGATGGTGCTTTAAACTTGTCC
    CCGTCGAACCTGAAAAAGTAGAAGAAGCAAATGAAGGCGAAAATAAT
    TCACTGCTCCACCCTATGTCACTGCACGGAATGGATGACCCCGAACGC
    GAAGTTCTGGTATGGAAATTTGATTCAAGACTTGCTTTTCACCACATGG
    CTAGAGAACTTCACCCCGAATATTATAAAGACTGTGAATTCACCAACG
    GCAGCATCACCGTGGCCGCCACCGCCCCCACCGTGACCCCCACCGTGA

TABLE 6-continued

SEQ
ID
NO: Full Sequence

```
    ACGCCACCCCCAGCGCCGCCCAATTCGCACAGCAAGCAGCAGCTGACA
    CAGGACACAGCAATCAGGTCAGCCAAAATTACCCTATAGTGCAGAACA
    TCCAGGGGCAAATGGTACATCAGGCCATATCACCTAGAACTTTAAATG
    CATGGGTAAAAGTAGTAGAAGAGAAGGCTTTCAGCCCAGAAGTGATA
    CCCATGTTTTCAGCATTATCAGAAGGAGCCACCCCACAAGATTTAAAC
    ACCATGCTAAACACAGTGGGGGGCACATCAAGCAGCCATGCAAATGTTA
    AAAGAGACCATCAATGAGGAAGCTGCAGAATGGGATAGAGTGCATCC
    AGTGCATGCAGGGCCTATTGCACCAGGCCAGATGAGAGAACCAAGGG
    GAAGTGACATAGCAGGAACTACTAGTACCCTTCAGGAACAAATAGGAT
    GGATGACACATAATCCACCTATCCCAGTAGGAGAAATCTATAAAAGGT
    GGATAATCCTGGGATTAAATAAAATAGTAAGAATGTATAGCCCTACCA
    GCATTCTGGACATAAGACAAGGACCAAAGGAACCCTTTAGAGACTATG
    TAGACCGATTCTATAAAACTCTAAGAGCCGAGCAAGCTTCACAAGAGG
    TAAAAAATTGGATGACAGAAACCTTGTTGGTCCAAAATGCGAACCCAG
    ATTGTAAGACTATTTTAAAAGCATTGGGACCAGGAGCGACACTAGAAG
    AAATGATGACAGCATGTCAGGGAGTGGGGCATCACCATCACCATCACT
    GA

53  TVTPTATATPSAIVTTITPTATTKP

54  TNGSITVAATAPTVTPTVNATPSAA

55  MHQKRTAMFQDPQERPRKLPQLCTELQTTIHDIILECVYCKQQLLRREVG
    DFAFRDLCIVYRDGNPYAVCDKCLKFYSKISEYRHYCYSVYGTTLEQQYN
    KPLCDLLIRCINCQKPLCPEASMHGDTPTLHEYMLDLQPETTDLYGYGQL
    NDSSEEEDEIDGPAGQAEPDRAHYNIVTFCCK

56  ASSSVSPTTSVHPTPTSVPPTPTKSSPAS

57  ASQTPTNTISVTPTNNSTPTNNSNPKPNPASMHQKRTAMFQDPQERPRKLP
    QLCTELQTTIHDIILECVYCKQQLLRREVGDFAFRDLCIVYRDGNPYAVCD
    KCLKFYSKISEYRHYCYSVYGTTLEQQYNKPLCDLLIRCINCQKPLCPEAS
    MHGDTPTLHEYMLDLQPETTDLYGYGQLNDSSEEEDEIDGPAGQAEPDR
    AHYNIVTFCCKASSSVSPTTSVHPTPTSVPPTPTKSSPAS

58  EVQLQQSGPELVKPGASVKMSCKASGYTFTDYVLHWVKQKPGQGLEWI
    GYINPYNDGTKYNEKFKGKATLTSDKSSSTAYMELSSLTSEDSAVYYCAR
    GYPAYSGYAMDYWGQGTSVTVSSAK

59  DIQMTQTTSSLSASLGDRVTISCRASQDISNYLNWYQQKPDGTVKLLIYYT
    SRLHSGVPSRFSGSGSGTDYSLTISNLEQEDIATYFCHHGNTLPWTFGGGT
    K

60  DVQLQESGPDLVKPSQSLSLTCTVTGYSITSDYSWHWIRQFPGNKLEWMG
    YIYYSGSTNYNPSLKSRISITRDTSKNQFFLQLNSVTTEDSATYFCARFYYG
    YSFFDYWGQGTTLTVSSAK

61  QIVLTQSPAFMSASPGEKVTMTCSASSSVSYMHWYQQKSGTSPKRWIYDT
    SKLASGVPARFSGSGSGTSYSLTISSMEAEDAATYYCQQWSSNPLTFGAGT
    K

62  QVQLVQSGAEVKKPGASVKVSCKASGYTFTGYYMHWVRQAPGQGLEW
    MGWINPDSGGTNYAQKFQGRVTMTRDTSISTAYMELNRLRSDDTAVYYC
    ARDQPLGYCTNGVCSYFDYWGQGTLVTVSSAS

63  DIQMTQSPSSVSASVGDRVTITCRASQGIYSWLAWYQQKPGKAPNLLIYT
    ASTLQSGVPSRFSGSGSGTDFTLTISSLQPEDFATYYCQQANIFPLTFGGGT
    K

64  EVQLVESGGGLVQPGGSLKLSCATSGFTFSDYYMYWVRQAPGKGLEWV
    AYINSGGGSTYYPDTVKGRFTISRDNAKNTLYLQMNSLRAEDTAVYYCA
    RRGLPFHAMDYWGQGTLVTVSSAK

65  DIQMTQSPSSLSASVGDRVTITCSASQGISNYLNWYQQKPGKAVKLLIYYT
    SILHSGVPSRFSGSGSGTDYTLTISSLQPEDFATYYCQQFNKLPPTFGGGTK

66  GAGGTCCAGCTGCAGCAGTCTGGACCTGAGCTGGTAAAGCCTGGGGCT
    TCAGTGAAGATGTCCTGCAAGGCTTCTGGATACACATTCACTGACTAT
    GTTTTGCACTGGGTGAAACAGAAGCCTGGGCAGGGCCTTGAGTGGATT
    GGATATATTAATCCTTACAATGATGGTACTAAGTACAATGAGAAGTTC
    AAAGGCAAGGCCACACTGACTTCAGACAAATCCTCCAGCACAGCCTAC
    ATGGAGCTCAGCAGCCTGACCTCTGAGGACTCTGCGGTCTATTACTGT
    GCAAGGGGCTATCCGGCCTACTCTGGGTATGCTATGGACTACTGGGGT
    CAAGGAACCTCAGTCACCGTCTCCTCAGCCAAA
```

TABLE 6-continued

| SEQ ID NO: | Full Sequence |
|---|---|

67 GATATCCAGATGACACAGACTACATCCTCCCTGTCTGCCTCTCTGGGAG
ACAGAGTCACCATCAGTTGCAGGGCAAGTCAGGACATTAGCAATTATT
TAAACTGGTATCAGCAGAAACCAGATGGAACTGTTAAACTCCTGATCT
ACTACACATCAAGATTACACTCAGGAGTCCCATCAAGGTTCAGTGGCA
GTGGGTCTGGAACAGATTATTCTCTCACCATTAGCAACCTGGAGCAAG
AAGATATTGCCACTTACTTTTGCCATCATGGTAATACGCTTCCGTGGAC
GTTCGGTGGAGGCACCAAG

68 GATGTGCAGCTTCAGGAGTCAGGACCTGACCTGGTGAAACCTTCTCAG
TCACTTTCACTCACCTGCACTGTCACTGGCTACTCCATCACCAGTGATT
ATAGCTGGCACTGGATCCGGCAGTTCCCAGGAAACAAACTGGAATGGA
TGGGCTACATATATTACAGTGGTAGCACTAACTACAACCCATCTCTCA
AAAGTCGAATCTCTATCACTCGAGACACATCCAAGAACCAGTTCTTCC
TGCAGTTGAATTCTGTGACTACTGAGGACTCAGCCACATATTTCTGTGC
AAGATTTTACTACGGTTATAGCTTCTTTGACTACTGGGGCCAAGGCACC
ACTCTCACAGTCTCCTCAGCCAAA

69 CAAATTGTTCTCACCCAGTCTCCAGCATTCATGTCTGCATCTCCAGGGG
AGAAGGTCACCATGACCTGCAGTGCCAGCTCAAGTGTCAGTTACATGC
ACTGGTACCAGCAGAAGTCAGGCACCTCCCCCAAAAGATGGATTTATG
ACACATCCAAACTGGCTTCTGGAGTCCCTGCTCGCTTCAGTGGCAGTG
GGTCTGGGACCTCTTACTCTCTCACAATCAGCAGCATGGAGGCTGAAG
ATGCTGCCACTTATTACTGCCAGCAGTGGAGTAGTAACCCACTCACGTT
CGGTGCTGGGACCAAG

70 CAAGTGCAGCTGGTTCAGTCTGGGGCTGAGGTGAAAAAGCCTGGGGCC
AGTGTCAAGGTCAGCTGCAAGGCCTCTGGCTACACATTTACTGGATAT
TACATGCATTGGGTTCGACAGGCCCCCGGACAGGGGCTCGAATGGATG
GGATGGATAAACCCAGACAGCGGCGGAACGAACTATGCCCAAAAATT
TCAGGGCAGGGTGACCATGACCCGGGACACCTCCATCAGCACAGCCTA
CATGGAGCTGAATAGACTTCGGAGTGACGATACAGCCGTCTACTATTG
CGCAAGGGATCAGCCGCTGGGCTACTGTACAAATGGCGTGTGTTCATA
CTTCGACTATTGGGGTCAGGGTACGCTCGTGACCGTGTCATCTGCGTCC

71 GACATTCAGATGACACAATCTCCCTCCTCCGTAAGCGCCTCTGTGGGC
GATCGCGTTACAATCACTTGCCGGGCTAGTCAGGGCATCTATAGCTGG
CTCGCTTGGTACCAGCAAAAGCCTGGCAAAGCGCCTAATCTGCTGATT
TATACCGCCTCTACGCTGCAGAGCGGGGTCCCAAGCAGATTTTCAGGG
TCCGGGTCAGGAACCGATTTCACTCTGACTATCAGCTCCCTGCAGCCCG
AGGACTTCGCAACCTACTACTGCCAGCAAGCCAACATATTCCCCCTGA
CCTTTGGTGGAGGTACAAAG

72 GAAGTGCAGCTGGTGGAGTCTGGGGGAGGCTTAGTGCAGCCCGGAGG
GTCCCTGAAACTCTCCTGTGCAACCTCTGGATTCACTTTCAGTGACTAT
TACATGTATTGGGTTCGCCAGGCCCCAGGCAAGGGCCTGGAGTGGGTC
GCATACATTAATTCTGGTGGTGGTAGCACCTATTATCCAGACACTGTAA
AGGGCCGATTCACCATCTCCAGAGACAATGCCAAGAACACCCTGTACC
TGCAAATGAACAGCCTGAGGGCCGAGGACACAGCCGTGTATTACTGTG
CAAGACGGGGGTTACCGTTCCATGCTATGGACTATTGGGGTCAAGGAA
CCCTGGTCACCGTCTCCTCAGCCAAA

73 GATATCCAGATGACACAGAGCCCTTCCTCCCTGTCTGCCTCTGTGGGAG
ACAGAGTCACCATCACCTGCAGTGCAAGTCAGGGCATTAGCAATTATT
TAAACTGGTATCAGCAGAAACCAGGCAAGGCCGTTAAACTCCTGATCT
ATTACACATCAATTTTACACTCAGGAGTCCCATCAAGGTTCAGTGGCA
GTGGGTCTGGGACAGATTATACCCTCACCATCAGCTCCCTGCAGCCTG
AAGATTTCGCCACTTACTATTGTCAGCAGTTTAATAAGCTTCCTCCGAC
GTTCGGTGGAGGCACCAAA

74 GYTFTDYVLH

75 YINPYNDGTKYNEKFKG

76 GYPAYSGYAMDY

77 RASQDISNYLN

78 YTSRLHS

79 HHGNTLPWT

80 GYSITSDYSWH

81 YIYYSGSTNYNPSLKS

TABLE 6-continued

| SEQ ID NO: | Full Sequence |
|---|---|

82 FYYGYSFFDY

83 SASSSVSYMH

84 DTSKLAS

85 QQWSSNPLT

86 GYTFTGYYMH

87 WINPDSGGTNYAQKFQG

88 DQPLGYCTNGVCSYFDY

89 RASQGIYSWLA

90 TASTLQS

91 QQANIFPLT

92 GFTFSDYYMY

93 YINSGGGSTYYPDTVKG

94 GLPFHAMDY

95 SASQGISNYLN

96 YTSILHS

97 QQFNKLPPT

98 EVQLQQSGPELVKPGASVKMSCKASGYTFTDYVLHWVKQKPGQGLEWI
GYINPYNDGTKYNEKFKGKATLTSDKSSTAYMELSSLTSEDSAVYYCA
RGYPAYSGYAMDYWGQGTSVTVSSAK

99 DIQMTQTTSSLSASLGDRVTISCRASQDISNYLNWYQQKPDGTVKLLIYY
TSRLHSGVPSRFSGSGSGTDYSLTISNLEQEDIATYFCHHGNTLPWTFGG
GTK

100 EVKLVESGGGLVQPGGSLKLSCATSGFTFSDYYMYWVRQTPEKRLEWV
AYINSGGGSTYYPDTVKGRFTISRDNAKNTLYLQMSRLKSEDTAMYYCA
RRGLPFHAMDYWGQGTSVTVSSAK

101 DIQMTQTTSSLSASLGDRVTISCSASQGISNYLNWYQQKPDGTVKLLIYY**T
SILHSGVPSRFSGSGSGTDYSLTIGNLEPEDIATYYCQQFNKLPPT**FGGGT
K

102 EVKLVESGGGLVQPGGSLKLSCATSGFTFSDYYMYWVRQAPGKGLEWV
AYINSGGGSTYYPDTVKGRFTISRDNAKNTLYLQMNSLRAEDTAVYYCA
RRGLPFHAMDYWGQGTLVTVSSAK

103 EVQLVESGGGLVQPGGSLKLSCATSGFTFSDYYMYWVRQAPGKGLEWV
AYINSGGGSTYYPDTVKGRFTISRDNAKNTLYLQMNSLRAEDTAVYYCA
RRGLPFHAMDYWGQGTLVTVSSAK

104 DIQMTQSPSSLSASVGDRVTITCSASQGISNYLNWYQQKPGKAVKLLIYY
TSILHSGVPSRFSGSGSGTDYTLTISSLQPEDFATYYCQQFNKLPPTFGGG
TK

105 QVQLVQSGAEVKKPGASVKVSCKASGYTFTGYYMHWVRQAPGQGLEW
MGWINPDSGGTNYAQKFQGRVTMTRDTSISTAYMELNRLRSDDTAVYY
CARDQPLGYCTNGVCSYFDYWGQGTLVTVSSAS

106 DIQMTQSPSSVSASVGDRVTITCRASQGIYSWLAWYQQKPGKAPNLLIYT
ASTLQSGVPSRFSGSGSGTDFTLTISSLQPEDFATYYCQQANIFPLTFGGG
TK

107 DVQLQESGPDLVKPSQSLSLTCTVTGYSITSDYSWHWIRQFPGNKLEWM
GYIYYSGSSTNYNPSLKSRISITRDTSKNQFFLQLNSVTTEDSATFYCAR**FY
YGYSFFDY**WGQGTTLTVSSAK

108 QIVLTQSPAFMSASPGEKVTMTCSASSSVSYMHWYQQKSGTSPKRWIYD
TSKLASGVPARFSGSGSGTSYSLTISSMEAEDAATYYCQQWSSNPLTFGA
GTK

TABLE 6-continued

| SEQ ID NO: | Full Sequence |
|---|---|

109 DVVMTQSPLSLPVTLGQPASISCRSSQSLVHSNGNTYLHWYQQRPGQSPR
LLIYKVSNRFSGVPDRFSGSGSGTDFTLKISRVEAEDVGVYFCSQSTHVP
WTFGGGTKLEIKRTVAAPSVFIFPPSDEQLKSGTASVVCLLNNFYPREAKV
QWKVDNALQSGNSQESVTEQDSKDSTYSLSSTLTLSKADYEKHKVYACE
VTHQGLSSPVTKSFNRGECASQTPTNTISVTPTNNSTPTNNSNPKPNPASM

QKGDQNPQIAAHVISEASSKTTSVLQNAEKGYYTMSNNLVTLENGKQLT

VKRQGLYYIYAQVTFCSNREASSQAPFIASLCLKSPGRPERILLRAANTHSS

AKPCGQQSIHLGGVFELQPGASVFVNVTDPSQVSHGTGFTSFGLLKL

110 EVQLVQSGAEVKKPGASVKISCKASGYSFTGYYMHWVKQAHGQGLEWI
GRINPYNGATSYNQNFKDRATLTVDKSTSTAYMELSSLRSEDTAVYYCA
REDYVYWGQGTTVTVSSAKTKGPSVFPLAPCSRSTSESTAALGCLVKDYF
PEPVTVSWNSGALTSGVHTFPAVLQSSGLYSLSSVVTVPSSSLGTKTYTCN
VDHKPSNTKVDKRVESKYGPPCPPCPAPEFEGGPSVFLFPPKPKDTLMISR
TPEVTCVVVDVSQEDPEVQFNWYVDGVEVHNAKTKPREEQFNSTYRVVS
VLTVLHQDWLNGKEYKCKVSNKGLPSSIEKTISKAKGQPREPQVYTLPPS
QEEMTKNQVSLTCLVKGFYPSDIAVEWESNGQPENNYKTTPPVLDSDGSF
FLYSRLTVDKSRWQEGNVFSCSVMHEALHNHYTQKSLSLSLGKASNSPQ
NEVLYGDVNDDGKVNSTDLTLLKRYVLKAVSTLPSSKAEKNADVNRDGR
VDSSDVTILSRYLIRVIEKLPI

111 NSPQNEVLYGDVNDDGKVNSTDLTLLKRYVLKAVSTLPSSKAEKNADVN
RDGRVDSSDVTILSRYLIRVIEKLPI

112 EKIRLRPGGKKKYKLKHIVASSSVSPTTSVHPTPTSVPPTPTKSSPASNPPIP
VGEIYKRWIILGLNKIVRMYSPTSILDASPTSTPADSSTITPTATPTATPTIKG
ASHTQGYFPDWQNYTPGPGVRYPLTFGWLYKLASTVTPTATATPSAIVTTI
TPTATTKPASVGFPVTPQVPLRPMTYKAAVDLSHFLKEKGGLASTNGSITV
AATAPTVTPTVNATPSAAASAIF'QSSMTKILEPFRKQNPDIVIYQYMDDLY
AS

113 GATGTTGTGATGACCCAATCTCCACTCTCCCTGCCTGTCACCCTTGGAC
AGCCGGCCTCCATCTCTTGCAGGTCTAGTCAGAGCCTTGTACACAGTA
ATGGAAACACCTATTTACATTGGTACCAGCAGAGACCAGGCCAGTCTC
CAAGGCTCCTGATCTACAAAGTTTCCAACCGATTTTCTGGGGTCCCAGA
CAGGTTCAGTGGCAGTGGATCAGGGACAGATTTCACACTCAAGATCAG
CAGAGTGGAGGCTGAAGATGTTGGAGTTTATTTCTGCTCTCAAAGTAC
ACATGTTCCTTGGACGTTCGGCGGAGGGACCAAGCTCGAGATCAAACG
AACTGTGGCTGCACCATCTGTCTTCATCTTCCCGCCATCTGATGAGCAG
TTGAAATCTGGAACTGCCTCTGTTGTGTGCCTGCTGAATAACTTCTATC
CCAGAGAGGCCAAAGTACAGTGGAAGGTGGATAACGCCCTCCAATCG
GGTAACTCCCAGGAGAGTGTCACAGAGCAGGACAGCAAGGACAGCAC
CTACAGCCTCAGCAGCACCCTGACGCTGAGCAAAGCAGACTACGAGA
AACACAAAGTCTATGCCTGCGAAGTCACCCATCAGGGCCTGAGCTCGC
CCGTCACAAAGAGCTTCAACAGGGGAGAGTGTGCTAGTCAGACCCCCA
CCAACACCATCAGCGTGACCCCCACCAACAACAGCACCCCCACCAACA
ACAGCAACCCCAAGCCCAACCCCGCTAGCATGCAGAAGGGAGACCAG
AACCCTCAGATCGCAGCTCACGTCATCTCCGAGGCTTCTTCCAAGACC
ACCTCCGTGCTCCAGTGGGCTGAAAAGGGATACTACACCATGAGCAAC
AACCTGGTGACACTGGAGAACGGCAAGCAGCTCACAGTCAAGCGGCA
GGGCCTTTACTACATCTATGCCCAGGTGACCTTCTGCTCCAACAGGGA
GGCCTCCAGCCAGGCCCCTTTCATTGCCTCTCTGTGTCTCAAGAGCCCA
GGCAGATTCGAGAGGATTCTCCTGCGCGCCGCCAATACACACAGCTCA
GCCAAACCCTGCGGGCAACAGTCAATTCACCTGGGGGGGGTCTTTGAG
TTGCAGCCAGGGGCCAGTGTCTTCGTGAACGTGACAGATCCCAGTCAG
GTGAGCCATGGCACTGGCTTTACTAGCTTTGGGTTGCTGAAACTGTGA

114 GAGGTCCAGCTGGTGCAATCTGGAGCTGAGGTGAAGAAGCCTGGGGCT
TCAGTGAAGATATCCTGCAAGGCTTCTGGATACTCCTTCACTGGCTACT
ACATGCACTGGGTGAAGCAGGCCCATGGACAAGGGCTTGAGTGGATTG
GAAGGATTAATCCTTACAATGGTGCTACTAGCTACAACCAGAACTTCA
AGGACAGAGCCACCTTGACTGTAGACAAGTCCACGAGCACAGCCTACA
TGGAGCTCAGCAGCCTGAGGTCTGAGGACACGGCAGTCTATTACTGTG
CAAGAGAGGACTACGTGTACTGGGGCCAAGGCACCACGGTCACCGTCT
CCTCAGCCAAAACGAAGGGCCCATCCGTCTTCCCCCTGGCGCCCTGCT
CCAGGAGCACCTCCGAGAGCACAGCCGCCCTGGGCTGCCTGGTCAAGG
ACTACTTCCCCGAACCGGTGACGGTGTCGTGGAACTCAGGCGCCCTGA
CCAGCGGCGTGCACACCTTCCCGGCTGTCCTACAGTCCTCAGGACTCTA
CTCCCTCAGCAGCGTGGTGACCGTGCCCTCCAGCAGCTTGGGCACGAA
GACCTACACCTGCAACGTAGATCACAAGCCCAGCAACACCAAGGTGG
ACAAGAGAGTTGAGTCCAAATATGGTCCCCCATGCCCACCCTGCCCAG
CACCTGAGTTCGAAGGGGGACCATCAGTCTTCCTGTTCCCCCCAAAAC

TABLE 6-continued

SEQ
ID
NO: Full Sequence

```
    CCAAGGACACTCTCATGATCTCCCGGACCCCTGAGGTCACGTGCGTGG
    TGGTGGACGTGAGCCAGGAAGACCCCGAGGTCCAGTTCAACTGGTACG
    TGGATGGCGTGGAGGTGCATAATGCCAAGACAAAGCCGCGGGAGGAG
    CAGTTCAACAGCACGTACCGTGTGGTCAGCGTCCTCACCGTCCTGCAC
    CAGGACTGGCTGAACGGCAAGGAGTACAAGTGCAAGGTCTCCAACAA
    AGGCCTCCCGTCCTCCATCGAGAAAACCATCTCCAAAGCCAAAGGGCA
    GCCCCGAGAGCCACAGGTGTACACCCTGCCCCCATCCCAGGAGGAGAT
    GACCAAGAACCAGGTCAGCCTGACCTGCCTGGTCAAAGGCTTCTACCC
    CAGCGACATCGCCGTGGAGTGGGAGAGCAATGGGCAGCCGGAGAACA
    ACTACAAGACCACGCCTCCCGTGCTGGACTCCGACGGCTCCTTCTTCCT
    CTACAGCAGGCTAACCGTGGACAAGAGCAGGTGGCAGGAGGGGAATG
    TCTTCTCATGCTCCGTGATGCATGAGGCTCTGCACAACCACTACACACA
    GAAGAGCCTCTCCCTGTCTCTGGGTAAAGCTAGCAATTCTCCTCAAAAT
    GAAGTACTGTACGGAGATGTGAATGATGACGGAAAAGTAAACTCCACT
    GACTTGACTTTGTTAAAAAGATATGTTCTTAAAGCCGTCTCAACTCTGC
    CTTCTTCCAAAGCTGAAAAGAACGCAGATGTAAATCGTGACGGAAGAG
    TTGACTCCAGTGATGTCACAATACTTTCAAGATATTTGATAAGGGTAAT
    CGAGAAATTACCAATATAA
```

```
115 GAGAAGATCCGGCTGCGGCCCGGCGGCAAGAAGAAGTACAAGCTGAA
    GCACATCGTGGCTAGTAGCAGCGTGAGCCCCACCACCAGCGTGCACCC
    CACCCCCACCAGCGTGCCCCCCACCCCCACCAAGAGCAGCCCCGCTAG
    TAACCCCCCCATCCCCGTGGGCGAGATCTACAAGCGGTGGATCATCCT
    GGGCCTGAACAAGATCGTGCGGATGTACAGCCCCACCAGCATCCTGGA
    CGCTAGTCCCACCAGCACCCCCGCCGACAGCAGCACCATCACCCCCAC
    CGCCACCCCCACCGCCACCCCCACCATCAAGGGCGCTAGTCACACCCA
    GGGCTACTTCCCCGACTGGCAGAACTACACCCCCGGCCCCGGCGTGCG
    GTACCCCCTGACCTTCGGCTGGCTGTACAAGCTGGCTAGTACCGTGAC
    CCCCACCGCCACCGCCACCCCCAGCGCCATCGTGACCACCATCACCCC
    CACCGCCACCACCAAGCCCGCTAGTGTGGGCTTCCCCGTGACCCCCCA
    GGTGCCCCTGCGGCCCATGACCTACAAGGCCGCCGTGGACCTGAGCCA
    CTTCCTGAAGGAGAAGGGCGGCCTGGCTAGTACCAACGGCAGCATCAC
    CGTGGCCGCCACCGCCCCCACCGTGACCCCCACCGTGAACGCCACCCC
    CAGCGCCGCCGCTAGTGCCATCTTCCAGAGCAGCATGACCAAGATCCT
    GGAGCCCTTCCGGAAGCAGAACCCCGACATCGTGATCTACCAGTACAT
    GGACGACCTGTACGCTAGCTGA
```

```
116 GCTAGTCAGACCCCCACCAACACCATCAGCGTGACCCCCACCAACAAC
    AGCACCCCCACCAACAACAGCAACCCCAAGCCCAACCCCGCTAGTATG
    CACCAAAAAAGGACCGCAATGTTTCAGGACCCCCAAGAGAGGCCCCG
    CAAACTGCCACAACTTTGCACGGAGCTGCAGACAACAATACATGACAT
    CATTCTCGAATGTGTTTACTGTAAGCAGCAGTTGTTGCGAAGAGAAGT
    GGGGAGACTTCGCTTTCAGAGACCTGTGTATCGTATATCGCGATGGCAA
    TCCTTATGCCGTCTGCGATAAATGCCTCAAGTTTTACTCCAAGATCAGC
    GAGTACCGGCACTACTGTTACTCTGTGTATGGGACTACCCTCGAACAG
    CAGTATAACAAGCCGCTGTGCGATCTCCTTATCCGGTGCATTAACTGCC
    AGAAGCCACTGTGTCCTGAGGCTAGTATGCACGGGGATACCCCCACAC
    TCCACGAATACATGCTTGATTTGCAACCTGAAACGACCGACCTGTACG
    GCTATGGTCAGCTGAATGACTCCAGCGAGGAAGAGGATGAGATTGAC
    GGACCGGCAGGCCAGGCCGAGCCAGACCGGGCTCATTATAACATCGTG
    ACTTTCTGCTGTAAGGCTAGTAGCAGCGTGAGCCCCACCACCAGCGTG
    CACCCCACCCCCACCAGCGTGCCCCCCACCCCCACCAAGAGCAGCCCC
    GCTAGCTGA
```

```
117 EVQLVQSGAEVKKPGASVKISCKASGYSFTGYYMHWVKQAHGQGLEWI
    GRINPYNGATSYNQNFKDRATLTVDKSTSTAYMELSSLRSEDTAVYYCAR
    EDYVYWGQGTTVTVSSAKTKGPSVFPLAPCSRSTSESTAALGCLVKDYFP
    EPVTVSWNSGALTSGVHTFPAVLQSSGLYSLSSVVTVPSSSLGTKTYTCNV
    DHKPSNTKVDKRVESKYGPPCPPCPAPEFEGGPSVFLFPPKPKDTLMISRTP
    EVTCVVVDVSQEDPEVQFNWYVDGVEVHNAKTKPREEQFNSTYRVVSVL
    TVLHQDWLNGKEYKCKVSNKGLPSSIEKTISKAKGQPREPQVYTLPPSQEE
    MTKNQVSLTCLVKGFYPSDIAVEWESNGQPENNYKTTPPVLDSDGSFFLY
    SRLTVDKSRWQEGNVFSCSVMHEALHNHYTQKSLSLSLGKASQTPTNTIS
    VTPTNNSTPTNNSNPKPNPASEKIRLRPGGKKKYKLKHIVASSSVSPTTSVH
    PTPTSVPPTPTKSSPASNPPIPVGEIYKRWIILGLNKIVRMYSPTSILDASPTS
    TPADSSTITPTATPTATPTIKGASHTQGYFPDWQNYTPGPGVRYPLTFGWL
    YKLASTVTPTATATPSAIVTTITPTATTKPASVGFPVTPQVPLRPMTYKAA
    VDLSHF'LKEKGGLASTNGSITVAATAPTVTPTVNATPSAAASAIFQSSMTK
    ILEPFRKQNPDIVIYQYMDDLYAS
```

```
118 GAGGTCCAGCTGGTGCAATCTGGAGCTGAGGTGAAGAAGCCTGGGGCT
    TCAGTGAAGATATCCTGCAAGGCTTCTGGATACTCCTTCACTGGCTACT
    ACATGCACTGGGTGAAGCAGGCCCATGGACAAGGGCTTGAGTGGATTG
    GAAGGATTAATCCTTACAATGGTGCTACTAGCTACAACCAGAACTTCA
    AGGACAGAGCCACCTTGACTGTAGACAAGTCCACGAGCACAGCCTACA
    TGGAGCTCAGCAGCCTGAGGTCTGAGGACACGGCAGTCTATTACTGTG
```

TABLE 6-continued

SEQ
ID
NO: Full Sequence

```
    CAAGAGAGGACTACGTGTACTGGGGCCAAGGCACCACGGTCACCGTCT
    CCTCAGCCAAAACGAAGGGCCCATCCGTCTTCCCCCTGGCGCCCTGCT
    CCAGGAGCACCTCCGAGAGCACAGCCGCCCTGGGCTGCCTGGTCAAGG
    ACTACTTCCCCGAACCGGTGACGGTGTCGTGGAACTCAGGCGCCCTGA
    CCAGCGGCGTGCACACCTTCCCGGCTGTCCTACAGTCCTCAGGACTCTA
    CTCCCTCAGCAGCGTGGTGACCGTGCCCTCCAGCAGCTTGGGCACGAA
    GACCTACACCTGCAACGTAGATCACAAGCCCAGCAACACCAAGGTGG
    ACAAGAGAGTTGAGTCCAAATATGGTCCCCCATGCCCACCCTGCCCAG
    CACCTGAGTTCGAAGGGGGACCATCAGTCTTCCTGTTCCCCCCAAAAC
    CCAAGGACACTCTCATGATCTCCCGGACCCCTGAGGTCACGTGCGTGG
    TGGTGGACGTGAGCCAGGAAGACCCCGAGGTCCAGTTCAACTGGTACG
    TGGATGGCGTGGAGGTGCATAATGCCAAGACAAAGCCGCGGGAGGAG
    CAGTTCAACAGCACGTACCGTGTGGTCAGCGTCCTCACCGTCCTGCAC
    CAGGACTGGCTGAACGGCAAGGAGTACAAGTGCAAGGTCTCCAACAA
    AGGCCTCCCGTCCTCCATCGAGAAACCATCTCCAAAGCCAAAGGGCA
    GCCCCGAGAGCCACAGGTGTACACCCTGCCCCCATCCCAGGAGGAGAT
    GACCAAGAACCAGGTCAGCCTGACCTGCCTGGTCAAAGGCTTCTACCC
    CAGCGACATCGCCGTGGAGTGGGAGAGCAATGGGCAGCCGGAGAACA
    ACTACAAGACCACGCCTCCCGTGCTGGACTCCGACGGCTCCTTCTTCCT
    CTACAGCAGGCTAACCGTGGACAAGAGCAGGTGGCAGGAGGGGAATG
    TCTTCTCATGCTCCGTGATGCATGAGGCTCTGCACAACCACTACACACA
    GAAGAGCCTCTCCCTGTCTCTGGGTAAAGCTAGTCAGACCCCCACCAA
    CACCATCAGCGTGACCCCCACCAACAACAGCACCCCCACCAACAACAG
    CAACCCCAAGCCCAACCCCGCTAGTGAGAAGATCCGGCTGCGGCCCGG
    CGGCAAGGAAGAAGTACAAGCTGAAGCACATCGTGGCTAGTAGCAGCG
    TGAGCCCCCACCACCAGCGTGCACCCCACCCCCACCAGCGTGCCCCCCA
    CCCCCACCAAGAGCAGCCCCGCTAGTAACCCCCCCATCCCCGTGGGCG
    AGATCTACAAGCGGTGGATCATCCTGGGCCTGAACAAGATCGTGCGGA
    TGTACAGCCCCACCAGCATCCTGGACGCTAGTCCCACCAGCACCCCCG
    CCGACAGCAGCACCATCACCCCCACCGCCACCCCCACCGCCACCCCCA
    CCATCAAGGGCGCTAGTCACACCCAGGGCTACTTCCCCGACTGGCAGA
    ACTACACCCCCGGCCCCGGCGTGCGGTACCCCCTGACCTTCGGCTGGC
    TGTACAAGCTGGCTAGTACCGTGACCCCCACCGCCACCGCCACCCCCA
    GCGCCATCGTGACCACCATCACCCCCACCGCCACCACCAAGCCCGCTA
    GTGTGGGCTTCCCCGTGACCCCCCAGGTGCCCCTGCCGGCCCATGACCT
    ACAAGGCCGCCGTGGACCTGAGCCACTTCCTGAAGGAGAAGGGCGGC
    CTGGCTAGTACCAACGGCAGCATCACCGTGGCCGCCACCGCCCCCACC
    GTGACCCCCACCGTGAACGCCACCCCCAGCGCCGCCGCTAGTGCCATC
    TTCCAGAGCAGCATGACCAAGATCCTGGAGCCCTTCCGGAAGCAGAAC
    CCCGACATCGTGATCTACCAGTACATGGACGACCTGTACGCTAGC̲T̲G̲A̲
```

119 DIQMTQTTSSLSASLGDRVTISCSAS̲Q̲G̲I̲S̲N̲Y̲L̲N̲WYQQKPDGTVKLLIYYT̲
    S̲I̲L̲H̲S̲GVPSRFSGSGSGTDYSLT̲I̲G̲N̲L̲E̲P̲E̲D̲IATYYCQ̲Q̲F̲N̲K̲L̲P̲P̲T̲FGGGTK

120 GATATCCAGATGACACAGACTACATCCTCCCTGTCTGCCTCTCTAGGAG
    ACAGAGTCACCATCAGTTGCAGTGCAAGTCAGGGCATTAGCAATTATT
    TAAACTGGTATCAGCAGAAACCAGATGGAACTGTTAAACTCCTGATCT
    ATTACACATCAATTTTACACTCAGGAGTCCCATCAAGGTTCAGTGGCA
    GTGGGTCTGGGACAGATTATTCTCTCACCATCGGCAACCTGGAACCTG
    AAGATATTGCCACTTACTATTGTCAGCAGTTTAATAAGCTTCCTCCGAC
    GTTCGGTGGAGGCACCAAA

121 EVQLVQSGAEVKKPGASVKVSCKASGYSFTGYYMHWVRQAPGQGLEWI
    GRINPNYNGATSYNQNFKDRVTLTVDKSTSTAYMELSSLRSEDTAVYYCAR
    EDYVYWGQGTTVTVSSAKTKGPSVFPLAPCSRSTSESTAALGCLVKDYFP
    EPVTVSWNSGALTSGVHTFPAVLQSSGLYSLSSVVTVPSSSLGTKTYTCNV
    DHKPSNTKVDKRVESKYGPPCPPCPAPEFEGGPSVFLEPPKPKDTLMISRTP
    EVTCVVVDVSQEDPEVQFNWYVDGVEVHNAKTKPREEQFNSTYRVVSVL
    TVLHQDWLNGKEYKCKVSNKGLPSSIEKTISKAKGQPREPQVYTLPPSQEE
    MTKNQVSLTCLVKGFYPSDIAVEWESNGQPENNYKTTPPVLDSDGSFFLY
    SRLTVDKSRWQEGNVFSCSVMHEALHNHYTQKSLSLSLGKAS

122 DVVMTQSPLSLPVTLGQPASISCRSSQSLVHSNGNTYLHWYQQRPGQSPR
    LLIYKVSNRFSGVPDRFSGSGSGTDFTLKISRVEAEDVGVYFCSQSTHVPW
    TFGGGTKLEIKRTVAAPSVFIFPPSDEQLKSGTASVVCLLNNFYPREAKVQ
    WKVDNALQSGNSQESVTEQDSKDSTYSLSSTLTLSKADYEKHKVYACEV
    THQGLSSPVTKSFNRGECAS

123 DVVMTQSPLSLPVTLGQPASISCRSSQSLVHSNGNTYLHWYQQRPGQSPR
    LLIYKVSNRFSGVPDRFSGSGSGTDFTLKISRVEAEDVGVYFCSQSTHVPW
    TFGGGTKLEIKRTVAAPSVFIFPPSDEQLKSGTASVVCLLNNFYPREAKVQ
    WKVDNALQSGNSQESVTEQDSKDSTYSLSSTLTLSKADYEKHKVYACEV
    THQGLSSPVTKSFNRGECASQTPTNTISVTPTNNSTPTNNSNPKPNPASMQ
    KGDQNPQIAAHVISEASSKTTSVLQWAEKGYYTMSNNLVTLENGKQLTV
    KRQGLYYIYAQVTFCSNREASSQAPFIASLCLKSPGRFERILLRAANTHSSA
    KPCGQQSIHLGGVFELQPGASVFVNVTDPSQVSHGTGFTSFGLLKL

TABLE 6-continued

| SEQ ID NO: | Full Sequence |
|---|---|

124 MDLDAVRIKVDTVNAKPGDTVNIPVRESGIPSKGIANADFVYSYDPNVLEI
    IEIKPGELIVDPNPTKSFDTAVYPDRKMIVFLFAEDSGTGAYAITKDGVFAT
    IVAKVKEGAPNGLSVIKFVEVGGFANNDLVEQKTQFFDGGVNVGDTTEPA
    TPTTPVTTPTTTDDLDAASLLTEVETYVLSIIPSGPLKAEIAQRLEDVFAGK
    NTDLEVLMEWLKTRPILSPLTKGILGFVFTLTVPSERGLQRRRFVQNALNG
    NGDPNNMDKAVKLYRKLKREITFHGAKEIALSYSAGALASCMGLIYNRM
    GAVTTEVAFGLVCATCEQIADSQHRSHRQMVTTTNPLIRHENRMVLASTT
    AKAMEQMAGSSEQAAEAMDIASQARQMVQAMRTIGTHPSSSAGLKDDL
    LENLQAYQKRMGVQMQRFKLEHHHHHH

125 ATGGATCTGGATGCAGTAAGGATTAAAGTGGACACAGTAAATGCAAA
    ACCGGGAGACACAGTAAATATACCTGTAAGATTCAGTGGTATACCATC
    CAAGGGAATAGCAAACGCTGACTTTGTATACAGCTATGACCCGAATGT
    ACTTGAGATAATAGAGATAAAACCGGGAGAATTGATAGTTGACCCGA
    ATCCTACCAAGAGCTTTGATACTGCAGTATATCCTGACAGAAAGATGA
    TAGTATTCCTGTTTGCGGAAGACAGCGGAACAGGAGCGTATGCAATAA
    CTAAAGACGGAGTATTTGCTACGATAGTAGCGAAAGTAAAAGAAGGA
    GCACCTAACGGGCTCAGTGTAATCAAATTTGTAGAAGTAGGCGGATTT
    GCGAACAATGACCTTGTAGAACAGAAGACACAGTTCTTTGACGGTGGA
    GTAAATGTTGGAGATACAACAGAACCTGCAACACCTACAACACCTGTA
    ACAACACCGACAACAACAGATGATCTGGATGCAGCTAGCCTTCTAACC
    GAGGTCGAAACGTACGTTCTCTCTATCATCCCGTCAGGCCCCCTCAAA
    GCCGAGATCGCACAGAGACTTGAAGATGTCTTTGCAGGGAAGAACACC
    GATCTTGAGGTTCTCATGGAATGGCTAAAGACAAGACCAATCCTGTCA
    CCTCTGACTAAGGGGATTTTAGGATTTGTGTTCACGCTCACCGTGCCCA
    GTGAGCGGGGACTGCAGCGTAGACGCTTTGTCCAAAATGCTCTTAATG
    GGAACGGAGATCCAAATAACATGGACAAAGCAGTTAAACTGTATAGG
    AAGCTTAAGAGGGAGATAACATTCCATGGGGCCAAAGAAATAGCACT
    CAGTTATTCTGCTGGTGCACTTGCCAGTTGTATGGGCCTCATATACAAC
    AGGATGGGGGCTGTGACCACTGAAGTGGCATTTGGCCTGGTATGCGCA
    ACCTGTAACAGATTGCTGACTCCCAGCATCGGTCTCATAGGCAAATG
    GTGACAACAACCAATCCACTAATCAGACATGAGAACAGAATGGTTCTA
    GCCAGCACTACAGCTAAGGCTATGGAGCAAATGGCTGGATCGAGTGA
    GCAAGCAGCAGAGGCCATGGATATTGCTAGTCAGGCCAGGCAAATGG
    TGCAGGCGATGAGAACCATTGGGACTCATCCTAGCTCCAGTGCTGGTC
    TAAAAGATGATCTTCTTGAAAATTTGCAGGCTTACCAGAAACGGATGG
    GGGTGCAGATGCAGCGATTCAAGCTCGAGCACCACCACCACCACCACT
    GA

126 GAAGTGAAGCTGGTGGAGTCTGGGGGAGGCTTAGTGCAGCCTGGAGG
    GTCCCTGAAACTCTCCTGTGCAACCTCTGGATTCACTTTCAGTGACTAT
    TACATGTATTGGGTTCGCCAGACTCCAGAGAAGAGGCTGGAGTGGGTC
    GCATACATTAATTCTGGTGGTGGTAGCACCTATTATCCAGACACTGTAA
    AGGGCCGATTCACCATCTCCAGAGACAATGCCAAGAACACCCTGTACC
    TGCAAATGAGCCGGCTGAAGTCTGAGGACACAGCCATGTATTACTGTG
    CAAGACGGGGGTTACCGTTCCATGCTATGGACTATTGGGGTCAAGGAA
    CCTCAGTCACCGTCTCCTCAGCCAAA

127 GAAGTGAAGCTGGTGGAGTCTGGGGGAGGCTTAGTGCAGCCCGGAGG
    GTCCCTGAAACTCTCCTGTGCAACCTCTGGATTCACTTTCAGTGACTAT
    TACATGTATTGGGTTCGCCAGGCCCCAGGCAAGGGCCTGGAGTGGGTC
    GCATACATTAATTCTGGTGGTGGTAGCACCTATTATCCAGACACTGTAA
    AGGGCCGATTCACCATCTCCAGAGACAATGCCAAGAACACCCTGTACC
    TGCAAATGAACAGCCTGAGGGCCGAGGACACAGCCGTGTATTACTGTG
    CAAGACGGGGGTTACCGTTCCATGCTATGGACTATTGGGGTCAAGGAA
    CCCTGGTCACCGTCTCCTCAGCCAAA

128 GAGGTCCAGCTGGTGCAATCTGGAGCTGAGGTGAAGAAGCCTGGGGCT
    TCAGTGAAGGTCTCCTGCAAGGCTTCTGGATACTCCTTCACTGGCTACT
    ACATGCACTGGGTGCGACAGGCCCCTGGACAAGGGCTTGAGTGGATTG
    GAAGGATTAATCCTTACAATGGTGCTACTAGCTACAACCAGAACTTCA
    AGGACAGAGTCACCTTGACTGTAGACAAGTCCACGAGCACAGCCTACA
    TGGAGCTCAGCAGCCTGAGGTCTGAGGACACGGCAGTCTATTACTGTG
    CAAGAGAGGACTACGTGTACTGGGGCCAAGGCACCACGGTCACCGTCT
    CCTCAGCCAAAACGAAGGGCCCATCCGTCTTCCCCCTGGCGCCCTGCT
    CCAGGAGCACCTCCGAGAGCACAGCCGCCCTGGGCTGCCTGGTCAAGG
    ACTACTTCCCCGAACCGGTGACGGTGTCGTGGAACTCAGGCGCCCTGA
    CCAGCGGCGTGCACACCTTCCCGGCTGTCCTACAGTCCTCAGGACTCTA
    CTCCCTCAGCAGCGTGGTGACCGTGCCCTCCAGCAGCTTGGGCACGAA
    GACCTACACCTGCAACGTAGATCACAAGCCCAGCAACACCAAGGTGG
    ACAAGAGAGTTGAGTCCAAATATGGTCCCCCATGCCCACCCTGCCCAG
    CACCTGAGTTCGAAGGGGGACCATCAGTCTTCCTGTTCCCCCCAAAAC
    CCAAGGACACTCTCATGATCTCCCGGACCCCTGAGGTCACGTGCGTGG
    TGGTGGACGTGAGCCAGGAAGACCCCGAGGTCCAGTTCAACTGGTACG
    TGGATGGCGTGGAGGTGCATAATGCCAAGACAAAGCCGCGGGAGGAG

TABLE 6-continued

| SEQ ID NO: | Full Sequence |
|---|---|

CAGTTCAACAGCACGTACCGTGTGGTCAGCGTCCTCACCGTCCTGCAC
CAGGACTGGCTGAACGGCAAGGAGTACAAGTGCAAGGTCTCCAACAA
AGGCCTCCCGTCCTCCATCGAGAAAACCATCTCCAAAGCCAAAGGGCA
GCCCCGAGAGCCACAGGTGTACACCCTGCCCCCATCCCAGGAGGAGAT
GACCAAGAACCAGGTCAGCCTGACCTGCCTGGTCAAAGGCTTCTACCC
CAGCGACATCGCCGTGGAGTGGGAGAGCAATGGGCAGCCGGAGAACA
ACTACAAGACCACGCCTCCCGTGCTGGACTCCGACGGCTCCTTCTTCCT
CTACAGCAGGCTAACCGTGGACAAGAGCAGGTGGCAGGAGGGGAATG
TCTTCTCATGCTCCGTGATGCATGAGGCTCTGCACAACCACTACACACA
GAAGAGCCTCTCCCTGTCTCTGGGTAAAGCTAGC<u>TGA</u>

129　GATGTTGTGATGACCCAATCTCCACTCTCCCTGCCTGTCACCCTTGGAC
AGCCGGCCTCCATCTCTTGCAGGTCTAGTCAGAGCCTTGTACACAGTA
ATGGAAACACCTATTTACATTGGTACCAGCAGAGACCAGGCCAGTCTC
CAAGGCTCCTGATCTACAAAGTTTCCAACCGATTTTCTGGGGTCCCAGA
CAGGTTCAGTGGCAGTGGATCAGGGACAGATTTCACACTCAAGATCAG
CAGAGTGGAGGCTGAAGATGTTGGAGTTTATTTCTGCTCTCAAAGTAC
ACATGTTCCTTGGACGTTCGGCGAGGGACCAAGCTCGAGATCAAACG
AACTGTGGCTGCACCATCTGTCTTCATCTTCCCGCCATCTGATGAGCAG
TTGAAATCTGGAACTGCCTCTGTTGTGTGCCTGCTGAATAACTTCTATC
CCAGAGAGGCCAAAGTACAGTGGAAGGTGGATAACGCCCTCCAATCG
GGTAACTCCCAGGAGAGTGTCACAGAGCAGGACAGCAAGGACAGCAC
CTACAGCCTCAGCAGCACCCTGACGCTGAGCAAAGCAGACTACGAGA
AACACAAAGTCTATGCCTGCGAAGTCACCCATCAGGGCCTGAGCTCGC
CCGTCACAAAGAGCTTCAACAGGGGAGAGTGTGCTAGC<u>TGA</u>

130　PTSTPADSSTITPTATPTATPTIKG

131　EVQLQQSGPELVKPGASVKISCKASGYSFTGYYMHWVKQSHVKSLEWIGRINPYNGATSYNQNFKDKASLTV
DKSSSTAYMELHSLTSEDSAVYYCAREDYVYWGQGTTLTVSSAKTKGPSVFPLAPCSRSTSESTAALGCLVK
DYEPEPVTVSWNSGALTSGVHTFPAVLQSSGLYSLSSVVTVPSSSLGTKTYTCNVDHKPSNTKVDKRVESKY
GPPCPPCPAPEFEGGPSVFLFPPKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQPREPQVYTLPPSQEEMTKNQVSLT
CLVKGFYPSDIAVEWESNGQPENNYKTTPPVLDSDGSFFLYSRLTVDKSRWQEGNVFSCSVMHEALHNHYTQ
KSLSLSLGKAS

132　<u>ATGGGATGGAGCTGGATCTTTCTCTTTCTCCTGTCAGGAACTGCAGGTGTCCTCTCTGAGGTCCAGCTGCAA</u>
CAGTCTGGACCTGAGCTGGTGAAGCCTGGGGCTTCAGTGAAGATATCCTGCAAGGCTTCTGGTTACTCATTC
ACTGGCTACTACATGCACTGGGTGAAGCAAAGCCATGTAAAGAGCCTTGAGTGGATTGGACGTATTAATCCT
TACAATGGTGCTACTAGCTACAACCAGAATTTCAAGGACAAGGCCAGCTTGACTGTAGATAAGTCCTCCAGC
ACAGCCTACATGGAGCTCCACAGCCTGACATCTGAGGACTCTGCAGTCTATTACTGTGCAAGAGAGGACTAC
GTCTACTGGGGCCAAGGCACCACTCTCACAGTCTCCTCAGCCAAAACGAAGGGCCCATCCGTCTTCCCCCTG
GCGCCCTGCTCCAGGAGCACCTCCGAGAGCACAGCCGCCCTGGGCTGCCTGGTCAAGGACTACTTCCCCGAA
CCGGTGACGGTGTCGTGGAACTCAGGCGCCCTGACCAGCGGCGTGCACACCTTCCCGGCTGTCCTACAGTCC
TCAGGACTCTACTCCCTCAGCAGCGTGGTGACCGTGCCCTCCAGCAGCTTGGGCACGAAGACCTACACCTGC
AACGTAGATCACAAGCCCAGCAACACCAAGGTGGACAAGAGAGTTGAGTCCAAATATGGTCCCCCATGCCCA
CCCTGCCCAGCACCTGAGTTCGAAGGGGGGACCATCAGTCTTCCTGTTCCCCCCAAAACCCAAGGACACTCTC
ATGATCTCCCGGACCCCTGAGGTCACGTGCGTGGTGGTGGACGTGAGCCAGGAAGACCCCGAGGTCCAGTTC
AACTGGTACGTGGATGGCGTGGAGGTGCATAATGCCAAGACAAAGCCGCGGGAGGAGCAGTTCAACAGCACG
TACCGTGTGGTCAGCGTCCTCACCGTCCTGCACCAGGACTGGCTGAACGGCAAGGAGTACAAGTGCAAGGTC
TCCAACAAAGGCCTCCCGTCCTCCATCGAGAAAACCATCTCCAAAGCCAAAGGGCAGCCCCGAGAGCCACAC
GTGTACACCCTGCCCCCATCCCAGGAGGAGATGACCAAGAACCAGGTCAGCCTGACCTGCCTGGTCAAAGGC
TTCTACCCCAGCGACATCGCCGTGGAGTGGGAGAGCAATGGGCAGCCGGAGAACAACTACAAGACCACGCCT
CCCGTGCTGGACTCCGACGGCTCCTTCTTCCTCTACAGCAGGCTAACCGTGGACAAGAGCAGGTGGCAGGAG
GGGAATGTCTTCTCATGCTCCGTGATGCATGAGGCTCTGCACAACCACTACACAGAAGAGCCTCTCCCTG
TCTCTGGGTAAAGCTAGCTGA

133　DVVMTQTPLSLPVSLGDQASISCRSSQSLVHSNGNTYLHWYLQKPGQSPKLLIYKVSNRFSGVPDRFSGSGS
GTDFALKISRVEAEDLGVYFCSQSTHVPWTFGGGTKLEIKRTVAAPSVFIFPPSDEQLKSGTASVVCLLNNF
YPREAKVQWKVDNALQSGNSQESVTEQDSKDSTYSLSSTLTLSKADYEKHKVYACEVTHQGLSSPVTKSFNR
GECASMQKGDQNPQIAAHVISEASSKTTSVLQWAEKGYYTMSNNLVTLENGKQLTVKRQGLYYIYAQVTFCS
NREASSQAPFIASLCLKSPGRFERILLRAANTHSSAKPCGQQSIHLGGVFELQPGASVFVNVTDPSQVSHGT
GFTSFGLLKL

134　ATGAAGTTGCCTGTTAGGCTGTTGGTGCTGATGTTCTGGATTCCTGCTTCCAGCAGTGATGTTGTGATGACC
CAAACTCCACTCTCCCTGCCTGTCAGTCTTGGAGATCAAGCCTCCATCTCTTGCCGGTCTAGTCAGAGCCTT
GTACACAGTAATGGAAACACCTATTTACATTGGTACCTGCAGAAGCCAGGCCAGTCTCCAAAGCTCCTGATC
TACAAAGTTTCCAACCGATTTTCTGGGGTCCCAGACAGGTTCAGTGGCAGTGGATCAGGGACAGATTTCGCA
CTCAAGATCAGTAGAGTGGAGGCCGAGGATCTGGGAGTTTATTTCTGCTCTCAAAGTACACATGTTCCGTGG
ACGTTCGGTGGAGGCACCAAGCTCGAGATCAAACGAACTGTGGCTGCACCATCTGTCTTCATCTTCCCGCCA
TCTGATGAGCAGTTGAAATCTGGAACTGCCTCTGTTGTGTGCCTGCTGAATAACTTCTATCCCAGAGAGGCC
AAAGTACAGTGGAAGGTGGATAACGCCCTCCAATCGGGTAACTCCCAGGAGAGTGTCACAGAGCAGGACAGC
AAGGACAGCACCTACAGCCTCAGCAGCACCCTGACGCTGAGCAAAGCAGACTACGAGAAACACAAAGTCTAT
GCCTGCGAAGTCACCCATCAGGGCCTGAGCTCGCCCGTCACAAAGAGCTTCAACAGGGGAGAGTGTGCTAGC
ATGCAGAAGGGAGACCAGAACCCTCAGATCGCAGCTCACGTCATCTCCGAGGCTTCTTCCAAGACCACCTCC
GTGCTCCAGTGGGCTGAAAAGGGATACTACACCATGAGCAACAACCTGGTGACACTGGAGAACGGCAAGCAG

TABLE 6-continued

SEQ
ID
NO: Full Sequence

```
    CTCACAGTCAAGCGGCAGGGCCTTTACTACATCTATGCCCAGGTGACCTTCTGCTCCAACAGGGAGGCCTCC
    AGCCAGGCCCCTTTCATTGCCTCTCTGTGTCTCAAGAGCCCAGGCAGATTCGAGAGGATTCTCCTGCGCGCC
    GCCAATACACACAGCTCAGCCAAACCCTGCGGGCAACAGTCAATTCACCTGGGGGGGGTCTTTGAGTTGCAG
    CCAGGGGCCAGTGTCTTCGTGAACGTGACAGATCCCAGTCAGGTGAGCCATGGCACTGGCTTTACTAGCTTT
    GGGTTGCTGAAACTGTGA

135 EVQLVQSGAEVKKPGASVKISCKASGYSFTGYYMHWVKQAHGQGLEWIGRINPYNGATSYNQNFKDRATLTV
    DKSTSTAYMELSSLRSEDTAVYYCAREDYVYWGQGTTVTVSSAKTKGPSVFPLAPCSRSTSESTAALGCLVK
    DYEPEPVTVSWNSGALTSGVHTFPAVLQSSGLYSLSSVVTVPSSSLGTKTYTCNVDHKPSNTKVDKRVESKY
    GPPCPPCPAPEFEGGPSVFLFPPKPKDTLMISRTPEVTCVVVDVSQEDPEVQFNWYVDGVEVHNAKTKPREE
    QFNSTYRVVSVLTVLHQDWLNGKEYKCKVSNKGLPSSIEKTISKAKGQPREPQVYTLPPSQEEMTKNQVSLT
    CLVKGFYPSDIAVEWESNGQPENNYKTTPPVLDSDGSFFLYSRLTVDKSRWQEGNVFSCSVMHEALHNHYTQ
    KSLSLSLGKASQTPTNTISVTPTNNSTPTNNSNPKPNPASMQKGDQNPQIAAHVISEASSKTTSVLQWAEKG
    YYTMSNNLVTLENGKQLTVKRQGLYYIYAQVTFCSNREASSQAPFIASLCLKSPGRFERILLRAANTHSSAK
    PCGQQSIHLGGVFELQPGASVFVNVTDPSQVSHGTGFTSFGLLKL

136 ATGGGATGGAGCTGGATCTTTCTCTTTCTCCTGTCAGGAACTGCAGGTGTCCTCTCTGAGGTCCAGCTGGTG
    CAATCTGGAGCTGAGGTGAAGAAGCCTGGGGCTTCAGTGAAGATATCCTGCAAGGCTTCTGGATACTCCTTC
    ACTGGCTACTACATGCACTGGGTGAAGCAGGCCCATGGACAAGGGCTTGAGTGGATTGGAAGGATTAATCCT
    TACAATGGTGCTACTAGCTACAACCAGAACTTCAAGGACAGAGCCACCTTGACTGTAGACAAGTCCACGAGC
    ACAGCCTACATGGAGCTCAGCAGCCTGAGGTCTGAGGACACGGCAGTCTATTACTGTGCAAGAGAGGACTAC
    GTGTACTGGGGCCAAGGCACCACGGTCACCGTCTCCTCAGCCAAAACGAAGGGCCCATCCGTCTTCCCCCTG
    GCGCCCTGCTCCAGGAGCACCTCCGAGAGCACAGCCGCCCTGGGCTGCCTGGTCAAGGACTACTTCCCCGAA
    CCGGTGACGGTGTCGTGGAACTCAGGCGCCCTGACCAGCGGCGTGCACACCTTCCCGGCTGTCCTACAGTCC
    TCAGGACTCTACTCCCTCAGCAGCGTGGTGACCGTGCCCTCCAGCAGCTTGGGCACGAAGACCTACACCTGC
    AACGTAGATCACAAGCCCAGCAACACCAAGGTGGACAAGAGAGTTGAGTCCAAATATGGTCCCCCATGCCCA
    CCCTGCCCAGCACCTGAGTTCGAAGGGGGGACCATCAGTCTTCCTGTTCCCCCCAAAACCCAAGGACACTCTC
    ATGATCTCCCGGACCCCTGAGGTCACGTGCGTGGTGGTGGACGTGAGCCAGGAAGACCCCGAGGTCCAGTTC
    AACTGGTACGTGGATGGCGTGGAGGTGCATAATGCCAAGACAAAGCCGCGGGAGGAGCAGTTCAACAGCACG
    TACCGTGTGGTCAGCGTCCTCACCGTCCTGCACCAGGACTGGCTGAACGGCAAGGAGTACAAGTGCAAGGTC
    TCCAACAAAGGCCTCCCGTCCTCCATCGAGAAAACCATCTCCAAAGCCAAAGGGCAGCCCCGAGAGCCACAG
    GTGTACACCCTGCCCCCATCCCAGGAGGAGATGACCAAGAACCAGGTCAGCCTGACCTGCCTGGTCAAAGGC
    TTCTACCCCAGCGACATCGCCGTGGAGTGGGAGAGCAATGGGCAGCCGGAGAACAACTACAAGACCACGCCT
    CCCGTGCTGGACTCCGACGGCTCCTTCTTCCTCTACAGCAGGCTAACCGTGGACAAGAGCAGGTGGCAGGAG
    GGGAATGTCTTCTCATGCTCCGTGATGCATGAGGCTCTGCACAACCACTACACACAGAAGAGCCTCTCCCTG
    TCTCTGGGTAAAGCTAGTCAGACCCCCACCAACACCATCAGCGTGACCCCCACCAACAACAGCAACCCCACC
    AACAACAGCAACCCCAAGCCCAACCCCGCTAGCATGCAGAAGGGAGACCAGAACCCTCAGATCGCAGCTCAC
    GTCATCTCCGAGGCTTCTTCCAAGACCACCTCCGTGCTCCAGTGGGCTGAAAAGGGATACTACACCATGAGC
    AACAACCTGGTGACACTGGAGAACGGCAAGCAGCTCACAGTCAAGCGGCAGGGCCTTTACTACATCTATGCC
    CAGGTGACCTTCTGCTCCAACAGGGAGGCCTCCAGCCAGGCCCCCTTTCATTGCCTCTCTGTGTCTCAAGAGC
    CCAGGCAGATTCGAGAGGATTCTCCTGCGCGCCGCCAATACACACAGCTCAGCCAAACCCTGCGGGCAACAG
    TCAATTCACCTGGGGGGGGTCTTTGAGTTGCAGCCAGGGGCCAGTGTCTTCGTGAACGTGACAGATCCCAGT
    CAGGTGAGCCATGGCACTGGCTTTACTAGCTTTGGGTTGCTGAAACTGTGA

137 DVVMTQSPLSLPVTLGQPASISCRSSQSLVHSNGNTYLHWYQQRPGQSPRLLIYKVSNRFSGVPDRFSGSGS
    GTDFTLKISRVEAEDVGVYFCSQSTHVPWTFGGGTKLEIKRTVAAPSVFIFPPSDEQLKSGTASVVCLLNNF
    YPREAKVQWKVDNALQSGNSQESVTEQDSKDSTYSLSSTLTLSKADYEKHKVYACEVTHQGLSSPVTKSFNR
    GECAS

138 ATGAAGTTGCCTGTTAGGCTGTTGGTGCTGATGTTCTGGATTCCTGCTTCCAGCAGTGATGTTGTGATGACC
    CAATCTCCACTCTCCCTGCCTGTCACCCTTGGACAGCCGGCCTCCATCTCTTGCAGGTCTAGTCAGAGCCTT
    GTACACAGTAATGGAAACACCTATTTACATTGGTACCAGCAGAGACCAGGCCAGTCTCCAAGGCTCCTGATC
    TACAAAGTTTCCAACCGATTTTCTGGGGTCCCAGACAGGTTCAGTGGCAGTGGATCAGGGACAGATTTCACA
    CTCAAGATCAGCAGAGTGGAGGCTGAAGATGTTGGAGTTTATTTCTGCTCTCAAAGTACACATGTTCCTTGG
    ACGTTCGGCGGAGGGACCAAGCTCGAGATCAAACGAACTGTGGCTGCACCATCTGTCTTCATCTTCCCGCCA
    TCTGATGAGCAGTTGAAATCTGGAACTGCCTCTGTTGTGTGCCTGCTGAATAACTTCTATCCCAGAGAGGCC
    AAAGTACAGTGGAAGGTGGATAACGCCCTCCAATCGGGTAACTCCCAGGAGAGTGTCACAGAGCAGGACAGC
    AAGGACAGCACCTACAGCCTCAGCAGCACCCTGACGCTGAGCAAAGCAGACTACGAGAAACACAAAGTCTAT
    GCCTGCGAAGTCACCCATCAGGGCCTGAGCTCGCCCGTCACAAAGAGCTTCAACAGGGGAGAGTGTGCTAGC
    TGA

139 DVVMTQSPLSLPVTLGQPASISCRSSQSLVHSNGNTYLHWYQQRPGQSPRLLIYKVSNRFSGVPDRFSGSGS
    GTDFTLKISRVEAEDVGVYFCSQSTHVPWTFGGGTKLEIKRTVAAPSVFIFPPSDEQLKSGTASVVCLLNNF
    YPREAKVQWKVDNALQSGNSQESVTEQDSKDSTYSLSSTLTLSKADYEKHKVYACEVTHQGLSSPVTKSFNR
    GECASQTPTNTISVTPTNNSTPTNNSNPKPNPASMQKGDQNPQIAAHVISEASSKTTSVLQWAEKGYYTMSN
    NLVTLENGKQLTVKRQGLYYIYAQVTFCSNREASSQAPFIASLCLKSPGRFERILLRAANTHSSAKPCGQQS
    IHLGGVFELQPGASVFVNVTDPSQVSHGTGFTSFGLLKL

140 ATGAAGTTGCCTGTTAGGCTGTTGGTGCTGATGTTCTGGATTCCTGCTTCCAGCAGTGATGTTGTGATGACC
    CAATCTCCACTCTCCCTGCCTGTCACCCTTGGACAGCCGGCCTCCATCTCTTGCAGGTCTAGTCAGAGCCTT
    GTACACAGTAATGGAAACACCTATTTACATTGGTACCAGCAGAGACCAGGCCAGTCTCCAAGGCTCCTGATC
    TACAAAGTTTCCAACCGATTTTCTGGGGTCCCAGACAGGTTCAGTGGCAGTGGATCAGGGACAGATTTCACA
    CTCAAGATCAGCAGAGTGGAGGCTGAAGATGTTGGAGTTTATTTCTGCTCTCAAAGTACACATGTTCCTTGG
    ACGTTCGGCGGAGGGACCAAGCTCGAGATCAAACGAACTGTGGCTGCACCATCTGTCTTCATCTTCCCGCCA
    TCTGATGAGCAGTTGAAATCTGGAACTGCCTCTGTTGTGTGCCTGCTGAATAACTTCTATCCCAGAGAGGCC
    AAAGTACAGTGGAAGGTGGATAACGCCCTCCAATCGGGTAACTCCCAGGAGAGTGTCACAGAGCAGGACAGC
```

TABLE 6-continued

SEQ
ID
NO: Full Sequence
```
    AAGGACAGCACCTACAGCCTCAGCAGCACCCTGACGCTGAGCAAAGCAGACTACGAGAAACACAAAGTCTAT
    GCCTGCGAAGTCACCCATCAGGGCCTGAGCTCGCCCGTCACAAAGAGCTTCAACAGGGGGAGAGTGTGCTAGT
    CAGACCCCCACCAACACCATCAGCGTGACCCCCACCAACAACAGCACCCCCACCAACAACAGCAACCCCAAG
    CCCAACCCCGCTAGCATGCAGAAGGGAGACCAGAACCCTCAGATCGCAGCTCAGCTCATCTCCGAGGCTTCT
    TCCAAGACCACCTCCGTGCTCCAGTGGGCTGAAAAGGGATACTACACCATGAGCAACAACCTGGTGACACTG
    GAGAACGGCAAGCAGCTCACAGTCAAGCGGCAGGGCCTTTACTACATCTATGCCCAGGTGACCTTCTGCTCC
    AACAGGGAGGCCTCCAGCCAGGCCCCCTTTCATTGCCTCTCTGTGTCTCAAGAGCCCAGGCAGATTCGAGAGG
    ATTCTCCTGCGCGCCGCCAATACACACAGCTCAGCCAAACCCTGCGGGCAACAGTCAATTCACCTGGGGGGG
    GTCTTTGAGTTGCAGCCAGGGGCCAGTGTCTTCGTGAACGTGACAGATCCCAGTCAGGTGAGCCATGGCACT
    GGCTTTACTAGCTTTGGGTTGCTGAAACTGTGA
```

141 EVQLVQSGAEVKKPGASVKVSCKASGYSFTGYYMHWVRQAPGQGLEWIGRINPYNGATSYNQNFKDRVTLTV
    DKSTSTAYMELSSLRSEDTAVYYCAREDYVYWGQGTTVTVSSAKTKGPSVFPLAPCSRSTSESTAALGCLVK
    DYEPEPVTVSWNSGALTSGVHTFPAVLQSSGLYSLSSVVTVPSSSLGTKTYTCNVDHKPSNTKVDKRVESKY
    GPPCPPCPAPEFEGGPSVFLFPPKPKDTLMISRTPEVTCVVVDVSQEDPEVQFNWYVDGVEVHNAKTKPREE
    QFNSTYRVVSVLTVLHQDWLNGKEYKCKVSNKGLPSSIEKTISKAKGQPREPQVYTLPPSQEEMTKNQVSLT
    CLVKGFYPSDIAVEWESNGQPENNYKTTPPVLDSDGSFFLYSRLTVDKSRWQEGNVFSCSVMHEALHNHYTQ
    KSLSLSLGKAS

142 ATGGGATGGAGCTGGATCTTTCTCTTTCTCCTGTCAGGAACTGCAGGTGTCCTCTCTGAGGTCCAGCTGGTG
    CAATCTGGAGCTGAGGTGAAGAAGCCTGGGGCTTCAGTGAAGGTCTCCTGCAAGGCTTCTGGATACTCCTTC
    ACTGGCTACTACATGCACTGGGTGCGACAGGCCCCTGGACAAGGGCTTGAGTGGATTGGAAGGATTAATCCT
    TACAATGGTGCTACTAGCTACAACCAGAACTTCAAGGACAGAGTCACCTTGACTGTAGACAAGTCCACGAGC
    ACAGCCTACATGGAGCTCAGCAGCCTGAGGTCTGAGGACACGGCAGTCTATTACTGTGCAAGAGAGGACTAC
    GTGTACTGGGGCCAAGGCACCACGGTCACCGTCTCCTCAGCCAAAACGAAGGGCCCATCCGTCTTCCCCCTG
    GCGCCCTGCTCCAGGAGCACCTCCGAGAGCACAGCCGCCCTGGGCTGCCTGGTCAAGGACTACTTCCCCGAA
    CCGGTGACGGTGTCGTGGAACTCAGGCGCCCTGACCAGCGGCGTGCACACCTTCCCGGCTGTCCTACAGTCC
    TCAGGACTCTACTCCCTCAGCAGCGTGGTGACCGTGCCCTCCAGCAGCTTGGGCACGAAGACCTACACCTGC
    AACGTAGATCACAAGCCCAGCAACACCAAGGTGGACAAGAGAGTTGAGTCCAAATATGGTCCCCCATGCCCA
    CCCTGCCCAGCACCTGAGTTCGAAGGGGGACCATCAGTCTTCCTGTTCCCCCCAAAACCCAAGGACACTCTC
    ATGATCTCCCGGACCCCTGAGGTCACGTGCGTGGTGGTGGACGTGAGCCAGGAAGACCCCGAGGTCCAGTTC
    AACTGGTACGTGGATGGCGTGGAGGTGCATAATGCCAAGACAAAGCCGCGGGAGGAGCAGTTCAACAGCACG
    TACCGTGTGGTCAGCGTCCTCACCGTCCTGCACCAGGACTGGCTGAACGGCAAGGAGTACAAGTGCAAGGTC
    TCCAACAAAGGCCTCCCGTCCTCCATCGAGAAAACCATCTCCAAAGCCAAAGGGCAGCCCCGAGAGCCACAG
    GTGTACACCCTGCCCCCATCCCAGGAGGAGATGACCAAGAACCAGGTCAGCCTGACCTGCCTGGTCAAAGGC
    TTCTACCCCAGCGACATCGCCGTGGAGTGGGAGAGCAATGGGCAGCCGGAGAACAACTACAAGACCACGCCT
    CCCGTGCTGGACTCCGACGGCTCCTTCTTCCTCTACAGCAGGCTAACCGTGGACAAGAGCAGGTGGCAGGAG
    GGGAATGTCTTCTCATGCTCCGTGATGCATGAGGCTCTGCACAACCACTACACAGAAGAGCCTCTCCCTG
    TCTCTGGGTAAAGCTAGCTGA

143 EVQLVQSGAEVKKPGASVKISCKASGYSFTGYYMHWKQAHGQGLEWIGRINPYNGATSYNQNFKDRATLTV
    DKSTSTAYMELSSLRSEDTAVYYCAREDYVYWGQGTTVTVSSAKTKGPSVFPLAPCSRSTSESTAALGCLVK
    DYEPEPVTVSWNSGALTSGVHTFPAVLQSSGLYSLSSVVTVPSSSLGTKTYTCNVDHKPSNTKVDKRVESKY
    GPPCPPCPAPEFEGGPSVFLFPPKPKDTLMISRTPEVTCVVVDVSQEDPEVQFNWYVDGVEVHNAKTKPREE
    QFNSTYRVVSVLTVLHQDWLNGKEYKCKVSNKGLPSSIEKTISKAKGQPREPQVYTLPPSQEEMTKNQVSLT
    CLVKGFYPSDIAVEWESNGQPENNYKTTPPVLDSDGSFFLYSRLTVDKSRWQEGNVFSCSVMHEALHNHYTQ
    KSLSLSLGKASMQKGDQNPQIAAHVISEASSKTTSVLQWAEKGYYTMSNNLVTLENGKQLTVKRQGLYYIYA
    QVTFCSNREASSQAPFIASLCLKSPGRFERILLRAANTHSSAKPCGQQSIHLGGVFELQPGASVFVNVTDPS
    QVSHGTGFTSFGLLKL

144 ATGGGATGGAGCTGGATCTTTCTCTTTCTCCTGTCAGGAACTGCAGGTGTCCTCTCTGAGGTCCAGCTGGTG
    CAATCTGGAGCTGAGGTGAAGAAGCCTGGGGCTTCAGTGAAGATATCCTGCAAGGCTTCTGGATACTCCTTC
    ACTGGCTACTACATGCACTGGGTGAAGCAGGCCCATGGACAAGGGCTTGAGTGGATTGGAAGGATTAATCCT
    TACAATGGTGCTACTAGCTACAACCAGAACTTCAAGGACAGAGCCACCTTGACTGTAGACAAGTCCACGAGC
    ACAGCCTACATGGAGCTCAGCAGCCTGAGGTCTGAGGACACGGCAGTCTATTACTGTGCAAGAGAGGACTAC
    GTGTACTGGGGCCAAGGCACCACGGTCACCGTCTCCTCAGCCAAAACGAAGGGCCCATCCGTCTTCCCCCTG
    GCGCCCTGCTCCAGGAGCACCTCCGAGAGCACAGCCGCCCTGGGCTGCCTGGTCAAGGACTACTTCCCCGAA
    CCGGTGACGGTGTCGTGGAACTCAGGCGCCCTGACCAGCGGCGTGCACACCTTCCCGGCTGTCCTACAGTCC
    TCAGGACTCTACTCCCTCAGCAGCGTGGTGACCGTGCCCTCCAGCAGCTTGGGCACGAAGACCTACACCTGC
    AACGTAGATCACAAGCCCAGCAACACCAAGGTGGACAAGAGAGTTGAGTCCAAATATGGTCCCCCATGCCCA
    CCCTGCCCAGCACCTGAGTTCGAAGGGGGACCATCAGTCTTCCTGTTCCCCCCAAAACCCAAGGACACTCTC
    ATGATCTCCCGGACCCCTGAGGTCACGTGCGTGGTGGTGGACGTGAGCCAGGAAGACCCCGAGGTCCAGTTC
    AACTGGTACGTGGATGGCGTGGAGGTGCATAATGCCAAGACAAAGCCGCGGGAGGAGCAGTTCAACAGCACG
    TACCGTGTGGTCAGCGTCCTCACCGTCCTGCACCAGGACTGGCTGAACGGCAAGGAGTACAAGTGCAAGGTC
    TCCAACAAAGGCCTCCCGTCCTCCATCGAGAAAACCATCTCCAAAGCCAAAGGGCAGCCCCGAGAGCCACAG
    GTGTACACCCTGCCCCCATCCCAGGAGGAGATGACCAAGAACCAGGTCAGCCTGACCTGCCTGGTCAAAGGC
    TTCTACCCCAGCGACATCGCCGTGGAGTGGGAGAGCAATGGGCAGCCGGAGAACAACTACAAGACCACGCCT
    CCCGTGCTGGACTCCGACGGCTCCTTCTTCCTCTACAGCAGGCTAACCGTGGACAAGAGCAGGTGGCAGGAG
    GGGAATGTCTTCTCATGCTCCGTGATGCATGAGGCTCTGCACAACCACTACACAGAAGAGCCTCTCCCTG
    TCTCTGGGTAAAGCTAGCATGCAGAAGGGAGACCAGAACCCTCAGATCGCAGCTCACGTCATCTCCGAGGCT
    TCTTCCAAGACCACCTCCGTGCTCCAGTGGGCTGAAAAGGGATACTACACCATGAGCAACAACCTGGTGACA
    CTGGAGAACGGCAAGCAGCTCACAGTCAAGCGGCAGGGCCTTTACTACATCTATGCCCAGGTGACCTTCTGC
    TCCAACAGGGAGGCCTCCAGCCAGGCCCCCTTTCATTGCCTCTCTGTGTCTCAAGAGCCCAGGCAGATTCGAG
    AGGATTCTCCTGCGCGCCGCCAATACACACAGCTCAGCCAAACCCTGCGGGCAACAGTCAATTCACCTGGGG
    GGGGTCTTTGAGTTGCAGCCAGGGGCCAGTGTCTTCGTGAACGTGACAGATCCCAGTCAGGTGAGCCATGGC
    ACTGGCTTTACTAGCTTTGGGTTGCTGAAACTGTGA

TABLE 6-continued

SEQ
ID
NO: Full Sequence

145 EVQLVQSGAEVKKPGASVKISCKASGYSFTGYYMHWVKQAHGQGLEWIGRINPYNGATSYNQNFKDRATLTV
DKSTSTAYMELSSLRSEDTAVYYCAREDYVYWGQGTTVTVSSAKTKGPSVFPLAPCSRSTSESTAALGCLVK
DYEPEPVTVSWNSGALTSGVHTFPAVLQSSGLYSLSSVVTVPSSSLGTKTYTCNVDHKPSNTKVDKRVESKY
GPPCPPCPAPEFEGGPSVFLFPPKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQPREPQVYTLPPSQEEMTKNQVSLT
CLVKGFYPSDIAVEWESNGQPENNYKTTPPVLDSDGSFFLYSRLTVDKSRWQEGNVFSCSVMHEALHNHYTQ
KSLSLSLGKAS

146 ATGGGATGGAGCTGGATCTTTCTCTTTCTCCTGTCAGGAACTGCAGGTGTCCTCTCTGAGGTCCAGCTGGTG
CAATCTGGAGCTGAGGTGAAGAAGCCTGGGGCTTCAGTGAAGATATCCTGCAAGGCTTCTGGATACTCCTTC
ACTGGCTACTACATGCACTGGGTGAAGCAGGCCCATGGACAAGGGCTTGAGTGGATTGGAAGGATTAATCCT
TACAATGGTGCTACTAGCTACAACCAGAACTTCAAGGACAGGCCACCTTGACTGTAGACAAGTCCACGAGC
ACAGCCTACATGGAGCTCAGCAGCCTGAGGTCTGAGGACACGGCAGTCTATTACTGTGCAAGAGAGGACTAC
GTGTACTGGGGCCAAGGCACCACGGTCACCGTCTCCTCAGCCAAAACGAAGGGCCCATCCGTCTTCCCCCTG
GCGCCCTGCTCCAGGAGCACCTCCGAGAGCACAGCCGCCCTGGGCTGCCTGGTCAAGGACTACTTCCCCGAA
CCGGTGACGGTGTCGTGGAACTCAGGCGCCCTGACCAGCGGCGTGCACACCTTCCCGGCTGTCCTACAGTCC
TCAGGACTCTACTCCCTCAGCAGCGTGGTGACCGTGCCCTCCAGCAGCTTGGGCACGAAGACCTACACCTGC
AACGTAGATCACAAGCCCAGCAACACCAAGGTGGACAAGAGAGTTGAGTCCAAATATGGTCCCCCATGCCCA
CCCTGCCCAGCACCTGAGTTCGAAGGGGGACCATCAGTCTTCCTGTTCCCCCCAAAACCCAAGGACACTCTC
ATGATCTCCCGGACCCCTGAGGTCACGTGCGTGGTGGTGGACGTGAGCCAGGAAGACCCCGAGGTCCAGTTC
AACTGGTACGTGGATGGCGTGGAGGTGCATAATGCCAAGACAAAGCCGCGGGAGGAGCAGTTCAACAGCACG
TACCGTGTGGTCAGCGTCCTCACCGTCCTGCACCAGGACTGGCTGAACGGCAAGGAGTACAAGTGCAAGGTC
TCCAACAAAGGCCTCCCGTCCTCCATCGAGAAAACCATCTCCAAAGCCAAAGGGCAGCCCCGAGAGCCACAG
GTGTACACCCTGCCCCCATCCCAGGAGGAGATGACCAAGAACCAGGTCAGCCTGACCTGCCTGGTCAAAGGC
TTCTACCCCAGCGACATCGCCGTGGAGTGGGAGAGCAATGGGCAGCCGGAGAACAACTACAAGACCACGCCT
CCCGTGCTGGACTCCGACGGCTCCTTCTTCCTCTACAGCAGGCTAACCGTGGACAAGAGCAGGTGGCAGGAG
GGGAATGTCTTCTCATGCTCCGTGATGCATGAGGCTCTGCACAACCACTACACACAGAAGAGCCTCTCCCTG
TCTCTGGGTAAAGCTAGCTGA

147 EVQLVQSGAEVKKPGASVKVSCKASGYSFTGYYMHWVRQAPGQGLEWIGRINPYNGATSYNQNFKDRVTLTV
DKSTSTAYMELSSLRSEDTAVYYCAREDYVYWGQGTTVTVSSAKTKGPSVFPLAPCSRSTSESTAALGCLVK
DYEPEPVTVSWNSGALTSGVHTFPAVLQSSGLYSLSSVVTVPSSSLGTKTYTCNVDHKPSNTKVDKRVESKY
GPPCPPCPAPEFEGGPSVFLFPPKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQPREPQVYTLPPSQEEMTKNQVSLT
CLVKGFYPSDIAVEWESNGQPENNYKTTPPVLDSDGSFFLYSRLTVDKSRWQEGNVFSCSVMHEALHNHYTQ
KSLSLSLGKAS

148 ATGGGATGGAGCTGGATCTTTCTCTTTCTCCTGTCAGGAACTGCAGGTGTCCTCTCTGAGGTCCAGCTGGTG
CAATCTGGAGCTGAGGTGAAGAAGCCTGGGGCTTCAGTGAAGGTCTCCTGCAAGGCTTCTGGATACTCCTTC
ACTGGCTACTACATGCACTGGGTGCGACAGGCCCCTGGACAAGGGCTTGAGTGGATTGGAAGGATTAATCCT
TACAATGGTGCTACTAGCTACAACCAGAACTTCAAGGACAGGCCACCTTGACTGTAGACAAGTCCACGAGC
ACAGCCTACATGGAGCTCAGCAGCCTGAGGTCTGAGGACACGGCAGTCTATTACTGTGCAAGAGAGGACTAC
GTGTACTGGGGCCAAGGCACCACGGTCACCGTCTCCTCAGCCAAAACGAAGGGCCCATCCGTCTTCCCCCTG
GCGCCCTGCTCCAGGAGCACCTCCGAGAGCACAGCCGCCCTGGGCTGCCTGGTCAAGGACTACTTCCCCGAA
CCGGTGACGGTGTCGTGGAACTCAGGCGCCCTGACCAGCGGCGTGCACACCTTCCCGGCTGTCCTACAGTCC
TCAGGACTCTACTCCCTCAGCAGCGTGGTGACCGTGCCCTCCAGCAGCTTGGGCACGAAGACCTACACCTGC
AACGTAGATCACAAGCCCAGCAACACCAAGGTGGACAAGAGAGTTGAGTCCAAATATGGTCCCCCATGCCCA
CCCTGCCCAGCACCTGAGTTCGAAGGGGGACCATCAGTCTTCCTGTTCCCCCCAAAACCCAAGGACACTCTC
ATGATCTCCCGGACCCCTGAGGTCACGTGCGTGGTGGTGGACGTGAGCCAGGAAGACCCCGAGGTCCAGTTC
AACTGGTACGTGGATGGCGTGGAGGTGCATAATGCCAAGACAAAGCCGCGGGAGGAGCAGTTCAACAGCACG
TACCGTGTGGTCAGCGTCCTCACCGTCCTGCACCAGGACTGGCTGAACGGCAAGGAGTACAAGTGCAAGGTC
TCCAACAAAGGCCTCCCGTCCTCCATCGAGAAAACCATCTCCAAAGCCAAAGGGCAGCCCCGAGAGCCACAG
GTGTACACCCTGCCCCCATCCCAGGAGGAGATGACCAAGAACCAGGTCAGCCTGACCTGCCTGGTCAAAGGC
TTCTACCCCAGCGACATCGCCGTGGAGTGGGAGAGCAATGGGCAGCCGGAGAACAACTACAAGACCACGCCT
CCCGTGCTGGACTCCGACGGCTCCTTCTTCCTCTACAGCAGGCTAACCGTGGACAAGAGCAGGTGGCAGGAG
GGGAATGTCTTCTCATGCTCCGTGATGCATGAGGCTCTGCACAACCACTACACACAGAAGAGCCTCTCCCTG
TCTCTGGGTAAAGCTAGCTGA

149 DVVMTQSPLSLPVTLGQPASISCRSSQSLVHSNGNTYLHWYQQRPGQSPRLLIYKVSNRFSGVPDRFSGSGS
GTDFTLKISRVEAEDVGVYFCSQSTHVPWTFGGGTKLEIKRTVAAPSVFIFPPSDEQLKSGTASVVCLLNNF
YPREAKVQWKVDNALQSGNSQESVTEQDSKDSTYSLSSTLTLSKADYEKHKVYACEVTHQGLSSPVTKSFNR
GECAS

150 ATGAAGTTGCCTGTTAGGCTGTTGGTGCTGATGTTCTGGATTCCTGCTTCCAGCAGTGATGTTGTGATGACC
CAATCTCCACTCTCCCTGCCTGTCACCCTTGGACAGCCGGCCTCCATCTCTTGCAGGTCTAGTCAGAGCCTT
GTACACAGTAATGGAAACACCTATTTACATTGGTACCAGCAGAGACCAGGCCAGTCTCCAAGGCTCCTGATC
TACAAAGTTTCCAACCGATTTTCTGGGGTCCCAGACAGGTTCAGTGGCAGTGGATCAGGGACAGATTTCACA
CTCAAGATCAGCAGAGTGGAGGCTGAAGATGTTGGAGTTTATTTCTGCTCTCAAAGTACACATGTTCCTTGG
ACGTTCGGCGGAGGGACCAAGCTCGAGATCAAACGAACTGTGGCTGCACCATCTGTCTTCATCTTCCCGCCA
TCTGATGAGCAGTTGAAATCTGGAACTGCCTCTGTTGTGTGCCTGCTGAATAACTTCTATCCCAGAGAGGCC
AAAGTACAGTGGAAGGTGGATAACGCCCTCCAATCGGGTAACTCCCAGGAGAGTGTCACAGAGCAGGACAGC
AAGGACAGCACCTACAGCCTCAGCAGCACCCTGACGCTGAGCAAAGCAGACTACGAGAAACACAAAGTCTAT
GCCTGCGAAGTCACCCATCAGGGCCTGAGCTCGCCCGTCACAAAGAGCTTCAACAGGGGAGAGTGTGCTAGC
TGA

TABLE 6-continued

| SEQ ID NO: | Full Sequence |
|---|---|
| 151 | EPPTACREKQYLINSQCCSLCQPGQKLVSDCTEFTETECLPCGESEFLDTWNRETHCHQHKYCDPNLGLRVQ QKGTSETDTICTCEEGWHCTSEACESCVLHRSCSPGFGVKQIATGVSDTICEPCPVGFFSNVSSAFEKCHPW TSCETKDLVVQQAGTNKTDVVCGPQDRLRVDSNLGWLCLLLLPIPLIVWVKRKEVQKTCRKHRKENQGSHES PTLNPETVAINLSDVDLSKYIATIAGVMTLSQVKGFVRKNGVNEAKIDEIKNDNVQDTAEQKVQLLRNWHQL HGKKEAYDTLIKDLKKANLCTLAEKIQTIILKDITSDSENSNFRNEIQSLV |
| 152 | ATGGTTCGTCTGCCTCTGCAGTGCGTCCTCTGGGGCTGCTTGCTGACCGCTGTCCATCCAGAACCACCCACT GCATGCAGAGAAAAACAGTACCTAATAAACAGTCAGTGCTGTTCTTTGTGCCAGCCAGGACAGAAACTGGTG AGTGACTGCACAGAGTTCACTGAAACGGAATGCCTTCCTTGCGGTGAAAGCGAATTCCTAGACACCTGGAAC AGAGAGACACACTGCCACCAGCACAAATACTGCGACCCCAACCTAGGGCTTCGGGTCCAGCAGAAGGGCACC TCAGAAACAGACACCATCTGCACCTGTGAAGAAGGCTGGCACTGTACGAGTGAGGCCTGTGAGAGCTGTGTC CTGCACCGCTCATGCTCGCCCGGCTTTGGGGTCAAGCAGATTGCTACAGGGGTTTCTGATACCATCTGCGAG CCCTGCCCAGTCGGCTTCTTCTCCAATGTGTCATCTGCTTTCGAAAAATGTCACCCTTGGACAAGCTGTGAG ACCAAGACCTGGTTGTGCAACAGGCAGGCACAAACAAGACTGATGTTGTCTGTGGTCCCCAGGATCGGCTG AGAGTCGACTCTAACTTGGGGTGGCTTTGTCTTCTTCTTTTGCCAATTCCACTAATTGTTTGGGTGAAGAGA AAGGAAGTACAGAAAACATGCAGAAAGCACAGAAAGGAAAACCAAGGTTCTCATGAATCTCCAACCTTAAAT CCTGAAACAGTGGCAATAAATTTATCTGATGTTGACTTGAGTAAATATATCGCCACTATTGCTGGAGTCATG ACACTAAGTCAAGTTAAAGGCTTTGTTCGAAAGAATGGTGTCAATGAAGCCAAAATAGATGAGATCAAGAAT GACAATGTCCAAGACACAGCAGAACAGAAAGTTCAACTGCTTCGTAATTGGCATCAACTTCATGGAAAGAAA GAAGCGTATGACACATTGATTAAAGATCTCAAAAAAGCCAATCTTTGTACTCTTGCAGAGAAAATTCAGACT ATCATCCTCAAGGACATTACTAGTGACTCAGAAAATTCAAACTTCAGAAATGAAATCCAAAGCTTGGTCTAG |
| 153 | PPTACREKQYLINSQ |
| 154 | QCCSLCQPGQ |
| 155 | DTWNRETHCHQHKYC |
| 156 | HRSCSPGFGVKQI |
| 157 | KCHPWTSCETKD |
| 158 | CHQHKYCDPNLGL |
| 159 | INSQCCSLCQPGQ |
| 160 | CLPCGESEFLDTWNR |
| 161 | DTWNRETHCH |
| 162 | CHQHKYCDPNLGLR |
| 163 | HCTSEACESCVLHR |
| 164 | LHRSCSPGFGVK |
| 165 | HPWTSCETKDLVVQQ |
| 166 | TNKTDVVCGPQDR |
| 167 | PTACREKQYLINSQ |
| 168 | EFASAEAGITGTWYNQHGSTFTVTAGADGNLTGQYENRAQGTGCQNSPYTLTGRYNGTKLEWRVEWNNSTEN CHSRTEWRGQYQGGAEARINTQWNLTYEGGSGPATEQGQDTFTKVKPSAASGSEPEA |
| 169 | GAGTTTGCTTCTGCTGAAGCTGGAATCACAGGCACATGGTATAATCAGCACGGCTCTACCTTTACAGTGACA GCCGGAGCTGATGGAAACCTGACCGGCCAGTATGAGAACAGAGCCCAGGGAACAGGATGTCAGAATAGTCCT TATACACTGACAGGCAGATATAACGGAACAAAGCTGGAGTGGAGAGTGGAGTGGAATAACTCTACAGAGAAC TGTCACTCTAGAACAGAGTGGAGAGGCCAGTACCAGGGCGGCGCTGAGGCTAGAATTAACACACAGTGGAAC CTGACATACGAGGGAGGCTCTGGACCTGCTACAGAACAGGGCCAGGATACATTCACAAAGGTGAAGCCTTCT GCTGCCTCTGGATCT |
| 170 | RLQLQESGPGLLKPSVTLSLTCTVSGDSVASSSYYWGWVRQPPGKGLEWIGTINFSGNMYYSPSLRSVTMS ADMSENSFYLKLDSVTAADTAVYYCAAGHLVMGFGAHWGQGKLVSVSPASTKGPSVFPLAPCSRSTSESTAA LGCLVKDYFPEPVTVSWNSGALTSGVHTFPAVLQSSGLYSLSSVVTVPSSSLGTKTYTCNVDHKPSNTKVDK |

TABLE 6-continued

| SEQ ID NO: | Full Sequence |
|---|---|
| | RVESKYGPPCPPCPAPEFEGGPSVFLFPPKPKDTLMISRTPEVTCVVVDVSQEDPEVQFNWYVDGVEVHNAK<br>TKPREEQFNSTYRVVSVLTVLHQDWLNGKEYKCKVSNKGLPSSIEKTISKAKGQPREPQVYTLPPSQEEMTK<br>NQVSLTCLVKGFYPSDIAVEWESNGQPENNYKTTPPVLDSDGSFFLYSRLTVDKSRWQEGNVFSCSVMHEAL<br>HNHYTQKSLSLSLGKASQTPTNTISVTPTNNSTPTNNSNPKPNPASEFASAEAGITGTWYNQHGSTFTVTAG<br>ADGNLTGQYENRAQGTGCQNSPYTLTGRYNGTKLEWRVEWNNSTENCHSRTEWRGQYQGGAEARINTQWNLT<br>YEGGSGPATEQGQDTFTKVKPSAASGSEPEA |
| 171 | ATGGACCTCCTGTGCAAGAACATGAAGCACCTGTGGTTCTTCCTCCTGCTGGTGGCGGCTCCCAGATGGGTC<br>CTGTCCCGGCTGCAGCTGCAGGAGTCGGGCCCAGGCCTGCTGAAGCCTTCGGTGACCCTGTCCCTCACCTGC<br>ACTGTCTCGGGTGACTCCGTCGCCAGTAGTTCTTATTACTGGGGCTGGGTCCGTCAGCCCCCAGGGAAGGGA<br>CTCGAGTGGATAGGGACTATCAATTTTAGTGGCAATATGTATTATAGTCCGTCCCTCAGGAGTCGAGTGACC<br>ATGTCGGCAGACATGTCCGAGAACTCCTTCTATCTGAAATTGGACTCTGTGACCGCAGCAGACACGGCCGTC<br>TATTATTGTGCGGCAGGACACCTCGTTATGGGATTTGGGGCCCACTGGGGACAGGGAAAACTGGTCTCCGTC<br>TCTCCAGCTTCCACCAAGGGCCCATCCGTCTTCCCCCTGGCGCCCTGCTCCAGGAGCACCTCCGAGAGCACA<br>GCCGCCCTGGGCTGCCTGGTCAAGGACTACTTCCCCGAACCGGTGACGGTGTCGTGGAACTCAGGCGCCCTG<br>ACCAGCGGCGTGCACACCTTCCCGGCTGTCCTACAGTCCTCAGGACTCTACTCCCTCAGCAGCGTGGTGACC<br>GTGCCCTCCAGCAGCTTGGGCACGAAGACCTACACCTGCAACGTAGATCACAAGCCCAGCAACACCAAGGTG<br>GACAAGAGAGTTGAGTCCAAATATGGTCCCCCATGCCCACCCTGCCCAGCACCTGAGTTCGAAGGGGGACCA<br>TCAGTCTTCCTGTTCCCCCCAAAACCCAAGGACACTCTCATGATCTCCCGGACCCCTGAGGTCACGTGCGTG<br>GTGGTGGACGTGAGCCAGGAAGACCCCGAGGTCCAGTTCAACTGGTACGTGGATGGCGTGGAGGTGCATAAT<br>GCCAAGACAAAGCCGCGGGAGGAGCAGTTCAACAGCACGTACCGTGTGGTCAGCGTCCTCACCGTCCTGCAC<br>CAGGACTGGCTGAACGGCAAGGAGTACAAGTGCAAGGTCTCCAACAAAGGCCTCCCGTCCTCCATCGAGAAA<br>ACCATCTCCAAAGCCAAAGGGCAGCCCCGAGAGCCACAGGTGTACACCCTGCCCCCATCCCAGGAGGAGATG<br>ACCAAGAACCAGGTCAGCCTGACCTGCCTGGTCAAAGGCTTCTACCCCAGCGACATCGCCGTGGAGTGGGAG<br>AGCAATGGGCAGCCGGAGAACAACTACAAGACCACGCCTCCCGTGCTGGACTCCGACGGCTCCTTCTTCCTC<br>TACAGCAGGCTAACCGTGGACAAGAGCAGGTGGCAGGAGGGGAATGTCTTCTCATGCTCCGTGATGCATGAG<br>GCTCTGCACAACCACTACACACAGAAGAGCCTCTCCCTGTCTCTGGGTAAAGCTAGTCAGACCCCCACCAAC<br>ACCATCAGCGTGACCCCCACCAACAACAGCACCCCCACCAACAACAGCAACCCCAAGCCCAACCCCGCTAGC<br>GAGTTTGCTTCTGCTGAAGCTGGAATCACAGGCACATGGTATAATCAGCACGGCTCTACCTTTACAGTGACA<br>GCCGGAGCTGATGGAAACCTGACCGGCCAGTATGAGAACAGAGCCCAGGGAACAGGATGTCAGAATAGTCCT<br>TATACACTGACAGGCAGATATAACGGAACAAAGCTGGAGTGGAGAGTGGAGTGGAATAACTCTACAGAGAAC<br>TGTCACTCTAGAACAGAGTGGAGAGGCCAGTACCAGGGCGGCGCTGAGGCTAGAATTAACACACAGTGGAAC<br>CTGACATACGAGGGAGGCTCTGGACCTGCTACAGAACAGGGCCAGGATACATTCACAAAGGTGAAGCCTTCT<br>GCTGCCTCTGGATCTGAGCCTGAGGCTTGA |

(for certain antibody sequences, CDRs are highlighted in bold font)

REFERENCES

Hivroz C, Chemin K, Tourret M, Bohineust A. Crosstalk between T lymphocytes and dendritic cells. Crit Rev Immunol. 2012; 32(2):139-55.

Daphne Y. Ma and Edward A. Clark. The role of CD40 and CD40L in Dendritic Cells Semin Immunol. 2009 October; 21(5): 265-272.

Elgueta R, Benson M J, de Vries V C, Wasiuk A, Guo Y, et al., Molecular mechanism and function of CD40/CD40L engagement in the immune system. Immunol Rev. 2009; 229(1): doi: 10.1111/j.1600-065X.2009.00782.x Therapeutic Activity of Agonistic, Human Anti-CD40 Monoclonal Antibodies Requires Selective FcγR Engagement. RonyDahan1Bryan C. Barnhart FubinLi Aaron P. Yamniuk Alan J. Korman Jeffrey V. Ravetch https://doi.org/10.1016/j.ccell.2016.05.001

Human Anti-CD40 Antibody and Poly IC:LC Adjuvant Combination Induces Potent T Cell Responses in the Lung of Non-Human Primates. Elizabeth A Thompson,*† Frank Liang,*† Gustaf Lindgren,* Kerrie J Sandgren,* Kylie M Quinn,† Patricia A Darrah,† Richard A Koup,† Robert A Seder,† Ross M Kedl,‡ and Karin Loré*† J Immunol. 2015 Aug. 1; 195(3): 1015-1024. doi: 10.4049/jimmunol.1500078

CDX-1140, a Novel Agonist CD40 Antibody with Potent Anti-Lymphoma Activity Li-Zhen He, James Testa, Wasiuk Anna, Weidlick Jeffery, Crystal Sisson, Laura A. Vitale, Thomas O'Neill, Andrea Crocker, Jenifer Widger, Joel Goldstein, Henry C. Marsh Jr. and Tibor Keler. Blood 2016 128:1848;

APX005MFDA https://www.fda.gov/downloads/Advisory-Committees/ . . . /Drugs/ . . . /UCM565257.pdf. Jun. 21, 2017—Presentation Overview. 2. Role of CD40 in the Immune System. Proposed Pediatric Development. Therapeutic Effects of Targeting CD40. CD40 Agonistic Antibody APX005M A potent adjuvant effect of CD40 antibody attached to antigen Tom A Barr, Adele L Mccormick, Jennifer Carlring, and Andrew W Heath Immunology. 2003 May; 109(1): 87-92. doi: 10.1046/j.1365-2567.2003.01634.x Functional Specialty of CD40 and Dendritic Cell Surface Lectins for Exogenous Antigen Presentation to CD8(+) and CD4(+) T Cells. Yin W1, Gorvel L2, Zurawski S3, Li D3, Ni L3, Duluc D3, Upchurch K1, Kim J3, Gu C1, Ouedraogo R3, Wang Z3, Xue Y3, Joo H1, Gorvel JP4, Zurawski G1, Oh S1. EBioMedicine. 2016 Jan. 28; 5:46-58. doi: 10.1016/j.ebiom.2016.01.029. eCollection 2016 March Chatterjee B., Smed-Sorensen A., Cohn L., Chalouni C., Vandlen R., Lee B. C., Widger J., Keler T., Delamarre L., Mellman I. Internalization and endosomal degradation of receptor-bound antigens regulate the efficiency of cross presentation by human dendritic cells. Blood. 2012; 120: 2011-2020.

Mangsbo et al, 2014; DOI: 10.1158/1078-0432.CCR-14-0913

The human agonistic CD40 antibody ADC-1013 eradicates bladder tumors and generates T cell dependent tumor immunity [Aligator]

Therapeutic Activity of Agonistic, Human Anti-CD40 Monoclonal Antibodies Requires Selective FcγR Engagement Rony Dahan Bryan C.Barnhart2FubinLi14Aaron P.Yamniuk3Alan J.Korman2Jeffrey V.Ravetch1 Cancer Cell Volume 29, Issue 6, 13 Jun. 2016, Pages 820-831

Gladue et al., The CD40 agonist antibody CP-870,893 enhances dendritic cell and B-cell activity and promotes anti-tumor efficacy in SCID-hu mice. Cancer Immunology and Immunotherapy 60(7):1009-17. July 2011

Zurawski G, Shen X, Zurawski S, Tomaras G D, Montefiori D C, Roederer M, et al. Superiority in Rhesus Macaques of Targeting HIV-1 Env Gp140 to CD40 Versus LOX-1 in Combination with Replication Competent NYVAC-KC for Induction of Env-Specific Antibody and T Cell Responses. J. Virol. 2017; doi: 10.1128/JVI.01596-16.

Cheng L, Zhang Z, Li G, Li F, Wang L, Zhang L, et al., Human innate responses and adjuvant activity of TLR ligands in vivo in mice reconstituted with a human immune system. Vaccine 2017; 35: 6143-6153.

Robert H. Vonderheide and Martin J. Glennie. Agonistic CD40 antibodies and cancer therapy. Clin Cancer Res. 2013 Mar. 1; 19(5): 1035-1043.

Vonderheide R H, Burg J M, Mick R, Trosko J A, Li D, Shaik M N, Tolcher A W, Hamid O. Phase I study of the CD40 agonist antibody CP-870,893 combined with carboplatin and paclitaxel in patients with advanced solid tumors. Oncoimmunology. 2013 Jan. 1; 2(1):e23033.

Yamniuk et al., Functional Antagonism of Human CD40 Achieved by Targeting a Unique Species-Specific Epitope. JMB 428, Issue 14, 17 Jul. 2016, Pages 2860-2879.

Daoussis Targeting CD40L: a Promising Therapeutic Approach. Clinical Vaccine Immunology 2004 vol. 11 no. 4 635-641.

Law C L, Gordon K A, Collier J, Klussman K, McEarchern J A, Cerveny C G, et al. Preclinical antilymphoma activity of a humanized anti-CD40 monoclonal antibody, SGN-40. Cancer Res 2005; 65:8331-8. Note this is the weak CD40 agonist S2C6-hIgG1.

Previous studies have shown that CD40L is most effective when it clusters its receptor, CD40, on the membranes of responding cells [45], [46]. Haswell L E, Glennie M J, Al-Shamkhani A (2001) Analysis of the oligomeric requirement for signaling by CD40 using soluble multimeric forms of its ligand, CD154. Eur J Immunol 31: 3094-3100.

Nanoparticle-Delivered Multimeric Soluble CD40L DNA Combined with Toll-Like Receptor Agonists as a Treatment for Melanoma Geoffrey W. Stone, Suzanne Barzee, Victoria Snarsky, Camila Santucci, Brian Tran, Robert Langer, Gregory T. Zugates, Daniel G. Anderson, Richard S. Kornbluth PLOS One Oct. 8, 2009 https://doi.org/10.1371/journal.pone.0007334

Bodmer J L, Schneider P, and Tschopp J. The molecular architecture of the TNF superfamily. Trends Biochem Sci. 2002; 27(1):19-26

Johnson et al., Clinical and Biological Effects of an Agonist Anti-CD40 Antibody: A Cancer Research UK Phase I Study. Clinical Cancer Research DOI: 10.1158/1078-0432.CCR-14-2355 Published March 2015

Induction of an Altered CD40 Signaling Complex by an Antagonistic Human Monoclonal Antibody to CD40 Katherine C. Bankert,*,1 Kyp L. Oxley,*,1,2 Sonja M. Smith,*,3 John P. Graham,†,2 Mark de Boer,‡ Marielle Thewissen,‡ Peter J. Simons,x and Gail A. Bishop doi: 10.4049/jimmunol.1402903

Richard S. Kornbluth, Mariusz Stempniak & Geoffrey W. Stone (2012) Design of CD40 Agonists and Their Use in Growing B Cells for Cancer Immunotherapy, International Reviews of Immunology, 31:4, 279-288, DOI: 10.3109/08830185.2012.703272

Michael D Oberst, Catherine Auge, Chad Morris, et al. Potent Immune Modulation by MEDI6383, an Engineered Human OX40 Ligand IgG4P Fc Fusion Protein. *Mol Cancer Ther* Published OnlineFirst Mar. 15, 2018.

Yu et al., Complex Interplay between Epitope Specificity and Isotype Dictates the Biological Activity of Anti-human CD40 Antibodies. 2018, Cancer Cell 33, 664-675 https://doi.org/10.1016/j.ccell.2018.02.009

Elegant studies using recombinant CD40L molecules of different stoichiometries have also demonstrated that higher-order clustering of CD40 can enhance signal intensity to levels above those observed with the trimeric ligand (Haswell, L. E., Glennie, M. J., Al-Shamkhani, A. (2001). Analysis of the olig-omeric requirement for signaling by CD40 using soluble multimeric forms of its ligand, CD154. Eur. J. Immunol. 31, 3094-3100).

A soluble hexameric form of CD40 ligand activates human dendritic cells and augments memory T cell response. Isabelle Miconnet and Giuseppe Pantaleo. Vaccine, 2008 Jul. 29, Volume 26, Issue 32, Pages 4006-4014

Design of CD40 Agonists and their use in growing B cells for cancer immunotherapy. Richard S. Kornbluth, Mariusz Stempniak, and Geoffrey W. Stone. Int Rev Immunol. 2012 August; 31(4): doi: 10.3109/08830185.2012.703272

Wang, Hui Ming, Qi Yan, Tao Yang, Hui Cheng, Juan Du, Katsuji Yoshioka, Sam K. P. Kung, and Guo Hua Ding. 2015. "Scaffold Protein JLP Is Critical for CD40 Signaling in B Lymphocytes." *Journal of Biological Chemistry* 290 (9): 5256-66. https://doi.org/10.1074/jbc.M114.618496

The invention claimed is:

1. A CD40 activating protein comprising at least the following protein domains: i) a CD40 agonist antibody or an antigen-binding fragment thereof (αCD40); and, ii) a CD40 binding-domain of CD40L wherein the CD40 agonist antibody is selected from: a) a humanized antibody comprising an HCDR1 of SEQ ID NO: 27, HCDR2 of SEQ ID NO: 28, HCDR3 of SEQ ID NO: 29, LCDR1 of SEQ ID NO: 30, LCDR2 of SEQ ID NO: 31 and LCDR3 of SEQ ID NO: 32; b) a humanized antibody comprising an HCDR1 of SEQ ID NO: 74, HCDR2 of SEQ ID NO: 75, HCDR3 of SEQ ID NO: 76, LCDR1 of SEQ ID NO: 77, LCDR2 of SEQ ID NO: 78 and LCDR3 of SEQ ID NO: 79; c) a humanized antibody comprising an HCDR1 of SEQ ID NO: 80, HCDR2 of SEQ ID NO: 81, HCDR3 of SEQ ID NO: 82, LCDR1 of SEQ ID NO: 83, LCDR2 of SEQ ID NO: 84 and LCDR3 of SEQ ID NO: 85; d) a humanized antibody comprising an HCDR1 of SEQ ID NO: 86, HCDR2 of SEQ ID NO: 87, HCDR3 of SEQ ID NO: 88, LCDR1 of SEQ ID NO: 89, LCDR2 of SEQ ID NO: 90 and LCDR3 of SEQ ID NO: 91; e) a humanized antibody comprising VH and VL domains of SEQ ID NO: 21 and SEQ ID NO: 22, respectively; f) a humanized antibody comprising VH and VL domains of SEQ ID NO: 23 and SEQ ID NO: 22, respectively; g) a humanized antibody comprising VH and VL domains of SEQ ID NO: 58 and SEQ ID NO: 59, respectively; h) a humanized antibody comprising VH and VL domains of SEQ ID NO: 60 and SEQ ID NO: 61, respectively; and i) a humanized antibody comprising VH and VL domains of SEQ ID NO: 62 and SEQ ID NO: 63, respectively; wherein the binding domain of CD40L is a fragment of CD40L comprising SEQ ID NO:14; and wherein the binding domain of CD40L is fused to the C-terminus of a light or a heavy chain of said CD40 agonist antibody or an antigen binding fragment thereof, optionally via a peptide linker.

2. The CD40 activating protein of claim 1, wherein said CD40 agonist antibody binds specifically to human CD40 and has at least one or more of the following properties:
i) it induces proliferation of B cells, as measured in vitro by flow cytometric analysis; or,
ii) it induces secretion of cytokines, as measured in vitro with a dendritic cell activation assay.

3. The CD40 activating protein of claim 1, wherein the CD40 agonist antibody is a CD40 agonist IgG antibody comprising a heavy and a light chain.

4. The CD40 activating protein of claim 1, comprising a peptide linker between the CD40 binding-domain of CD40L and the light or the heavy chain of said CD40 agonist antibody or the antigen-binding fragment thereof.

5. The CD40 activating protein of claim 1, wherein said CD40 agonist antibody is selected from the following antibodies: a) a humanized antibody comprising the HCDR1 of SEQ ID NO: 27, HCDR2 of SEQ ID NO: 28, HCDR3 of SEQ ID NO: 29, LCDR1 of SEQ ID NO: 30, LCDR2 of SEQ ID NO: 31 and LCDR3 of SEQ ID NO: 32; or b) a humanized antibody comprising VH and VL domains of SEQ ID NO: 21 and SEQ ID NO: 22, respectively.

6. The CD40 activating protein of claim 1, wherein one or more antigens are fused to the heavy or the light chain of said CD40 agonist antibody or the antigen-binding fragment thereof.

7. The CD40 activating protein of claim 6, wherein the one or more antigens are viral antigens or cancer antigens.

8. The CD40 activating protein of claim 1, comprising a light chain of the formula αCD40Light-PL-CD40L and a heavy chain of the formula αCD40Heavy-(PL-Ag)x, wherein αCD40Light is the light chain of said CD40 agonist antibody;

αCD40Heavy is the heavy chain of said CD40 agonist antibody;

PL is a bond or a peptide linker;

Ag is a viral antigen or a cancer antigen;

x is an integer from 1 to 20;

CD40L is the CD40 binding-domain of CD40L comprising SEQ ID NO: 14; and,

– is a bond.

9. The CD40 activating protein of claim 8, wherein said viral antigen is an HIV peptide antigen.

10. A pharmaceutical composition, comprising the CD40 activating protein of claim 1 and one or more pharmaceutically acceptable excipients.

11. A vaccine composition comprising the CD40 activating protein of claim 1 and a pharmaceutically acceptable vehicle.

12. A method of enhancing a T cell specific response in a subject in need thereof, comprising, administering to the subject a therapeutically effective amount of the CD40 activating protein of claim 1.

13. A method of eliciting B cell proliferation and/or inducing cytokine secretion of dendritic cells in a subject in need thereof, comprising, administering to the subject a therapeutically effective amount of the CD40 activating protein of claim 1.

14. The CD40 activating protein of claim 2, wherein the cytokines are IL-6, IL-12 and/or IL-15 cytokines.

15. The CD40 activating protein of claim 3, wherein the CD40 agonist IgG antibody is an IgG4 antibody or a mutated silent IgG antibody.

16. The CD40 activating protein of claim 4, wherein the peptide linker is the flexible linker FlexV1 consisting of the amino acid sequence of SEQ ID NO: 15.

17. The CD40 activating protein of claim 9, wherein the HIV peptide antigen is GNG consisting of the amino acid sequence of SEQ ID NO: 48 or HIV5pep consisting of the amino acid sequence of SEQ ID NO: 112.

* * * * *

SEQUENCE LISTING

<160> NUMBER OF SEQ ID NOS: 173

<210> SEQ ID NO 1
<211> LENGTH: 443
<212> TYPE: PRT
<213> ORGANISM: Artificial Sequence
<220> FEATURE:
<223> OTHER INFORMATION: Synthetic Recombinant

<400> SEQUENCE: 1

Glu Val Gln Leu Val Gln Ser Gly Ala Glu Val Lys Lys Pro Gly Ala
1               5                   10                  15

Ser Val Lys Ile Ser Cys Lys Ala Ser Gly Tyr Ser Phe Thr Gly Tyr

-continued

```
                20                25                30

Tyr Met His Trp Val Lys Gln Ala His Gly Gln Gly Leu Glu Trp Ile
            35                40                45

Gly Arg Ile Asn Pro Tyr Asn Gly Ala Thr Ser Tyr Asn Gln Asn Phe
        50                55                60

Lys Asp Arg Ala Thr Leu Thr Val Asp Lys Ser Thr Ser Thr Ala Tyr
65                70                75                80

Met Glu Leu Ser Ser Leu Arg Ser Glu Asp Thr Ala Val Tyr Tyr Cys
                85                90                95

Ala Arg Glu Asp Tyr Val Tyr Trp Gly Gln Gly Thr Thr Val Thr Val
            100               105               110

Ser Ser Ala Lys Thr Lys Gly Pro Ser Val Phe Pro Leu Ala Pro Cys
        115               120               125

Ser Arg Ser Thr Ser Glu Ser Thr Ala Ala Leu Gly Cys Leu Val Lys
        130               135               140

Asp Tyr Phe Pro Glu Pro Val Thr Val Ser Trp Asn Ser Gly Ala Leu
145               150               155               160

Thr Ser Gly Val His Thr Phe Pro Ala Val Leu Gln Ser Ser Gly Leu
            165               170               175

Tyr Ser Leu Ser Ser Val Val Thr Val Pro Ser Ser Ser Leu Gly Thr
            180               185               190

Lys Thr Tyr Thr Cys Asn Val Asp His Lys Pro Ser Asn Thr Lys Val
            195               200               205

Asp Lys Arg Val Glu Ser Lys Tyr Gly Pro Pro Cys Pro Pro Cys Pro
        210               215               220

Ala Pro Glu Phe Glu Gly Gly Pro Ser Val Phe Leu Phe Pro Pro Lys
225               230               235               240

Pro Lys Asp Thr Leu Met Ile Ser Arg Thr Pro Glu Val Thr Cys Val
            245               250               255

Val Val Asp Val Ser Gln Glu Asp Pro Glu Val Gln Phe Asn Trp Tyr
            260               265               270

Val Asp Gly Val Glu Val His Asn Ala Lys Thr Lys Pro Arg Glu Glu
            275               280               285

Gln Phe Asn Ser Thr Tyr Arg Val Val Ser Val Leu Thr Val Leu His
        290               295               300

Gln Asp Trp Leu Asn Gly Lys Glu Tyr Lys Cys Lys Val Ser Asn Lys
305               310               315               320

Gly Leu Pro Ser Ser Ile Glu Lys Thr Ile Ser Lys Ala Lys Gly Gln
            325               330               335

Pro Arg Glu Pro Gln Val Tyr Thr Leu Pro Pro Ser Gln Glu Glu Met
            340               345               350

Thr Lys Asn Gln Val Ser Leu Thr Cys Leu Val Lys Gly Phe Tyr Pro
            355               360               365

Ser Asp Ile Ala Val Glu Trp Glu Ser Asn Gly Gln Pro Glu Asn Asn
        370               375               380

Tyr Lys Thr Thr Pro Pro Val Leu Asp Ser Asp Gly Ser Phe Phe Leu
385               390               395               400

Tyr Ser Arg Leu Thr Val Asp Lys Ser Arg Trp Gln Glu Gly Asn Val
            405               410               415

Phe Ser Cys Ser Val Met His Glu Ala Leu His Asn His Tyr Thr Gln
            420               425               430

Lys Ser Leu Ser Leu Ser Leu Gly Lys Ala Ser
            435               440
```

```
<210> SEQ ID NO 2
<211> LENGTH: 221
<212> TYPE: PRT
<213> ORGANISM: Artificial Sequence
<220> FEATURE:
<223> OTHER INFORMATION: Synthetic recombinant

<400> SEQUENCE: 2

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Trp Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Ala Ser
    210                 215                 220

<210> SEQ ID NO 3
<211> LENGTH: 443
<212> TYPE: PRT
<213> ORGANISM: Artificial Sequence
<220> FEATURE:
<223> OTHER INFORMATION: Synthetic recombinant

<400> SEQUENCE: 3

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Gly Leu Glu Trp Ile
        35                  40                  45

Gly Arg Ile Asn Pro Tyr Asn Gly Ala Thr Ser Tyr Asn Gln Asn Phe
    50                  55                  60

Lys Asp Arg Val Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
```

-continued

```
                   85                90                95

Ala Arg Glu Asp Tyr Val Tyr Trp Gly Gln Gly Thr Thr Val Thr Val
                100               105               110

Ser Ser Ala Lys Thr Lys Gly Pro Ser Val Phe Pro Leu Ala Pro Cys
            115               120               125

Ser Arg Ser Thr Ser Glu Ser Thr Ala Ala Leu Gly Cys Leu Val Lys
        130               135               140

Asp Tyr Phe Pro Glu Pro Val Thr Val Ser Trp Asn Ser Gly Ala Leu
145               150               155               160

Thr Ser Gly Val His Thr Phe Pro Ala Val Leu Gln Ser Ser Gly Leu
            165               170               175

Tyr Ser Leu Ser Ser Val Val Thr Val Pro Ser Ser Ser Leu Gly Thr
            180               185               190

Lys Thr Tyr Thr Cys Asn Val Asp His Lys Pro Ser Asn Thr Lys Val
            195               200               205

Asp Lys Arg Val Glu Ser Lys Tyr Gly Pro Pro Cys Pro Pro Cys Pro
        210               215               220

Ala Pro Glu Phe Glu Gly Gly Pro Ser Val Phe Leu Phe Pro Pro Lys
225               230               235               240

Pro Lys Asp Thr Leu Met Ile Ser Arg Thr Pro Glu Val Thr Cys Val
            245               250               255

Val Val Asp Val Ser Gln Glu Asp Pro Glu Val Gln Phe Asn Trp Tyr
            260               265               270

Val Asp Gly Val Glu Val His Asn Ala Lys Thr Lys Pro Arg Glu Glu
            275               280               285

Gln Phe Asn Ser Thr Tyr Arg Val Val Ser Val Leu Thr Val Leu His
        290               295               300

Gln Asp Trp Leu Asn Gly Lys Glu Tyr Lys Cys Lys Val Ser Asn Lys
305               310               315               320

Gly Leu Pro Ser Ser Ile Glu Lys Thr Ile Ser Lys Ala Lys Gly Gln
            325               330               335

Pro Arg Glu Pro Gln Val Tyr Thr Leu Pro Pro Ser Gln Glu Glu Met
            340               345               350

Thr Lys Asn Gln Val Ser Leu Thr Cys Leu Val Lys Gly Phe Tyr Pro
            355               360               365

Ser Asp Ile Ala Val Glu Trp Glu Ser Asn Gly Gln Pro Glu Asn Asn
        370               375               380

Tyr Lys Thr Thr Pro Pro Val Leu Asp Ser Asp Gly Ser Phe Phe Leu
385               390               395               400

Tyr Ser Arg Leu Thr Val Asp Lys Ser Arg Trp Gln Glu Gly Asn Val
            405               410               415

Phe Ser Cys Ser Val Met His Glu Ala Leu His Asn His Tyr Thr Gln
            420               425               430

Lys Ser Leu Ser Leu Ser Leu Gly Lys Ala Ser
            435               440
```

<210> SEQ ID NO 4
<211> LENGTH: 221
<212> TYPE: PRT
<213> ORGANISM: Artificial Sequence
<220> FEATURE:
<223> OTHER INFORMATION: Synthetic recombinant

<400> SEQUENCE: 4

Asp Val Val Met Thr Gln Ser Pro Leu Ser Leu Pro Val Thr Leu Gly

-continued

```
1                   5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Gln Gln Arg Pro Gly Gln Ser
            35                  40                  45

Pro Arg Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Trp Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys Ala Ser
        210                 215                 220

<210> SEQ ID NO 5
<211> LENGTH: 399
<212> TYPE: PRT
<213> ORGANISM: Artificial Sequence
<220> FEATURE:
<223> OTHER INFORMATION: Synthetic recombinant

<400> SEQUENCE: 5

Asp Val Val Met Thr Gln Ser Pro Leu Ser Leu Pro Val Thr Leu Gly
1                   5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Gln Gln Arg Pro Gly Gln Ser
            35                  40                  45

Pro Arg Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Trp Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
```

-continued

```
145              150              155              160

Ser Gly Asn Ser Gln Glu Ser Val Thr Glu Gln Asp Ser Lys Asp Ser
            165              170              175

Thr Tyr Ser Leu Ser Ser Thr Leu Thr Leu Ser Lys Ala Asp Tyr Glu
            180              185              190

Lys His Lys Val Tyr Ala Cys Glu Val Thr His Gln Gly Leu Ser Ser
        195              200              205

Pro Val Thr Lys Ser Phe Asn Arg Gly Glu Cys Ala Ser Gln Thr Pro
    210              215              220

Thr Asn Thr Ile Ser Val Thr Pro Thr Asn Asn Ser Thr Pro Thr Asn
225              230              235              240

Asn Ser Asn Pro Lys Pro Asn Pro Ala Ser Met Gln Lys Gly Asp Gln
            245              250              255

Asn Pro Gln Ile Ala Ala His Val Ile Ser Glu Ala Ser Ser Lys Thr
            260              265              270

Thr Ser Val Leu Gln Trp Ala Glu Lys Gly Tyr Tyr Thr Met Ser Asn
        275              280              285

Asn Leu Val Thr Leu Glu Asn Gly Lys Gln Leu Thr Val Lys Arg Gln
    290              295              300

Gly Leu Tyr Tyr Ile Tyr Ala Gln Val Thr Phe Cys Ser Asn Arg Glu
305              310              315              320

Ala Ser Ser Gln Ala Pro Phe Ile Ala Ser Leu Cys Leu Lys Ser Pro
            325              330              335

Gly Arg Phe Glu Arg Ile Leu Leu Arg Ala Ala Asn Thr His Ser Ser
            340              345              350

Ala Lys Pro Cys Gly Gln Gln Ser Ile His Leu Gly Gly Val Phe Glu
        355              360              365

Leu Gln Pro Gly Ala Ser Val Phe Val Asn Val Thr Asp Pro Ser Gln
    370              375              380

Val Ser His Gly Thr Gly Phe Thr Ser Phe Gly Leu Leu Lys Leu
385              390              395
```

<210> SEQ ID NO 6
<211> LENGTH: 443
<212> TYPE: PRT
<213> ORGANISM: Artificial Sequence
<220> FEATURE:
<223> OTHER INFORMATION: Synthetic recombinant

<400> SEQUENCE: 6

```
Glu Val Gln Leu Val Gln Ser Gly Ala Glu Val Lys Lys Pro Gly Ala
1                5               10               15

Ser Val Lys Ile Ser Cys Lys Ala Ser Gly Tyr Ser Phe Thr Gly Tyr
            20               25               30

Tyr Met His Trp Val Lys Gln Ala His Gly Gln Gly Leu Glu Trp Ile
        35               40               45

Gly Arg Ile Asn Pro Tyr Asn Gly Ala Thr Ser Tyr Asn Gln Asn Phe
    50               55               60

Lys Asp Arg Ala Thr Leu Thr Val Asp Lys Ser Thr Ser Thr Ala Tyr
65               70               75               80

Met Glu Leu Ser Ser Leu Arg Ser Glu Asp Thr Ala Val Tyr Tyr Cys
            85               90               95

Ala Arg Glu Asp Tyr Val Tyr Trp Gly Gln Gly Thr Thr Val Thr Val
            100              105              110

Ser Ser Ala Lys Thr Lys Gly Pro Ser Val Phe Pro Leu Ala Pro Cys
```

-continued

```
          115               120               125
Ser Arg Ser Thr Ser Glu Ser Thr Ala Ala Leu Gly Cys Leu Val Lys
    130               135               140

Asp Tyr Phe Pro Glu Pro Val Thr Val Ser Trp Asn Ser Gly Ala Leu
145               150               155               160

Thr Ser Gly Val His Thr Phe Pro Ala Val Leu Gln Ser Ser Gly Leu
                165               170               175

Tyr Ser Leu Ser Ser Val Val Thr Val Pro Ser Ser Ser Leu Gly Thr
                180               185               190

Lys Thr Tyr Thr Cys Asn Val Asp His Lys Pro Ser Asn Thr Lys Val
                195               200               205

Asp Lys Arg Val Glu Ser Lys Tyr Gly Pro Pro Cys Pro Pro Cys Pro
    210               215               220

Ala Pro Glu Phe Glu Gly Gly Pro Ser Val Phe Leu Phe Pro Pro Lys
225               230               235               240

Pro Lys Asp Thr Leu Met Ile Ser Arg Thr Pro Glu Val Thr Cys Val
                245               250               255

Val Val Asp Val Ser Gln Glu Asp Pro Glu Val Gln Phe Asn Trp Tyr
                260               265               270

Val Asp Gly Val Glu Val His Asn Ala Lys Thr Lys Pro Arg Glu Glu
                275               280               285

Gln Phe Asn Ser Thr Tyr Arg Val Val Ser Val Leu Thr Val Leu His
    290               295               300

Gln Asp Trp Leu Asn Gly Lys Glu Tyr Lys Cys Lys Val Ser Asn Lys
305               310               315               320

Gly Leu Pro Ser Ser Ile Glu Lys Thr Ile Ser Lys Ala Lys Gly Gln
                325               330               335

Pro Arg Glu Pro Gln Val Tyr Thr Leu Pro Pro Ser Gln Glu Glu Met
                340               345               350

Thr Lys Asn Gln Val Ser Leu Thr Cys Leu Val Lys Gly Phe Tyr Pro
                355               360               365

Ser Asp Ile Ala Val Glu Trp Glu Ser Asn Gly Gln Pro Glu Asn Asn
    370               375               380

Tyr Lys Thr Thr Pro Pro Val Leu Asp Ser Asp Gly Ser Phe Phe Leu
385               390               395               400

Tyr Ser Arg Leu Thr Val Asp Lys Ser Arg Trp Gln Glu Gly Asn Val
                405               410               415

Phe Ser Cys Ser Val Met His Glu Ala Leu His Asn His Tyr Thr Gln
                420               425               430

Lys Ser Leu Ser Leu Ser Leu Gly Lys Ala Ser
    435               440
```

```
<210> SEQ ID NO 7
<211> LENGTH: 831
<212> TYPE: DNA
<213> ORGANISM: Homo sapiens

<400> SEQUENCE: 7
atggttcgtc tgcctctgca gtgcgtcctc tggggctgct tgctgaccgc tgtccatcca        60
gaaccaccca ctgcatgcag agaaaaacag tacctaataa acagtcagtg ctgttctttg       120
tgccagccag acagaaaact ggtgagtgac tgcacagagt tcactgaaac ggaatgcctt       180
ccttgcggtg aaagcgaatt cctagacacc tggaacagag agacacactg ccaccagcac       240
aaatactgcg accccaacct agggcttcgg gtccagcaga agggcacctc agaaacagac       300
```

-continued

```
accatctgca cctgtgaaga aggctggcac tgtacgagtg aggcctgtga gagctgtgtc      360
ctgcaccgct catgctcgcc cggctttggg gtcaagcaga ttgctacagg ggtttctgat      420
accatctgcg agccctgccc agtcggcttc ttctccaatg tgtcatctgc tttcgaaaaa      480
tgtcacccct tggacaagct gtgagaccaaa gacctggttg tgcaacaggc aggcacaaac     540
aagactgatg ttgtctgtgg tccccaggat cggctgagag ccctggtggt gatccccatc      600
atcttcggga tcctgtttgc catcctcttg gtgctggtct ttatcaaaaa ggtggccaag      660
aagccaacca ataaggcccc ccacccaag caggaacccc aggagatcaa ttttcccgac       720
gatcttcctg ctccaacac tgctgctcca gtgcaggaga ctttacatgg atgccaaccg        780
gtcacccagg aggatggcaa agagagtcgc atctcagtgc aggagagaca g               831
```

```
<210> SEQ ID NO 8
<211> LENGTH: 443
<212> TYPE: PRT
<213> ORGANISM: Artificial Sequence
<220> FEATURE:
<223> OTHER INFORMATION: Synthetic recombinant

<400> SEQUENCE: 8

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Gly Leu Glu Trp Ile
        35                  40                  45

Gly Arg Ile Asn Pro Tyr Asn Gly Ala Thr Ser Tyr Asn Gln Asn Phe
    50                  55                  60

Lys Asp Arg Val Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Tyr Val Tyr Trp Gly Gln Gly Thr Thr Val Thr Val
            100                 105                 110

Ser Ser Ala Lys Thr Lys Gly Pro Ser Val Phe Pro Leu Ala Pro Cys
        115                 120                 125

Ser Arg Ser Thr Ser Glu Ser Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Lys Thr Tyr Thr Cys Asn Val Asp His Lys Pro Ser Asn Thr Lys Val
        195                 200                 205

Asp Lys Arg Val Glu Ser Lys Tyr Gly Pro Pro Cys Pro Pro Cys Pro
    210                 215                 220

Ala Pro Glu Phe Glu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser Gln Glu Asp Pro Glu Val Gln Phe Asn Trp Tyr
                260                 265                 270
```

-continued

```
Val Asp Gly Val Glu Val His Asn Ala Lys Thr Lys Pro Arg Glu Glu
        275             280             285

Gln Phe Asn Ser Thr Tyr Arg Val Val Ser Val Leu Thr Val Leu His
    290             295             300

Gln Asp Trp Leu Asn Gly Lys Glu Tyr Lys Cys Lys Val Ser Asn Lys
305             310             315             320

Gly Leu Pro Ser Ser Ile Glu Lys Thr Ile Ser Lys Ala Lys Gly Gln
            325             330             335

Pro Arg Glu Pro Gln Val Tyr Thr Leu Pro Pro Ser Gln Glu Glu Met
            340             345             350

Thr Lys Asn Gln Val Ser Leu Thr Cys Leu Val Lys Gly Phe Tyr Pro
        355             360             365

Ser Asp Ile Ala Val Glu Trp Glu Ser Asn Gly Gln Pro Glu Asn Asn
    370             375             380

Tyr Lys Thr Thr Pro Pro Val Leu Asp Ser Asp Gly Ser Phe Phe Leu
385             390             395             400

Tyr Ser Arg Leu Thr Val Asp Lys Ser Arg Trp Gln Glu Gly Asn Val
            405             410             415

Phe Ser Cys Ser Val Met His Glu Ala Leu His Asn His Tyr Thr Gln
            420             425             430

Lys Ser Leu Ser Leu Ser Leu Gly Lys Ala Ser
        435             440
```

```
<210> SEQ ID NO 9
<211> LENGTH: 734
<212> TYPE: PRT
<213> ORGANISM: Artificial Sequence
<220> FEATURE:
<223> OTHER INFORMATION: Synthetic recombinant

<400> SEQUENCE: 9
```

```
Glu Val Gln Leu Val Gln Ser Gly Ala Glu Val Lys Lys Pro Gly Ala
1               5               10              15

Ser Val Lys Ile Ser Cys Lys Ala Ser Gly Tyr Ser Phe Thr Gly Tyr
            20              25              30

Tyr Met His Trp Val Lys Gln Ala His Gly Gln Gly Leu Glu Trp Ile
        35              40              45

Gly Arg Ile Asn Pro Tyr Asn Gly Ala Thr Ser Tyr Asn Gln Asn Phe
    50              55              60

Lys Asp Arg Ala Thr Leu Thr Val Asp Lys Ser Thr Ser Thr Ala Tyr
65              70              75              80

Met Glu Leu Ser Ser Leu Arg Ser Glu Asp Thr Ala Val Tyr Tyr Cys
            85              90              95

Ala Arg Glu Asp Tyr Val Tyr Trp Gly Gln Gly Thr Thr Val Thr Val
            100             105             110

Ser Ser Ala Lys Thr Lys Gly Pro Ser Val Phe Pro Leu Ala Pro Cys
        115             120             125

Ser Arg Ser Thr Ser Glu Ser Thr Ala Ala Leu Gly Cys Leu Val Lys
        130             135             140

Asp Tyr Phe Pro Glu Pro Val Thr Val Ser Trp Asn Ser Gly Ala Leu
145             150             155             160

Thr Ser Gly Val His Thr Phe Pro Ala Val Leu Gln Ser Ser Gly Leu
            165             170             175

Tyr Ser Leu Ser Ser Val Val Thr Val Pro Ser Ser Ser Leu Gly Thr
        180             185             190
```

```
Lys Thr Tyr Thr Cys Asn Val Asp His Lys Pro Ser Asn Thr Lys Val
        195                 200             205

Asp Lys Arg Val Glu Ser Lys Tyr Gly Pro Pro Cys Pro Pro Cys Pro
    210             215             220

Ala Pro Glu Phe Glu Gly Gly Pro Ser Val Phe Leu Phe Pro Pro Lys
225             230             235             240

Pro Lys Asp Thr Leu Met Ile Ser Arg Thr Pro Glu Val Thr Cys Val
        245             250             255

Val Val Asp Val Ser Gln Glu Asp Pro Glu Val Gln Phe Asn Trp Tyr
        260             265             270

Val Asp Gly Val Glu Val His Asn Ala Lys Thr Lys Pro Arg Glu Glu
        275             280             285

Gln Phe Asn Ser Thr Tyr Arg Val Val Ser Val Leu Thr Val Leu His
    290             295             300

Gln Asp Trp Leu Asn Gly Lys Glu Tyr Lys Cys Lys Val Ser Asn Lys
305             310             315             320

Gly Leu Pro Ser Ser Ile Glu Lys Thr Ile Ser Lys Ala Lys Gly Gln
            325             330             335

Pro Arg Glu Pro Gln Val Tyr Thr Leu Pro Pro Ser Gln Glu Glu Met
        340             345             350

Thr Lys Asn Gln Val Ser Leu Thr Cys Leu Val Lys Gly Phe Tyr Pro
        355             360             365

Ser Asp Ile Ala Val Glu Trp Glu Ser Asn Gly Gln Pro Glu Asn Asn
    370             375             380

Tyr Lys Thr Thr Pro Pro Val Leu Asp Ser Asp Gly Ser Phe Phe Leu
385             390             395             400

Tyr Ser Arg Leu Thr Val Asp Lys Ser Arg Trp Gln Glu Gly Asn Val
            405             410             415

Phe Ser Cys Ser Val Met His Glu Ala Leu His Asn His Tyr Thr Gln
            420             425             430

Lys Ser Leu Ser Leu Ser Leu Gly Lys Ala Ser Gln Thr Pro Thr Asn
        435             440             445

Thr Ile Ser Val Thr Pro Thr Asn Asn Ser Thr Pro Thr Asn Asn Ser
    450             455             460

Asn Pro Lys Pro Asn Pro Ala Ser Glu Lys Ile Arg Leu Arg Pro Gly
465             470             475             480

Gly Lys Lys Lys Tyr Lys Leu Lys His Ile Val Ala Ser Ser Val
            485             490             495

Ser Pro Thr Thr Ser Val His Pro Thr Pro Thr Ser Val Pro Pro Thr
        500             505             510

Pro Thr Lys Ser Ser Pro Ala Ser Asn Pro Pro Ile Pro Val Gly Glu
        515             520             525

Ile Tyr Lys Arg Trp Ile Ile Leu Gly Leu Asn Lys Ile Val Arg Met
    530             535             540

Tyr Ser Pro Thr Ser Ile Leu Asp Ala Ser Pro Thr Ser Thr Pro Ala
545             550             555             560

Asp Ser Ser Thr Ile Thr Pro Thr Ala Thr Pro Thr Ala Thr Pro Thr
            565             570             575

Ile Lys Gly Ala Ser His Thr Gln Gly Tyr Phe Pro Asp Trp Gln Asn
        580             585             590

Tyr Thr Pro Gly Pro Gly Val Arg Tyr Pro Leu Thr Phe Gly Trp Leu
        595             600             605
```

```
Tyr Lys Leu Ala Ser Thr Val Thr Pro Thr Ala Thr Ala Thr Pro Ser
    610             615             620

Ala Ile Val Thr Thr Ile Thr Pro Thr Ala Thr Thr Lys Pro Ala Ser
625             630             635             640

Val Gly Phe Pro Val Thr Pro Gln Val Pro Leu Arg Pro Met Thr Tyr
            645             650             655

Lys Ala Ala Val Asp Leu Ser His Phe Leu Lys Glu Lys Gly Gly Leu
            660             665             670

Ala Ser Thr Asn Gly Ser Ile Thr Val Ala Ala Thr Ala Pro Thr Val
            675             680             685

Thr Pro Thr Val Asn Ala Thr Pro Ser Ala Ala Ala Ser Ala Ile Phe
    690             695             700

Gln Ser Ser Met Thr Lys Ile Leu Glu Pro Phe Arg Lys Gln Asn Pro
705             710             715             720

Asp Ile Val Ile Tyr Gln Tyr Met Asp Asp Leu Tyr Ala Ser
            725             730

<210> SEQ ID NO 10
<211> LENGTH: 221
<212> TYPE: PRT
<213> ORGANISM: Artificial Sequence
<220> FEATURE:
<223> OTHER INFORMATION: Synthetic recombinant

<400> SEQUENCE: 10

Asp Val Val Met Thr Gln Ser Pro Leu Ser Leu Pro Val Thr Leu Gly
1               5               10              15

Gln Pro Ala Ser Ile Ser Cys Arg Ser Ser Gln Ser Leu Val His Ser
            20              25              30

Asn Gly Asn Thr Tyr Leu His Trp Tyr Gln Gln Arg Pro Gly Gln Ser
            35              40              45

Pro Arg Leu Leu Ile Tyr Lys Val Ser Asn Arg Phe Ser Gly Val Pro
    50              55              60

Asp Arg Phe Ser Gly Ser Gly Ser Gly Thr Asp Phe Thr Leu Lys Ile
65              70              75              80

Ser Arg Val Glu Ala Glu Asp Val Gly Val Tyr Phe Cys Ser Gln Ser
            85              90              95

Thr His Val Pro Trp Thr Phe Gly Gly Gly Thr Lys Leu Glu Ile Lys
            100             105             110

Arg Thr Val Ala Ala Pro Ser Val Phe Ile Phe Pro Pro Ser Asp Glu
            115             120             125

Gln Leu Lys Ser Gly Thr Ala Ser Val Val Cys Leu Leu Asn Asn Phe
    130             135             140

Tyr Pro Arg Glu Ala Lys Val Gln Trp Lys Val Asp Asn Ala Leu Gln
145             150             155             160

Ser Gly Asn Ser Gln Glu Ser Val Thr Glu Gln Asp Ser Lys Asp Ser
            165             170             175

Thr Tyr Ser Leu Ser Ser Thr Leu Thr Leu Ser Lys Ala Asp Tyr Glu
            180             185             190

Lys His Lys Val Tyr Ala Cys Glu Val Thr His Gln Gly Leu Ser Ser
            195             200             205

Pro Val Thr Lys Ser Phe Asn Arg Gly Glu Cys Ala Ser
    210             215             220

<210> SEQ ID NO 11
<211> LENGTH: 734
```

<212> TYPE: PRT
<213> ORGANISM: Artificial Sequence
<220> FEATURE:
<223> OTHER INFORMATION: Synthetic recombinant

<400> SEQUENCE: 11

Glu Val Gln Leu Val Gln Ser Gly Ala Glu Val Lys Lys Pro Gly Ala
1               5                   10                  15

Ser Val Lys Ile Ser Cys Lys Ala Ser Gly Tyr Ser Phe Thr Gly Tyr
                20                  25                  30

Tyr Met His Trp Val Lys Gln Ala His Gly Gln Gly Leu Glu Trp Ile
            35                  40                  45

Gly Arg Ile Asn Pro Tyr Asn Gly Ala Thr Ser Tyr Asn Gln Asn Phe
        50                  55                  60

Lys Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Tyr Val Tyr Trp Gly Gln Gly Thr Thr Val Thr Val
            100                 105                 110

Ser Ser Ala Lys Thr Lys Gly Pro Ser Val Phe Pro Leu Ala Pro Cys
            115                 120                 125

Ser Arg Ser Thr Ser Glu Ser Thr Ala Ala Leu Gly Cys Leu Val Lys
        130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Lys Thr Tyr Thr Cys Asn Val Asp His Lys Pro Ser Asn Thr Lys Val
            195                 200                 205

Asp Lys Arg Val Glu Ser Lys Tyr Gly Pro Pro Cys Pro Pro Cys Pro
        210                 215                 220

Ala Pro Glu Phe Glu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser Gln Glu Asp Pro Glu Val Gln Phe Asn Trp Tyr
            260                 265                 270

Val Asp Gly Val Glu Val His Asn Ala Lys Thr Lys Pro Arg Glu Glu
            275                 280                 285

Gln Phe Asn Ser Thr Tyr Arg Val Val Ser Val Leu Thr Val Leu His
        290                 295                 300

Gln Asp Trp Leu Asn Gly Lys Glu Tyr Lys Cys Lys Val Ser Asn Lys
305                 310                 315                 320

Gly Leu Pro Ser Ser Ile Glu Lys Thr Ile Ser Lys Ala Lys Gly Gln
                325                 330                 335

Pro Arg Glu Pro Gln Val Tyr Thr Leu Pro Pro Ser Gln Glu Glu Met
            340                 345                 350

Thr Lys Asn Gln Val Ser Leu Thr Cys Leu Val Lys Gly Phe Tyr Pro
            355                 360                 365

Ser Asp Ile Ala Val Glu Trp Glu Ser Asn Gly Gln Pro Glu Asn Asn
        370                 375                 380

-continued

```
Tyr Lys Thr Thr Pro Pro Val Leu Asp Ser Asp Gly Ser Phe Phe Leu
385                 390                 395                 400

Tyr Ser Arg Leu Thr Val Asp Lys Ser Arg Trp Gln Glu Gly Asn Val
                405                 410                 415

Phe Ser Cys Ser Val Met His Glu Ala Leu His Asn His Tyr Thr Gln
                420                 425                 430

Lys Ser Leu Ser Leu Ser Leu Gly Lys Ala Ser Gln Thr Pro Thr Asn
            435                 440                 445

Thr Ile Ser Val Thr Pro Thr Asn Asn Ser Thr Pro Thr Asn Asn Ser
            450                 455                 460

Asn Pro Lys Pro Asn Pro Ala Ser Glu Lys Ile Arg Leu Arg Pro Gly
465                 470                 475                 480

Gly Lys Lys Lys Tyr Lys Leu Lys His Ile Val Ala Ser Ser Ser Val
                485                 490                 495

Ser Pro Thr Thr Ser Val His Pro Thr Pro Thr Ser Val Pro Pro Thr
                500                 505                 510

Pro Thr Lys Ser Ser Pro Ala Ser Asn Pro Pro Ile Pro Val Gly Glu
            515                 520                 525

Ile Tyr Lys Arg Trp Ile Ile Leu Gly Leu Asn Lys Ile Val Arg Met
        530                 535                 540

Tyr Ser Pro Thr Ser Ile Leu Asp Ala Ser Pro Thr Ser Thr Pro Ala
545                 550                 555                 560

Asp Ser Ser Thr Ile Thr Pro Thr Ala Thr Pro Thr Ala Thr Pro Thr
                565                 570                 575

Ile Lys Gly Ala Ser His Thr Gln Gly Tyr Phe Pro Asp Trp Gln Asn
                580                 585                 590

Tyr Thr Pro Gly Pro Gly Val Arg Tyr Pro Leu Thr Phe Gly Trp Leu
            595                 600                 605

Tyr Lys Leu Ala Ser Thr Val Thr Pro Thr Ala Thr Ala Thr Pro Ser
            610                 615                 620

Ala Ile Val Thr Thr Ile Thr Pro Thr Ala Thr Thr Lys Pro Ala Ser
625                 630                 635                 640

Val Gly Phe Pro Val Thr Pro Gln Val Pro Leu Arg Pro Met Thr Tyr
                645                 650                 655

Lys Ala Ala Val Asp Leu Ser His Phe Leu Lys Glu Lys Gly Gly Leu
            660                 665                 670

Ala Ser Thr Asn Gly Ser Ile Thr Val Ala Ala Thr Ala Pro Thr Val
            675                 680                 685

Thr Pro Thr Val Asn Ala Thr Pro Ser Ala Ala Ala Ser Ala Ile Phe
            690                 695                 700

Gln Ser Ser Met Thr Lys Ile Leu Glu Pro Phe Arg Lys Gln Asn Pro
705                 710                 715                 720

Asp Ile Val Ile Tyr Gln Tyr Met Asp Asp Leu Tyr Ala Ser
                725                 730
```

```
<210> SEQ ID NO 12
<211> LENGTH: 399
<212> TYPE: PRT
<213> ORGANISM: Artificial Sequence
<220> FEATURE:
<223> OTHER INFORMATION: Synthetic recombinant

<400> SEQUENCE: 12

Asp Val Val Met Thr Gln Ser Pro Leu Ser Leu Pro Val Thr Leu Gly
1               5                   10                  15
```

```
Gln Pro Ala Ser Ile Ser Cys Arg Ser Ser Gln Ser Leu Val His Ser
            20              25              30

Asn Gly Asn Thr Tyr Leu His Trp Tyr Gln Gln Arg Pro Gly Gln Ser
        35              40              45

Pro Arg Leu Leu Ile Tyr Lys Val Ser Asn Arg Phe Ser Gly Val Pro
    50              55              60

Asp Arg Phe Ser Gly Ser Gly Ser Gly Thr Asp Phe Thr Leu Lys Ile
65              70              75              80

Ser Arg Val Glu Ala Glu Asp Val Gly Val Tyr Phe Cys Ser Gln Ser
            85              90              95

Thr His Val Pro Trp Thr Phe Gly Gly Gly Thr Lys Leu Glu Ile Lys
            100             105             110

Arg Thr Val Ala Ala Pro Ser Val Phe Ile Phe Pro Pro Ser Asp Glu
            115             120             125

Gln Leu Lys Ser Gly Thr Ala Ser Val Val Cys Leu Leu Asn Asn Phe
    130             135             140

Tyr Pro Arg Glu Ala Lys Val Gln Trp Lys Val Asp Asn Ala Leu Gln
145             150             155             160

Ser Gly Asn Ser Gln Glu Ser Val Thr Glu Gln Asp Ser Lys Asp Ser
            165             170             175

Thr Tyr Ser Leu Ser Ser Thr Leu Thr Leu Ser Lys Ala Asp Tyr Glu
            180             185             190

Lys His Lys Val Tyr Ala Cys Glu Val Thr His Gln Gly Leu Ser Ser
            195             200             205

Pro Val Thr Lys Ser Phe Asn Arg Gly Glu Cys Ala Ser Gln Thr Pro
    210             215             220

Thr Asn Thr Ile Ser Val Thr Pro Thr Asn Asn Ser Thr Pro Thr Asn
225             230             235             240

Asn Ser Asn Pro Lys Pro Asn Pro Ala Ser Met Gln Lys Gly Asp Gln
            245             250             255

Asn Pro Gln Ile Ala Ala His Val Ile Ser Glu Ala Ser Ser Lys Thr
            260             265             270

Thr Ser Val Leu Gln Trp Ala Glu Lys Gly Tyr Tyr Thr Met Ser Asn
            275             280             285

Asn Leu Val Thr Leu Glu Asn Gly Lys Gln Leu Thr Val Lys Arg Gln
    290             295             300

Gly Leu Tyr Tyr Ile Tyr Ala Gln Val Thr Phe Cys Ser Asn Arg Glu
305             310             315             320

Ala Ser Ser Gln Ala Pro Phe Ile Ala Ser Leu Cys Leu Lys Ser Pro
            325             330             335

Gly Arg Phe Glu Arg Ile Leu Leu Arg Ala Ala Asn Thr His Ser Ser
            340             345             350

Ala Lys Pro Cys Gly Gln Gln Ser Ile His Leu Gly Gly Val Phe Glu
            355             360             365

Leu Gln Pro Gly Ala Ser Val Phe Val Asn Val Thr Asp Pro Ser Gln
    370             375             380

Val Ser His Gly Thr Gly Phe Thr Ser Phe Gly Leu Leu Lys Leu
385             390             395
```

<210> SEQ ID NO 13
<211> LENGTH: 277
<212> TYPE: PRT
<213> ORGANISM: Homo sapiens

<400> SEQUENCE: 13

-continued

```
Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
            115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
            165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
            195                 200                 205

Leu Leu Val Leu Val Phe Ile Lys Lys Val Ala Lys Lys Pro Thr Asn
    210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
            260                 265                 270

Val Gln Glu Arg Gln
            275
```

<210> SEQ ID NO 14
<211> LENGTH: 149
<212> TYPE: PRT
<213> ORGANISM: Homo sapiens

<400> SEQUENCE: 14

```
Met Gln Lys Gly Asp Gln Asn Pro Gln Ile Ala Ala His Val Ile Ser
1               5                   10                  15

Glu Ala Ser Ser Lys Thr Thr Ser Val Leu Gln Trp Ala Glu Lys Gly
            20                  25                  30

Tyr Tyr Thr Met Ser Asn Asn Leu Val Thr Leu Glu Asn Gly Lys Gln
        35                  40                  45

Leu Thr Val Lys Arg Gln Gly Leu Tyr Tyr Ile Tyr Ala Gln Val Thr
    50                  55                  60

Phe Cys Ser Asn Arg Glu Ala Ser Ser Gln Ala Pro Phe Ile Ala Ser
65                  70                  75                  80

Leu Cys Leu Lys Ser Pro Gly Arg Phe Glu Arg Ile Leu Leu Arg Ala
```

-continued

```
                85                  90                  95
Ala Asn Thr His Ser Ser Ala Lys Pro Cys Gly Gln Gln Ser Ile His
            100                 105                 110

Leu Gly Gly Val Phe Glu Leu Gln Pro Gly Ala Ser Val Phe Val Asn
            115                 120                 125

Val Thr Asp Pro Ser Gln Val Ser His Gly Thr Gly Phe Thr Ser Phe
        130                 135                 140

Gly Leu Leu Lys Leu
145

<210> SEQ ID NO 15
<211> LENGTH: 27
<212> TYPE: PRT
<213> ORGANISM: Artificial Sequence
<220> FEATURE:
<223> OTHER INFORMATION: Synthetic recombinant

<400> SEQUENCE: 15

Gln Thr Pro Thr Asn Thr Ile Ser Val Thr Pro Thr Asn Asn Ser Thr
1               5                   10                  15

Pro Thr Asn Asn Ser Asn Pro Lys Pro Asn Pro
            20                  25

<210> SEQ ID NO 16
<211> LENGTH: 19
<212> TYPE: PRT
<213> ORGANISM: Human immunodeficiency virus

<400> SEQUENCE: 16

Glu Lys Ile Arg Leu Arg Pro Gly Gly Lys Lys Lys Tyr Lys Leu Lys
1               5                   10                  15

His Ile Val

<210> SEQ ID NO 17
<211> LENGTH: 32
<212> TYPE: PRT
<213> ORGANISM: Human immunodeficiency virus

<400> SEQUENCE: 17

Asn Pro Pro Ile Pro Val Gly Glu Ile Tyr Lys Arg Trp Ile Ile Leu
1               5                   10                  15

Gly Leu Asn Lys Ile Val Arg Met Tyr Ser Pro Thr Ser Ile Leu Asp
            20                  25                  30

<210> SEQ ID NO 18
<211> LENGTH: 30
<212> TYPE: PRT
<213> ORGANISM: Human immunodeficiency virus

<400> SEQUENCE: 18

His Thr Gln Gly Tyr Phe Pro Asp Trp Gln Asn Tyr Thr Pro Gly Pro
1               5                   10                  15

Gly Val Arg Tyr Pro Leu Thr Phe Gly Trp Leu Tyr Lys Leu
            20                  25                  30

<210> SEQ ID NO 19
<211> LENGTH: 31
<212> TYPE: PRT
<213> ORGANISM: Human immunodeficiency virus

<400> SEQUENCE: 19
```

Ala Ile Phe Gln Ser Ser Met Thr Lys Ile Leu Glu Pro Phe Arg Lys
1               5                   10                  15

Gln Asn Pro Asp Ile Val Ile Tyr Gln Tyr Met Asp Asp Leu Tyr
            20                  25                  30

<210> SEQ ID NO 20
<211> LENGTH: 32
<212> TYPE: PRT
<213> ORGANISM: Human immunodeficiency virus

<400> SEQUENCE: 20

Val Gly Phe Pro Val Thr Pro Gln Val Pro Leu Arg Pro Met Thr Tyr
1               5                   10                  15

Lys Ala Ala Val Asp Leu Ser His Phe Leu Lys Glu Lys Gly Gly Leu
            20                  25                  30

<210> SEQ ID NO 21
<211> LENGTH: 443
<212> TYPE: PRT
<213> ORGANISM: Artificial Sequence
<220> FEATURE:
<223> OTHER INFORMATION: Synthetic recombinant

<400> SEQUENCE: 21

Glu Val Gln Leu Val Gln Ser Gly Ala Glu Val Lys Lys Pro Gly Ala
1               5                   10                  15

Ser Val Lys Ile Ser Cys Lys Ala Ser Gly Tyr Ser Phe Thr Gly Tyr
            20                  25                  30

Tyr Met His Trp Val Lys Gln Ala His Gly Gln Gly Leu Glu Trp Ile
        35                  40                  45

Gly Arg Ile Asn Pro Tyr Asn Gly Ala Thr Ser Tyr Asn Gln Asn Phe
    50                  55                  60

Lys Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Tyr Val Tyr Trp Gly Gln Gly Thr Thr Val Thr Val
            100                 105                 110

Ser Ser Ala Lys Thr Lys Gly Pro Ser Val Phe Pro Leu Ala Pro Cys
            115                 120                 125

Ser Arg Ser Thr Ser Glu Ser Thr Ala Ala Leu Gly Cys Leu Val Lys
        130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Lys Thr Tyr Thr Cys Asn Val Asp His Lys Pro Ser Asn Thr Lys Val
        195                 200                 205

Asp Lys Arg Val Glu Ser Lys Tyr Gly Pro Pro Cys Pro Pro Cys Pro
    210                 215                 220

Ala Pro Glu Phe Glu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser Gln Glu Asp Pro Glu Val Gln Phe Asn Trp Tyr

-continued

```
            260             265             270

Val Asp Gly Val Glu Val His Asn Ala Lys Thr Lys Pro Arg Glu Glu
        275             280             285

Gln Phe Asn Ser Thr Tyr Arg Val Val Ser Val Leu Thr Val Leu His
    290             295             300

Gln Asp Trp Leu Asn Gly Lys Glu Tyr Lys Cys Lys Val Ser Asn Lys
305             310             315             320

Gly Leu Pro Ser Ser Ile Glu Lys Thr Ile Ser Lys Ala Lys Gly Gln
            325             330             335

Pro Arg Glu Pro Gln Val Tyr Thr Leu Pro Pro Ser Gln Glu Glu Met
            340             345             350

Thr Lys Asn Gln Val Ser Leu Thr Cys Leu Val Lys Gly Phe Tyr Pro
            355             360             365

Ser Asp Ile Ala Val Glu Trp Glu Ser Asn Gly Gln Pro Glu Asn Asn
            370             375             380

Tyr Lys Thr Thr Pro Pro Val Leu Asp Ser Asp Gly Ser Phe Phe Leu
385             390             395             400

Tyr Ser Arg Leu Thr Val Asp Lys Ser Arg Trp Gln Glu Gly Asn Val
            405             410             415

Phe Ser Cys Ser Val Met His Glu Ala Leu His Asn His Tyr Thr Gln
            420             425             430

Lys Ser Leu Ser Leu Ser Leu Gly Lys Ala Ser
            435             440
```

```
<210> SEQ ID NO 22
<211> LENGTH: 221
<212> TYPE: PRT
<213> ORGANISM: Artificial Sequence
<220> FEATURE:
<223> OTHER INFORMATION: Synthetic recombinant

<400> SEQUENCE: 22

Asp Val Val Met Thr Gln Ser Pro Leu Ser Leu Pro Val Thr Leu Gly
1               5               10              15

Gln Pro Ala Ser Ile Ser Cys Arg Ser Ser Gln Ser Leu Val His Ser
            20              25              30

Asn Gly Asn Thr Tyr Leu His Trp Tyr Gln Gln Arg Pro Gly Gln Ser
        35              40              45

Pro Arg Leu Leu Ile Tyr Lys Val Ser Asn Arg Phe Ser Gly Val Pro
    50              55              60

Asp Arg Phe Ser Gly Ser Gly Ser Gly Thr Asp Phe Thr Leu Lys Ile
65              70              75              80

Ser Arg Val Glu Ala Glu Asp Val Gly Val Tyr Phe Cys Ser Gln Ser
            85              90              95

Thr His Val Pro Trp Thr Phe Gly Gly Gly Thr Lys Leu Glu Ile Lys
            100             105             110

Arg Thr Val Ala Ala Pro Ser Val Phe Ile Phe Pro Pro Ser Asp Glu
            115             120             125

Gln Leu Lys Ser Gly Thr Ala Ser Val Val Cys Leu Leu Asn Asn Phe
    130             135             140

Tyr Pro Arg Glu Ala Lys Val Gln Trp Lys Val Asp Asn Ala Leu Gln
145             150             155             160

Ser Gly Asn Ser Gln Glu Ser Val Thr Glu Gln Asp Ser Lys Asp Ser
            165             170             175

Thr Tyr Ser Leu Ser Ser Thr Leu Thr Leu Ser Lys Ala Asp Tyr Glu
```

-continued

```
              180              185              190

Lys His Lys Val Tyr Ala Cys Glu Val Thr His Gln Gly Leu Ser Ser
         195              200              205

Pro Val Thr Lys Ser Phe Asn Arg Gly Glu Cys Ala Ser
    210              215              220

<210> SEQ ID NO 23
<211> LENGTH: 443
<212> TYPE: PRT
<213> ORGANISM: Artificial Sequence
<220> FEATURE:
<223> OTHER INFORMATION: Synthetic recombinant

<400> SEQUENCE: 23

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
         20                  25                  30

Tyr Met His Trp Val Arg Gln Ala Pro Gly Gln Gly Leu Glu Trp Ile
         35                  40                  45

Gly Arg Ile Asn Pro Tyr Asn Gly Ala Thr Ser Tyr Asn Gln Asn Phe
    50                  55                  60

Lys Asp Arg Val Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                 85                  90                  95

Ala Arg Glu Asp Tyr Val Tyr Trp Gly Gln Gly Thr Thr Val Thr Val
         100                 105                 110

Ser Ser Ala Lys Thr Lys Gly Pro Ser Val Phe Pro Leu Ala Pro Cys
         115                 120                 125

Ser Arg Ser Thr Ser Glu Ser Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
             165                 170                 175

Tyr Ser Leu Ser Ser Val Val Thr Val Pro Ser Ser Ser Leu Gly Thr
         180                 185                 190

Lys Thr Tyr Thr Cys Asn Val Asp His Lys Pro Ser Asn Thr Lys Val
         195                 200                 205

Asp Lys Arg Val Glu Ser Lys Tyr Gly Pro Pro Cys Pro Pro Cys Pro
    210                 215                 220

Ala Pro Glu Phe Glu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
             245                 250                 255

Val Val Asp Val Ser Gln Glu Asp Pro Glu Val Gln Phe Asn Trp Tyr
             260                 265                 270

Val Asp Gly Val Glu Val His Asn Ala Lys Thr Lys Pro Arg Glu Glu
         275                 280                 285

Gln Phe Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Gly Leu Pro Ser Ser Ile Glu Lys Thr Ile Ser Lys Ala Lys Gly Gln
```

```
                     325                 330                 335
Pro Arg Glu Pro Gln Val Tyr Thr Leu Pro Pro Ser Gln Glu Glu Met
            340                 345                 350

Thr Lys Asn Gln Val Ser Leu Thr Cys Leu Val Lys Gly Phe Tyr Pro
            355                 360                 365

Ser Asp Ile Ala Val Glu Trp Glu Ser Asn Gly Gln Pro Glu Asn Asn
            370                 375                 380

Tyr Lys Thr Thr Pro Pro Val Leu Asp Ser Asp Gly Ser Phe Phe Leu
385                 390                 395                 400

Tyr Ser Arg Leu Thr Val Asp Lys Ser Arg Trp Gln Glu Gly Asn Val
                405                 410                 415

Phe Ser Cys Ser Val Met His Glu Ala Leu His Asn His Tyr Thr Gln
                420                 425                 430

Lys Ser Leu Ser Leu Ser Leu Gly Lys Ala Ser
            435                 440
```

<210> SEQ ID NO 24
<211> LENGTH: 1332
<212> TYPE: DNA
<213> ORGANISM: Artificial Sequence
<220> FEATURE:
<223> OTHER INFORMATION: Synthetic recombinant

<400> SEQUENCE: 24

```
gaggtccagc tggtgcaatc tggagctgag gtgaagaagc ctggggcttc agtgaagata      60
tcctgcaagg cttctggata ctccttcact ggctactaca tgcactgggt gaagcaggcc     120
catggacaag ggcttgagtg gattggaagg attaatcctt acaatggtgc tactagctac     180
aaccagaact tcaaggacag agccaccttg actgtagaca gtccacgag cacagcctac      240 atggagctca gcagcctgag gtctgaggac acggcagtct attactgtgc aagagaggac     300
tacgtgtact ggggccaagg caccacggtc accgtctcct cagccaaaac gaagggccca     360
tccgtcttcc ccctggcgcc ctgctccagg agcacctccg agagcacagc cgccctgggc     420
tgcctggtca aggactactt ccccgaaccg gtgacggtgt cgtggaactc aggcgccctg     480
accagcggcg tgcacacctt cccggctgtc ctacagtcct caggactcta ctccctcagc     540
agcgtggtga ccgtgccctc agcagcttg ggcacgaaga cctacacctg caacgtagat      600
cacaagccca gcaacaccaa ggtggacaag agagttgagt ccaaatatgg tcccccatgc     660
ccaccctgcc cagcacctga gttcgaaggg ggaccatcag tcttcctgtt ccccccaaaa     720
cccaaggaca ctctcatgat ctcccggacc cctgaggtca cgtgcgtggt ggtggacgtg     780
agccaggaag accccgaggt ccagttcaac tggtacgtgg atggcgtgga ggtgcataat     840
gccaagacaa agccgcggga ggagcagttc aacagcacgt accgtgtggt cagcgtcctc     900
accgtcctgc accaggactg gctgaacggc aaggagtaca agtgcaaggt ctccaacaaa     960
ggcctcccgt cctccatcga gaaaaccatc tccaaagcca aagggcagcc cgagagccca    1020
caggtgtaca ccctgccccc atcccaggag gagatgacca gaaccaggt cagcctgacc     1080 tgcctggtca aaggcttcta ccccagcgac atcgccgtgg agtgggagag caatgggcag    1140
ccggagaaca actacaagac cacgcctccc gtgctggact ccgacggctc cttcttcctc    1200
tacagcaggc taaccgtgga caagagcagg tggcaggagg ggaatgtctt ctcatgctcc    1260
gtgatgcatg aggctctgca caaccactac acacagaaga gcctctccct gtctctgggt    1320
aaagctagct ga                                                         1332
```

-continued

```
<210> SEQ ID NO 25
<211> LENGTH: 666
<212> TYPE: DNA
<213> ORGANISM: Artificial Sequence
<220> FEATURE:
<223> OTHER INFORMATION: Synthetic recombinant

<400> SEQUENCE: 25
gatgttgtga tgacccaatc tccactctcc ctgcctgtca cccttggaca gccggcctcc        60
atctcttgca ggtctagtca gagccttgta cacagtaatg gaaacaccta tttacattgg       120
taccagcaga gaccaggcca gtctccaagg ctcctgatct acaaagtttc caaccgattt       180
tctggggtcc cagacaggtt cagtggcagt ggatcaggga cagatttcac actcaagatc       240
agcagagtgg aggctgaaga tgttggagtt tatttctgct ctcaaagtac acatgttcct       300
tggacgttcg gcggagggac caagctcgag atcaaacgaa ctgtggctgc accatctgtc       360
ttcatcttcc cgccatctga tgagcagttg aaatctggaa ctgcctctgt tgtgtgcctg       420
ctgaataact ctatcccag agaggccaaa gtacagtgga aggtggataa cgccctccaa       480
tcgggtaact cccaggagag tgtcacagag caggacagca aggacagcac ctacagcctc       540
agcagcaccc tgacgctgag caaagcagac tacgagaaac acaaagtcta tgcctgcgaa       600
gtcacccatc agggcctgag ctcgcccgtc acaaagagct tcaacagggg agagtgtgct       660
agctga                                                                    666

<210> SEQ ID NO 26
<211> LENGTH: 1332
<212> TYPE: DNA
<213> ORGANISM: Artificial Sequence
<220> FEATURE:
<223> OTHER INFORMATION: Synthetic recombinant

<400> SEQUENCE: 26
gaggtccagc tggtgcaatc tggagctgag gtgaagaagc ctgggggcttc agtgaaggtc        60 tcctgcaagg cttctggata tccttcact ggctactaca tgcactgggt gcgacaggcc       120
cctggacaag ggcttgagtg gattggaagg attaatcctt acaatggtgc tactagctac       180
aaccagaact tcaaggacag agtcaccttg actgtagaca gtccacgag cacagcctac       240 atggagctca gcagcctgag gtctgaggac acggcagtct attactgtgc aagagaggac       300
tacgtgtact ggggccaagg caccacggtc accgtctcct cagccaaaac gaagggccca       360
tccgtcttcc cctggcgcc ctgctccagg agcacctccg agagcacagc cgccctgggc       420
tgcctggtca aggactactt ccccgaaccg gtgacggtgt cgtggaactc aggcgccctg       480
accagcggcg tgcacaccct cccggctgtc ctacagtcct caggactcta ctccctcagc       540
agcgtggtga ccgtgccctc cagcagcttg ggcacgaaga cctacacctg caacgtagat       600
cacaagccca gcaacaccaa ggtggacaag agagttgagt ccaaatatgg tcccccatgc       660
ccaccctgcc cagcacctga gttcgaaggg ggaccatcag tcttcctgtt ccccccaaaa       720
cccaaggaca ctctcatgat ctcccggacc cctgaggtca cgtgcgtggt ggtggacgtg       780
agccaggaag accccgaggt ccagttcaac tggtacgtgg atggcgtgga ggtgcataat       840
gccaagacaa agccgcggga ggagcagttc aacagcacgt accgtgtggt cagcgtcctc       900
accgtcctgc accaggactg gctgaacggc aaggagtaca agtgcaaggt ctccaacaaa       960
ggcctcccgt cctccatcga gaaaaccatc tccaaagcca agggcagcc ccgagagcca       1020 caggtgtaca ccctgccccc atcccaggag gagatgacca gaaccaggt cagcctgacc       1080
```

-continued

```
tgcctggtca aaggcttcta ccccagcgac atcgccgtgg agtgggagag caatgggcag     1140
ccggagaaca actacaagac cacgcctccc gtgctggact ccgacggctc cttcttcctc     1200
tacagcaggc taaccgtgga caagagcagg tggcaggagg ggaatgtctt ctcatgctcc     1260
gtgatgcatg aggctctgca caaccactac acacagaaga gcctctccct gtctctgggt     1320
aaagctagct ga                                                         1332
```

<210> SEQ ID NO 27
<211> LENGTH: 10
<212> TYPE: PRT
<213> ORGANISM: Artificial Sequence
<220> FEATURE:
<223> OTHER INFORMATION: Synthetic recombinant

<400> SEQUENCE: 27

```
Gly Tyr Ser Phe Thr Gly Tyr Tyr Met His
1               5                   10
```

<210> SEQ ID NO 28
<211> LENGTH: 18
<212> TYPE: PRT
<213> ORGANISM: Artificial Sequence
<220> FEATURE:
<223> OTHER INFORMATION: Synthetic recombinant

<400> SEQUENCE: 28

```
Arg Ile Asn Pro Tyr Asn Gly Ala Thr Ser Tyr Asn Gln Asn Phe Lys
1               5                   10                  15

Asp Arg
```

<210> SEQ ID NO 29
<211> LENGTH: 5
<212> TYPE: PRT
<213> ORGANISM: Artificial Sequence
<220> FEATURE:
<223> OTHER INFORMATION: Synthetic recombinant

<400> SEQUENCE: 29

```
Glu Asp Tyr Val Tyr
1               5
```

<210> SEQ ID NO 30
<211> LENGTH: 16
<212> TYPE: PRT
<213> ORGANISM: Artificial Sequence
<220> FEATURE:
<223> OTHER INFORMATION: Synthetic recombinant

<400> SEQUENCE: 30

```
Arg Ser Ser Gln Ser Leu Val His Ser Asn Gly Asn Thr Tyr Leu His
1               5                   10                  15
```

<210> SEQ ID NO 31
<211> LENGTH: 7
<212> TYPE: PRT
<213> ORGANISM: Artificial Sequence
<220> FEATURE:
<223> OTHER INFORMATION: Synthetic recombinant

<400> SEQUENCE: 31

```
Lys Val Ser Asn Arg Phe Ser
1               5
```

```
<210> SEQ ID NO 32
<211> LENGTH: 9
<212> TYPE: PRT
<213> ORGANISM: Artificial Sequence
<220> FEATURE:
<223> OTHER INFORMATION: Synthetic recombinant

<400> SEQUENCE: 32

Ser Gln Ser Thr His Val Pro Trp Thr
1               5

<210> SEQ ID NO 33
<211> LENGTH: 1332
<212> TYPE: DNA
<213> ORGANISM: Artificial Sequence
<220> FEATURE:
<223> OTHER INFORMATION: Synthetic recombinant

<400> SEQUENCE: 33
gaggtccagc tggtgcaatc tggagctgag gtgaagaagc ctggggcttc agtgaagata     60
tcctgcaagg cttctggata ctccttcact ggctactaca tgcactgggt gaagcaggcc    120
catggacaag gcttgagtg gattggaagg attaatcctt acaatggtgc tactagctac    180
aaccagaact tcaaggacag agccaccttg actgtagaca gtccacgag cacagcctac    240 atggagctca gcagcctgag gtctgaggac acggcagtct attactgtgc aagagaggac    300
tacgtgtact ggggccaagg caccacggtc accgtctcct cagccaaaac gaagggccca    360
tccgtcttcc ccctggcgcc ctgctccagg agcacctccg agagcacagc cgccctgggc    420
tgcctggtca aggactactt ccccgaaccg gtgacggtgt cgtggaactc aggcgccctg    480
accagcggcg tgcacacctt cccggctgtc ctacagtcct caggactcta ctccctcagc    540
agcgtggtga ccgtgccctc cagcagcttg ggcacgaaga cctacacctg caacgtagat    600
cacaagccca gcaacaccaa ggtggacaag agagttgagt ccaaatatgg tcccccatgc    660
ccaccctgcc cagcacctga gttcgaaggg ggaccatcag tcttcctgtt cccccccaaaa    720 cccaaggaca ctctcatgat ctcccggacc cctgaggtca cgtgcgtggt ggtggacgtg    780
agccaggaag accccgaggt ccagttcaac tggtacgtgg atggcgtgga ggtgcataat    840
gccaagacaa agccgcggga ggagcagttc aacagcacgt accgtgtggt cagcgtcctc    900
accgtcctgc accaggactg gctgaacggc aaggagtaca agtgcaaggt ctccaacaaa    960
ggcctcccgt cctccatcga gaaaaccatc tccaaagcca agggcagcc ccgagagcca   1020 caggtgtaca ccctgccccc atcccaggag gagatgacca gaaccaggt cagcctgacc   1080 tgcctggtca aaggcttcta ccccagcgac atcgccgtgg agtgggagag caatgggcag   1140
ccggagaaca actacaagac cacgcctccc gtgctggact ccgacggctc cttcttcctc   1200
tacagcaggc taaccgtgga caagagcagg tggcaggagg ggaatgtctt ctcatgctcc   1260
gtgatgcatg aggctctgca caaccactac acacagaaga gcctctccct gtctctgggt   1320
aaagctagct ga                                                        1332

<210> SEQ ID NO 34
<211> LENGTH: 666
<212> TYPE: DNA
<213> ORGANISM: Artificial Sequence
<220> FEATURE:
<223> OTHER INFORMATION: Synthetic recombinant

<400> SEQUENCE: 34
gatgttgtga tgacccaatc tccactctcc ctgcctgtca cccttggaca gccggcctcc     60
```

```
atctcttgca ggtctagtca gagccttgta cacagtaatg gaaacaccta tttacattgg      120
taccagcaga gaccaggcca gtctccaagg ctcctgatct acaaagtttc caaccgattt      180
tctggggtcc cagacaggtt cagtggcagt ggatcaggga cagatttcac actcaagatc      240
agcagagtgg aggctgaaga tgttggagtt tatttctgct ctcaaagtac acatgttcct      300
tggacgttcg gcggagggac caagctcgag atcaaacgaa ctgtggctgc accatctgtc      360
ttcatcttcc cgccatctga tgagcagttg aaatctggaa ctgcctctgt tgtgtgcctg      420
ctgaataact ctatcccag agaggccaaa gtacagtgga aggtggataa cgccctccaa      480
tcgggtaact cccaggagag tgtcacagag caggacagca aggacagcac ctacagcctc      540
agcagcaccc tgacgctgag caaagcagac tacgagaaac acaaagtcta tgcctgcgaa      600
gtcacccatc agggcctgag ctcgcccgtc acaaagagct tcaacagggg agagtgtgct      660
agctga                                                                  666

<210> SEQ ID NO 35
<211> LENGTH: 1332
<212> TYPE: DNA
<213> ORGANISM: Artificial Sequence
<220> FEATURE:
<223> OTHER INFORMATION: Synthetic recombinant

<400> SEQUENCE: 35
gaggtccagc tggtgcaatc tggagctgag gtgaagaagc ctggggcttc agtgaaggtc       60
tcctgcaagg cttctggata tcccttcact ggctactaca tgcactgggt gcgacaggcc      120
cctggacaag ggcttgagtg gattggaagg attaatcctt acaatggtgc tactagctac      180
aaccagaact tcaaggacag agtcaccttg actgtagaca gtccacgag cacagcctac       240 atggagctca gcagcctgag gtctgaggac acggcagtct attactgtgc aagagaggac      300
tacgtgtact ggggccaagg caccacggtc accgtctcct cagccaaaac gaagggccca      360
tccgtcttcc ccctggcgcc ctgctccagg agcacctccg agagcacagc cgccctgggc      420
tgcctggtca aggactactt ccccgaaccg gtgacggtgt cgtggaactc aggcgccctg      480
accagcggcg tgcacacctt cccggctgtc ctacagtcct caggactcta ctccctcagc      540
agcgtggtga ccgtgccctc cagcagcttg ggcacgaaga cctacacctg caacgtagat      600
cacaagccca gcaacaccaa ggtggacaag agagttgagt ccaaatatgg tcccccatgc      660
ccaccctgcc cagcacctga gttcgaaggg ggaccatcag tcttcctgtt ccccccaaaa      720
cccaaggaca ctctcatgat ctcccggacc cctgaggtca cgtgcgtggt ggtggacgtg      780
agccaggaag accccgaggt ccagttcaac tggtacgtgg atggcgtgga ggtgcataat      840
gccaagacaa agccgcggga ggagcagttc aacagcacgt accgtgtggt cagcgtcctc      900
accgtcctgc accaggactg gctgaacggc aaggagtaca agtgcaaggt ctccaacaaa      960
ggcctcccgt cctccatcga gaaaaccatc tccaaagcca aagggcagcc ccgagagcca     1020
caggtgtaca ccctgccccc atcccaggag gagatgacca gaaccaggt cagcctgacc      1080 tgcctggtca aaggcttcta ccccagcgac atcgccgtgg agtgggagag caatgggcag     1140
ccggagaaca actacaagac cacgcctccc gtgctggact ccgacggctc cttcttcctc     1200
tacagcaggc taaccgtgga caagagcagg tggcaggagg ggaatgtctt ctcatgctcc     1260
gtgatgcatg aggctctgca caaccactac acacagaaga gcctctccct gtctctgggt     1320
aaagctagct ga                                                         1332
```

```
<210> SEQ ID NO 36
<211> LENGTH: 666
<212> TYPE: DNA
<213> ORGANISM: Artificial Sequence
<220> FEATURE:
<223> OTHER INFORMATION: Synthetic recombinant

<400> SEQUENCE: 36
gatgttgtga tgacccaatc tccactctcc ctgcctgtca cccttggaca gccggcctcc      60
atctcttgca ggtctagtca gagccttgta cacagtaatg gaaacaccta tttacattgg     120
taccagcaga gaccaggcca gtctccaagg ctcctgatct acaaagtttc caaccgattt     180
tctggggtcc cagacaggtt cagtggcagt ggatcaggga cagatttcac actcaagatc     240
agcagagtgg aggctgaaga tgttggagtt tatttctgct ctcaaagtac acatgttcct     300
tggacgttcg gcggagggac caagctcgag atcaaacgaa ctgtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta tgcctgcgaa     600
gtcacccatc agggcctgag ctcgcccgtc acaaagagct tcaacagggg agagtgtgct     660
agctga                                                                666

<210> SEQ ID NO 37
<211> LENGTH: 1200
<212> TYPE: DNA
<213> ORGANISM: Artificial Sequence
<220> FEATURE:
<223> OTHER INFORMATION: Synthetic recombinant

<400> SEQUENCE: 37
gatgttgtga tgacccaatc tccactctcc ctgcctgtca cccttggaca gccggcctcc      60
atctcttgca ggtctagtca gagccttgta cacagtaatg gaaacaccta tttacattgg     120
taccagcaga gaccaggcca gtctccaagg ctcctgatct acaaagtttc caaccgattt     180
tctggggtcc cagacaggtt cagtggcagt ggatcaggga cagatttcac actcaagatc     240
agcagagtgg aggctgaaga tgttggagtt tatttctgct ctcaaagtac acatgttcct     300
tggacgttcg gcggagggac caagctcgag atcaaacgaa ctgtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta tgcctgcgaa     600
gtcacccatc agggcctgag ctcgcccgtc acaaagagct tcaacagggg agagtgtgct     660
agtcagaccc ccaccaacac catcagcgtg accccccacca acaacagcac ccccaccaac     720
aacagcaacc ccaagcccaa ccccgctagc atgcagaagg agaccagaa ccctcagatc      780 gcagctcacg tcatctccga ggcttcttcc aagaccacct ccgtgctcca gtgggctgaa     840
aagggatact acaccatgag caacaacctg gtgacactgg agaacggcaa gcagctcaca     900
gtcaagcggc agggcctttta ctacatctat gcccaggtga ccttctgctc caacagggag     960
gcctccagcc aggccccttt cattgcctct ctgtgtctca gagcccagg cagattcgag     1020 aggattctcc tgcgcgccgc caatacacac agctcagcca aaccctgcgg gcaacagtca     1080
```
attcacctgg ggggggtctt tgagttgcag ccaggggcca gtgtcttcgt gaacgtgaca     1140
gatcccagtc aggtgagcca tggcactggc tttactagct ttgggttgct gaaactgtga     1200

<210> SEQ ID NO 38
<211> LENGTH: 1332
<212> TYPE: DNA
<213> ORGANISM: Artificial Sequence
<220> FEATURE:
<223> OTHER INFORMATION: Synthetic recombinant

<400> SEQUENCE: 38
gaggtccagc tggtgcaatc tggagctgag gtgaagaagc ctgggggcttc agtgaagata      60 tcctgcaagg cttctggata ctccttcact ggctactaca tgcactgggt gaagcaggcc     120
catggacaag ggcttgagtg gattggaagg attaatcctt acaatggtgc tactagctac     180
aaccagaact tcaaggacag agccaccttg actgtagaca agtccacgag cacagcctac     240
atggagctca gcagcctgag gtctgaggac acggcagtct attactgtgc aagagaggac     300
tacgtgtact ggggccaagg caccacggtc accgtctcct cagccaaaac gaagggccca     360
tccgtcttcc ccctggcgcc ctgctccagg agcacctccg agagcacagc cgccctgggc     420
tgcctggtca aggactactt ccccgaaccg gtgacggtgt cgtggaactc aggcgccctg     480
accagcggcg tgcacacctt cccggctgtc ctacagtcct caggactcta ctccctcagc     540
agcgtggtga ccgtgccctc cagcagcttg ggcacgaaga cctacacctg caacgtagat     600
cacaagccca gcaacaccaa ggtggacaag agagttgagt ccaaatatgg tcccccatgc     660 ccacctgcc cagcacctga gttcgaaggg ggaccatcag tcttcctgtt cccccccaaaa     720 cccaaggaca ctctcatgat ctcccggacc cctgaggtca cgtgcgtggt ggtggacgtg     780
agccaggaag accccgaggt ccagttcaac tggtacgtgg atggcgtgga ggtgcataat     840
gccaagacaa agccgcggga ggagcagttc aacagcacgt accgtgtggt cagcgtcctc     900
accgtcctgc accaggactg gctgaacggc aaggagtaca agtgcaaggt ctccaacaaa     960
ggcctcccgt cctccatcga gaaaaccatc tccaaagcca aagggcagcc ccgagagcca    1020
caggtgtaca ccctgccccc atcccaggag gagatgacca agaaccaggt cagcctgacc    1080
tgcctggtca aaggcttcta ccccagcgac atcgccgtgg agtgggagag caatgggcag    1140
ccggagaaca actacaagac cacgcctccc gtgctggact ccgacggctc cttcttcctc    1200
tacagcaggc taaccgtgga caagagcagg tggcaggagg ggaatgtctt ctcatgctcc    1260
gtgatgcatg aggctctgca caaccactac acacagaaga gcctctccct gtctctgggt    1320
aaagctagct ga                                                       1332

<210> SEQ ID NO 39
<211> LENGTH: 1200
<212> TYPE: DNA
<213> ORGANISM: Artificial Sequence
<220> FEATURE:
<223> OTHER INFORMATION: Synthetic recombinant

<400> SEQUENCE: 39
gatgttgtga tgacccaatc tccactctcc ctgcctgtca cccttggaca gccggcctcc      60
atctcttgca ggtctagtca gagccttgta cacagtaatg gaaacaccta tttacattgg     120
taccagcaga gaccaggcca gtctccaagg ctcctgatct acaaagtttc caaccgattt     180
tctggggtcc cagacaggtt cagtggcagt ggatcaggga cagatttcac actcaagatc     240

```
agcagagtgg aggctgaaga tgttggagtt tatttctgct ctcaaagtac acatgttcct      300
tggacgttcg gcggagggac caagctcgag atcaaacgaa ctgtggctgc accatctgtc      360
ttcatcttcc cgccatctga tgagcagttg aaatctggaa ctgcctctgt tgtgtgcctg      420
ctgaataact tctatcccag agaggccaaa gtacagtgga aggtggataa cgccctccaa      480
tcgggtaact cccaggagag tgtcacagag caggacagca aggacagcac ctacagcctc      540
agcagcaccc tgacgctgag caaagcagac tacgagaaac acaaagtcta tgcctgcgaa      600
gtcacccatc agggcctgag ctcgcccgtc acaaagagct tcaacagggg agagtgtgct      660
agtcagaccc ccaccaacac catcagcgtg accccaccacca acaacagcac ccccaccaac      720
aacagcaacc ccaagcccaa ccccgctagc atgcagaagg agaccagaa ccctcagatc      780 gcagctcacg tcatctccga ggcttcttcc aagaccacct ccgtgctcca gtgggctgaa      840
aagggatact acaccatgag caacaacctg gtgacactgg agaacggcaa gcagctcaca      900
gtcaagcggc agggccttta ctacatctat gcccaggtga ccttctgctc caacagggag      960
gcctccagcc aggcccctt cattgcctct ctgtgtctca gagcccagg cagattcgag      1020 aggattctcc tgcgcgccgc caatacacac agctcagcca accctgcgg gcaacagtca      1080 attcacctgg gggggtctt tgagttgcag ccaggggcca gtgtcttcgt gaacgtgaca      1140
gatcccagtc aggtgagcca tggcactggc tttactagct ttgggttgct gaaactgtga      1200
```

```
<210> SEQ ID NO 40
<211> LENGTH: 121
<212> TYPE: PRT
<213> ORGANISM: Artificial Sequence
<220> FEATURE:
<223> OTHER INFORMATION: Synthetic recombinant

<400> SEQUENCE: 40

Glu Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Tyr Ile Asn Ser Gly Gly Gly Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Arg Leu Lys Ser Glu Asp Thr Ala Met Tyr Tyr Cys
                85                  90                  95

Ala Arg Arg Gly Leu Pro Phe His Ala Met Asp Tyr Trp Gly Gln Gly
            100                 105                 110

Thr Ser Val Thr Val Ser Ser Ala Lys
        115                 120
```

```
<210> SEQ ID NO 41
<211> LENGTH: 1332
<212> TYPE: DNA
<213> ORGANISM: Artificial Sequence
<220> FEATURE:
<223> OTHER INFORMATION: Synthetic recombinant

<400> SEQUENCE: 41
gaggtccagc tggtgcaatc tggagctgag gtgaagaagc ctggggcttc agtgaaggtc       60
tcctgcaagg cttctggata tcccttcact ggctactaca tgcactgggt gcgacaggcc      120
```

```
cctggacaag ggcttgagtg gattggaagg attaatcctt acaatggtgc tactagctac      180
aaccagaact tcaaggacag agtcaccttg actgtagaca agtccacgag cacagcctac      240
atggagctca gcagcctgag gtctgaggac acggcagtct attactgtgc aagagaggac      300
tacgtgtact ggggccaagg caccacggtc accgtctcct cagccaaaac gaagggccca      360
tccgtcttcc ccctggcgcc ctgctccagg agcacctccg agagcacagc cgccctgggc      420
tgcctggtca aggactactt ccccgaaccg gtgacggtgt cgtggaactc aggcgccctg      480
accagcggcg tgcacacctt cccggctgtc ctacagtcct caggactcta ctccctcagc      540
agcgtggtga ccgtgccctc cagcagcttg ggcacgaaga cctacacctg caacgtagat      600
cacaagccca gcaacaccaa ggtggacaag agagttgagt ccaaatatgg tcccccatgc      660 ccacctgcc cagcacctga gttcgaaggg ggaccatcag tcttcctgtt ccccccaaaa      720
cccaaggaca ctctcatgat ctcccggacc cctgaggtca cgtgcgtggt ggtggacgtg      780
agccaggaag accccgaggt ccagttcaac tggtacgtgg atggcgtgga ggtgcataat      840
gccaagacaa agccgcggga ggagcagttc aacagcacgt accgtgtggt cagcgtcctc      900
accgtcctgc accaggactg gctgaacggc aaggagtaca agtgcaaggt ctccaacaaa      960
ggcctcccgt cctccatcga gaaaaccatc tccaaagcca aagggcagcc cgagagcca     1020 caggtgtaca ccctgccccc atcccaggag gagatgacca gaaccaggt cagcctgacc     1080 tgcctggtca aaggcttcta ccccagcgac atcgccgtgg agtgggagag caatgggcag     1140
ccggagaaca actacaagac cacgcctccc gtgctggact ccgacggctc cttcttcctc     1200
tacagcaggc taaccgtgga caagagcagg tggcaggagg ggaatgtctt ctcatgctcc     1260
gtgatgcatg aggctctgca caaccactac acacagaaga gcctctccct gtctctgggt     1320
aaagctagct ga                                                         1332

<210> SEQ ID NO 42
<211> LENGTH: 666
<212> TYPE: DNA
<213> ORGANISM: Artificial Sequence
<220> FEATURE:
<223> OTHER INFORMATION: Synthetic recombinant

<400> SEQUENCE: 42
gatgttgtga tgacccaatc tccactctcc ctgcctgtca cccttggaca gccggcctcc       60
atctcttgca ggtctagtca gagccttgta cacagtaatg gaaacaccta tttacattgg      120
taccagcaga gaccaggcca gtctccaagg ctcctgatct acaaagtttc caaccgattt      180
tctggggtcc cagacaggtt cagtggcagt ggatcaggga cagatttcac actcaagatc      240
agcagagtgg aggctgaaga tgttggagtt tatttctgct ctcaaagtac acatgttcct      300
tggacgttcg gcggagggac caagctcgag atcaaacgaa ctgtggctgc accatctgtc      360
ttcatcttcc cgccatctga tgagcagttg aaatctggaa ctgcctctgt tgtgtgcctg      420
ctgaataact ctatcccag agaggccaaa gtacagtgga aggtggataa cgccctccaa      480
tcgggtaact cccaggagag tgtcacagag caggacagca aggacagcac ctacagcctc      540
agcagcaccc tgacgctgag caaagcagac tacgagaaac acaaagtcta tgcctgcgaa      600
gtcacccatc agggcctgag ctcgcccgtc acaaagagct tcaacagggg agagtgtgct      660
agctga                                                                 666

<210> SEQ ID NO 43
```

<211> LENGTH: 2205
<212> TYPE: DNA
<213> ORGANISM: Artificial Sequence
<220> FEATURE:
<223> OTHER INFORMATION: Synthetic recombinant

<400> SEQUENCE: 43
gaggtccagc tggtgcaatc tggagctgag gtgaagaagc ctggggcttc agtgaagata      60
tcctgcaagg cttctggata ctccttcact ggctactaca tgcactgggt gaagcaggcc     120
catggacaag ggcttgagtg gattggaagg attaatcctt acaatggtgc tactagctac     180
aaccagaact tcaaggacag agccaccttg actgtagaca gtccacgag cacagcctac      240 atggagctca gcagcctgag gtctgaggac acggcagtct attactgtgc aagagaggac     300
tacgtgtact ggggccaagg caccacggtc accgtctcct cagccaaaac gaagggccca     360
tccgtcttcc ccctggcgcc ctgctccagg agcacctccg agagcacagc cgccctgggc     420
tgcctggtca aggactactt ccccgaaccg gtgacggtgt cgtggaactc aggcgccctg     480
accagcggcg tgcacacctt cccggctgtc ctacagtcct caggactcta ctccctcagc     540
agcgtggtga ccgtgccctc cagcagcttg ggcacgaaga cctacacctg caacgtagat     600
cacaagccca gcaacaccaa ggtggacaag agagttgagt ccaaatatgg tcccccatgc     660
ccaccctgcc cagcacctga gttcgaaggg ggaccatcag tcttcctgtt cccccaaaa     720 cccaaggaca ctctcatgat ctcccggacc cctgaggtca cgtgcgtggt ggtggacgtg     780
agccaggaag accccgaggt ccagttcaac tggtacgtgg atggcgtgga ggtgcataat     840
gccaagacaa agccgcggga ggagcagttc aacagcacgt accgtgtggt cagcgtcctc     900
accgtcctgc accaggactg gctgaacggc aaggagtaca gtgcaaggt ctccaacaaa      960 ggcctcccgt cctccatcga gaaaaccatc tccaaagcca aagggcagcc ccgagagcca    1020
caggtgtaca ccctgccccc atcccaggag gagatgacca gaaccaggt cagcctgacc     1080 tgcctggtca aaggcttcta ccccagcgac atcgccgtgg agtgggagag caatgggcag    1140
ccggagaaca actacaagac cacgcctccc gtgctggact ccgacggctc cttcttcctc    1200
tacagcaggc taaccgtgga caagagcagg tggcaggagg ggaatgtctt ctcatgctcc    1260
gtgatgcatg aggctctgca caaccactac acacagaaga gcctctccct gtctctgggt    1320
aaagctagtc agaccccac caacaccatc agcgtgaccc ccaccaacaa cagcaccccc    1380
accaacaaca gcaaccccaa gcccaacccc gctagtgaga agatccggct gcggcccggc    1440
ggcaagaaga agtacaagct gaagcacatc gtggctagta gcagcgtgag ccccaccacc    1500
agcgtgcacc ccacccccac cagcgtgccc cccaccccca ccaagagcag ccccgctagt    1560
aaccccccca tccccgtggg cgagatctac aagcggtgga tcatcctggg cctgaacaag    1620
atcgtgcgga tgtacagccc caccagcatc ctggacgcta gtcccaccag cacccccgcc    1680
gacagcagca ccatcacccc caccgccacc cccaccgcca cccccaccat caagggcgct    1740
agtcacaccc agggctactt ccccgactgg cagaactaca ccccccggccc cggcgtgcgg    1800 tacccctga ccttcggctg gctgtacaag ctggctagta ccgtgacccc caccgccacc     1860 gccacccca gcgccatcgt gaccaccatc acccccaccg ccaccaccaa gcccgctagt    1920
gtgggcttcc ccgtgacccc ccaggtgccc ctgcggccca tgacctacaa ggccgccgtg    1980
gacctgagcc acttcctgaa ggagaagggc ggcctggcta gtaccaacgg cagcatcacc    2040
gtggccgcca ccgcccccac cgtgacccc accgtgaacg ccaccccag cgccgccgct      2100 agtgccatct tccagagcag catgaccaag atcctggagc ccttccggaa gcagaacccc    2160

-continued gacatcgtga tctaccagta catggacgac ctgtacgcta gctga                        2205

<210> SEQ ID NO 44
<211> LENGTH: 1200
<212> TYPE: DNA
<213> ORGANISM: Artificial Sequence
<220> FEATURE:
<223> OTHER INFORMATION: Synthetic recombinant

<400> SEQUENCE: 44
gatgttgtga tgacccaatc tccactctcc ctgcctgtca cccttggaca gccggcctcc          60
atctcttgca ggtctagtca gagccttgta cacagtaatg aaacaccta tttacattgg         120 taccagcaga gaccaggcca gtctccaagg ctcctgatct acaaagtttc caaccgattt         180
tctggggtcc cagacaggtt cagtggcagt ggatcaggga cagatttcac actcaagatc        240
agcagagtgg aggctgaaga tgttggagtt tatttctgct ctcaaagtac acatgttcct        300
tggacgttcg gcggagggac caagctcgag atcaaacgaa ctgtggctgc accatctgtc        360
ttcatcttcc cgccatctga tgagcagttg aaatctggaa ctgcctctgt tgtgtgcctg        420
ctgaataact tctatcccag agaggccaaa gtacagtgga aggtggataa cgccctccaa        480
tcgggtaact cccaggagag tgtcacagag caggacagca aggacagcac ctacagcctc        540
agcagcaccc tgacgctgag caaagcagac tacgagaaac acaaagtcta tgcctgcgaa        600
gtcacccatc agggcctgag ctcgcccgtc acaaagagct tcaacagggg agagtgtgct        660
agtcagaccc ccaccaacac catcagcgtg accccccacca acaacagcac ccccaccaac        720
aacagcaacc ccaagcccaa ccccgctagc atgcagaagg gagaccagaa ccctcagatc        780
gcagctcacg tcatctccga ggcttcttcc aagaccacct ccgtgctcca gtgggctgaa        840
aagggatact acaccatgag caacaacctg gtgacactgg agaacggcaa gcagctcaca        900
gtcaagcggc agggccttta ctacatctat gcccaggtga ccttctgctc caacagggag        960
gcctccagcc aggccccttt cattgcctct ctgtgtctca gagcccagg cagattcgag       1020 aggattctcc tgcgcgccgc caatacacac agctcagcca aaccctgcgg gcaacagtca       1080
attcacctgg gggggtctt tgagttgcag ccaggggcca gtgtcttcgt gaacgtgaca       1140
gatcccagtc aggtgagcca tggcactggc tttactagct ttgggttgct gaaactgtga       1200

<210> SEQ ID NO 45
<211> LENGTH: 240
<212> TYPE: PRT
<213> ORGANISM: Human immunodeficiency virus

<400> SEQUENCE: 45

Ala Gln Gln Ala Ala Ala Asp Thr Gly His Ser Asn Gln Val Ser Gln
1               5                   10                  15

Asn Tyr Pro Ile Val Gln Asn Ile Gln Gly Gln Met Val His Gln Ala
            20                  25                  30

Ile Ser Pro Arg Thr Leu Asn Ala Trp Val Lys Val Val Glu Glu Lys
        35                  40                  45

Ala Phe Ser Pro Glu Val Ile Pro Met Phe Ser Ala Leu Ser Glu Gly
    50                  55                  60

Ala Thr Pro Gln Asp Leu Asn Thr Met Leu Asn Thr Val Gly Gly His
65                  70                  75                  80

Gln Ala Ala Met Gln Met Leu Lys Glu Thr Ile Asn Glu Glu Ala Ala
                85                  90                  95

-continued

```
Glu Trp Asp Arg Val His Pro Val His Ala Gly Pro Ile Ala Pro Gly
        100                 105                 110

Gln Met Arg Glu Pro Arg Gly Ser Asp Ile Ala Gly Thr Thr Ser Thr
        115                 120                 125

Leu Gln Glu Gln Ile Gly Trp Met Thr His Asn Pro Pro Ile Pro Val
        130                 135                 140

Gly Glu Ile Tyr Lys Arg Trp Ile Ile Leu Gly Leu Asn Lys Ile Val
145                 150                 155                 160

Arg Met Tyr Ser Pro Thr Ser Ile Leu Asp Ile Arg Gln Gly Pro Lys
                165                 170                 175

Glu Pro Phe Arg Asp Tyr Val Asp Arg Phe Tyr Lys Thr Leu Arg Ala
        180                 185                 190

Glu Gln Ala Ser Gln Glu Val Lys Asn Trp Met Thr Glu Thr Leu Leu
        195                 200                 205

Val Gln Asn Ala Asn Pro Asp Cys Lys Thr Ile Leu Lys Ala Leu Gly
        210                 215                 220

Pro Gly Ala Thr Leu Glu Glu Met Met Thr Ala Cys Gln Gly Val Gly
225                 230                 235                 240
```

<210> SEQ ID NO 46
<211> LENGTH: 206
<212> TYPE: PRT
<213> ORGANISM: Human immunodeficiency virus

<400> SEQUENCE: 46

```
Met Gly Gly Lys Trp Ser Lys Arg Ser Val Val Gly Trp Pro Thr Val
1               5                   10                  15

Arg Glu Arg Met Arg Arg Ala Glu Pro Ala Ala Asp Gly Val Gly Ala
        20                  25                  30

Val Ser Arg Asp Leu Glu Lys His Gly Ala Ile Thr Ser Ser Asn Thr
        35                  40                  45

Ala Ala Asn Asn Ala Asp Cys Ala Trp Leu Glu Ala Gln Glu Glu Glu
        50                  55                  60

Glu Val Gly Phe Pro Val Arg Pro Gln Val Pro Leu Arg Pro Met Thr
65                  70                  75                  80

Tyr Lys Gly Ala Leu Asp Leu Ser His Phe Leu Lys Glu Lys Gly Gly
                85                  90                  95

Leu Glu Gly Leu Ile Tyr Ser Gln Lys Arg Gln Asp Ile Leu Asp Leu
        100                 105                 110

Trp Val Tyr His Thr Gln Gly Tyr Phe Pro Asp Trp Gln Asn Tyr Thr
        115                 120                 125

Pro Gly Pro Gly Ile Arg Tyr Pro Leu Thr Phe Gly Trp Cys Phe Lys
        130                 135                 140

Leu Val Pro Val Glu Pro Glu Lys Val Glu Glu Ala Asn Glu Gly Glu
145                 150                 155                 160

Asn Asn Ser Leu Leu His Pro Met Ser Leu His Gly Met Asp Asp Pro
                165                 170                 175

Glu Arg Glu Val Leu Val Trp Lys Phe Asp Ser Arg Leu Ala Phe His
        180                 185                 190

His Met Ala Arg Glu Leu His Pro Glu Tyr Tyr Lys Asp Cys
        195                 200                 205
```

<210> SEQ ID NO 47
<211> LENGTH: 111
<212> TYPE: PRT
<213> ORGANISM: Human immunodeficiency virus -continued

<400> SEQUENCE: 47

```
Met Gly Ala Arg Ala Ser Ile Leu Ser Gly Gly Glu Leu Asp Arg Trp
1               5                   10                  15

Glu Lys Ile Arg Leu Arg Pro Gly Gly Asn Lys Gln Tyr Lys Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Asp Lys Ile Glu Glu Glu Gln Asn Lys Ser
            100                 105                 110
```

<210> SEQ ID NO 48
<211> LENGTH: 654
<212> TYPE: PRT
<213> ORGANISM: Artificial Sequence
<220> FEATURE:
<223> OTHER INFORMATION: Synthetic recombinant

<400> SEQUENCE: 48

```
Ala Ser Gln Thr Pro Thr Asn Thr Ile Ser Val Thr Pro Thr Asn Asn
1               5                   10                  15

Ser Thr Pro Thr Asn Asn Ser Asn Pro Lys Pro Asn Pro Ala Ser Leu
            20                  25                  30

Glu Met Gly Ala Arg Ala Ser Ile Leu Ser Gly Gly Glu Leu Asp Arg
        35                  40                  45

Trp Glu Lys Ile Arg Leu Arg Pro Gly Gly Asn Lys Gln Tyr Lys Leu
    50                  55                  60

Lys His Ile Val Trp Ala Ser Arg Glu Leu Glu Arg Phe Ala Val Asn
65                  70                  75                  80

Pro Gly Leu Leu Glu Thr Ser Glu Gly Cys Arg Gln Ile Leu Gly Gln
                85                  90                  95

Leu Gln Pro Ser Leu Gln Thr Gly Ser Glu Glu Leu Arg Ser Leu Tyr
            100                 105                 110

Asn Thr Val Ala Thr Leu Tyr Cys Val His Gln Arg Ile Glu Ile Lys
            115                 120                 125

Asp Thr Lys Glu Ala Leu Asp Lys Ile Glu Glu Glu Gln Asn Lys Ser
    130                 135                 140

Val Asp Thr Val Thr Pro Thr Ala Thr Ala Thr Pro Ser Ala Ile Val
145                 150                 155                 160

Thr Thr Ile Thr Pro Thr Ala Thr Thr Lys Pro Val Asp Met Gly Gly
                165                 170                 175

Lys Trp Ser Lys Arg Ser Val Val Gly Trp Pro Thr Val Arg Glu Arg
            180                 185                 190

Met Arg Arg Ala Glu Pro Ala Ala Asp Gly Val Gly Ala Val Ser Arg
            195                 200                 205

Asp Leu Glu Lys His Gly Ala Ile Thr Ser Ser Asn Thr Ala Ala Asn
    210                 215                 220

Asn Ala Asp Cys Ala Trp Leu Glu Ala Gln Glu Glu Glu Glu Val Gly
225                 230                 235                 240
```

```
Phe Pro Val Arg Pro Gln Val Pro Leu Arg Pro Met Thr Tyr Lys Gly
            245                 250                 255

Ala Leu Asp Leu Ser His Phe Leu Lys Glu Lys Gly Gly Leu Glu Gly
            260                 265                 270

Leu Ile Tyr Ser Gln Lys Arg Gln Asp Ile Leu Asp Leu Trp Val Tyr
            275                 280                 285

His Thr Gln Gly Tyr Phe Pro Asp Trp Gln Asn Tyr Thr Pro Gly Pro
    290                 295                 300

Gly Ile Arg Tyr Pro Leu Thr Phe Gly Trp Cys Phe Lys Leu Val Pro
305                 310                 315                 320

Val Glu Pro Glu Lys Val Glu Glu Ala Asn Glu Gly Glu Asn Asn Ser
            325                 330                 335

Leu Leu His Pro Met Ser Leu His Gly Met Asp Asp Pro Glu Arg Glu
            340                 345                 350

Val Leu Val Trp Lys Phe Asp Ser Arg Leu Ala Phe His His Met Ala
            355                 360                 365

Arg Glu Leu His Pro Glu Tyr Tyr Lys Asp Cys Glu Phe Thr Asn Gly
    370                 375                 380

Ser Ile Thr Val Ala Ala Thr Ala Pro Thr Val Thr Pro Thr Val Asn
385                 390                 395                 400

Ala Thr Pro Ser Ala Ala Gln Phe Ala Gln Gln Ala Ala Ala Asp Thr
            405                 410                 415

Gly His Ser Asn Gln Val Ser Gln Asn Tyr Pro Ile Val Gln Asn Ile
            420                 425                 430

Gln Gly Gln Met Val His Gln Ala Ile Ser Pro Arg Thr Leu Asn Ala
            435                 440                 445

Trp Val Lys Val Val Glu Glu Lys Ala Phe Ser Pro Glu Val Ile Pro
    450                 455                 460

Met Phe Ser Ala Leu Ser Glu Gly Ala Thr Pro Gln Asp Leu Asn Thr
465                 470                 475                 480

Met Leu Asn Thr Val Gly Gly His Gln Ala Ala Met Gln Met Leu Lys
            485                 490                 495

Glu Thr Ile Asn Glu Glu Ala Ala Glu Trp Asp Arg Val His Pro Val
            500                 505                 510

His Ala Gly Pro Ile Ala Pro Gly Gln Met Arg Glu Pro Arg Gly Ser
            515                 520                 525

Asp Ile Ala Gly Thr Thr Ser Thr Leu Gln Glu Gln Ile Gly Trp Met
    530                 535                 540

Thr His Asn Pro Pro Ile Pro Val Gly Glu Ile Tyr Lys Arg Trp Ile
545                 550                 555                 560

Ile Leu Gly Leu Asn Lys Ile Val Arg Met Tyr Ser Pro Thr Ser Ile
            565                 570                 575

Leu Asp Ile Arg Gln Gly Pro Lys Glu Pro Phe Arg Asp Tyr Val Asp
            580                 585                 590

Arg Phe Tyr Lys Thr Leu Arg Ala Glu Gln Ala Ser Gln Glu Val Lys
            595                 600                 605

Asn Trp Met Thr Glu Thr Leu Leu Val Gln Asn Ala Asn Pro Asp Cys
    610                 615                 620

Lys Thr Ile Leu Lys Ala Leu Gly Pro Gly Ala Thr Leu Glu Glu Met
625                 630                 635                 640

Met Thr Ala Cys Gln Gly Val Gly His His His His His
            645                 650
```

-continued

```
<210> SEQ ID NO 49
<211> LENGTH: 720
<212> TYPE: DNA
<213> ORGANISM: Human immunodeficiency virus

<400> SEQUENCE: 49
gcacagcaag cagcagctga cacaggacac agcaatcagg tcagccaaaa ttaccctata      60
gtgcagaaca tccaggggca aatggtacat caggccatat cacctagaac tttaaatgca     120
tgggtaaaag tagtagaaga gaaggctttc agcccagaag tgatacccat gttttcagca     180
ttatcagaag gagccacccc acaagattta aacaccatgc taaacacagt ggggggacat     240
caagcagcca tgcaaatgtt aaaagagacc atcaatgagg aagctgcaga atgggataga     300
gtgcatccag tgcatgcagg gcctattgca ccaggccaga tgagagaacc aaggggaagt     360
gacatagcag gaactactag tacccttcag gaacaaatag gatggatgac acataatcca     420
cctatcccag taggagaaat ctataaaagg tggataatcc tgggattaaa taaaatagta     480
agaatgtata gccctaccag cattctggac ataagacaag gaccaaagga accctttaga     540
gactatgtag accgattcta taaaactcta agagccgagc aagcttcaca agaggtaaaa     600
aattggatga cagaaacctt gttggtccaa aatgcgaacc cagattgtaa gactatttta     660
aaagcattgg gaccaggagc gacactagaa gaaatgatga cagcatgtca gggagtgggg     720

<210> SEQ ID NO 50
<211> LENGTH: 618
<212> TYPE: DNA
<213> ORGANISM: Human immunodeficiency virus

<400> SEQUENCE: 50
atgggaggca aatggagtaa aagaagtgtt gtgggttggc caactgtgag agaaagaatg      60
agaagggctg aaccagccgc tgatggtgta ggtgctgtgt cacgagatct ggaaaaacac     120
ggagcaataa catcctctaa taccgccgca aataacgcag actgtgcctg gctcgaagct     180
caagaagaag aagaagtcgg attccccgtg cgaccccaag ttcccctcag accaatgact     240
tataaaggcg ctctggatct tagccacttt cttaaagaaa aaggaggact ggaaggactt     300
atttattcac aaaaaagaca agacatcctc gatttgtggg tatatcatac tcaaggttat     360
ttcccagact ggcaaaatta tactcctgga cccggcattc gatatcccct tacctttgga     420
tggtgcttta aacttgtccc cgtcgaacct gaaaaagtag aagaagcaaa tgaaggcgaa     480
aataattcac tgctccaccc tatgtcactg cacggaatgg atgacccga acgcgaagtt     540 ctggtatgga aatttgattc aagacttgct tttcaccaca tggctagaga acttcacccc     600
gaatattata aagactgt                                                  618

<210> SEQ ID NO 51
<211> LENGTH: 333
<212> TYPE: DNA
<213> ORGANISM: Human immunodeficiency virus

<400> SEQUENCE: 51
atgggtgcga gagcgtcaat attaagcggt ggcgaattag atagatggga aaaaattcgg      60
ttaaggccag gggaaacaa acaatataaa ttaaaacata gtatgggc aagcagggag     120 ctagaacgat tcgcagttaa tcctggcctg ttagaaacat cagaaggctg tagacaaata     180
ctgggacagc tacaaccatc ccttcagaca ggatcagaag aacttagatc attatataat     240
acagtagcaa ccctctattg tgtgcatcaa aggatagaga taaaagacac caaggaagct     300
```

```
ttagacaaga tagaggaaga gcaaaacaaa agt                                    333

<210> SEQ ID NO 52
<211> LENGTH: 1965
<212> TYPE: DNA
<213> ORGANISM: Artificial Sequence
<220> FEATURE:
<223> OTHER INFORMATION: Synthetic recombinant

<400> SEQUENCE: 52
gctagtcaga ccccaccaa caccatcagc gtgaccccca ccaacaacag cacccccacc         60
aacaacagca accccaagcc caaccccgct agcctcgaga tgggtgcgag agcgtcaata       120
ttaagcggtg gcgaattaga tagatgggaa aaaattcggt taaggccagg gggaaacaaa       180
caatataaat taaaacatat agtatgggca agcagggagc tagaacgatt cgcagttaat       240
cctggcctgt tagaaacatc agaaggctgt agacaaatac tgggacagct acaaccatcc       300
cttcagacag gatcagaaga acttagatca ttatataata cagtagcaac cctctattgt       360
gtgcatcaaa ggatagagat aaaagacacc aaggaagctt tagacaagat agaggaagag       420
caaaacaaaa gtgtcgatac cgtgacccccc accgccaccg ccacccccag cgccatcgtg       480
accaccatca ccccaccgc caccaccaag cccgtcgaca tgggaggcaa atggagtaaa       540
agaagtgttg tgggttggcc aactgtgaga gaaagaatga gaagggctga accagccgct       600
gatggtgtag gtgctgtgtc acgagatctg gaaaaacacg gagcaataac atcctctaat       660
accgccgcaa ataacgcaga ctgtgcctgg ctcgaagctc aagaagaaga agaagtcgga       720
ttccccgtgc gacccaagt tccctcaga ccaatgactt ataaaggcgc tctggatctt       780
agccactttc ttaaagaaaa aggaggactg gaaggactta tttattcaca aaaaagacaa       840
gacatcctcg atttgtgggt atatcatact caaggttatt tcccagactg gcaaaattat       900
actcctggac ccggcattcg atatccctt acctttggat ggtgctttaa acttgtcccc       960
gtcgaacctg aaaaagtaga agaagcaaat gaaggcgaaa ataattcact gctccaccct      1020
atgtcactgc acggaatgga tgacccgaa cgcgaagttc tggtatggaa atttgattca      1080
agacttgctt ttcaccacat ggctagagaa cttcaccccg aatattataa agactgtgaa      1140
ttcaccaacg gcagcatcac cgtggccgcc accgcccca ccgtgacccc caccgtgaac      1200 gccacccca gcgccgccca attcgcacag caagcagcag ctgacacagg acacagcaat      1260
caggtcagcc aaaattaccc tatagtgcag aacatccagg ggcaaatggt acatcaggcc      1320
atatcaccta gaactttaaa tgcatgggta aaagtagtag aagagaaggc tttcagccca      1380
gaagtgatac ccatgttttc agcattatca gaaggagcca ccccacaaga tttaaacacc      1440
atgctaaaca gtgggggg acatcaagca gccatgcaaa tgttaaaaga gaccatcaat      1500
gaggaagctg cagaatggga tagagtgcat ccagtgcatg cagggcctat tgcaccaggc      1560
cagatgagag aaccaagggg aagtgacata gcaggaacta ctagtaccct tcaggaacaa      1620
ataggatgga tgacacataa tccacctatc ccagtaggag aaatctataa aaggtggata      1680
atcctgggat taaataaaat agtaagaatg tatagcccta ccagcattct ggacataaga      1740
caaggaccaa aggaacccctt tagagactat gtagaccgat tctataaaac tctaagagcc      1800
gagcaagctt cacaagaggt aaaaaattgg atgacagaaa ccttgttggt ccaaaatgcg      1860
aacccagatt gtaagactat tttaaaagca ttgggaccag gagcgacact agaagaaatg      1920
atgacagcat gtcagggagt ggggcatcac catcaccatc actga                     1965
```

<210> SEQ ID NO 53
<211> LENGTH: 25
<212> TYPE: PRT
<213> ORGANISM: Artificial Sequence
<220> FEATURE:
<223> OTHER INFORMATION: Synthetic recombinant

<400> SEQUENCE: 53

Thr Val Thr Pro Thr Ala Thr Ala Thr Pro Ser Ala Ile Val Thr Thr
1               5                   10                  15

Ile Thr Pro Thr Ala Thr Thr Lys Pro
            20                  25

<210> SEQ ID NO 54
<211> LENGTH: 25
<212> TYPE: PRT
<213> ORGANISM: Artificial Sequence
<220> FEATURE:
<223> OTHER INFORMATION: Synthetic recombinant

<400> SEQUENCE: 54

Thr Asn Gly Ser Ile Thr Val Ala Ala Thr Ala Pro Thr Val Thr Pro
1               5                   10                  15

Thr Val Asn Ala Thr Pro Ser Ala Ala
            20                  25

<210> SEQ ID NO 55
<211> LENGTH: 182
<212> TYPE: PRT
<213> ORGANISM: Artificial Sequence
<220> FEATURE:
<223> OTHER INFORMATION: Synthetic recombinant

<400> SEQUENCE: 55

Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
            20                  25                  30

Ile Ile Leu Glu Cys Val Tyr Cys Lys Gln Gln Leu Leu Arg Arg Glu
        35                  40                  45

Val Gly Asp Phe Ala Phe Arg Asp Leu Cys Ile Val Tyr Arg Asp Gly
    50                  55                  60

Asn Pro Tyr Ala Val Cys Asp Lys Cys Leu Lys Phe Tyr Ser Lys Ile
65                  70                  75                  80

Ser Glu Tyr Arg His Tyr Cys Tyr Ser Val Tyr Gly Thr Thr Leu Glu
                85                  90                  95

Gln Gln Tyr Asn Lys Pro Leu Cys Asp Leu Leu Ile Arg Cys Ile Asn
            100                 105                 110

Cys Gln Lys Pro Leu Cys Pro Glu Ala Ser Met His Gly Asp Thr Pro
            115                 120                 125

Thr Leu His Glu Tyr Met Leu Asp Leu Gln Pro Glu Thr Thr Asp Leu
    130                 135                 140

Tyr Gly Tyr Gly Gln Leu Asn Asp Ser Ser Glu Glu Glu Asp Glu Ile
145                 150                 155                 160

Asp Gly Pro Ala Gly Gln Ala Glu Pro Asp Arg Ala His Tyr Asn Ile
                165                 170                 175

Val Thr Phe Cys Cys Lys
            180

<210> SEQ ID NO 56

<211> LENGTH: 29
<212> TYPE: PRT
<213> ORGANISM: Artificial Sequence
<220> FEATURE:
<223> OTHER INFORMATION: Synthetic recombinant

<400> SEQUENCE: 56

Ala Ser Ser Ser Val Ser Pro Thr Thr Ser Val His Pro Thr Pro Thr
1               5                   10                  15

Ser Val Pro Pro Thr Pro Thr Lys Ser Ser Pro Ala Ser
            20                  25

<210> SEQ ID NO 57
<211> LENGTH: 242
<212> TYPE: PRT
<213> ORGANISM: Artificial Sequence
<220> FEATURE:
<223> OTHER INFORMATION: Synthetic recombinant

<400> SEQUENCE: 57

Ala Ser Gln Thr Pro Thr Asn Thr Ile Ser Val Thr Pro Thr Asn Asn
1               5                   10                  15

Ser Thr Pro Thr Asn Asn Ser Asn Pro Lys Pro Asn Pro Ala Ser Met
            20                  25                  30

His Gln Lys Arg Thr Ala Met Phe Gln Asp Pro Gln Glu Arg Pro Arg
        35                  40                  45

Lys Leu Pro Gln Leu Cys Thr Glu Leu Gln Thr Thr Ile His Asp Ile
    50                  55                  60

Ile Leu Glu Cys Val Tyr Cys Lys Gln Gln Leu Leu Arg Arg Glu Val
65                  70                  75                  80

Gly Asp Phe Ala Phe Arg Asp Leu Cys Ile Val Tyr Arg Asp Gly Asn
            85                  90                  95

Pro Tyr Ala Val Cys Asp Lys Cys Leu Lys Phe Tyr Ser Lys Ile Ser
            100                 105                 110

Glu Tyr Arg His Tyr Cys Tyr Ser Val Tyr Gly Thr Thr Leu Glu Gln
        115                 120                 125

Gln Tyr Asn Lys Pro Leu Cys Asp Leu Leu Ile Arg Cys Ile Asn Cys
        130                 135                 140

Gln Lys Pro Leu Cys Pro Glu Ala Ser Met His Gly Asp Thr Pro Thr
145                 150                 155                 160

Leu His Glu Tyr Met Leu Asp Leu Gln Pro Glu Thr Thr Asp Leu Tyr
            165                 170                 175

Gly Tyr Gly Gln Leu Asn Asp Ser Ser Glu Glu Glu Asp Glu Ile Asp
            180                 185                 190

Gly Pro Ala Gly Gln Ala Glu Pro Asp Arg Ala His Tyr Asn Ile Val
        195                 200                 205

Thr Phe Cys Cys Lys Ala Ser Ser Ser Val Ser Pro Thr Thr Ser Val
    210                 215                 220

His Pro Thr Pro Thr Ser Val Pro Pro Thr Pro Thr Lys Ser Ser Pro
225                 230                 235                 240

Ala Ser

<210> SEQ ID NO 58
<211> LENGTH: 123
<212> TYPE: PRT
<213> ORGANISM: Artificial Sequence
<220> FEATURE:
<223> OTHER INFORMATION: Synthetic recombinant

<400> SEQUENCE: 58

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
                20                  25                  30

Val Leu His Trp Val Lys Gln Lys Pro Gly Gln Gly Leu Glu Trp Ile
            35                  40                  45

Gly Tyr Ile Asn Pro Tyr Asn Asp Gly Thr Lys Tyr Asn Glu Lys Phe
        50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Tyr Pro Ala Tyr Ser Gly Tyr Ala Met Asp Tyr Trp Gly
                100                 105                 110

Gln Gly Thr Ser Val Thr Val Ser Ser Ala Lys
        115                 120

<210> SEQ ID NO 59
<211> LENGTH: 103
<212> TYPE: PRT
<213> ORGANISM: Artificial Sequence
<220> FEATURE:
<223> OTHER INFORMATION: Synthetic recombinant

<400> SEQUENCE: 59

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
                20                  25                  30

Leu Asn Trp Tyr Gln Gln Lys Pro Asp Gly Thr Val Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys His His Gly Asn Thr Leu Pro Trp
                85                  90                  95

Thr Phe Gly Gly Gly Thr Lys
        100

<210> SEQ ID NO 60
<211> LENGTH: 121
<212> TYPE: PRT
<213> ORGANISM: Artificial Sequence
<220> FEATURE:
<223> OTHER INFORMATION: Synthetic recombinant

<400> SEQUENCE: 60

Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Asp
                20                  25                  30

Tyr Ser Trp His Trp Ile Arg Gln Phe Pro Gly Asn Lys Leu Glu Trp
            35                  40                  45

Met Gly Tyr Ile Tyr Tyr Ser Gly Ser Thr Asn Tyr Asn Pro Ser Leu
        50                  55                  60

```
Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Ser Ala Thr Tyr Phe Cys
                85                  90                  95

Ala Arg Phe Tyr Tyr Gly Tyr Ser Phe Phe Asp Tyr Trp Gly Gln Gly
            100                 105                 110

Thr Thr Leu Thr Val Ser Ser Ala Lys
        115                 120
```

<210> SEQ ID NO 61
<211> LENGTH: 102
<212> TYPE: PRT
<213> ORGANISM: Artificial Sequence
<220> FEATURE:
<223> OTHER INFORMATION: Synthetic recombinant

<400> SEQUENCE: 61

```
Gln Ile Val Leu Thr Gln Ser Pro Ala Phe Met Ser Ala Ser Pro Gly
1               5                   10                  15

Glu Lys Val Thr Met Thr Cys Ser Ala Ser Ser Ser Val Ser Tyr Met
                20                  25                  30

His Trp Tyr Gln Gln Lys Ser Gly Thr Ser Pro Lys Arg Trp Ile Tyr
            35                  40                  45

Asp Thr Ser Lys Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys
            100
```

<210> SEQ ID NO 62
<211> LENGTH: 128
<212> TYPE: PRT
<213> ORGANISM: Artificial Sequence
<220> FEATURE:
<223> OTHER INFORMATION: Synthetic recombinant

<400> SEQUENCE: 62

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asp Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Asn Arg Leu Arg Ser Asp Asp Thr Ala Val Tyr Tyr Cys
                85                  90                  95

Ala Arg Asp Gln Pro Leu Gly Tyr Cys Thr Asn Gly Val Cys Ser Tyr
            100                 105                 110

Phe Asp Tyr Trp Gly Gln Gly Thr Leu Val Thr Val Ser Ser Ala Ser
        115                 120                 125
```

<210> SEQ ID NO 63

```
<211> LENGTH: 103
<212> TYPE: PRT
<213> ORGANISM: Artificial Sequence
<220> FEATURE:
<223> OTHER INFORMATION: Synthetic recombinant

<400> SEQUENCE: 63

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Tyr Ser Trp
                20                  25                  30

Leu Ala Trp Tyr Gln Gln Lys Pro Gly Lys Ala Pro Asn Leu Leu Ile
            35                  40                  45

Tyr Thr Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ile Phe Pro Leu
                85                  90                  95

Thr Phe Gly Gly Gly Thr Lys
                100

<210> SEQ ID NO 64
<211> LENGTH: 121
<212> TYPE: PRT
<213> ORGANISM: Artificial Sequence
<220> FEATURE:
<223> OTHER INFORMATION: Synthetic recombinant

<400> SEQUENCE: 64

Glu Val Gln Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
                20                  25                  30

Tyr Met Tyr Trp Val Arg Gln Ala Pro Gly Lys Gly Leu Glu Trp Val
            35                  40                  45

Ala Tyr Ile Asn Ser Gly Gly Gly Ser Thr Tyr Tyr Pro Asp Thr Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Leu Pro Phe His Ala Met Asp Tyr Trp Gly Gln Gly
            100                 105                 110

Thr Leu Val Thr Val Ser Ser Ala Lys
        115                 120

<210> SEQ ID NO 65
<211> LENGTH: 103
<212> TYPE: PRT
<213> ORGANISM: Artificial Sequence
<220> FEATURE:
<223> OTHER INFORMATION: Synthetic recombinant

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Gly Ile Ser Asn Tyr
                20                  25                  30
```

```
Leu Asn Trp Tyr Gln Gln Lys Pro Gly Lys Ala Val Lys Leu Leu Ile
        35                  40                  45

Tyr Tyr Thr Ser Ile Leu His Ser Gly Val Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Phe Asn Lys Leu Pro Pro
                85                  90                  95

Thr Phe Gly Gly Gly Thr Lys
            100
```

<210> SEQ ID NO 66
<211> LENGTH: 369
<212> TYPE: DNA
<213> ORGANISM: Artificial Sequence
<220> FEATURE:
<223> OTHER INFORMATION: Synthetic recombinant

<400> SEQUENCE: 66

```
gaggtccagc tgcagcagtc tggacctgag ctggtaaagc ctggggcttc agtgaagatg      60
tcctgcaagg cttctggata cacattcact gactatgttt tgcactgggt gaaacagaag     120
cctgggcagg gccttgagtg gattggatat attaatcctt acaatgatgg tactaagtac     180
aatgagaagt tcaaaggcaa ggccacactg acttcagaca atcctccag cacagcctac      240 atggagctca gcagcctgac ctctgaggac tctgcggtct attactgtgc aaggggctat     300
ccggcctact ctgggtatgc tatggactac tggggtcaag aacctcagt caccgtctcc      360 tcagccaaa                                                             369
```

<210> SEQ ID NO 67
<211> LENGTH: 309
<212> TYPE: DNA
<213> ORGANISM: Artificial Sequence
<220> FEATURE:
<223> OTHER INFORMATION: Synthetic recombinant

<400> SEQUENCE: 67

```
gatatccaga tgacacagac tacatcctcc ctgtctgcct ctctgggaga cagagtcacc      60
atcagttgca gggcaagtca ggacattagc aattatttaa actggtatca gcagaaacca     120
gatggaactg ttaaactcct gatctactac acatcaagat tacactcagg agtcccatca     180
aggttcagtg gcagtgggtc tggaacagat tattctctca ccattagcaa cctggagcaa     240
gaagatattg ccacttactt ttgccatcat ggtaatacgc ttccgtggac gttcggtgga     300
ggcaccaag                                                             309
```

<210> SEQ ID NO 68
<211> LENGTH: 363
<212> TYPE: DNA
<213> ORGANISM: Artificial Sequence
<220> FEATURE:
<223> OTHER INFORMATION: Synthetic recombinant

<400> SEQUENCE: 68

```
gatgtgcagc ttcaggagtc aggacctgac ctggtgaaac cttctcagtc actttcactc      60
acctgcactg tcactggcta ctccatcacc agtgattata ctggcactg atccggcag      120 ttcccaggaa acaaactgga atggatgggc tacatatatt acagtggtag cactaactac     180
aacccatctc tcaaaagtcg aatctctatc actcgagaca catccaagaa ccagttcttc     240
```

```
ctgcagttga attctgtgac tactgaggac tcagccacat atttctgtgc aagattttac      300
tacggttata gcttctttga ctactggggc caaggcacca ctctcacagt ctcctcagcc      360
aaa                                                                     363

<210> SEQ ID NO 69
<211> LENGTH: 306
<212> TYPE: DNA
<213> ORGANISM: Artificial Sequence
<220> FEATURE:
<223> OTHER INFORMATION: Synthetic recombinant

<400> SEQUENCE: 69
caaattgttc tcacccagtc tccagcattc atgtctgcat ctccagggga gaaggtcacc       60
atgacctgca gtgccagctc aagtgtcagt tacatgcact ggtaccagca gaagtcaggc      120
acctccccca aaagatggat ttatgacaca tccaaactgg cttctggagt ccctgctcgc      180
ttcagtggca gtgggtctgg gacctcttac tctctcacaa tcagcagcat ggaggctgaa      240
gatgctgcca cttattactg ccagcagtgg agtagtaacc cactcacgtt cggtgctggg      300
accaag                                                                 306

<210> SEQ ID NO 70
<211> LENGTH: 384
<212> TYPE: DNA
<213> ORGANISM: Artificial Sequence
<220> FEATURE:
<223> OTHER INFORMATION: Synthetic recombinant

<400> SEQUENCE: 70
caagtgcagc tggttcagtc tggggctgag gtgaaaaagc ctggggccag tgtcaaggtc       60
agctgcaagg cctctggcta cacatttact ggatattaca tgcattgggt tcgacaggcc      120
cccggacagg ggctcgaatg gatgggatgg ataaacccag acagcggcgg aacgaactat      180
gcccaaaaat ttcagggcag ggtgaccatg acccgggaca cctccatcag cacagcctac      240
atggagctga atagacttcg gagtgacgat acagccgtct actattgcgc aagggatcag      300
ccgctgggct actgtacaaa tggcgtgtgt tcatacttcg actattgggg tcagggtacg      360
ctcgtgaccg tgtcatctgc gtcc                                             384

<210> SEQ ID NO 71
<211> LENGTH: 309
<212> TYPE: DNA
<213> ORGANISM: Artificial Sequence
<220> FEATURE:
<223> OTHER INFORMATION: Synthetic recombinant

<400> SEQUENCE: 71
gacattcaga tgacacaatc tccctcctcc gtaagcgcct ctgtgggcga tcgcgttaca       60
atcacttgcc gggctagtca gggcatctat agctggctcg cttggtacca gcaaaagcct      120
ggcaaagcgc ctaatctgct gatttatacc gcctctacgc tgcagagcgg ggtcccaagc      180
agattttcag gtccgggtc aggaaccgat ttcactctga ctatcagctc cctgcagccc       240
gaggacttcg caacctacta ctgccagcaa gccaacatat tccccctgac ctttggtgga      300
ggtacaaag                                                              309

<210> SEQ ID NO 72
<211> LENGTH: 363
<212> TYPE: DNA
<213> ORGANISM: Artificial Sequence
```

-continued

```
<220> FEATURE:
<223> OTHER INFORMATION: Synthetic recombinant

<400> SEQUENCE: 72
gaagtgcagc tggtggagtc tggggggaggc ttagtgcagc ccggagggtc cctgaaactc     60
tcctgtgcaa cctctggatt cactttcagt gactattaca tgtattgggt tcgccaggcc    120
ccaggcaagg gcctggagtg ggtcgcatac attaattctg gtggtggtag cacctattat    180
ccagacactg taaagggccg attcaccatc tccagagaca tgccaagaa caccctgtac    240 ctgcaaatga acagcctgag ggccgaggac acagccgtgt attactgtgc aagacggggg    300
ttaccgttcc atgctatgga ctattggggt caaggaaccc tggtcaccgt ctcctcagcc    360
aaa                                                                   363

<210> SEQ ID NO 73
<211> LENGTH: 309
<212> TYPE: DNA
<213> ORGANISM: Artificial Sequence
<220> FEATURE:
<223> OTHER INFORMATION: Synthetic recombinant

<400> SEQUENCE: 73
gatatccaga tgacacagag cccttcctcc ctgtctgcct ctgtgggaga cagagtcacc     60
atcacctgca gtgcaagtca gggcattagc aattatttaa actggtatca gcagaaacca    120
ggcaaggccg ttaaactcct gatctattac acatcaattt tacactcagg agtcccatca    180
aggttcagtg gcagtgggtc tgggacagat tataccctca ccatcagctc cctgcagcct    240
gaagatttcg ccacttacta ttgtcagcag tttaataagc ttcctccgac gttcggtgga    300
ggcaccaaa                                                             309

<210> SEQ ID NO 74
<211> LENGTH: 10
<212> TYPE: PRT
<213> ORGANISM: Artificial Sequence
<220> FEATURE:
<223> OTHER INFORMATION: Synthetic recombinant

<400> SEQUENCE: 74

Gly Tyr Thr Phe Thr Asp Tyr Val Leu His
1               5                   10

<210> SEQ ID NO 75
<211> LENGTH: 17
<212> TYPE: PRT
<213> ORGANISM: Artificial Sequence
<220> FEATURE:
<223> OTHER INFORMATION: Synthetic recombinant

<400> SEQUENCE: 75

Tyr Ile Asn Pro Tyr Asn Asp Gly Thr Lys Tyr Asn Glu Lys Phe Lys
1               5                   10                  15

Gly

<210> SEQ ID NO 76
<211> LENGTH: 12
<212> TYPE: PRT
<213> ORGANISM: Artificial Sequence
<220> FEATURE:
<223> OTHER INFORMATION: Synthetic recombinant

<400> SEQUENCE: 76
```

```
Gly Tyr Pro Ala Tyr Ser Gly Tyr Ala Met Asp Tyr
1               5                   10

<210> SEQ ID NO 77
<211> LENGTH: 11
<212> TYPE: PRT
<213> ORGANISM: Artificial Sequence
<220> FEATURE:
<223> OTHER INFORMATION: Synthetic recombinant

<400> SEQUENCE: 77

Arg Ala Ser Gln Asp Ile Ser Asn Tyr Leu Asn
1               5                   10

<210> SEQ ID NO 78
<211> LENGTH: 7
<212> TYPE: PRT
<213> ORGANISM: Artificial Sequence
<220> FEATURE:
<223> OTHER INFORMATION: Synthetic recombinant

<400> SEQUENCE: 78

Tyr Thr Ser Arg Leu His Ser
1               5

<210> SEQ ID NO 79
<211> LENGTH: 9
<212> TYPE: PRT
<213> ORGANISM: Artificial Sequence
<220> FEATURE:
<223> OTHER INFORMATION: Synthetic recombinant

<400> SEQUENCE: 79

His His Gly Asn Thr Leu Pro Trp Thr
1               5

<210> SEQ ID NO 80
<211> LENGTH: 11
<212> TYPE: PRT
<213> ORGANISM: Artificial Sequence
<220> FEATURE:
<223> OTHER INFORMATION: Synthetic recombinant

<400> SEQUENCE: 80

Gly Tyr Ser Ile Thr Ser Asp Tyr Ser Trp His
1               5                   10

<210> SEQ ID NO 81
<211> LENGTH: 16
<212> TYPE: PRT
<213> ORGANISM: Artificial Sequence
<220> FEATURE:
<223> OTHER INFORMATION: Synthetic recombinant

<400> SEQUENCE: 81

Tyr Ile Tyr Tyr Ser Gly Ser Thr Asn Tyr Asn Pro Ser Leu Lys Ser
1               5                   10                  15

<210> SEQ ID NO 82
<211> LENGTH: 10
<212> TYPE: PRT
<213> ORGANISM: Artificial Sequence
<220> FEATURE:
<223> OTHER INFORMATION: Synthetic recombinant

<400> SEQUENCE: 82

Phe Tyr Tyr Gly Tyr Ser Phe Phe Asp Tyr
```

-continued

```
1               5                10

<210> SEQ ID NO 83
<211> LENGTH: 10
<212> TYPE: PRT
<213> ORGANISM: Artificial Sequence
<220> FEATURE:
<223> OTHER INFORMATION: Synthetic recombinant

<400> SEQUENCE: 83

Ser Ala Ser Ser Ser Val Ser Tyr Met His
1               5                10

<210> SEQ ID NO 84
<211> LENGTH: 7
<212> TYPE: PRT
<213> ORGANISM: Artificial Sequence
<220> FEATURE:
<223> OTHER INFORMATION: Synthetic recombinant

<400> SEQUENCE: 84

Asp Thr Ser Lys Leu Ala Ser
1               5

<210> SEQ ID NO 85
<211> LENGTH: 9
<212> TYPE: PRT
<213> ORGANISM: Artificial Sequence
<220> FEATURE:
<223> OTHER INFORMATION: Synthetic recombinant

<400> SEQUENCE: 85

Gln Gln Trp Ser Ser Asn Pro Leu Thr
1               5

<210> SEQ ID NO 86
<211> LENGTH: 10
<212> TYPE: PRT
<213> ORGANISM: Artificial Sequence
<220> FEATURE:
<223> OTHER INFORMATION: Synthetic recombinant

<400> SEQUENCE: 86

Gly Tyr Thr Phe Thr Gly Tyr Tyr Met His
1               5                10

<210> SEQ ID NO 87
<211> LENGTH: 17
<212> TYPE: PRT
<213> ORGANISM: Artificial Sequence
<220> FEATURE:
<223> OTHER INFORMATION: Synthetic recombinant

<400> SEQUENCE: 87

Trp Ile Asn Pro Asp Ser Gly Gly Thr Asn Tyr Ala Gln Lys Phe Gln
1               5                10               15

Gly

<210> SEQ ID NO 88
<211> LENGTH: 17
<212> TYPE: PRT
<213> ORGANISM: Artificial Sequence
<220> FEATURE:
<223> OTHER INFORMATION: Synthetic recombinant

<400> SEQUENCE: 88
```

-continued

```
Asp Gln Pro Leu Gly Tyr Cys Thr Asn Gly Val Cys Ser Tyr Phe Asp
1               5                   10                  15

Tyr

<210> SEQ ID NO 89
<211> LENGTH: 11
<212> TYPE: PRT
<213> ORGANISM: Artificial Sequence
<220> FEATURE:
<223> OTHER INFORMATION: Synthetic recombinant

<400> SEQUENCE: 89

Arg Ala Ser Gln Gly Ile Tyr Ser Trp Leu Ala
1               5                   10

<210> SEQ ID NO 90
<211> LENGTH: 7
<212> TYPE: PRT
<213> ORGANISM: Artificial Sequence
<220> FEATURE:
<223> OTHER INFORMATION: Synthetic recombinant

<400> SEQUENCE: 90

Thr Ala Ser Thr Leu Gln Ser
1               5

<210> SEQ ID NO 91
<211> LENGTH: 9
<212> TYPE: PRT
<213> ORGANISM: Artificial Sequence
<220> FEATURE:
<223> OTHER INFORMATION: Synthetic recombinant

<400> SEQUENCE: 91

Gln Gln Ala Asn Ile Phe Pro Leu Thr
1               5

<210> SEQ ID NO 92
<211> LENGTH: 10
<212> TYPE: PRT
<213> ORGANISM: Artificial Sequence
<220> FEATURE:
<223> OTHER INFORMATION: Synthetic recombinant

<400> SEQUENCE: 92

Gly Phe Thr Phe Ser Asp Tyr Tyr Met Tyr
1               5                   10

<210> SEQ ID NO 93
<211> LENGTH: 17
<212> TYPE: PRT
<213> ORGANISM: Artificial Sequence
<220> FEATURE:
<223> OTHER INFORMATION: Synthetic recombinant

<400> SEQUENCE: 93

Tyr Ile Asn Ser Gly Gly Gly Ser Thr Tyr Tyr Pro Asp Thr Val Lys
1               5                   10                  15

Gly

<210> SEQ ID NO 94
<211> LENGTH: 9
<212> TYPE: PRT
<213> ORGANISM: Artificial Sequence
<220> FEATURE:
<223> OTHER INFORMATION: Synthetic recombinant
```

<400> SEQUENCE: 94

Gly Leu Pro Phe His Ala Met Asp Tyr
1               5

<210> SEQ ID NO 95
<211> LENGTH: 11
<212> TYPE: PRT
<213> ORGANISM: Artificial Sequence
<220> FEATURE:
<223> OTHER INFORMATION: Synthetic recombinant

<400> SEQUENCE: 95

Ser Ala Ser Gln Gly Ile Ser Asn Tyr Leu Asn
1               5                   10

<210> SEQ ID NO 96
<211> LENGTH: 7
<212> TYPE: PRT
<213> ORGANISM: Artificial Sequence
<220> FEATURE:
<223> OTHER INFORMATION: Synthetic recombinant

<400> SEQUENCE: 96

Tyr Thr Ser Ile Leu His Ser
1               5

<210> SEQ ID NO 97
<211> LENGTH: 9
<212> TYPE: PRT
<213> ORGANISM: Artificial Sequence
<220> FEATURE:
<223> OTHER INFORMATION: Synthetic recombinant

<400> SEQUENCE: 97

Gln Gln Phe Asn Lys Leu Pro Pro Thr
1               5

<210> SEQ ID NO 98
<211> LENGTH: 123
<212> TYPE: PRT
<213> ORGANISM: Artificial Sequence
<220> FEATURE:
<223> OTHER INFORMATION: Synthetic recombinant

<400> SEQUENCE: 98

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Val Leu His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Tyr Pro Ala Tyr Ser Gly Tyr Ala Met Asp Tyr Trp Gly
            100                 105                 110

Gln Gly Thr Ser Val Thr Val Ser Ser Ala Lys
        115                 120

-continued

<210> SEQ ID NO 99
<211> LENGTH: 103
<212> TYPE: PRT
<213> ORGANISM: Artificial Sequence
<220> FEATURE:
<223> OTHER INFORMATION: Synthetic recombinant

<400> SEQUENCE: 99

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
                20                  25                  30

Leu Asn Trp Tyr Gln Gln Lys Pro Asp Gly Thr Val Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys His His Gly Asn Thr Leu Pro Trp
                85                  90                  95

Thr Phe Gly Gly Gly Thr Lys
            100

<210> SEQ ID NO 100
<211> LENGTH: 121
<212> TYPE: PRT
<213> ORGANISM: Artificial Sequence
<220> FEATURE:
<223> OTHER INFORMATION: Synthetic recombinant

<400> SEQUENCE: 100

Glu Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
                20                  25                  30

Tyr Met Tyr Trp Val Arg Gln Thr Pro Glu Lys Arg Leu Glu Trp Val
        35                  40                  45

Ala Tyr Ile Asn Ser Gly Gly Gly Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Arg Leu Lys Ser Glu Asp Thr Ala Met Tyr Tyr Cys
                85                  90                  95

Ala Arg Arg Gly Leu Pro Phe His Ala Met Asp Tyr Trp Gly Gln Gly
            100                 105                 110

Thr Ser Val Thr Val Ser Ser Ala Lys
        115                 120

<210> SEQ ID NO 101
<211> LENGTH: 103
<212> TYPE: PRT
<213> ORGANISM: Artificial Sequence
<220> FEATURE:
<223> OTHER INFORMATION: Synthetic recombinant

<400> SEQUENCE: 101

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr

-continued

```
                20                  25                  30

Leu Asn Trp Tyr Gln Gln Lys Pro Asp Gly Thr Val Lys Leu Leu Ile
        35                  40                  45

Tyr Tyr Thr Ser Ile Leu His Ser Gly Val Pro Ser Arg Phe Ser Gly
    50                  55                  60

Ser Gly Ser Gly Thr Asp Tyr Ser Leu Thr Ile Gly Asn Leu Glu Pro
65                  70                  75                  80

Glu Asp Ile Ala Thr Tyr Tyr Cys Gln Gln Phe Asn Lys Leu Pro Pro
                85                  90                  95

Thr Phe Gly Gly Gly Thr Lys
            100

<210> SEQ ID NO 102
<211> LENGTH: 121
<212> TYPE: PRT
<213> ORGANISM: Artificial Sequence
<220> FEATURE:
<223> OTHER INFORMATION: Synthetic recombinant

<400> SEQUENCE: 102

Glu Val Lys Leu Val Glu Ser Gly Gly Gly Leu Val Gln Pro Gly Gly
1               5                  10                  15

Ser Leu Lys Leu Ser Cys Ala Thr Ser Gly Phe Thr Phe Ser Asp Tyr
            20                  25                  30

Tyr Met Tyr Trp Val Arg Gln Ala Pro Gly Lys Gly Leu Glu Trp Val
        35                  40                  45

Ala Tyr Ile Asn Ser Gly Gly Gly Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Leu Pro Phe His Ala Met Asp Tyr Trp Gly Gln Gly
            100                 105                 110

Thr Leu Val Thr Val Ser Ser Ala Lys
        115                 120

<210> SEQ ID NO 103
<211> LENGTH: 121
<212> TYPE: PRT
<213> ORGANISM: Artificial Sequence
<220> FEATURE:
<223> OTHER INFORMATION: Synthetic recombinant

<400> SEQUENCE: 103

Glu Val Gln Leu Val Glu Ser Gly Gly Gly Leu Val Gln Pro Gly Gly
1               5                  10                  15

Ser Leu Lys Leu Ser Cys Ala Thr Ser Gly Phe Thr Phe Ser Asp Tyr
            20                  25                  30

Tyr Met Tyr Trp Val Arg Gln Ala Pro Gly Lys Gly Leu Glu Trp Val
        35                  40                  45

Ala Tyr Ile Asn Ser Gly Gly Gly Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Arg Arg Gly Leu Pro Phe His Ala Met Asp Tyr Trp Gly Gln Gly
            100                 105                 110

Thr Leu Val Thr Val Ser Ser Ala Lys
        115                 120

<210> SEQ ID NO 104
<211> LENGTH: 103
<212> TYPE: PRT
<213> ORGANISM: Artificial Sequence
<220> FEATURE:
<223> OTHER INFORMATION: Synthetic recombinant

<400> SEQUENCE: 104

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Gly Ile Ser Asn Tyr
            20                  25                  30

Leu Asn Trp Tyr Gln Gln Lys Pro Gly Lys Ala Val Lys Leu Leu Ile
        35                  40                  45

Tyr Tyr Thr Ser Ile Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Phe Asn Lys Leu Pro Pro
                85                  90                  95

Thr Phe Gly Gly Gly Thr Lys
            100

<210> SEQ ID NO 105
<211> LENGTH: 128
<212> TYPE: PRT
<213> ORGANISM: Artificial Sequence
<220> FEATURE:
<223> OTHER INFORMATION: Synthetic recombinant

<400> SEQUENCE: 105

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asp Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Asn Arg Leu Arg Ser Asp Asp Thr Ala Val Tyr Tyr Cys
                85                  90                  95

Ala Arg Asp Gln Pro Leu Gly Tyr Cys Thr Asn Gly Val Cys Ser Tyr
            100                 105                 110

Phe Asp Tyr Trp Gly Gln Gly Thr Leu Val Thr Val Ser Ser Ala Ser
        115                 120                 125

<210> SEQ ID NO 106
<211> LENGTH: 103
<212> TYPE: PRT
<213> ORGANISM: Artificial Sequence
<220> FEATURE:
<223> OTHER INFORMATION: Synthetic recombinant -continued

<400> SEQUENCE: 106

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Tyr Ser Trp
            20                  25                  30

Leu Ala Trp Tyr Gln Gln Lys Pro Gly Lys Ala Pro Asn Leu Leu Ile
        35                  40                  45

Tyr Thr Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ile Phe Pro Leu
                85                  90                  95

Thr Phe Gly Gly Gly Thr Lys
            100

<210> SEQ ID NO 107
<211> LENGTH: 121
<212> TYPE: PRT
<213> ORGANISM: Artificial Sequence
<220> FEATURE:
<223> OTHER INFORMATION: Synthetic recombinant

<400> SEQUENCE: 107

Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ser Trp His Trp Ile Arg Gln Phe Pro Gly Asn Lys Leu Glu Trp
        35                  40                  45

Met Gly Tyr Ile Tyr Tyr Ser Gly Ser Thr Asn Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Ser Ala Thr Tyr Phe Cys
                85                  90                  95

Ala Arg Phe Tyr Tyr Gly Tyr Ser Phe Phe Asp Tyr Trp Gly Gln Gly
            100                 105                 110

Thr Thr Leu Thr Val Ser Ser Ala Lys
        115                 120

<210> SEQ ID NO 108
<211> LENGTH: 102
<212> TYPE: PRT
<213> ORGANISM: Artificial Sequence
<220> FEATURE:
<223> OTHER INFORMATION: Synthetic recombinant

<400> SEQUENCE: 108

Gln Ile Val Leu Thr Gln Ser Pro Ala Phe Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

-continued

```
Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys
                100
```

```
<210> SEQ ID NO 109
<211> LENGTH: 399
<212> TYPE: PRT
<213> ORGANISM: Artificial Sequence
<220> FEATURE:
<223> OTHER INFORMATION: Synthetic recombinant

<400> SEQUENCE: 109
```

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
                20                  25                  30

Asn Gly Asn Thr Tyr Leu His Trp Tyr Gln Gln Arg Pro Gly Gln Ser
            35                  40                  45

Pro Arg Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Trp Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys Ala Ser Gln Thr Pro
        210                 215                 220

Thr Asn Thr Ile Ser Val Thr Pro Thr Asn Asn Ser Thr Pro Thr Asn
225                 230                 235                 240

Asn Ser Asn Pro Lys Pro Asn Pro Ala Ser Met Gln Lys Gly Asp Gln
            245                 250                 255

Asn Pro Gln Ile Ala Ala His Val Ile Ser Glu Ala Ser Ser Lys Thr
            260                 265                 270

Thr Ser Val Leu Gln Trp Ala Glu Lys Gly Tyr Tyr Thr Met Ser Asn
        275                 280                 285

Asn Leu Val Thr Leu Glu Asn Gly Lys Gln Leu Thr Val Lys Arg Gln
        290                 295                 300

Gly Leu Tyr Tyr Ile Tyr Ala Gln Val Thr Phe Cys Ser Asn Arg Glu
305                 310                 315                 320
```

Ala Ser Ser Gln Ala Pro Phe Ile Ala Ser Leu Cys Leu Lys Ser Pro
                325                     330                     335

Gly Arg Phe Glu Arg Ile Leu Leu Arg Ala Ala Asn Thr His Ser Ser
                340                     345                     350

Ala Lys Pro Cys Gly Gln Gln Ser Ile His Leu Gly Gly Val Phe Glu
                355                     360                     365

Leu Gln Pro Gly Ala Ser Val Phe Val Asn Val Thr Asp Pro Ser Gln
        370                     375                     380

Val Ser His Gly Thr Gly Phe Thr Ser Phe Gly Leu Leu Lys Leu
385                     390                     395

<210> SEQ ID NO 110
<211> LENGTH: 518
<212> TYPE: PRT
<213> ORGANISM: Artificial Sequence
<220> FEATURE:
<223> OTHER INFORMATION: Synthetic recombinant

<400> SEQUENCE: 110

Glu Val Gln Leu Val Gln Ser Gly Ala Glu Val Lys Lys Pro Gly Ala
1               5                       10                      15

Ser Val Lys Ile Ser Cys Lys Ala Ser Gly Tyr Ser Phe Thr Gly Tyr
                20                      25                      30

Tyr Met His Trp Val Lys Gln Ala His Gly Gln Gly Leu Glu Trp Ile
            35                      40                      45

Gly Arg Ile Asn Pro Tyr Asn Gly Ala Thr Ser Tyr Asn Gln Asn Phe
        50                      55                      60

Lys Asp Arg Ala Thr Leu Thr Val Asp Lys Ser Thr Ser Thr Ala Tyr
65                      70                      75                      80

Met Glu Leu Ser Ser Leu Arg Ser Glu Asp Thr Ala Val Tyr Tyr Cys
                85                      90                      95

Ala Arg Glu Asp Tyr Val Tyr Trp Gly Gln Gly Thr Thr Val Thr Val
                100                     105                     110

Ser Ser Ala Lys Thr Lys Gly Pro Ser Val Phe Pro Leu Ala Pro Cys
                115                     120                     125

Ser Arg Ser Thr Ser Glu Ser Thr Ala Ala Leu Gly Cys Leu Val Lys
        130                     135                     140

Asp Tyr Phe Pro Glu Pro Val Thr Val Ser Trp Asn Ser Gly Ala Leu
145                     150                     155                     160

Thr Ser Gly Val His Thr Phe Pro Ala Val Leu Gln Ser Ser Gly Leu
                165                     170                     175

Tyr Ser Leu Ser Ser Val Val Thr Val Pro Ser Ser Ser Leu Gly Thr
                180                     185                     190

Lys Thr Tyr Thr Cys Asn Val Asp His Lys Pro Ser Asn Thr Lys Val
                195                     200                     205

Asp Lys Arg Val Glu Ser Lys Tyr Gly Pro Pro Cys Pro Pro Cys Pro
        210                     215                     220

Ala Pro Glu Phe Glu Gly Gly Pro Ser Val Phe Leu Phe Pro Pro Lys
225                     230                     235                     240

Pro Lys Asp Thr Leu Met Ile Ser Arg Thr Pro Glu Val Thr Cys Val
                245                     250                     255

Val Val Asp Val Ser Gln Glu Asp Pro Glu Val Gln Phe Asn Trp Tyr
                260                     265                     270

Val Asp Gly Val Glu Val His Asn Ala Lys Thr Lys Pro Arg Glu Glu
                275                     280                     285

-continued

```
Gln Phe Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Gly Leu Pro Ser Ser Ile Glu Lys Thr Ile Ser Lys Ala Lys Gly Gln
            325                 330                 335

Pro Arg Glu Pro Gln Val Tyr Thr Leu Pro Pro Ser Gln Glu Glu Met
            340                 345                 350

Thr Lys Asn Gln Val Ser Leu Thr Cys Leu Val Lys Gly Phe Tyr Pro
            355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Arg Leu Thr Val Asp Lys Ser Arg Trp Gln Glu Gly Asn Val
                405                 410                 415

Phe Ser Cys Ser Val Met His Glu Ala Leu His Asn His Tyr Thr Gln
            420                 425                 430

Lys Ser Leu Ser Leu Ser Leu Gly Lys Ala Ser Asn Ser Pro Gln Asn
            435                 440                 445

Glu Val Leu Tyr Gly Asp Val Asn Asp Asp Gly Lys Val Asn Ser Thr
    450                 455                 460

Asp Leu Thr Leu Leu Lys Arg Tyr Val Leu Lys Ala Val Ser Thr Leu
465                 470                 475                 480

Pro Ser Ser Lys Ala Glu Lys Asn Ala Asp Val Asn Arg Asp Gly Arg
                485                 490                 495

Val Asp Ser Ser Asp Val Thr Ile Leu Ser Arg Tyr Leu Ile Arg Val
                500                 505                 510

Ile Glu Lys Leu Pro Ile
        515
```

<210> SEQ ID NO 111
<211> LENGTH: 75
<212> TYPE: PRT
<213> ORGANISM: Artificial Sequence
<220> FEATURE:
<223> OTHER INFORMATION: Synthetic recombinant

<400> SEQUENCE: 111

```
Asn Ser Pro Gln Asn Glu Val Leu Tyr Gly Asp Val Asn Asp Asp Gly
1               5                   10                  15

Lys Val Asn Ser Thr Asp Leu Thr Leu Leu Lys Arg Tyr Val Leu Lys
            20                  25                  30

Ala Val Ser Thr Leu Pro Ser Ser Lys Ala Glu Lys Asn Ala Asp Val
            35                  40                  45

Asn Arg Asp Gly Arg Val Asp Ser Ser Asp Val Thr Ile Leu Ser Arg
    50                  55                  60

Tyr Leu Ile Arg Val Ile Glu Lys Leu Pro Ile
65                  70                  75
```

<210> SEQ ID NO 112
<211> LENGTH: 262
<212> TYPE: PRT
<213> ORGANISM: Artificial Sequence
<220> FEATURE:
<223> OTHER INFORMATION: Synthetic recombinant

<400> SEQUENCE: 112

```
Glu Lys Ile Arg Leu Arg Pro Gly Gly Lys Lys Tyr Lys Leu Lys
1               5                   10                  15

His Ile Val Ala Ser Ser Ser Val Ser Pro Thr Thr Ser Val His Pro
            20                  25                  30

Thr Pro Thr Ser Val Pro Pro Thr Pro Thr Lys Ser Ser Pro Ala Ser
        35                  40                  45

Asn Pro Pro Ile Pro Val Gly Glu Ile Tyr Lys Arg Trp Ile Ile Leu
    50                  55                  60

Gly Leu Asn Lys Ile Val Arg Met Tyr Ser Pro Thr Ser Ile Leu Asp
65                  70                  75                  80

Ala Ser Pro Thr Ser Thr Pro Ala Asp Ser Ser Thr Ile Thr Pro Thr
                85                  90                  95

Ala Thr Pro Thr Ala Thr Pro Thr Ile Lys Gly Ala Ser His Thr Gln
            100                 105                 110

Gly Tyr Phe Pro Asp Trp Gln Asn Tyr Thr Pro Gly Pro Gly Val Arg
            115                 120                 125

Tyr Pro Leu Thr Phe Gly Trp Leu Tyr Lys Leu Ala Ser Thr Val Thr
    130                 135                 140

Pro Thr Ala Thr Ala Thr Pro Ser Ala Ile Val Thr Thr Ile Thr Pro
145                 150                 155                 160

Thr Ala Thr Thr Lys Pro Ala Ser Val Gly Phe Pro Val Thr Pro Gln
            165                 170                 175

Val Pro Leu Arg Pro Met Thr Tyr Lys Ala Ala Val Asp Leu Ser His
            180                 185                 190

Phe Leu Lys Glu Lys Gly Gly Leu Ala Ser Thr Asn Gly Ser Ile Thr
            195                 200                 205

Val Ala Ala Thr Ala Pro Thr Val Thr Pro Thr Val Asn Ala Thr Pro
    210                 215                 220

Ser Ala Ala Ala Ser Ala Ile Phe Gln Ser Ser Met Thr Lys Ile Leu
225                 230                 235                 240

Glu Pro Phe Arg Lys Gln Asn Pro Asp Ile Val Ile Tyr Gln Tyr Met
            245                 250                 255

Asp Asp Leu Tyr Ala Ser
            260
```

<210> SEQ ID NO 113
<211> LENGTH: 1200
<212> TYPE: DNA
<213> ORGANISM: Artificial Sequence
<220> FEATURE:
<223> OTHER INFORMATION: Synthetic recombinant

<400> SEQUENCE: 113

```
gatgttgtga tgacccaatc tccactctcc ctgcctgtca cccttggaca gccggcctcc        60
atctcttgca ggtctagtca gagccttgta cacagtaatg aaacaccta tttacattgg        120 taccagcaga gaccaggcca gtctccaagg ctcctgatct acaaagtttc caaccgattt        180
tctggggtcc cagacaggtt cagtggcagt ggatcaggga cagatttcac actcaagatc        240
agcagagtgg aggctgaaga tgttggagtt tatttctgct ctcaaagtac acatgttcct        300
tggacgttcg gcggagggac caagctcgag atcaaacgaa ctgtggctgc accatctgtc        360
ttcatcttcc cgccatctga tgagcagttg aaatctggaa ctgcctctgt tgtgtgcctg        420
ctgaataact ctatcccag agaggccaaa gtacagtgga aggtggataa cgccctccaa        480
tcgggtaact cccaggagag tgtcacagag caggacagca aggacagcac ctacagcctc        540
```

-continued

```
agcagcaccc tgacgctgag caaagcagac tacgagaaac acaaagtcta tgcctgcgaa      600
gtcacccatc agggcctgag ctcgcccgtc acaaagagct tcaacagggg agagtgtgct      660
agtcagaccc ccaccaacac catcagcgtg accccccacca acaacagcac ccccaccaac      720
aacagcaacc ccaagcccaa ccccgctagc atgcagaagg gagaccagaa ccctcagatc      780
gcagctcacg tcatctccga ggcttcttcc aagaccacct ccgtgctcca gtgggctgaa      840
aagggatact acaccatgag caacaacctg gtgacactgg agaacggcaa gcagctcaca      900
gtcaagcggc agggcctttta ctacatctat gcccaggtga ccttctgctc caacagggag      960
gcctccagcc aggccccttt cattgcctct ctgtgtctca gagcccagg cagattcgag     1020 aggattctcc tgcgcgccgc caatacacac agctcagcca aaccctgcgg gcaacagtca     1080
attcacctgg gggggggtctt tgagttgcag ccaggggcca gtgtcttcgt gaacgtgaca     1140
gatcccagtc aggtgagcca tggcactggc tttactagct ttgggttgct gaaactgtga     1200
```

```
<210> SEQ ID NO 114
<211> LENGTH: 1557
<212> TYPE: DNA
<213> ORGANISM: Artificial Sequence
<220> FEATURE:
<223> OTHER INFORMATION: Synthetic recombinant

<400> SEQUENCE: 114
```

```
gaggtccagc tggtgcaatc tggagctgag gtgaagaagc ctggggcttc agtgaagata       60
tcctgcaagg cttctggata tcccttcact ggctactaca tgcactgggt gaagcaggcc      120
catggacaag ggcttgagtg gattggaagg attaatcctt acaatggtgc tactagctac      180
aaccagaact tcaaggacag agccaccttg actgtagaca gtccacgag cacagcctac      240 atggagctca gcagcctgag gtctgaggac acggcagtct attactgtgc aagagaggac      300
tacgtgtact ggggccaagg caccacggtc accgtctcct cagccaaaac gaagggccca      360
tccgtcttcc ccctggcgcc ctgctccagg agcacctccg agagcacagc cgccctgggc      420
tgcctggtca aggactactt ccccgaaccg gtgacggtgt cgtggaactc aggcgccctg      480
accagcggcg tgcacacctt cccggctgtc ctacagtcct caggactcta ctccctcagc      540
agcgtggtga ccgtgccctc cagcagcttg ggcacgaaga cctacacctg caacgtagat      600
cacaagccca gcaacaccaa ggtggacaag agagttgagt ccaaatatgg tcccccatgc      660
ccaccctgcc cagcacctga gttcgaaggg ggaccatcag tcttcctgtt cccccccaaaa      720 cccaaggaca ctctcatgat ctcccggacc cctgaggtca cgtgcgtggt ggtggacgtg      780
agccaggaag accccgaggt ccagttcaac tggtacgtgg atggcgtgga ggtgcataat      840
gccaagacaa agccgcggga ggagcagttc aacagcacgt accgtgtggt cagcgtcctc      900
accgtcctgc accaggactg gctgaacggc aaggagtaca agtgcaaggt ctccaacaaa      960
ggcctcccgt cctccatcga gaaaaccatc tccaaagcca aagggcagcc ccgagagcca     1020
caggtgtaca ccctgccccc atcccaggag gagatgacca gaaccaggt cagcctgacc     1080 tgcctggtca aaggcttcta ccccagcgac atcgccgtgg agtgggagag caatgggcag     1140
ccggagaaca actacaagac cacgcctccc gtgctggact ccgacggctc cttcttcctc     1200
tacagcaggc taaccgtgga caagagcagg tggcaggagg ggaatgtctt ctcatgctcc     1260
gtgatgcatg aggctctgca caaccactac acacagaaga gcctctccct gtctctgggt     1320
aaagctagca attctcctca aaatgaagta ctgtacggag atgtgaatga tgacggaaaa     1380
```

-continued

```
gtaaactcca ctgacttgac tttgttaaaa agatatgttc ttaaagccgt ctcaactctg      1440
ccttcttcca aagctgaaaa gaacgcagat gtaaatcgtg acggaagagt tgactccagt      1500
gatgtcacaa tactttcaag atatttgata agggtaatcg agaaattacc aatataa        1557

<210> SEQ ID NO 115
<211> LENGTH: 789
<212> TYPE: DNA
<213> ORGANISM: Artificial Sequence
<220> FEATURE:
<223> OTHER INFORMATION: Synthetic recombinant

<400> SEQUENCE: 115
gagaagatcc ggctgcggcc cggcggcaag aagaagtaca agctgaagca catcgtggct        60
agtagcagcg tgagccccac caccagcgtg cacccccccc ccaccagcgt gcccccccacc      120 cccaccaaga gcagccccgc tagtaacccc cccatccccg tgggcgagat ctacaagcgg       180
tggatcatcc tgggcctgaa caagatcgtg cggatgtaca gccccaccag catcctggac       240
gctagtccca ccagcacccc cgccgacagc agcaccatca cccccaccgc cacccccacc       300 gccacccccca ccatcaaggg cgctagtcac acccagggct acttccccga ctggcagaac      360
tacacccccg gccccggcgt gcggtacccc ctgaccttcg gctggctgta caagctggct       420
agtaccgtga cccccaccgc caccgccacc cccagcgcca tcgtgaccac catcacccccc      480 accgccacca ccaagcccgc tagtgtgggc ttccccgtga cccccaggt gcccctgcgg        540 cccatgacct acaaggccgc cgtggacctg agccacttcc tgaaggagaa gggcggcctg       600
gctagtacca acggcagcat caccgtggcc gccaccgccc ccaccgtgac ccccaccgtg       660
aacgccaccc ccagcgccgc cgctagtgcc atcttccaga gcagcatgac caagatcctg       720
gagcccttcc ggaagcagaa ccccgacatc gtgatctacc agtacatgga cgacctgtac       780
gctagctga                                                              789

<210> SEQ ID NO 116
<211> LENGTH: 729
<212> TYPE: DNA
<213> ORGANISM: Artificial Sequence
<220> FEATURE:
<223> OTHER INFORMATION: Synthetic recombinant

<400> SEQUENCE: 116
gctagtcaga cccccaccaa caccatcagc gtgacccccca ccaacaacag cacccccacc       60
aacaacagca accccaagcc caaccccgct agtatgcacc aaaaaaggac cgcaatgttt       120 caggacccccc aagagaggcc ccgcaaactg ccacaacttt gcacggagct gcagacaaca      180
atacatgaca tcattctcga atgtgtttac tgtaagcagc agttgttgcg aagagaagtg       240
ggagacttcg ctttcagaga cctgtgtatc gtatatcgcg atggcaatcc ttatgccgtc       300
tgcgataaat gcctcaagtt ttactccaag atcagcgagt accggcacta ctgttactct       360
gtgtatggga ctaccctcga acagcagtat aacaagccgc tgtgcgatct ccttatccgg       420
tgcattaact gccagaagcc actgtgtcct gaggctagta tgcacgggga tacccccaca       480
ctccacgaat acatgcttga tttgcaacct gaaacgaccg acctgtacgg ctatggtcag       540
ctgaatgact ccagcgagga agaggatgag attgacggac cggcaggcca ggccgagcca       600
gaccgggctc attataacat cgtgactttc tgctgtaagg ctagtagcag cgtgagccccc      660 accaccagcg tgcaccccac ccccaccagc gtgcccccca ccccccaccaa gagcagcccc      720 gctagctga                                                              729
```

-continued

```
<210> SEQ ID NO 117
<211> LENGTH: 734
<212> TYPE: PRT
<213> ORGANISM: Artificial Sequence
<220> FEATURE:
<223> OTHER INFORMATION: Synthetic recombinant

<400> SEQUENCE: 117

Glu Val Gln Leu Val Gln Ser Gly Ala Glu Val Lys Lys Pro Gly Ala
1               5                   10                  15

Ser Val Lys Ile Ser Cys Lys Ala Ser Gly Tyr Ser Phe Thr Gly Tyr
            20                  25                  30

Tyr Met His Trp Val Lys Gln Ala His Gly Gln Gly Leu Glu Trp Ile
        35                  40                  45

Gly Arg Ile Asn Pro Tyr Asn Gly Ala Thr Ser Tyr Asn Gln Asn Phe
    50                  55                  60

Lys Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Tyr Val Tyr Trp Gly Gln Gly Thr Thr Val Thr Val
            100                 105                 110

Ser Ser Ala Lys Thr Lys Gly Pro Ser Val Phe Pro Leu Ala Pro Cys
        115                 120                 125

Ser Arg Ser Thr Ser Glu Ser Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Lys Thr Tyr Thr Cys Asn Val Asp His Lys Pro Ser Asn Thr Lys Val
        195                 200                 205

Asp Lys Arg Val Glu Ser Lys Tyr Gly Pro Pro Cys Pro Pro Cys Pro
    210                 215                 220

Ala Pro Glu Phe Glu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser Gln Glu Asp Pro Glu Val Gln Phe Asn Trp Tyr
            260                 265                 270

Val Asp Gly Val Glu Val His Asn Ala Lys Thr Lys Pro Arg Glu Glu
        275                 280                 285

Gln Phe Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Gly Leu Pro Ser Ser Ile Glu Lys Thr Ile Ser Lys Ala Lys Gly Gln
                325                 330                 335

Pro Arg Glu Pro Gln Val Tyr Thr Leu Pro Pro Ser Gln Glu Glu Met
            340                 345                 350

Thr Lys Asn Gln Val Ser Leu Thr Cys Leu Val Lys Gly Phe Tyr Pro
        355                 360                 365
```

-continued

```
Ser Asp Ile Ala Val Glu Trp Glu Ser Asn Gly Gln Pro Glu Asn Asn
    370             375             380

Tyr Lys Thr Thr Pro Pro Val Leu Asp Ser Asp Gly Ser Phe Phe Leu
385             390             395             400

Tyr Ser Arg Leu Thr Val Asp Lys Ser Arg Trp Gln Glu Gly Asn Val
            405             410             415

Phe Ser Cys Ser Val Met His Glu Ala Leu His Asn His Tyr Thr Gln
            420             425             430

Lys Ser Leu Ser Leu Ser Leu Gly Lys Ala Ser Gln Thr Pro Thr Asn
    435             440             445

Thr Ile Ser Val Thr Pro Thr Asn Asn Ser Thr Pro Thr Asn Asn Ser
    450             455             460

Asn Pro Lys Pro Asn Pro Ala Ser Glu Lys Ile Arg Leu Arg Pro Gly
465             470             475             480

Gly Lys Lys Lys Tyr Lys Leu Lys His Ile Val Ala Ser Ser Ser Val
            485             490             495

Ser Pro Thr Thr Ser Val His Pro Thr Pro Thr Ser Val Pro Pro Thr
            500             505             510

Pro Thr Lys Ser Ser Pro Ala Ser Asn Pro Pro Ile Pro Val Gly Glu
            515             520             525

Ile Tyr Lys Arg Trp Ile Ile Leu Gly Leu Asn Lys Ile Val Arg Met
    530             535             540

Tyr Ser Pro Thr Ser Ile Leu Asp Ala Ser Pro Thr Ser Thr Pro Ala
545             550             555             560

Asp Ser Ser Thr Ile Thr Pro Thr Ala Thr Pro Thr Ala Thr Pro Thr
            565             570             575

Ile Lys Gly Ala Ser His Thr Gln Gly Tyr Phe Pro Asp Trp Gln Asn
            580             585             590

Tyr Thr Pro Gly Pro Gly Val Arg Tyr Pro Leu Thr Phe Gly Trp Leu
            595             600             605

Tyr Lys Leu Ala Ser Thr Val Thr Pro Thr Ala Thr Ala Thr Pro Ser
    610             615             620

Ala Ile Val Thr Thr Ile Thr Pro Thr Ala Thr Thr Lys Pro Ala Ser
625             630             635             640

Val Gly Phe Pro Val Thr Pro Gln Val Pro Leu Arg Pro Met Thr Tyr
            645             650             655

Lys Ala Ala Val Asp Leu Ser His Phe Leu Lys Glu Lys Gly Gly Leu
            660             665             670

Ala Ser Thr Asn Gly Ser Ile Thr Val Ala Ala Thr Ala Pro Thr Val
            675             680             685

Thr Pro Thr Val Asn Ala Thr Pro Ser Ala Ala Ala Ser Ala Ile Phe
    690             695             700

Gln Ser Ser Met Thr Lys Ile Leu Glu Pro Phe Arg Lys Gln Asn Pro
705             710             715             720

Asp Ile Val Ile Tyr Gln Tyr Met Asp Asp Leu Tyr Ala Ser
            725             730
```

<210> SEQ ID NO 118
<211> LENGTH: 2205
<212> TYPE: DNA
<213> ORGANISM: Artificial Sequence
<220> FEATURE:
<223> OTHER INFORMATION: Synthetic recombinant

<400> SEQUENCE: 118

```
gaggtccagc tggtgcaatc tggagctgag gtgaagaagc ctggggcttc agtgaagata      60
tcctgcaagg cttctggata ctccttcact ggctactaca tgcactgggt gaagcaggcc     120
catggacaag ggcttgagtg gattggaagg attaatcctt acaatggtgc tactagctac     180
aaccagaact tcaaggacag agccaccttg actgtagaca gtccacgag cacagcctac      240 atggagctca gcagcctgag gtctgaggac acggcagtct attactgtgc aagagaggac     300
tacgtgtact ggggccaagg caccacggtc accgtctcct cagccaaaac gaagggccca     360
tccgtcttcc ccctggcgcc ctgctccagg agcacctccg agagcacagc cgccctgggc     420
tgcctggtca aggactactt ccccgaaccg gtgacggtgt cgtggaactc aggcgccctg     480
accagcggcg tgcacacctt cccggctgtc ctacagtcct caggactcta ctccctcagc     540
agcgtggtga ccgtgccctc agcagcttg ggcacgaaga cctacacctg caacgtagat      600
cacaagccca gcaacaccaa ggtggacaag agagttgagt ccaaatatgg tcccccatgc     660
ccaccctgcc cagcacctga gttcgaaggg ggaccatcag tcttcctgtt ccccccaaaa     720
cccaaggaca ctctcatgat ctcccggacc cctgaggtca cgtgcgtggt ggtggacgtg     780
agccaggaag accccgaggt ccagttcaac tggtacgtgg atggcgtgga ggtgcataat     840
gccaagacaa agccgcggga ggagcagttc aacagcacgt accgtgtggt cagcgtcctc     900
accgtcctgc accaggactg gctgaacggc aaggagtaca gtgcaaggt ctccaacaaa      960 ggcctcccgt cctccatcga gaaaaccatc tccaaagcca aagggcagcc ccgagagcca    1020
caggtgtaca ccctgccccc atcccaggag gagatgacca gaaccaggt cagcctgacc     1080 tgcctggtca aaggcttcta ccccagcgac atcgccgtgg agtgggagag caatgggcag    1140
ccggagaaca actacaagac cacgcctccc gtgctggact ccgacggctc cttcttcctc    1200
tacagcaggc taaccgtgga caagagcagg tggcaggagg ggaatgtctt ctcatgctcc    1260
gtgatgcatg aggctctgca caaccactac acacagaaga gcctctccct gtctctgggt    1320
aaagctagtc agaccccac caacaccatc agcgtgaccc ccaccaacaa cagcacccc     1380 accaacaaca gcaaccccaa gcccaacccc gctagtgaga agatccggct gcggcccggc    1440
ggcaagaaga agtacaagct gaagcacatc gtggctagta gcagcgtgag ccccaccacc    1500
agcgtgcacc ccaccccac cagcgtgccc cccaccccca ccaagagcag ccccgctagt    1560 aacccccca tccccgtggg cgagatctac aagcggtgga tcatcctggg cctgaacaag    1620
atcgtgcgga tgtacagccc caccagcatc ctggacgcta gtcccaccag cacccccgcc    1680
gacagcagca ccatcacccc caccgccacc cccaccgcca cccccaccat caagggcgct    1740
agtcacaccc agggctactt ccccgactgg cagaactaca ccccggccc cggcgtgcgg    1800 tacccctga ccttcggctg gctgtacaag ctggctagta ccgtgacccc caccgccacc    1860 gccacccca gcgccatcgt gaccaccatc acccccaccg ccaccaccaa gcccgctagt    1920
gtgggcttcc ccgtgacccc ccaggtgccc ctgcggccca tgacctacaa ggccgccgtg    1980
gacctgagcc acttcctgaa ggagaagggc ggcctggcta gtaccaacgg cagcatcacc    2040
gtggccgcca ccgcccccac cgtgaccccc accgtgaacg ccaccccag cgccgccgct    2100 agtgccatct ccagagcag catgaccaag atcctggagc ccttccggaa gcagaacccc    2160
gacatcgtga tctaccagta catggacgac ctgtacgcta gctga                    2205
```

<210> SEQ ID NO 119
<211> LENGTH: 103
<212> TYPE: PRT

<213> ORGANISM: Artificial Sequence
<220> FEATURE:
<223> OTHER INFORMATION: Synthetic recombinant

<400> SEQUENCE: 119

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ile Leu His Ser Gly Val Pro Ser Arg Phe Ser Gly
    50                  55                  60

Ser Gly Ser Gly Thr Asp Tyr Ser Leu Thr Ile Gly Asn Leu Glu Pro
65                  70                  75                  80

Glu Asp Ile Ala Thr Tyr Tyr Cys Gln Gln Phe Asn Lys Leu Pro Pro
                85                  90                  95

Thr Phe Gly Gly Gly Thr Lys
            100

<210> SEQ ID NO 120
<211> LENGTH: 309
<212> TYPE: DNA
<213> ORGANISM: Artificial Sequence
<220> FEATURE:
<223> OTHER INFORMATION: Synthetic recombinant

<400> SEQUENCE: 120
gatatccaga tgacacagac tacatcctcc ctgtctgcct ctctaggaga cagagtcacc        60
atcagttgca gtgcaagtca gggcattagc aattatttaa actggtatca gcagaaacca       120
gatggaactg ttaaactcct gatctattac acatcaattt tacactcagg agtcccatca       180
aggttcagtg gcagtgggtc tgggacagat tattctctca ccatcggcaa cctggaacct       240
gaagatattg ccacttacta ttgtcagcag tttaataagc ttcctccgac gttcggtgga       300
ggcaccaaa                                                               309

<210> SEQ ID NO 121
<211> LENGTH: 443
<212> TYPE: PRT
<213> ORGANISM: Artificial Sequence
<220> FEATURE:
<223> OTHER INFORMATION: Synthetic recombinant

<400> SEQUENCE: 121

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Gly Leu Glu Trp Ile
        35                  40                  45

Gly Arg Ile Asn Pro Tyr Asn Gly Ala Thr Ser Tyr Asn Gln Asn Phe
    50                  55                  60

Lys Asp Arg Val Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Tyr Val Tyr Trp Gly Gln Gly Thr Thr Val Thr Val
            100                 105                 110

-continued

```
Ser Ser Ala Lys Thr Lys Gly Pro Ser Val Phe Pro Leu Ala Pro Cys
        115                 120                 125

Ser Arg Ser Thr Ser Glu Ser Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
                180                 185                 190

Lys Thr Tyr Thr Cys Asn Val Asp His Lys Pro Ser Asn Thr Lys Val
                195                 200                 205

Asp Lys Arg Val Glu Ser Lys Tyr Gly Pro Pro Cys Pro Pro Cys Pro
    210                 215                 220

Ala Pro Glu Phe Glu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser Gln Glu Asp Pro Glu Val Gln Phe Asn Trp Tyr
                260                 265                 270

Val Asp Gly Val Glu Val His Asn Ala Lys Thr Lys Pro Arg Glu Glu
                275                 280                 285

Gln Phe Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Gly Leu Pro Ser Ser Ile Glu Lys Thr Ile Ser Lys Ala Lys Gly Gln
                325                 330                 335

Pro Arg Glu Pro Gln Val Tyr Thr Leu Pro Pro Ser Gln Glu Glu Met
                340                 345                 350

Thr Lys Asn Gln Val Ser Leu Thr Cys Leu Val Lys Gly Phe Tyr Pro
                355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Arg Leu Thr Val Asp Lys Ser Arg Trp Gln Glu Gly Asn Val
                405                 410                 415

Phe Ser Cys Ser Val Met His Glu Ala Leu His Asn His Tyr Thr Gln
                420                 425                 430

Lys Ser Leu Ser Leu Ser Leu Gly Lys Ala Ser
        435                 440
```

```
<210> SEQ ID NO 122
<211> LENGTH: 221
<212> TYPE: PRT
<213> ORGANISM: Artificial Sequence
<220> FEATURE:
<223> OTHER INFORMATION: Synthetic recombinant

<400> SEQUENCE: 122

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
        20                  25                  30
```

```
Asn Gly Asn Thr Tyr Leu His Trp Tyr Gln Gln Arg Pro Gly Gln Ser
        35                  40                  45

Pro Arg Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Trp Thr Phe Gly Gly Gly Thr Lys Leu Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys Ala Ser
        210                 215                 220

<210> SEQ ID NO 123
<211> LENGTH: 399
<212> TYPE: PRT
<213> ORGANISM: Artificial Sequence
<220> FEATURE:
<223> OTHER INFORMATION: Synthetic recombinant

<400> SEQUENCE: 123

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
                20                  25                  30

Asn Gly Asn Thr Tyr Leu His Trp Tyr Gln Gln Arg Pro Gly Gln Ser
        35                  40                  45

Pro Arg Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Trp Thr Phe Gly Gly Gly Thr Lys Leu Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175
```

```
Thr Tyr Ser Leu Ser Ser Thr Leu Thr Leu Ser Lys Ala Asp Tyr Glu
        180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Ala Ser Gln Thr Pro
        210                 215                 220

Thr Asn Thr Ile Ser Val Thr Pro Thr Asn Asn Ser Thr Pro Thr Asn
225                 230                 235                 240

Asn Ser Asn Pro Lys Pro Asn Pro Ala Ser Met Gln Lys Gly Asp Gln
                245                 250                 255

Asn Pro Gln Ile Ala Ala His Val Ile Ser Glu Ala Ser Ser Lys Thr
                260                 265                 270

Thr Ser Val Leu Gln Trp Ala Glu Lys Gly Tyr Tyr Thr Met Ser Asn
        275                 280                 285

Asn Leu Val Thr Leu Glu Asn Gly Lys Gln Leu Thr Val Lys Arg Gln
        290                 295                 300

Gly Leu Tyr Tyr Ile Tyr Ala Gln Val Thr Phe Cys Ser Asn Arg Glu
305                 310                 315                 320

Ala Ser Ser Gln Ala Pro Phe Ile Ala Ser Leu Cys Leu Lys Ser Pro
                325                 330                 335

Gly Arg Phe Glu Arg Ile Leu Leu Arg Ala Ala Asn Thr His Ser Ser
                340                 345                 350

Ala Lys Pro Cys Gly Gln Gln Ser Ile His Leu Gly Gly Val Phe Glu
        355                 360                 365

Leu Gln Pro Gly Ala Ser Val Phe Val Asn Val Thr Asp Pro Ser Gln
        370                 375                 380

Val Ser His Gly Thr Gly Phe Thr Ser Phe Gly Leu Leu Lys Leu
385                 390                 395
```

```
<210> SEQ ID NO 124
<211> LENGTH: 430
<212> TYPE: PRT
<213> ORGANISM: Artificial Sequence
<220> FEATURE:
<223> OTHER INFORMATION: Synthetic recombinant

<400> SEQUENCE: 124

Met Asp Leu Asp Ala Val Arg Ile Lys Val Asp Thr Val Asn Ala Lys
1               5                   10                  15

Pro Gly Asp Thr Val Asn Ile Pro Val Arg Phe Ser Gly Ile Pro Ser
        20                  25                  30

Lys Gly Ile Ala Asn Ala Asp Phe Val Tyr Ser Tyr Asp Pro Asn Val
        35                  40                  45

Leu Glu Ile Ile Glu Ile Lys Pro Gly Glu Leu Ile Val Asp Pro Asn
        50                  55                  60

Pro Thr Lys Ser Phe Asp Thr Ala Val Tyr Pro Asp Arg Lys Met Ile
65                  70                  75                  80

Val Phe Leu Phe Ala Glu Asp Ser Gly Thr Gly Ala Tyr Ala Ile Thr
                85                  90                  95

Lys Asp Gly Val Phe Ala Thr Ile Val Ala Lys Val Lys Glu Gly Ala
        100                 105                 110

Pro Asn Gly Leu Ser Val Ile Lys Phe Val Glu Val Gly Gly Phe Ala
        115                 120                 125

Asn Asn Asp Leu Val Glu Gln Lys Thr Gln Phe Phe Asp Gly Gly Val
        130                 135                 140
```

```
Asn Val Gly Asp Thr Thr Glu Pro Ala Thr Pro Thr Thr Pro Val Thr
145                 150                 155                 160

Thr Pro Thr Thr Thr Asp Asp Leu Asp Ala Ala Ser Leu Leu Thr Glu
                165                 170                 175

Val Glu Thr Tyr Val Leu Ser Ile Ile Pro Ser Gly Pro Leu Lys Ala
                180                 185                 190

Glu Ile Ala Gln Arg Leu Glu Asp Val Phe Ala Gly Lys Asn Thr Asp
                195                 200                 205

Leu Glu Val Leu Met Glu Trp Leu Lys Thr Arg Pro Ile Leu Ser Pro
        210                 215                 220

Leu Thr Lys Gly Ile Leu Gly Phe Val Phe Thr Leu Thr Val Pro Ser
225                 230                 235                 240

Glu Arg Gly Leu Gln Arg Arg Arg Phe Val Gln Asn Ala Leu Asn Gly
                245                 250                 255

Asn Gly Asp Pro Asn Asn Met Asp Lys Ala Val Lys Leu Tyr Arg Lys
                260                 265                 270

Leu Lys Arg Glu Ile Thr Phe His Gly Ala Lys Glu Ile Ala Leu Ser
        275                 280                 285

Tyr Ser Ala Gly Ala Leu Ala Ser Cys Met Gly Leu Ile Tyr Asn Arg
        290                 295                 300

Met Gly Ala Val Thr Thr Glu Val Ala Phe Gly Leu Val Cys Ala Thr
305                 310                 315                 320

Cys Glu Gln Ile Ala Asp Ser Gln His Arg Ser His Arg Gln Met Val
                325                 330                 335

Thr Thr Thr Asn Pro Leu Ile Arg His Glu Asn Arg Met Val Leu Ala
                340                 345                 350

Ser Thr Thr Ala Lys Ala Met Glu Gln Met Ala Gly Ser Ser Glu Gln
        355                 360                 365

Ala Ala Glu Ala Met Asp Ile Ala Ser Gln Ala Arg Gln Met Val Gln
        370                 375                 380

Ala Met Arg Thr Ile Gly Thr His Pro Ser Ser Ser Ala Gly Leu Lys
385                 390                 395                 400

Asp Asp Leu Leu Glu Asn Leu Gln Ala Tyr Gln Lys Arg Met Gly Val
                405                 410                 415

Gln Met Gln Arg Phe Lys Leu Glu His His His His His
                420                 425                 430
```

```
<210> SEQ ID NO 125
<211> LENGTH: 1293
<212> TYPE: DNA
<213> ORGANISM: Artificial Sequence
<220> FEATURE:
<223> OTHER INFORMATION: Synthetic recombinant

<400> SEQUENCE: 125
atggatctgg atgcagtaag gattaaagtg gacacagtaa atgcaaaacc gggagacaca        60
gtaaatatac ctgtaagatt cagtggtata ccatccaagg gaatagcaaa cgctgacttt       120
gtatacagct atgacccgaa tgtacttgag ataatagaga taaaaccggg agaattgata       180
gttgacccga atcctaccaa gagctttgat actgcagtat atcctgacag aaagatgata       240
gtattcctgt ttgcggaaga cagcggaaca ggagcgtatg caataactaa agacggagta       300
tttgctacga tagtagcgaa agtaaaagaa ggagcaccta cgggctcag tgtaatcaaa        360 tttgtagaag taggcggatt tgcgaacaat gaccttgtag aacagaagac acagttcttt       420
```

-continued

```
gacggtggag taaatgttgg agatacaaca gaacctgcaa cacctacaac acctgtaaca      480
acaccgacaa caacagatga tctggatgca gctagccttc taaccgaggt cgaaacgtac      540
gttctctcta tcatcccgtc aggccccctc aaagccgaga tcgcacagag acttgaagat      600
gtctttgcag ggaagaacac cgatcttgag gttctcatgg aatggctaaa gacaagacca      660
atcctgtcac ctctgactaa ggggattttta ggatttgtgt tcacgctcac cgtgcccagt      720
gagcggggac tgcagcgtag acgctttgtc caaaatgctc ttaatgggaa cggagatcca      780
aataacatgg acaaagcagt taaactgtat aggaagctta agagggagat aacattccat      840
ggggccaaag aaatagcact cagttattct gctggtgcac ttgccagttg tatgggcctc      900
atatacaaca ggatgggggc tgtgaccact gaagtggcat ttggcctggt atgcgcaacc      960
tgtgaacaga ttgctgactc ccagcatcgg tctcataggc aaatggtgac aacaaccaat     1020
ccactaatca gacatgagaa cagaatggtt ctagccagca ctacagctaa ggctatggag     1080
caaatggctg gatcgagtga gcaagcagca gaggccatgg atattgctag tcaggccagg     1140
caaatggtgc aggcgatgag aaccattggg actcatccta gctccagtgc tggtctaaaa     1200
gatgatcttc ttgaaaattt gcaggcttac cagaaacgga tggggtgca gatgcagcga     1260 ttcaagctcg agcaccacca ccaccaccac tga                                 1293
```

```
<210> SEQ ID NO 126
<211> LENGTH: 363
<212> TYPE: DNA
<213> ORGANISM: Artificial Sequence
<220> FEATURE:
<223> OTHER INFORMATION: Synthetic recombinant

<400> SEQUENCE: 126
gaagtgaagc tggtggagtc tggggggaggc ttagtgcagc ctggagggtc cctgaaactc       60
tcctgtgcaa cctctggatt cactttcagt gactattaca tgtattgggt tcgccagact      120
ccagagaaga ggctggagtg ggtcgcatac attaattctg gtggtggtag cacctattat      180
ccagacactg taaagggccg attcaccatc tccagagaca atgccaagaa caccctgtac      240
ctgcaaatga gccggctgaa gtctgaggac acagccatgt attactgtgc aagacggggg      300
ttaccgttcc atgctatgga ctattggggt caaggaacct cagtcaccgt ctcctcagcc      360
aaa                                                                   363
```

```
<210> SEQ ID NO 127
<211> LENGTH: 363
<212> TYPE: DNA
<213> ORGANISM: Artificial Sequence
<220> FEATURE:
<223> OTHER INFORMATION: Synthetic recombinant

<400> SEQUENCE: 127
gaagtgaagc tggtggagtc tggggggaggc ttagtgcagc ccggagggtc cctgaaactc       60
tcctgtgcaa cctctggatt cactttcagt gactattaca tgtattgggt tcgccaggcc      120
ccaggcaagg gcctggagtg ggtcgcatac attaattctg gtggtggtag cacctattat      180
ccagacactg taaagggccg attcaccatc tccagagaca atgccaagaa caccctgtac      240
ctgcaaatga acagcctgag ggccgaggac acagccgtgt attactgtgc aagacggggg      300
ttaccgttcc atgctatgga ctattggggt caaggaaccc tggtcaccgt ctcctcagcc      360
aaa                                                                   363
```

```
<210> SEQ ID NO 128
<211> LENGTH: 1332
<212> TYPE: DNA
<213> ORGANISM: Artificial Sequence
<220> FEATURE:
<223> OTHER INFORMATION: Synthetic recombinant

<400> SEQUENCE: 128
gaggtccagc tggtgcaatc tggagctgag gtgaagaagc ctggggcttc agtgaaggtc        60
tcctgcaagg cttctggata ctccttcact ggctactaca tgcactgggt gcgacaggcc       120
cctggacaag ggcttgagtg gattggaagg attaatcctt acaatggtgc tactagctac       180
aaccagaact tcaaggacag agtcaccttg actgtagaca gtccacgag cacagcctac        240 atggagctca gcagcctgag gtctgaggac acggcagtct attactgtgc aagagaggac       300
tacgtgtact ggggccaagg caccacggtc accgtctcct cagccaaaac gaagggccca       360
tccgtcttcc ccctggcgcc ctgctccagg agcacctccg agagcacagc cgccctgggc       420
tgcctggtca aggactactt ccccgaaccg gtgacggtgt cgtggaactc aggcgccctg       480
accagcggcg tgcacacctt cccggctgtc ctacagtcct caggactcta ctccctcagc       540
agcgtggtga ccgtgccctc cagcagcttg ggcacgaaga cctacacctg caacgtagat       600
cacaagccca gcaacaccaa ggtggacaag agagttgagt ccaaatatgg tcccccatgc       660
ccaccctgcc cagcacctga gttcgaaggg ggaccatcag tcttcctgtt ccccccaaaa       720
cccaaggaca ctctcatgat ctcccggacc cctgaggtca cgtgcgtggt ggtggacgtg       780
agccaggaag accccgaggt ccagttcaac tggtacgtgg atggcgtgga ggtgcataat       840
gccaagacaa agccgcggga ggagcagttc aacagcacgt accgtgtggt cagcgtcctc       900
accgtcctgc accaggactg gctgaacggc aaggagtaca gtgcaaggt ctccaacaaa        960 ggcctcccgt cctccatcga gaaaaccatc tccaaagcca aagggcagcc ccgagagcca      1020
caggtgtaca ccctgcccccc atcccaggag gagatgacca gaaccaggt cagcctgacc      1080 tgcctggtca aaggcttcta ccccagcgac atcgccgtgg agtgggagag caatgggcag      1140
ccggagaaca actacaagac cacgcctccc gtgctggact ccgacggctc cttcttcctc      1200
tacagcaggc taaccgtgga caagagcagg tggcaggagg ggaatgtctt ctcatgctcc      1260
gtgatgcatg aggctctgca caaccactac acacagaaga gcctctccct gtctctgggt      1320
aaagctagct ga                                                         1332

<210> SEQ ID NO 129
<211> LENGTH: 666
<212> TYPE: DNA
<213> ORGANISM: Artificial Sequence
<220> FEATURE:
<223> OTHER INFORMATION: Synthetic recombinant

<400> SEQUENCE: 129
gatgttgtga tgacccaatc tccactctcc ctgcctgtca cccttggaca gccggcctcc        60
atctcttgca ggtctagtca gagccttgta cacagtaatg gaaacaccta tttacattgg       120
taccagcaga gaccaggcca gtctccaagg ctcctgatct acaaagtttc caaccgattt       180
tctggggtcc cagacaggtt cagtggcagt ggatcaggga cagatttcac actcaagatc       240
agcagagtgg aggctgaaga tgttggagtt tatttctgct ctcaaagtac acatgttcct       300
tggacgttcg gcgagggac caagctcgag atcaaacgaa ctgtggctgc accatctgtc        360
ttcatcttcc cgccatctga tgagcagttg aaatctggaa ctgcctctgt tgtgtgcctg       420
```

-continued

```
ctgaataact tctatcccag agaggccaaa gtacagtgga aggtggataa cgccctccaa      480
tcgggtaact cccaggagag tgtcacagag caggacagca aggacagcac ctacagcctc      540
agcagcaccc tgacgctgag caaagcagac tacgagaaac acaaagtcta tgcctgcgaa      600
gtcacccatc agggcctgag ctcgcccgtc acaaagagct tcaacagggg agagtgtgct      660
agctga                                                                 666
```

```
<210> SEQ ID NO 130
<211> LENGTH: 25
<212> TYPE: PRT
<213> ORGANISM: Artificial Sequence
<220> FEATURE:
<223> OTHER INFORMATION: Synthetic recombinant

<400> SEQUENCE: 130

Pro Thr Ser Thr Pro Ala Asp Ser Ser Thr Ile Thr Pro Thr Ala Thr
1               5                   10                  15

Pro Thr Ala Thr Pro Thr Ile Lys Gly
            20                  25
```

```
<210> SEQ ID NO 131
<211> LENGTH: 443
<212> TYPE: PRT
<213> ORGANISM: Artificial Sequence
<220> FEATURE:
<223> OTHER INFORMATION: Synthetic Fusion protein

<400> SEQUENCE: 131

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Tyr Met His Trp Val Lys Gln Ser His Val Lys Ser Leu Glu Trp Ile
        35                  40                  45

Gly Arg Ile Asn Pro Tyr Asn Gly Ala Thr Ser Tyr Asn Gln Asn Phe
    50                  55                  60

Lys Asp Lys Ala Ser Leu Thr Val Asp Lys Ser Ser Ser Thr Ala Tyr
65                  70                  75                  80

Met Glu Leu His Ser Leu Thr Ser Glu Asp Ser Ala Val Tyr Tyr Cys
                85                  90                  95

Ala Arg Glu Asp Tyr Val Tyr Trp Gly Gln Gly Thr Thr Leu Thr Val
            100                 105                 110

Ser Ser Ala Lys Thr Lys Gly Pro Ser Val Phe Pro Leu Ala Pro Cys
        115                 120                 125

Ser Arg Ser Thr Ser Glu Ser Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Lys Thr Tyr Thr Cys Asn Val Asp His Lys Pro Ser Asn Thr Lys Val
            195                 200                 205

Asp Lys Arg Val Glu Ser Lys Tyr Gly Pro Pro Cys Pro Pro Cys Pro
    210                 215                 220

Ala Pro Glu Phe Glu Gly Gly Pro Ser Val Phe Leu Phe Pro Pro Lys
```

```
225                 230                 235                 240

Pro Lys Asp Thr Leu Met Ile Ser Arg Thr Pro Glu Val Thr Cys Val
            245                 250                 255

Val Val Asp Val Ser Gln Glu Asp Pro Glu Val Gln Phe Asn Trp Tyr
            260                 265                 270

Val Asp Gly Val Glu Val His Asn Ala Lys Thr Lys Pro Arg Glu Glu
        275                 280                 285

Gln Phe Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Gly Leu Pro Ser Ser Ile Glu Lys Thr Ile Ser Lys Ala Lys Gly Gln
            325                 330                 335

Pro Arg Glu Pro Gln Val Tyr Thr Leu Pro Pro Ser Gln Glu Glu Met
            340                 345                 350

Thr Lys Asn Gln Val Ser Leu Thr Cys Leu Val Lys Gly Phe Tyr Pro
            355                 360                 365

Ser Asp Ile Ala Val Glu Trp Glu Ser Asn Gly Gln Pro Glu Asn Asn
        370                 375                 380

Tyr Lys Thr Thr Pro Pro Val Leu Asp Ser Asp Gly Ser Phe Phe Leu
385                 390                 395                 400

Tyr Ser Arg Leu Thr Val Asp Lys Ser Arg Trp Gln Glu Gly Asn Val
            405                 410                 415

Phe Ser Cys Ser Val Met His Glu Ala Leu His Asn His Tyr Thr Gln
            420                 425                 430

Lys Ser Leu Ser Leu Ser Leu Gly Lys Ala Ser
        435                 440
```

```
<210> SEQ ID NO 132
<211> LENGTH: 1389
<212> TYPE: DNA
<213> ORGANISM: Artificial Sequence
<220> FEATURE:
<223> OTHER INFORMATION: Synthetic Fusion protein

<400> SEQUENCE: 132
atgggatgga gctggatctt tctctttctc ctgtcaggaa ctgcaggtgt cctctctgag      60
gtccagctgc aacagtctgg acctgagctg gtgaagcctg gggcttcagt gaagatatcc     120
tgcaaggctt ctggttactc attcactggc tactacatgc actgggtgaa gcaaagccat     180
gtaaagagcc ttgagtggat tggacgtatt aatccttaca tggtgctac tagctacaac     240 cagaatttca aggacaaggc cagcttgact gtagataagt cctccagcac agcctacatg     300
gagctccaca gcctgacatc tgaggactct gcagtctatt actgtgcaag agaggactac     360
gtctactggg gccaaggcac cactctcaca gtctcctcag ccaaaacgaa gggcccatcc     420
gtcttccccc tggcgccctg ctccaggagc acctccgaga gcacagccgc cctgggctgc     480
ctggtcaagg actacttccc cgaaccggtg acggtgtcgt ggaactcagg cgccctgacc     540
agcggcgtgc acaccttccc ggctgtccta cagtcctcag gactctactc cctcagcagc     600
gtggtgaccg tgccctccag cagcttgggc acgaagacct acacctgcaa cgtagatcac     660
aagcccagca acaccaaggt ggacaagaga gttgagtcca aatatggtcc cccatgccca     720
ccctgcccag cacctgagtt cgaaggggga ccatcagtct tcctgttccc cccaaaaccc     780
aaggacactc tcatgatctc ccggacccct gaggtcacgt gcgtggtggt ggacgtgagc     840
```

-continued

```
caggaagacc ccgaggtcca gttcaactgg tacgtggatg gcgtggaggt gcataatgcc      900
aagacaaagc cgcgggagga gcagttcaac agcacgtacc gtgtggtcag cgtcctcacc      960
gtcctgcacc aggactggct gaacggcaag gagtacaagt gcaaggtctc caacaaaggc     1020
ctcccgtcct ccatcgagaa aaccatctcc aaagccaaag ggcagccccg agagccacag     1080
gtgtacaccc tgcccccatc ccaggaggag atgaccaaga accaggtcag cctgacctgc     1140
ctggtcaaag gcttctaccc cagcgacatc gccgtggagt gggagagcaa tgggcagccg     1200
gagaacaact acaagaccac gcctcccgtg ctggactccg acggctcctt cttcctctac     1260
agcaggctaa ccgtggacaa gagcaggtgg caggagggga atgtcttctc atgctccgtg     1320
atgcatgagg ctctgcacaa ccactacaca cagaagagcc tctccctgtc tctgggtaaa     1380
gctagctga                                                             1389
```

```
<210> SEQ ID NO 133
<211> LENGTH: 370
<212> TYPE: PRT
<213> ORGANISM: Artificial Sequence
<220> FEATURE:
<223> OTHER INFORMATION: Synthetic Fusion protein

<400> SEQUENCE: 133

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Ala Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Ala Ser Met Gln Lys
    210                 215                 220

Gly Asp Gln Asn Pro Gln Ile Ala Ala His Val Ile Ser Glu Ala Ser
225                 230                 235                 240

Ser Lys Thr Thr Ser Val Leu Gln Trp Ala Glu Lys Gly Tyr Tyr Thr
                245                 250                 255

Met Ser Asn Asn Leu Val Thr Leu Glu Asn Gly Lys Gln Leu Thr Val
```

```
                260              265              270
Lys Arg Gln Gly Leu Tyr Tyr Ile Tyr Ala Gln Val Thr Phe Cys Ser
        275              280              285

Asn Arg Glu Ala Ser Ser Gln Ala Pro Phe Ile Ala Ser Leu Cys Leu
    290              295              300

Lys Ser Pro Gly Arg Phe Glu Arg Ile Leu Leu Arg Ala Ala Asn Thr
305              310              315              320

His Ser Ser Ala Lys Pro Cys Gly Gln Gln Ser Ile His Leu Gly Gly
                325              330              335

Val Phe Glu Leu Gln Pro Gly Ala Ser Val Phe Val Asn Val Thr Asp
            340              345              350

Pro Ser Gln Val Ser His Gly Thr Gly Phe Thr Ser Phe Gly Leu Leu
        355              360              365

Lys Leu
    370
```

```
<210> SEQ ID NO 134
<211> LENGTH: 1170
<212> TYPE: DNA
<213> ORGANISM: Artificial Sequence
<220> FEATURE:
<223> OTHER INFORMATION: Synthetic Fusion protein

<400> SEQUENCE: 134
atgaagttgc tgttaggct gttggtgctg atgttctgga ttcctgcttc cagcagtgat      60
gttgtgatga cccaaactcc actctccctg cctgtcagtc ttggagatca agcctccatc     120
tcttgccggt ctagtcagag ccttgtacac agtaatggaa acacctattt acattggtac     180
ctgcagaagc caggccagtc tccaaagctc ctgatctaca agtttccaa ccgattttct     240 ggggtcccag acaggttcag tggcagtgga tcagggacag atttcgcact caagatcagt     300
agagtggagg ccgaggatct gggagtttat ttctgctctc aaagtacaca tgttccgtgg     360
acgttcggtg gaggcaccaa gctcgagatc aaacgaactg tggctgcacc atctgtcttc     420
atcttcccgc catctgatga gcagttgaaa tctggaactg cctctgttgt gtgcctgctg     480
aataacttct atcccagaga ggccaaagta cagtggaagg tggataacgc cctccaatcg     540
ggtaactccc aggagagtgt cacagagcag gacagcaagg acagcaccta cagcctcagc     600
agcaccctga cgctgagcaa agcagactac gagaaacaca agtctatgc ctgcgaagtc     660 acccatcagg gcctgagctc gcccgtcaca aagagcttca cagggggaga gtgtgctagc     720
atgcagaagg gagaccagaa ccctcagatc gcagctcacg tcatctccga ggcttcttcc     780
aagaccacct ccgtgctcca gtgggctgaa aagggatact acaccatgag caacaacctg     840
gtgacactgg agaacggcaa gcagctcaca gtcaagcggc agggccttta ctacatctat     900
gcccaggtga ccttctgctc caacagggag gcctccagcc aggcccttt cattgcctct     960 ctgtgtctca agagcccagg cagattcgag aggattctcc tgcgcgccgc caatacacac    1020
agctcagcca aaccctgcgg gcaacagtca attcacctgg ggggggtctt tgagttgcag    1080
ccaggggcca gtgtcttcgt gaacgtgaca gatcccagtc aggtgagcca tggcactggc    1140
tttactagct ttgggttgct gaaactgtga                                     1170
```

```
<210> SEQ ID NO 135
<211> LENGTH: 621
<212> TYPE: PRT
<213> ORGANISM: Artificial Sequence
<220> FEATURE:
```

-continued

<223> OTHER INFORMATION: Synthetic Fusion protein

<400> SEQUENCE: 135

```
Glu Val Gln Leu Val Gln Ser Gly Ala Glu Val Lys Lys Pro Gly Ala
1               5                   10                  15

Ser Val Lys Ile Ser Cys Lys Ala Ser Gly Tyr Ser Phe Thr Gly Tyr
            20                  25                  30

Tyr Met His Trp Val Lys Gln Ala His Gly Gln Gly Leu Glu Trp Ile
        35                  40                  45

Gly Arg Ile Asn Pro Tyr Asn Gly Ala Thr Ser Tyr Asn Gln Asn Phe
    50                  55                  60

Lys Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Tyr Val Tyr Trp Gly Gln Gly Thr Thr Val Thr Val
            100                 105                 110

Ser Ser Ala Lys Thr Lys Gly Pro Ser Val Phe Pro Leu Ala Pro Cys
        115                 120                 125

Ser Arg Ser Thr Ser Glu Ser Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Lys Thr Tyr Thr Cys Asn Val Asp His Lys Pro Ser Asn Thr Lys Val
        195                 200                 205

Asp Lys Arg Val Glu Ser Lys Tyr Gly Pro Pro Cys Pro Pro Cys Pro
    210                 215                 220

Ala Pro Glu Phe Glu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser Gln Glu Asp Pro Glu Val Gln Phe Asn Trp Tyr
            260                 265                 270

Val Asp Gly Val Glu Val His Asn Ala Lys Thr Lys Pro Arg Glu Glu
        275                 280                 285

Gln Phe Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Gly Leu Pro Ser Ser Ile Glu Lys Thr Ile Ser Lys Ala Lys Gly Gln
                325                 330                 335

Pro Arg Glu Pro Gln Val Tyr Thr Leu Pro Pro Ser Gln Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400
```

```
Tyr Ser Arg Leu Thr Val Asp Lys Ser Arg Trp Gln Glu Gly Asn Val
                405             410                 415

Phe Ser Cys Ser Val Met His Glu Ala Leu His Asn His Tyr Thr Gln
            420             425                 430

Lys Ser Leu Ser Leu Ser Leu Gly Lys Ala Ser Gln Thr Pro Thr Asn
        435             440                 445

Thr Ile Ser Val Thr Pro Thr Asn Asn Ser Thr Pro Thr Asn Asn Ser
    450             455                 460

Asn Pro Lys Pro Asn Pro Ala Ser Met Gln Lys Gly Asp Gln Asn Pro
465             470             475                 480

Gln Ile Ala Ala His Val Ile Ser Glu Ala Ser Ser Lys Thr Thr Ser
            485             490                 495

Val Leu Gln Trp Ala Glu Lys Gly Tyr Tyr Thr Met Ser Asn Asn Leu
            500             505                 510

Val Thr Leu Glu Asn Gly Lys Gln Leu Thr Val Lys Arg Gln Gly Leu
        515             520                 525

Tyr Tyr Ile Tyr Ala Gln Val Thr Phe Cys Ser Asn Arg Glu Ala Ser
    530             535                 540

Ser Gln Ala Pro Phe Ile Ala Ser Leu Cys Leu Lys Ser Pro Gly Arg
545             550             555                 560

Phe Glu Arg Ile Leu Leu Arg Ala Ala Asn Thr His Ser Ser Ala Lys
            565             570                 575

Pro Cys Gly Gln Gln Ser Ile His Leu Gly Gly Val Phe Glu Leu Gln
            580             585                 590

Pro Gly Ala Ser Val Phe Val Asn Val Thr Asp Pro Ser Gln Val Ser
            595             600                 605

His Gly Thr Gly Phe Thr Ser Phe Gly Leu Leu Lys Leu
    610             615                 620
```

```
<210> SEQ ID NO 136
<211> LENGTH: 1923
<212> TYPE: DNA
<213> ORGANISM: Artificial Sequence
<220> FEATURE:
<223> OTHER INFORMATION: Synthetic Fusion protein

<400> SEQUENCE: 136
atgggatgga gctggatctt tctctttctc ctgtcaggaa ctgcaggtgt cctctctgag      60
gtccagctgg tgcaatctgg agctgaggtg aagaagcctg gggcttcagt gaagatatcc     120
tgcaaggctt ctggatactc cttcactggc tactacatgc actgggtgaa gcaggcccat     180
ggacaagggc ttgagtggat tggaaggatt aatccttaca atggtgctac tagctacaac     240
cagaacttca ggacagagc caccttgact gtagacaagt ccacgagcac agcctacatg     300
gagctcagca gcctgaggtc tgaggacacg gcagtctatt actgtgcaag agaggactac     360
gtgtactggg gccaaggcac cacggtcacc gtctcctcag ccaaaacgaa gggcccatcc     420
gtcttccccc tggcgccctg ctccaggagc acctccgaga gcacagccgc cctgggctgc     480
ctggtcaagg actacttccc cgaaccggtg acggtgtcgt ggaactcagg cgccctgacc     540
agcggcgtgc acaccttccc ggctgtccta cagtcctcag gactctactc cctcagcagc     600
gtggtgaccg tgccctccag cagcttgggc acgaagacct acacctgcaa cgtagatcac     660
aagcccagca acaccaaggt ggacaagaga gttgagtcca atatggtccc cccatgccca     720
ccctgcccag cacctgagtt cgaagggggga ccatcagtct tcctgttccc cccaaaaccc     780
aaggacactc tcatgatctc ccggacccct gaggtcacgt gcgtggtggt ggacgtgagc     840
```

-continued

```
caggaagacc ccgaggtcca gttcaactgg tacgtggatg gcgtggaggt gcataatgcc      900
aagacaaagc cgcgggagga gcagttcaac agcacgtacc gtgtggtcag cgtcctcacc      960
gtcctgcacc aggactggct gaacggcaag gagtacaagt gcaaggtctc caacaaaggc     1020
ctcccgtcct ccatcgagaa aaccatctcc aaagccaaag gcagccccg agagccacag      1080 gtgtacaccc tgcccccatc ccaggaggag atgaccaaga accaggtcag cctgacctgc     1140
ctggtcaaag gcttctaccc cagcgacatc gccgtggagt gggagagcaa tgggcagccg     1200
gagaacaact acaagaccac gcctcccgtg ctggactccg acggctcctt cttcctctac     1260
agcaggctaa ccgtggacaa gagcaggtgg caggagggga atgtcttctc atgctccgtg     1320
atgcatgagg ctctgcacaa ccactacaca cagaagagcc tctccctgtc tctgggtaaa     1380
gctagtcaga cccccaccaa caccatcagc gtgaccccca ccaacaacag caccccacc      1440 aacaacagca accccaagcc caaccccgct agcatgcaga agggagacca gaaccctcag     1500
atcgcagctc acgtcatctc cgaggcttct tccaagacca cctccgtgct ccagtgggct     1560
gaaaagggat actacaccat gagcaacaac ctggtgacac tggagaacgg caagcagctc     1620
acagtcaagc ggcagggcct ttactacatc tatgcccagg tgaccttctg ctccaacagg     1680
gaggcctcca gccaggcccc tttcattgcc tctctgtgtc tcaagagccc aggcagattc     1740
gagaggattc tcctgcgcgc cgccaataca cacagctcag ccaaaccctg cgggcaacag     1800
tcaattcacc tggggggggt ctttgagttg cagccagggg ccagtgtctt cgtgaacgtg     1860
acagatccca gtcaggtgag ccatggcact ggctttacta gctttgggtt gctgaaactg     1920
tga                                                                   1923
```

<210> SEQ ID NO 137
<211> LENGTH: 221
<212> TYPE: PRT
<213> ORGANISM: Artificial Sequence
<220> FEATURE:
<223> OTHER INFORMATION: Synthetic Fusion protein

<400> SEQUENCE: 137

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Trp Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160
```

```
Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Ala Ser
    210                 215                 220

<210> SEQ ID NO 138
<211> LENGTH: 723
<212> TYPE: PRT
<213> ORGANISM: Artificial Sequence
<220> FEATURE:
<223> OTHER INFORMATION: Synthetic Fusion protein

<400> SEQUENCE: 138

Ala Thr Gly Ala Ala Gly Thr Thr Gly Cys Cys Thr Gly Thr Thr Ala
1               5                   10                  15

Gly Gly Cys Thr Gly Thr Thr Gly Gly Thr Gly Cys Thr Gly Ala Thr
            20                  25                  30

Gly Thr Thr Cys Thr Gly Gly Ala Thr Thr Cys Cys Thr Gly Cys Thr
        35                  40                  45

Thr Cys Cys Ala Gly Cys Ala Gly Thr Gly Ala Thr Gly Thr Thr Gly
    50                  55                  60

Thr Gly Ala Thr Gly Ala Cys Cys Cys Ala Ala Thr Cys Thr Cys Cys
65                  70                  75                  80

Ala Cys Thr Cys Thr Cys Cys Cys Thr Gly Cys Cys Thr Gly Thr Cys
                85                  90                  95

Ala Cys Cys Cys Thr Thr Gly Gly Ala Cys Ala Gly Cys Cys Gly Gly
            100                 105                 110

Cys Cys Thr Cys Cys Ala Thr Cys Thr Cys Thr Thr Gly Cys Ala Gly
            115                 120                 125

Gly Thr Cys Thr Ala Gly Thr Cys Ala Gly Ala Gly Cys Cys Thr Thr
        130                 135                 140

Gly Thr Ala Cys Ala Cys Ala Gly Thr Ala Ala Thr Gly Gly Ala Ala
145                 150                 155                 160

Ala Cys Ala Cys Cys Thr Ala Thr Thr Ala Cys Ala Thr Thr Gly
                165                 170                 175

Gly Thr Ala Cys Cys Ala Gly Cys Ala Gly Ala Gly Ala Cys Cys Ala
            180                 185                 190

Gly Gly Cys Cys Ala Gly Thr Cys Thr Cys Cys Ala Ala Gly Gly Cys
            195                 200                 205

Thr Cys Cys Thr Gly Ala Thr Cys Thr Ala Cys Ala Ala Ala Gly Thr
    210                 215                 220

Thr Thr Cys Cys Ala Ala Cys Cys Gly Ala Thr Thr Thr Thr Cys Thr
225                 230                 235                 240

Gly Gly Gly Gly Thr Cys Cys Cys Ala Gly Ala Cys Ala Gly Gly Thr
                245                 250                 255

Thr Cys Ala Gly Thr Gly Gly Cys Ala Gly Thr Gly Gly Ala Thr Cys
            260                 265                 270

Ala Gly Gly Gly Ala Cys Ala Gly Ala Thr Thr Thr Cys Ala Cys Ala
            275                 280                 285

Cys Thr Cys Ala Ala Gly Ala Thr Cys Ala Gly Cys Ala Gly Ala Gly
    290                 295                 300
```

```
Thr Gly Gly Ala Gly Gly Cys Thr Gly Ala Ala Gly Ala Thr Gly Thr
305                 310                 315                 320

Thr Gly Gly Ala Gly Thr Thr Thr Ala Thr Thr Thr Cys Thr Gly Cys
                325                 330                 335

Thr Cys Thr Cys Ala Ala Ala Gly Thr Ala Cys Ala Cys Ala Thr Gly
                340                 345                 350

Thr Thr Cys Cys Thr Thr Gly Gly Ala Cys Gly Thr Thr Cys Gly Gly
                355                 360                 365

Cys Gly Gly Ala Gly Gly Gly Ala Cys Cys Ala Ala Gly Cys Thr Cys
                370                 375                 380

Gly Ala Gly Ala Thr Cys Ala Ala Ala Cys Gly Ala Ala Cys Thr Gly
385                 390                 395                 400

Thr Gly Gly Cys Thr Gly Cys Ala Cys Cys Ala Thr Cys Thr Gly Thr
                405                 410                 415

Cys Thr Thr Cys Ala Thr Cys Thr Thr Cys Cys Cys Gly Cys Cys Ala
                420                 425                 430

Thr Cys Thr Gly Ala Thr Gly Ala Gly Cys Ala Gly Thr Thr Gly Ala
                435                 440                 445

Ala Ala Thr Cys Thr Gly Gly Ala Ala Cys Thr Gly Cys Cys Thr Cys
                450                 455                 460

Thr Gly Thr Thr Gly Thr Gly Thr Gly Cys Cys Thr Gly Cys Thr Gly
465                 470                 475                 480

Ala Ala Thr Ala Ala Cys Thr Thr Cys Thr Ala Thr Cys Cys Cys Ala
                485                 490                 495

Gly Ala Gly Ala Gly Gly Cys Cys Ala Ala Ala Gly Thr Ala Cys Ala
                500                 505                 510

Gly Thr Gly Gly Ala Ala Gly Gly Thr Gly Gly Ala Thr Ala Ala Cys
                515                 520                 525

Gly Cys Cys Cys Thr Cys Cys Ala Ala Thr Cys Gly Gly Gly Thr Ala
                530                 535                 540

Ala Cys Thr Cys Cys Cys Ala Gly Gly Ala Gly Ala Gly Thr Gly Thr
545                 550                 555                 560

Cys Ala Cys Ala Gly Ala Gly Cys Ala Gly Gly Ala Cys Ala Gly Cys
                565                 570                 575

Ala Ala Gly Gly Ala Cys Ala Gly Cys Ala Cys Cys Thr Ala Cys Ala
                580                 585                 590

Gly Cys Cys Thr Cys Ala Gly Cys Ala Gly Cys Ala Cys Cys Cys Thr
                595                 600                 605

Gly Ala Cys Gly Cys Thr Gly Ala Gly Cys Ala Ala Ala Gly Cys Ala
                610                 615                 620

Gly Ala Cys Thr Ala Cys Gly Ala Gly Ala Ala Ala Cys Ala Cys Ala
625                 630                 635                 640

Ala Ala Gly Thr Cys Thr Ala Thr Gly Cys Cys Thr Gly Cys Gly Ala
                645                 650                 655

Ala Gly Thr Cys Ala Cys Cys Cys Ala Thr Cys Ala Gly Gly Gly Cys
                660                 665                 670

Cys Thr Gly Ala Gly Cys Thr Cys Gly Cys Cys Cys Gly Thr Cys Ala
                675                 680                 685

Cys Ala Ala Ala Gly Ala Gly Cys Thr Thr Cys Ala Ala Cys Ala Gly
                690                 695                 700

Gly Gly Gly Ala Gly Ala Gly Thr Gly Thr Gly Cys Thr Ala Gly Cys
705                 710                 715                 720

Thr Gly Ala
```

<210> SEQ ID NO 139
<211> LENGTH: 399
<212> TYPE: PRT
<213> ORGANISM: Artificial Sequence
<220> FEATURE:
<223> OTHER INFORMATION: Synthetic Fusion protein

<400> SEQUENCE: 139

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Trp Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys Ala Ser Gln Thr Pro
    210                 215                 220

Thr Asn Thr Ile Ser Val Thr Pro Thr Asn Asn Ser Thr Pro Thr Asn
225                 230                 235                 240

Asn Ser Asn Pro Lys Pro Asn Pro Ala Ser Met Gln Lys Gly Asp Gln
            245                 250                 255

Asn Pro Gln Ile Ala Ala His Val Ile Ser Glu Ala Ser Ser Lys Thr
            260                 265                 270

Thr Ser Val Leu Gln Trp Ala Glu Lys Gly Tyr Tyr Thr Met Ser Asn
        275                 280                 285

Asn Leu Val Thr Leu Glu Asn Gly Lys Gln Leu Thr Val Lys Arg Gln
    290                 295                 300

Gly Leu Tyr Tyr Ile Tyr Ala Gln Val Thr Phe Cys Ser Asn Arg Glu
305                 310                 315                 320

Ala Ser Ser Gln Ala Pro Phe Ile Ala Ser Leu Cys Leu Lys Ser Pro
                325                 330                 335

Gly Arg Phe Glu Arg Ile Leu Leu Arg Ala Ala Asn Thr His Ser Ser
            340                 345                 350

Ala Lys Pro Cys Gly Gln Gln Ser Ile His Leu Gly Gly Val Phe Glu
            355                 360                 365
```

-continued

```
Leu Gln Pro Gly Ala Ser Val Phe Val Asn Val Thr Asp Pro Ser Gln
    370                 375                 380

Val Ser His Gly Thr Gly Phe Thr Ser Phe Gly Leu Leu Lys Leu
385                 390                 395

<210> SEQ ID NO 140
<211> LENGTH: 1257
<212> TYPE: DNA
<213> ORGANISM: Artificial Sequence
<220> FEATURE:
<223> OTHER INFORMATION: Synthetic Fusion protein

<400> SEQUENCE: 140
atgaagttgc ctgttaggct gttggtgctg atgttctgga ttcctgcttc cagcagtgat      60
gttgtgatga cccaatctcc actctccctg cctgtcaccc ttggacagcc ggcctccatc     120
tcttgcaggt ctagtcagag ccttgtacac agtaatggaa acacctattt acattggtac     180
cagcagagac caggccagtc tccaaggctc ctgatctaca agtttccaa ccgatttct      240 ggggtcccag acaggttcag tggcagtgga tcagggacag atttcacact caagatcagc     300
agagtggagc tgaagatgt tggagtttat ttctgctctc aaagtacaca tgttccttgg     360
acgttcggcg agggaccaa gctcgagatc aaacgaactg tggctgcacc atctgtcttc     420
atcttcccgc catctgatga gcagttgaaa tctggaactg cctctgttgt gtgcctgctg     480
aataacttct atcccagaga ggccaaagta cagtggaagg tggataacgc cctccaatcg     540
ggtaactccc aggagagtgt cacagagcag gacagcaagg acagcaccta cagcctcagc     600
agcaccctga cgctgagcaa agcagactac gagaaacaca agtctatgc ctgcgaagtc     660 acccatcagg gcctgagctc gcccgtcaca aagagcttca caggggaga gtgtgctagt     720 cagacccca ccaacaccat cagcgtgacc cccaccaaca acagcacccc caccaacaac     780 agcaaccca agcccaaccc cgctagcatg cagaagggag accagaaccc tcagatcgca     840
gctcacgtca tctccgaggc ttcttccaag accacctccg tgctccagtg ggctgaaaag     900
ggatactaca ccatgagcaa caacctggtg cactggaga acggcaagca gctcacagtc     960
aagcggcagg gcctttacta catctatgcc caggtgacct tctgctccaa cagggaggcc    1020
tccagccagg ccccttttcat tgcctctctg tgtctcaaga gcccaggcag attcgagagg    1080
attctcctgc gcgccgccaa tacacacagc tcagccaaac cctgcgggca acagtcaatt    1140
cacctggggg gggtctttga gttgcagcca ggggccagtg tcttcgtgaa cgtgacagat    1200
cccagtcagg tgagccatgg cactggcttt actagctttg ggttgctgaa actgtga      1257

<210> SEQ ID NO 141
<211> LENGTH: 443
<212> TYPE: PRT
<213> ORGANISM: Artificial Sequence
<220> FEATURE:
<223> OTHER INFORMATION: Synthetic Fusion Protein

<400> SEQUENCE: 141

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Gly Leu Glu Trp Ile
        35                  40                  45

Gly Arg Ile Asn Pro Tyr Asn Gly Ala Thr Ser Tyr Asn Gln Asn Phe
```

-continued

|  | | 50 | | | | 55 | | | | 60 | | |

Lys Asp Arg Val Thr Leu Thr Val Asp Lys Ser Thr Ser Thr Ala Tyr
65              70                  75                  80

Met Glu Leu Ser Ser Leu Arg Ser Glu Asp Thr Ala Val Tyr Tyr Cys
                85                  90                  95

Ala Arg Glu Asp Tyr Val Tyr Trp Gly Gln Gly Thr Thr Val Thr Val
            100                 105                 110

Ser Ser Ala Lys Thr Lys Gly Pro Ser Val Phe Pro Leu Ala Pro Cys
        115                 120                 125

Ser Arg Ser Thr Ser Glu Ser Thr Ala Ala Leu Gly Cys Leu Val Lys
        130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
                180                 185                 190

Lys Thr Tyr Thr Cys Asn Val Asp His Lys Pro Ser Asn Thr Lys Val
                195                 200                 205

Asp Lys Arg Val Glu Ser Lys Tyr Gly Pro Pro Cys Pro Pro Cys Pro
        210                 215                 220

Ala Pro Glu Phe Glu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser Gln Glu Asp Pro Glu Val Gln Phe Asn Trp Tyr
                260                 265                 270

Val Asp Gly Val Glu Val His Asn Ala Lys Thr Lys Pro Arg Glu Glu
                275                 280                 285

Gln Phe Asn Ser Thr Tyr Arg Val Val Ser Val Leu Thr Val Leu His
        290                 295                 300

Gln Asp Trp Leu Asn Gly Lys Glu Tyr Lys Cys Lys Val Ser Asn Lys
305                 310                 315                 320

Gly Leu Pro Ser Ser Ile Glu Lys Thr Ile Ser Lys Ala Lys Gly Gln
                325                 330                 335

Pro Arg Glu Pro Gln Val Tyr Thr Leu Pro Pro Ser Gln Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
        370                 375                 380

Tyr Lys Thr Thr Pro Pro Val Leu Asp Ser Asp Gly Ser Phe Phe Leu
385                 390                 395                 400

Tyr Ser Arg Leu Thr Val Asp Lys Ser Arg Trp Gln Glu Gly Asn Val
                405                 410                 415

Phe Ser Cys Ser Val Met His Glu Ala Leu His Asn His Tyr Thr Gln
                420                 425                 430

Lys Ser Leu Ser Leu Ser Leu Gly Lys Ala Ser
        435                 440

<210> SEQ ID NO 142
<211> LENGTH: 1389
<212> TYPE: DNA
<213> ORGANISM: Artificial Sequence

```
<220> FEATURE:
<223> OTHER INFORMATION: Synthetic Fusion Protein

<400> SEQUENCE: 142
atgggatgga gctggatctt tctctttctc ctgtcaggaa ctgcaggtgt cctctctgag      60
gtccagctgg tgcaatctgg agctgaggtg aagaagcctg gggcttcagt gaaggtctcc     120
tgcaaggctt ctggatactc cttcactggc tactacatgc actgggtgcg acaggcccct     180
ggacaagggc ttgagtggat tggaaggatt aatccttaca atggtgctac tagctacaac     240
cagaacttca aggacagagt caccttgact gtagacaagt ccacgagcac agcctacatg     300
gagctcagca gcctgaggtc tgaggacacg gcagtctatt actgtgcaag agaggactac     360
gtgtactggg gccaaggcac cacggtcacc gtctcctcag ccaaaacgaa gggcccatcc     420
gtcttccccc tggcgccctg ctccaggagc acctccgaga gcacagccgc cctgggctgc     480
ctggtcaagg actacttccc cgaaccggtg acggtgtcgt ggaactcagg cgccctgacc     540
agcggcgtgc acaccttccc ggctgtccta cagtcctcag gactctactc cctcagcagc     600
gtggtgaccg tgccctccag cagcttgggc acgaagacct acacctgcaa cgtagatcac     660
aagcccagca acaccaaggt ggacaagaga gttgagtcca atatggtcc cccatgccca      720 ccctgcccag cacctgagtt cgaaggggga ccatcagtct tcctgttccc cccaaaaccc     780
aaggacactc tcatgatctc ccggacccct gaggtcacgt gcgtggtggt ggacgtgagc     840
caggaagacc ccgaggtcca gttcaactgg tacgtggatg gcgtggaggt gcataatgcc     900
aagacaaagc cgcgggagga gcagttcaac agcacgtacc gtgtggtcag cgtcctcacc     960
gtcctgcacc aggactggct gaacggcaag gagtacaagt gcaaggtctc caacaaaggc    1020
ctcccgtcct ccatcgagaa aaccatctcc aaagccaaag gcagccccg agagccacag     1080 gtgtacaccc tgcccccatc ccaggaggag atgaccaaga accaggtcag cctgacctgc    1140
ctggtcaaag gcttctaccc cagcgacatc gccgtggagt gggagagcaa tgggcagccg    1200
gagaacaact acaagaccac gcctcccgtg ctggactccg acggctcctt cttcctctac    1260
agcaggctaa ccgtggacaa gagcaggtgg caggagggga atgtcttctc atgctccgtg    1320
atgcatgagg ctctgcacaa ccactacaca cagaagagcc tctccctgtc tctgggtaaa    1380
gctagctga                                                          1389

<210> SEQ ID NO 143
<211> LENGTH: 592
<212> TYPE: PRT
<213> ORGANISM: Artificial Sequence
<220> FEATURE:
<223> OTHER INFORMATION: Synthetic Fusion Protein

<400> SEQUENCE: 143

Glu Val Gln Leu Val Gln Ser Gly Ala Glu Val Lys Lys Pro Gly Ala
1               5                   10                  15

Ser Val Lys Ile Ser Cys Lys Ala Ser Gly Tyr Ser Phe Thr Gly Tyr
                20                  25                  30

Tyr Met His Trp Val Lys Gln Ala His Gly Gln Gly Leu Glu Trp Ile
            35                  40                  45

Gly Arg Ile Asn Pro Tyr Asn Gly Ala Thr Ser Tyr Asn Gln Asn Phe
        50                  55                  60

Lys Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
```

```
                      85                   90                   95
Ala Arg Glu Asp Tyr Val Tyr Trp Gly Gln Gly Thr Thr Val Thr Val
            100                 105                 110

Ser Ser Ala Lys Thr Lys Gly Pro Ser Val Phe Pro Leu Ala Pro Cys
            115                 120                 125

Ser Arg Ser Thr Ser Glu Ser Thr Ala Ala Leu Gly Cys Leu Val Lys
            130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
                180                 185                 190

Lys Thr Tyr Thr Cys Asn Val Asp His Lys Pro Ser Asn Thr Lys Val
                195                 200                 205

Asp Lys Arg Val Glu Ser Lys Tyr Gly Pro Pro Cys Pro Pro Cys Pro
            210                 215                 220

Ala Pro Glu Phe Glu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser Gln Glu Asp Pro Glu Val Gln Phe Asn Trp Tyr
                260                 265                 270

Val Asp Gly Val Glu Val His Asn Ala Lys Thr Lys Pro Arg Glu Glu
                275                 280                 285

Gln Phe Asn Ser Thr Tyr Arg Val Val Ser Val Leu Thr Val Leu His
            290                 295                 300

Gln Asp Trp Leu Asn Gly Lys Glu Tyr Lys Cys Lys Val Ser Asn Lys
305                 310                 315                 320

Gly Leu Pro Ser Ser Ile Glu Lys Thr Ile Ser Lys Ala Lys Gly Gln
                325                 330                 335

Pro Arg Glu Pro Gln Val Tyr Thr Leu Pro Pro Ser Gln Glu Glu Met
                340                 345                 350

Thr Lys Asn Gln Val Ser Leu Thr Cys Leu Val Lys Gly Phe Tyr Pro
            355                 360                 365

Ser Asp Ile Ala Val Glu Trp Glu Ser Asn Gly Gln Pro Glu Asn Asn
            370                 375                 380

Tyr Lys Thr Thr Pro Pro Val Leu Asp Ser Asp Gly Ser Phe Phe Leu
385                 390                 395                 400

Tyr Ser Arg Leu Thr Val Asp Lys Ser Arg Trp Gln Glu Gly Asn Val
                405                 410                 415

Phe Ser Cys Ser Val Met His Glu Ala Leu His Asn His Tyr Thr Gln
            420                 425                 430

Lys Ser Leu Ser Leu Ser Leu Gly Lys Ala Ser Met Gln Lys Gly Asp
            435                 440                 445

Gln Asn Pro Gln Ile Ala Ala His Val Ile Ser Glu Ala Ser Ser Lys
            450                 455                 460

Thr Thr Ser Val Leu Gln Trp Ala Glu Lys Gly Tyr Tyr Thr Met Ser
465                 470                 475                 480

Asn Asn Leu Val Thr Leu Glu Asn Gly Lys Gln Leu Thr Val Lys Arg
                485                 490                 495

Gln Gly Leu Tyr Tyr Ile Tyr Ala Gln Val Thr Phe Cys Ser Asn Arg
            500                 505                 510
```

-continued

```
Glu Ala Ser Ser Gln Ala Pro Phe Ile Ala Ser Leu Cys Leu Lys Ser
        515                 520                 525

Pro Gly Arg Phe Glu Arg Ile Leu Leu Arg Ala Ala Asn Thr His Ser
    530                 535                 540

Ser Ala Lys Pro Cys Gly Gln Gln Ser Ile His Leu Gly Gly Val Phe
545                 550                 555                 560

Glu Leu Gln Pro Gly Ala Ser Val Phe Val Asn Val Thr Asp Pro Ser
                565                 570                 575

Gln Val Ser His Gly Thr Gly Phe Thr Ser Phe Gly Leu Leu Lys Leu
                580                 585                 590

<210> SEQ ID NO 144
<211> LENGTH: 1836
<212> TYPE: DNA
<213> ORGANISM: Artificial Sequence
<220> FEATURE:
<223> OTHER INFORMATION: Synthetic Fusion protein

<400> SEQUENCE: 144
atgggatgga gctggatctt tctctttctc ctgtcaggaa ctgcaggtgt cctctctgag       60
gtccagctgg tgcaatctgg agctgaggtg aagaagcctg gggcttcagt gaagatatcc      120
tgcaaggctt ctggatactc cttcactggc tactacatgc actgggtgaa gcaggcccat      180
ggacaagggc ttgagtggat tggaaggatt aatccttaca tggtgctac tagctacaac      240 cagaacttca ggacagagc caccttgact gtagacaagt ccacgagcac agcctacatg      300
gagctcagca gcctgaggtc tgaggacacg gcagtctatt actgtgcaag agaggactac      360
gtgtactggg gccaaggcac cacggtcacc gtctcctcag ccaaaacgaa gggcccatcc      420
gtcttccccc tggcgccctg ctccaggagc acctccgaga gcacagccgc cctgggctgc      480
ctggtcaagg actacttccc cgaaccggtg acggtgtcgt ggaactcagg cgccctgacc      540
agcggcgtgc acaccttccc ggctgtccta cagtcctcag gactctactc cctcagcagc      600
gtggtgaccg tgccctccag cagcttgggc acgaagacct acacctgcaa cgtagatcac      660
aagcccagca acaccaaggt ggacaagaga gttgagtcca atatggtcc cccatgccca      720 ccctgcccag cacctgagtt cgaagggggga ccatcagtct tcctgttccc cccaaaaccc      780
aaggacactc tcatgatctc ccggaccccT gaggtcacgt gcgtggtggt ggacgtgagc      840
caggaagacc ccgaggtcca gttcaactgg tacgtggatg gcgtggaggt gcataatgcc      900
aagacaaagc cgcgggagga gcagttcaac agcacgtacc gtgtggtcag cgtcctcacc      960
gtcctgcacc aggactggct gaacggcaag gagtacaagt gcaaggtctc caacaaaggc     1020
ctcccgtcct ccatcgagaa aaccatctcc aaagccaaag gcagccccg agagccacag     1080 gtgtacaccc tgcccccatc ccaggaggag atgaccaaga ccaggtcag cctgacctgc     1140 ctggtcaaag gcttctaccc cagcgacatc gccgtggagt gggagagcaa tgggcagccg     1200
gagaacaact acaagaccac gcctcccgtg ctggactccg acggctcctt cttcctctac     1260
agcaggctaa ccgtggacaa gagcaggtgg caggagggga atgtcttctc atgctccgtg     1320
atgcatgagg ctctgcacaa ccactacaca cagaagagcc tctccctgtc tctgggtaaa     1380
gctagcatgc agaagggaga ccagaaccct cagatcgcag ctcacgtcat ctccgaggct     1440
tcttccaaga ccacctccgt gctccagtgg gctgaaaagg atactacac catgagcaac     1500 aacctggtga cactggagaa cggcaagcag ctcacagtca agcggcaggg cctttactac     1560
atctatgccc aggtgacctt ctgctccaac agggaggcct ccagccaggc cccttttcatt     1620
```

```
gcctctctgt gtctcaagag cccaggcaga ttcgagagga ttctcctgcg cgccgccaat    1680
acacacagct cagccaaacc ctgcgggcaa cagtcaattc acctggggggg ggtctttgag    1740 ttgcagccag gggccagtgt cttcgtgaac gtgacagatc ccagtcaggt gagccatggc    1800
actggcttta ctagctttgg gttgctgaaa ctgtga                              1836
```

<210> SEQ ID NO 145
<211> LENGTH: 443
<212> TYPE: PRT
<213> ORGANISM: Artificial Sequence
<220> FEATURE:
<223> OTHER INFORMATION: Synthetic Fusion Protein

<400> SEQUENCE: 145

```
Glu Val Gln Leu Val Gln Ser Gly Ala Glu Val Lys Lys Pro Gly Ala
1               5                   10                  15

Ser Val Lys Ile Ser Cys Lys Ala Ser Gly Tyr Ser Phe Thr Gly Tyr
                20                  25                  30

Tyr Met His Trp Val Lys Gln Ala His Gly Gln Gly Leu Glu Trp Ile
            35                  40                  45

Gly Arg Ile Asn Pro Tyr Asn Gly Ala Thr Ser Tyr Asn Gln Asn Phe
        50                  55                  60

Lys Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Tyr Val Tyr Trp Gly Gln Gly Thr Thr Val Thr Val
            100                 105                 110

Ser Ser Ala Lys Thr Lys Gly Pro Ser Val Phe Pro Leu Ala Pro Cys
        115                 120                 125

Ser Arg Ser Thr Ser Glu Ser Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Lys Thr Tyr Thr Cys Asn Val Asp His Lys Pro Ser Asn Thr Lys Val
        195                 200                 205

Asp Lys Arg Val Glu Ser Lys Tyr Gly Pro Pro Cys Pro Pro Cys Pro
    210                 215                 220

Ala Pro Glu Phe Glu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser Gln Glu Asp Pro Glu Val Gln Phe Asn Trp Tyr
            260                 265                 270

Val Asp Gly Val Glu Val His Asn Ala Lys Thr Lys Pro Arg Glu Glu
        275                 280                 285

Gln Phe Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320
```

```
Gly Leu Pro Ser Ser Ile Glu Lys Thr Ile Ser Lys Ala Lys Gly Gln
            325                 330                 335

Pro Arg Glu Pro Gln Val Tyr Thr Leu Pro Pro Ser Gln Glu Glu Met
            340                 345                 350

Thr Lys Asn Gln Val Ser Leu Thr Cys Leu Val Lys Gly Phe Tyr Pro
            355                 360                 365

Ser Asp Ile Ala Val Glu Trp Glu Ser Asn Gly Gln Pro Glu Asn Asn
            370                 375                 380

Tyr Lys Thr Thr Pro Pro Val Leu Asp Ser Asp Gly Ser Phe Phe Leu
385                 390                 395                 400

Tyr Ser Arg Leu Thr Val Asp Lys Ser Arg Trp Gln Glu Gly Asn Val
            405                 410                 415

Phe Ser Cys Ser Val Met His Glu Ala Leu His Asn His Tyr Thr Gln
            420                 425                 430

Lys Ser Leu Ser Leu Ser Leu Gly Lys Ala Ser
            435                 440
```

<210> SEQ ID NO 146
<211> LENGTH: 1389
<212> TYPE: DNA
<213> ORGANISM: Artificial Sequence
<220> FEATURE:
<223> OTHER INFORMATION: Synthetic Fusion Protein

<400> SEQUENCE: 146

```
atgggatgga gctggatctt tctctttctc ctgtcaggaa ctgcaggtgt cctctctgag      60
gtccagctgg tgcaatctgg agctgaggtg aagaagcctg gggcttcagt gaagatatcc     120
tgcaaggctt ctggatactc cttcactggc tactacatgc actgggtgaa gcaggcccat     180
ggacaagggc ttgagtggat tggaaggatt aatccttaca atggtgctac tagctacaac     240
cagaacttca aggacagagc caccttgact gtagacaagt ccacgagcac agcctacatg     300
gagctcagca gcctgaggtc tgaggacacg gcagtctatt actgtgcaag agaggactac     360
gtgtactggg gccaaggcac cacggtcacc gtctcctcag ccaaaacgaa gggcccatcc     420
gtcttccccc tggcgccctg ctccaggagc acctccgaga gcacagccgc cctgggctgc     480
ctggtcaagg actacttccc cgaaccggtg acggtgtcgt ggaactcagg cgccctgacc     540
agcggcgtgc acaccttccc ggctgtccta cagtcctcag gactctactc cctcagcagc     600
gtggtgaccg tgccctccag cagcttgggc acgaagacct acacctgcaa cgtagatcac     660
aagcccagca acaccaaggt ggacaagaga gttgagtcca atatggtcc cccatgccca     720 ccctgcccag cacctgagtt cgaaggggga ccatcagtct tcctgttccc cccaaaaccc     780
aaggacactc tcatgatctc ccggacccct gaggtcacgt gcgtggtggt ggacgtgagc     840
caggaagacc ccgaggtcca gttcaactgg tacgtggatg gcgtggaggt gcataatgcc     900
aagacaaagc cgcgggagga gcagttcaac agcacgtacc gtgtggtcag cgtcctcacc     960
gtcctgcacc aggactggct gaacggcaag gagtacaagt gcaaggtctc caacaaaggc    1020
ctcccgtcct ccatcgagaa aaccatctcc aaagccaaag gcagccccg agagccacag     1080 gtgtacaccc tgcccccatc ccaggaggag atgaccaaga accaggtcag cctgacctgc    1140
ctggtcaaag gcttctaccc cagcgacatc gccgtggagt gggagagcaa tgggcagccg    1200
gagaacaact acaagaccac gcctcccgtg ctggactccg acggctcctt cttcctctac    1260
agcaggctaa ccgtggacaa gagcaggtgg caggagggga atgtcttctc atgctccgtg    1320
atgcatgagg ctctgcacaa ccactacaca cagaagagcc tctccctgtc tctgggtaaa    1380
```

-continued gctagctga                                                                1389

<210> SEQ ID NO 147
<211> LENGTH: 443
<212> TYPE: PRT
<213> ORGANISM: Artificial Sequence
<220> FEATURE:
<223> OTHER INFORMATION: Synthetic Fusion Protein

<400> SEQUENCE: 147

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Gly Leu Glu Trp Ile
        35                  40                  45

Gly Arg Ile Asn Pro Tyr Asn Gly Ala Thr Ser Tyr Asn Gln Asn Phe
    50                  55                  60

Lys Asp Arg Val Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Tyr Val Tyr Trp Gly Gln Gly Thr Thr Val Thr Val
            100                 105                 110

Ser Ser Ala Lys Thr Lys Gly Pro Ser Val Phe Pro Leu Ala Pro Cys
        115                 120                 125

Ser Arg Ser Thr Ser Glu Ser Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Lys Thr Tyr Thr Cys Asn Val Asp His Lys Pro Ser Asn Thr Lys Val
            195                 200                 205

Asp Lys Arg Val Glu Ser Lys Tyr Gly Pro Pro Cys Pro Pro Cys Pro
    210                 215                 220

Ala Pro Glu Phe Glu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser Gln Glu Asp Pro Glu Val Gln Phe Asn Trp Tyr
            260                 265                 270

Val Asp Gly Val Glu Val His Asn Ala Lys Thr Lys Pro Arg Glu Glu
        275                 280                 285

Gln Phe Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Gly Leu Pro Ser Ser Ile Glu Lys Thr Ile Ser Lys Ala Lys Gly Gln
                325                 330                 335

Pro Arg Glu Pro Gln Val Tyr Thr Leu Pro Pro Ser Gln Glu Glu Met
            340                 345                 350

-continued

```
Thr Lys Asn Gln Val Ser Leu Thr Cys Leu Val Lys Gly Phe Tyr Pro
    355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Arg Leu Thr Val Asp Lys Ser Arg Trp Gln Glu Gly Asn Val
            405                 410                 415

Phe Ser Cys Ser Val Met His Glu Ala Leu His Asn His Tyr Thr Gln
            420                 425                 430

Lys Ser Leu Ser Leu Ser Leu Gly Lys Ala Ser
    435                 440
```

```
<210> SEQ ID NO 148
<211> LENGTH: 1389
<212> TYPE: DNA
<213> ORGANISM: Artificial Sequence
<220> FEATURE:
<223> OTHER INFORMATION: Synthetic Fusion Protein

<400> SEQUENCE: 148
atgggatgga gctggatctt tctctttctc ctgtcaggaa ctgcaggtgt cctctctgag      60
gtccagctgg tgcaatctgg agctgaggtg aagaagcctg gggcttcagt gaaggtctcc     120
tgcaaggctt ctggatactc cttcactggc tactacatgc actgggtgcg acaggcccct     180
ggacaagggc ttgagtggat tggaaggatt aatccttaca atggtgctac tagctacaac     240
cagaacttca ggacagagt caccttgact gtagacaagt ccacgagcac agcctacatg     300
gagctcagca gcctgaggtc tgaggacacg gcagtctatt actgtgcaag agaggactac     360
gtgtactggg gccaaggcac cacggtcacc gtctcctcag ccaaaacgaa gggcccatcc     420
gtcttccccc tggcgccctg ctccaggagc acctccgaga gcacagccgc cctgggctgc     480
ctggtcaagg actacttccc cgaaccggtg acggtgtcgt ggaactcagg cgccctgacc     540
agcggcgtgc acaccttccc ggctgtccta cagtcctcag gactctactc cctcagcagc     600
gtggtgaccg tgccctccag cagcttgggc acgaagacct acacctgcaa cgtagatcac     660
aagcccagca acaccaaggt ggacaagaga gttgagtcca aatatggtcc cccatgccca     720
ccctgcccag cacctgagtt cgaaggggga ccatcagtct tcctgttccc cccaaaaccc     780
aaggacactc tcatgatctc ccggacccct gaggtcacgt gcgtggtggt ggacgtgagc     840
caggaagacc ccgaggtcca gttcaactgg tacgtggatg gcgtggaggt gcataatgcc     900
aagacaaagc cgcgggagga gcagttcaac agcacgtacc gtgtggtcag cgtcctcacc     960
gtcctgcacc aggactggct gaacggcaag gagtacaagt gcaaggtctc caacaaaggc    1020
ctcccgtcct ccatcgagaa aaccatctcc aaagccaaag gcagccccg agagccacag    1080 gtgtacaccc tgcccccatc ccaggaggag atgaccaaga accaggtcag cctgacctgc    1140
ctggtcaaag gcttctaccc cagcgacatc gccgtggagt gggagagcaa tgggcagccg    1200
gagaacaact acaagaccac gcctcccgtg ctggactccg acggctcctt cttcctctac    1260
agcaggctaa ccgtggacaa gagcaggtgg caggagggga atgtcttctc atgctccgtg    1320
atgcatgagg ctctgcacaa ccactacaca cagaagagcc tctccctgtc tctgggtaaa    1380
gctagctga                                                           1389
```

```
<210> SEQ ID NO 149
<211> LENGTH: 221
```

<212> TYPE: PRT
<213> ORGANISM: Artificial Sequence
<220> FEATURE:
<223> OTHER INFORMATION: Synthetic Fusion Protein

<400> SEQUENCE: 149

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Trp Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Ala Ser
    210                 215                 220
```

<210> SEQ ID NO 150
<211> LENGTH: 723
<212> TYPE: DNA
<213> ORGANISM: Artificial Sequence
<220> FEATURE:
<223> OTHER INFORMATION: Synthetic Fusion protein

<400> SEQUENCE: 150

```
atgaagttgc ctgttaggct gttggtgctg atgttctgga ttcctgcttc cagcagtgat      60
gttgtgatga cccaatctcc actctccctg cctgtcaccc ttggacagcc ggcctccatc     120
tcttgcaggt ctagtcagag ccttgtacac agtaatggaa acacctattt acattggtac     180
cagcagagac caggccagtc tccaaggctc ctgatctaca agtttccaa ccgattttct     240 ggggtcccag acaggttcag tggcagtgga tcagggacag atttcacact caagatcagc     300
agagtggagg ctgaagatgt ggagttttat ttctgctctc aaagtacaca tgttccttgg     360
acgttcggcg agggaccaa gctcgagatc aaacgaactg tggctgcacc atctgtcttc     420
atcttcccgc catctgatga gcagttgaaa tctggaactg cctctgttgt gtgcctgctg     480
aataacttct atcccagaga ggccaaagta cagtggaagg tggataacgc cctccaatcg     540
ggtaactccc aggagagtgt cacagagcag gacagcaagg acagcaccta cagcctcagc     600
```
agcaccctga cgctgagcaa agcagactac gagaaacaca aagtctatgc ctgcgaagtc     660
acccatcagg gcctgagctc gcccgtcaca aagagcttca acaggggaga gtgtgctagc     720
tga                                                                   723

<210> SEQ ID NO 151
<211> LENGTH: 339
<212> TYPE: PRT
<213> ORGANISM: Artificial Sequence
<220> FEATURE:
<223> OTHER INFORMATION: Synthetic Fusion Protein

<400> SEQUENCE: 151

Glu Pro Pro Thr Ala Cys Arg Glu Lys Gln Tyr Leu Ile Asn Ser Gln
1               5                   10                  15

Cys Cys Ser Leu Cys Gln Pro Gly Gln Lys Leu Val Ser Asp Cys Thr
                20                  25                  30

Glu Phe Thr Glu Thr Glu Cys Leu Pro Cys Gly Glu Ser Glu Phe Leu
            35                  40                  45

Asp Thr Trp Asn Arg Glu Thr His Cys His Gln His Lys Tyr Cys Asp
        50                  55                  60

Pro Asn Leu Gly Leu Arg Val Gln Gln Lys Gly Thr Ser Glu Thr Asp
65                  70                  75                  80

Thr Ile Cys Thr Cys Glu Glu Gly Trp His Cys Thr Ser Glu Ala Cys
                85                  90                  95

Glu Ser Cys Val Leu His Arg Ser Cys Ser Pro Gly Phe Gly Val Lys
            100                 105                 110

Gln Ile Ala Thr Gly Val Ser Asp Thr Ile Cys Glu Pro Cys Pro Val
            115                 120                 125

Gly Phe Phe Ser Asn Val Ser Ser Ala Phe Glu Lys Cys His Pro Trp
        130                 135                 140

Thr Ser Cys Glu Thr Lys Asp Leu Val Val Gln Gln Ala Gly Thr Asn
145                 150                 155                 160

Lys Thr Asp Val Val Cys Gly Pro Gln Asp Arg Leu Arg Val Asp Ser
                165                 170                 175

Asn Leu Gly Trp Leu Cys Leu Leu Leu Leu Pro Ile Pro Leu Ile Val
            180                 185                 190

Trp Val Lys Arg Lys Glu Val Gln Lys Thr Cys Arg Lys His Arg Lys
            195                 200                 205

Glu Asn Gln Gly Ser His Glu Ser Pro Thr Leu Asn Pro Glu Thr Val
        210                 215                 220

Ala Ile Asn Leu Ser Asp Val Asp Leu Ser Lys Tyr Ile Ala Thr Ile
225                 230                 235                 240

Ala Gly Val Met Thr Leu Ser Gln Val Lys Gly Phe Val Arg Lys Asn
                245                 250                 255

Gly Val Asn Glu Ala Lys Ile Asp Glu Ile Lys Asn Asp Asn Val Gln
            260                 265                 270

Asp Thr Ala Glu Gln Lys Val Gln Leu Leu Arg Asn Trp His Gln Leu
        275                 280                 285

His Gly Lys Lys Glu Ala Tyr Asp Thr Leu Ile Lys Asp Leu Lys Lys
        290                 295                 300

Ala Asn Leu Cys Thr Leu Ala Glu Lys Ile Gln Thr Ile Ile Leu Lys
305                 310                 315                 320

Asp Ile Thr Ser Asp Ser Glu Asn Ser Asn Phe Arg Asn Glu Ile Gln
                325                 330                 335

Ser Leu Val

<210> SEQ ID NO 152
<211> LENGTH: 1080
<212> TYPE: DNA
<213> ORGANISM: Artificial Sequence
<220> FEATURE:
<223> OTHER INFORMATION: Synthetic Fusion Protein

<400> SEQUENCE: 152
atggttcgtc tgcctctgca gtgcgtcctc tggggctgct tgctgaccgc tgtccatcca        60
gaaccaccca ctgcatgcag agaaaaacag tacctaataa acagtcagtg ctgttctttg       120
tgccagccag gacagaaact ggtgagtgac tgcacagagt tcactgaaac ggaatgcctt       180
ccttgcggtg aaagcgaatt cctagacacc tggaacagag agacacactg ccaccagcac       240
aaatactgcg accccaacct agggcttcgg gtccagcaga agggcacctc agaaacagac       300
accatctgca cctgtgaaga aggctggcac tgtacgagtg aggcctgtga gagctgtgtc       360
ctgcaccgct catgctcgcc cggctttggg gtcaagcaga ttgctacagg ggtttctgat       420
accatctgcg agccctgccc agtcggcttc ttctccaatg tgtcatctgc tttcgaaaaa       480
tgtcacccct ggacaagctg tgagaccaaa gacctggttg tgcaacaggc aggcacaaac       540
aagactgatg ttgtctgtgg tccccaggat cggctgagag tcgactctaa cttggggtgg       600
ctttgtcttc ttctttgcc aattccacta attgtttggg tgaagagaaa ggaagtacag       660
aaaacatgca gaaagcacag aaaggaaaac caaggttctc atgaatctcc aaccttaaat       720
cctgaaacag tggcaataaa tttatctgat gttgacttga gtaaatatat cgccactatt       780
gctggagtca tgacactaag tcaagttaaa ggctttgttc gaaagaatgg tgtcaatgaa       840
gccaaaatag atgagatcaa gaatgacaat gtccaagaca cagcagaaca gaaagttcaa       900
ctgcttcgta attggcatca acttcatgga aagaagaag cgtatgacac attgattaaa       960
gatctcaaaa aagccaatct ttgtactctt gcagagaaaa ttcagactat catcctcaag      1020
gacattacta gtgactcaga aaattcaaac ttcagaaatg aaatccaaag cttggtctag      1080

<210> SEQ ID NO 153
<211> LENGTH: 15
<212> TYPE: PRT
<213> ORGANISM: Homo sapiens

<400> SEQUENCE: 153

Pro Pro Thr Ala Cys Arg Glu Lys Gln Tyr Leu Ile Asn Ser Gln
1               5                   10                  15

<210> SEQ ID NO 154
<211> LENGTH: 10
<212> TYPE: PRT
<213> ORGANISM: Homo sapiens

<400> SEQUENCE: 154

Gln Cys Cys Ser Leu Cys Gln Pro Gly Gln
1               5                   10

<210> SEQ ID NO 155
<211> LENGTH: 15
<212> TYPE: PRT
<213> ORGANISM: Homo sapiens

<400> SEQUENCE: 155

Asp Thr Trp Asn Arg Glu Thr His Cys His Gln His Lys Tyr Cys

-continued

```
1               5               10              15

<210> SEQ ID NO 156
<211> LENGTH: 13
<212> TYPE: PRT
<213> ORGANISM: Homo sapiens

<400> SEQUENCE: 156

His Arg Ser Cys Ser Pro Gly Phe Gly Val Lys Gln Ile
1               5               10

<210> SEQ ID NO 157
<211> LENGTH: 12
<212> TYPE: PRT
<213> ORGANISM: Homo sapiens

<400> SEQUENCE: 157

Lys Cys His Pro Trp Thr Ser Cys Glu Thr Lys Asp
1               5               10

<210> SEQ ID NO 158
<211> LENGTH: 13
<212> TYPE: PRT
<213> ORGANISM: Homo sapiens

<400> SEQUENCE: 158

Cys His Gln His Lys Tyr Cys Asp Pro Asn Leu Gly Leu
1               5               10

<210> SEQ ID NO 159
<211> LENGTH: 13
<212> TYPE: PRT
<213> ORGANISM: Homo sapiens

<400> SEQUENCE: 159

Ile Asn Ser Gln Cys Cys Ser Leu Cys Gln Pro Gly Gln
1               5               10

<210> SEQ ID NO 160
<211> LENGTH: 15
<212> TYPE: PRT
<213> ORGANISM: Homo sapiens

<400> SEQUENCE: 160

Cys Leu Pro Cys Gly Glu Ser Glu Phe Leu Asp Thr Trp Asn Arg
1               5               10              15

<210> SEQ ID NO 161
<211> LENGTH: 10
<212> TYPE: PRT
<213> ORGANISM: Homo sapiens

<400> SEQUENCE: 161

Asp Thr Trp Asn Arg Glu Thr His Cys His
1               5               10

<210> SEQ ID NO 162
<211> LENGTH: 14
<212> TYPE: PRT
<213> ORGANISM: Homo sapiens

<400> SEQUENCE: 162

Cys His Gln His Lys Tyr Cys Asp Pro Asn Leu Gly Leu Arg
1               5               10
```

<210> SEQ ID NO 163
<211> LENGTH: 14
<212> TYPE: PRT
<213> ORGANISM: Homo sapiens

<400> SEQUENCE: 163

His Cys Thr Ser Glu Ala Cys Glu Ser Cys Val Leu His Arg
1               5                   10

<210> SEQ ID NO 164
<211> LENGTH: 12
<212> TYPE: PRT
<213> ORGANISM: Homo sapiens

<400> SEQUENCE: 164

Leu His Arg Ser Cys Ser Pro Gly Phe Gly Val Lys
1               5                   10

<210> SEQ ID NO 165
<211> LENGTH: 15
<212> TYPE: PRT
<213> ORGANISM: Homo sapiens

<400> SEQUENCE: 165

His Pro Trp Thr Ser Cys Glu Thr Lys Asp Leu Val Val Gln Gln
1               5                   10                  15

<210> SEQ ID NO 166
<211> LENGTH: 13
<212> TYPE: PRT
<213> ORGANISM: Homo sapiens

<400> SEQUENCE: 166

Thr Asn Lys Thr Asp Val Val Cys Gly Pro Gln Asp Arg
1               5                   10

<210> SEQ ID NO 167
<211> LENGTH: 14
<212> TYPE: PRT
<213> ORGANISM: Homo sapiens

<400> SEQUENCE: 167

Pro Thr Ala Cys Arg Glu Lys Gln Tyr Leu Ile Asn Ser Gln
1               5                   10

<210> SEQ ID NO 168
<211> LENGTH: 129
<212> TYPE: PRT
<213> ORGANISM: Artificial Sequence
<220> FEATURE:
<223> OTHER INFORMATION: Synthetic Fusion protein

<400> SEQUENCE: 168

Glu Phe Ala Ser Ala Glu Ala Gly Ile Thr Gly Thr Trp Tyr Asn Gln
1               5                   10                  15

His Gly Ser Thr Phe Thr Val Thr Ala Gly Ala Asp Gly Asn Leu Thr
            20                  25                  30

Gly Gln Tyr Glu Asn Arg Ala Gln Gly Thr Gly Cys Gln Asn Ser Pro
        35                  40                  45

Tyr Thr Leu Thr Gly Arg Tyr Asn Gly Thr Lys Leu Glu Trp Arg Val
    50                  55                  60

Glu Trp Asn Asn Ser Thr Glu Asn Cys His Ser Arg Thr Glu Trp Arg
65                  70                  75                  80

```
Gly Gln Tyr Gln Gly Gly Ala Glu Ala Arg Ile Asn Thr Gln Trp Asn
            85                  90                  95

Leu Thr Tyr Glu Gly Gly Ser Gly Pro Ala Thr Glu Gln Gly Gln Asp
            100                 105                 110

Thr Phe Thr Lys Val Lys Pro Ser Ala Ala Ser Gly Ser Glu Pro Glu
        115                 120                 125

Ala
```

```
<210> SEQ ID NO 169
<211> LENGTH: 375
<212> TYPE: DNA
<213> ORGANISM: Artificial Sequence
<220> FEATURE:
<223> OTHER INFORMATION: Synthetic Fusion protein

<400> SEQUENCE: 169
gagtttgctt ctgctgaagc tggaatcaca ggcacatggt ataatcagca cggctctacc      60
tttacagtga cagccggagc tgatggaaac ctgaccggcc agtatgagaa cagagcccag     120
ggaacaggat gtcagaatag tccttataca ctgacaggca gatataacgg aacaaagctg     180
gagtggagag tggagtggaa taactctaca gagaactgtc actctagaac agagtggaga     240
ggccagtacc agggcggcgc tgaggctaga attaacacac agtggaacct gacatacgag     300
ggaggctctg gacctgctac agaacagggc caggatacat tcacaaaggt gaagccttct     360
gctgcctctg gatct                                                      375
```

```
<210> SEQ ID NO 170
<211> LENGTH: 607
<212> TYPE: PRT
<213> ORGANISM: Artificial Sequence
<220> FEATURE:
<223> OTHER INFORMATION: Synthetic Fusion protein

<400> SEQUENCE: 170

Arg Leu Gln Leu Gln Glu Ser Gly Pro Gly Leu Leu Lys Pro Ser Val
1               5                   10                  15

Thr Leu Ser Leu Thr Cys Thr Val Ser Gly Asp Ser Val Ala Ser Ser
            20                  25                  30

Ser Tyr Tyr Trp Gly Trp Val Arg Gln Pro Pro Gly Lys Gly Leu Glu
        35                  40                  45

Trp Ile Gly Thr Ile Asn Phe Ser Gly Asn Met Tyr Tyr Ser Pro Ser
    50                  55                  60

Leu Arg Ser Arg Val Thr Met Ser Ala Asp Met Ser Glu Asn Ser Phe
65                  70                  75                  80

Tyr Leu Lys Leu Asp Ser Val Thr Ala Ala Asp Thr Ala Val Tyr Tyr
            85                  90                  95

Cys Ala Ala Gly His Leu Val Met Gly Phe Gly Ala His Trp Gly Gln
            100                 105                 110

Gly Lys Leu Val Ser Val Ser Pro Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175
```

```
Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Glu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
            405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys Ala
            435                 440                 445

Ser Gln Thr Pro Thr Asn Thr Ile Ser Val Thr Pro Thr Asn Asn Ser
    450                 455                 460

Thr Pro Thr Asn Asn Ser Asn Pro Lys Pro Asn Pro Ala Ser Glu Phe
465                 470                 475                 480

Ala Ser Ala Glu Ala Gly Ile Thr Gly Thr Trp Tyr Asn Gln His Gly
            485                 490                 495

Ser Thr Phe Thr Val Thr Ala Gly Ala Asp Gly Asn Leu Thr Gly Gln
            500                 505                 510

Tyr Glu Asn Arg Ala Gln Gly Thr Gly Cys Gln Asn Ser Pro Tyr Thr
            515                 520                 525

Leu Thr Gly Arg Tyr Asn Gly Thr Lys Leu Glu Trp Arg Val Glu Trp
    530                 535                 540

Asn Asn Ser Thr Glu Asn Cys His Ser Arg Thr Glu Trp Arg Gly Gln
545                 550                 555                 560

Tyr Gln Gly Gly Ala Glu Ala Arg Ile Asn Thr Gln Trp Asn Leu Thr
            565                 570                 575

Tyr Glu Gly Gly Ser Gly Pro Ala Thr Glu Gln Gly Gln Asp Thr Phe
            580                 585                 590

Thr Lys Val Lys Pro Ser Ala Ala Ser Gly Ser Glu Pro Glu Ala
```

-continued

```
        595              600              605

<210> SEQ ID NO 171
<211> LENGTH: 1902
<212> TYPE: DNA
<213> ORGANISM: Artificial Sequence
<220> FEATURE:
<223> OTHER INFORMATION: Synthetic Fusion protein

<400> SEQUENCE: 171
atggacctcc tgtgcaagaa catgaagcac ctgtggttct tcctcctgct ggtggcggct          60
cccagatggg tcctgtcccg gctgcagctg caggagtcgg gcccaggcct gctgaagcct         120
tcggtgaccc tgtccctcac ctgcactgtc tcgggtgact ccgtcgccag tagttcttat         180
tactggggct gggtccgtca gccccaggg aagggactcg agtggatagg gactatcaat         240
tttagtggca atatgtatta tagtccgtcc ctcaggagtc gagtgaccat gtcggcagac         300
atgtccgaga actccttcta tctgaaattg actctgtga ccgcagcaga cacggccgtc         360
tattattgtg cggcaggaca cctcgttatg ggatttgggg cccactgggg acagggaaaa         420
ctggtctccg tctctccagc ttccaccaag ggcccatccg tcttcccct ggcgccctgc         480 tccaggagca cctccgagag cacagccgcc ctgggctgcc tggtcaagga ctacttcccc         540
gaaccggtga cggtgtcgtg gaactcaggc gccctgacca gcggcgtgca caccttcccg         600
gctgtcctac agtcctcagg actctactcc ctcagcagcg tggtgaccgt gccctccagc         660
agcttgggca cgaagaccta cacctgcaac gtagatcaca gcccagcaa caccaaggtg         720 gacaagagag ttgagtccaa atatggtccc ccatgcccac cctgcccagc acctgagttc         780 gaaggggac catcagtctt cctgttcccc ccaaaaccca aggacactct catgatctcc         840
cggacccctg aggtcacgtg cgtggtggtg acgtgagcc aggaagaccc cgaggtccag         900
ttcaactggt acgtggatgg cgtggaggtg cataatgcca agacaaagcc gcgggaggag         960
cagttcaaca gcacgtaccg tgtggtcagc gtcctcaccg tcctgcacca ggactggctg        1020
aacggcaagg agtacaagtg caaggtctcc aacaaaggcc tcccgtcctc catcgagaaa        1080
accatctcca aagccaaagg gcagccccga gagccacagg tgtacaccct gcccccatcc        1140
caggaggaga tgaccaagaa ccaggtcagc ctgacctgcc tggtcaaagg cttctacccc        1200
agcgacatcg ccgtggagtg ggagagcaat gggcagccgg agaacaacta caagaccacg        1260
cctcccgtgc tggactccga cggctccttc ttcctctaca gcaggctaac cgtggacaag        1320
agcaggtggc aggagggaa tgtcttctca tgctccgtga tgcatgaggc tctgcacaac        1380
cactacacac agaagagcct ctccctgtct ctgggtaaag ctagtcagac ccccaccaac        1440
accatcagcg tgacccccac caacaacagc accccaccaac aacagcaa ccccaagccc        1500 aaccccgcta gcgagtttgc ttctgctgaa gctggaatca caggcacatg gtataatcag        1560
cacggctcta cctttacagt gacagccgga gctgatggaa acctgaccgg ccagtatgag        1620
aacagagccc agggaacagg atgtcagaat agtccttata cactgacagg cagatataac        1680
ggaacaaagc tggagtggag agtggagtgg aataactcta cagagaactg tcactctaga        1740
acagagtgga gaggccagta ccagggcggc gctgaggcta gaattaacac acagtggaac        1800
ctgacatacg agggaggctc tggacctgct acagaacagg ccaggatac attcacaaag        1860 gtgaagcctt ctgctgcctc tggatctgag cctgaggctt ga                          1902

<210> SEQ ID NO 172
<211> LENGTH: 174
```

```
<212> TYPE: PRT
<213> ORGANISM: Artificial Sequence
<220> FEATURE:
<223> OTHER INFORMATION: Synthetic Recombinant

<400> SEQUENCE: 172

Arg Glu Lys Gln Tyr Leu Ile Asn Ser Gln Cys Cys Ser Leu Cys Gln
1               5                   10                  15

Pro Gly Gln Lys Leu Val Ser Asp Cys Thr Glu Phe Thr Glu Thr Glu
            20                  25                  30

Cys Leu Pro Cys Gly Glu Ser Glu Phe Leu Asp Thr Trp Asn Arg Glu
        35                  40                  45

Thr His Cys His Gln His Lys Tyr Cys Asp Pro Asn Leu Gly Leu Arg
    50                  55                  60

Val Gln Gln Lys Gly Thr Ser Glu Thr Asp Thr Ile Cys Thr Cys Glu
65                  70                  75                  80

Glu Gly Trp His Cys Thr Ser Glu Ala Cys Glu Ser Cys Val Leu His
                85                  90                  95

Arg Ser Cys Ser Pro Gly Phe Gly Val Lys Gln Ile Ala Thr Gly Val
            100                 105                 110

Ser Asp Thr Ile Cys Glu Pro Cys Pro Val Gly Phe Phe Ser Asn Val
            115                 120                 125

Ser Ser Ala Phe Glu Lys Cys His Pro Trp Thr Ser Cys Glu Thr Lys
    130                 135                 140

Asp Leu Val Val Gln Gln Ala Gly Thr Asn Lys Thr Asp Val Val Cys
145                 150                 155                 160

Gly Pro Gln Asp Arg Leu Arg Ala Leu Val Val Ile Pro Ile
                165                 170

<210> SEQ ID NO 173
<211> LENGTH: 6
<212> TYPE: PRT
<213> ORGANISM: Artificial Sequence
<220> FEATURE:
<223> OTHER INFORMATION: Synthetic recombinant

<400> SEQUENCE: 173

His His His His His His
1               5
```